US 11,501,440 B2

(12) United States Patent
Weisenfeld et al.

(10) Patent No.: US 11,501,440 B2
(45) Date of Patent: *Nov. 15, 2022

(54) SYSTEMS AND METHODS FOR SPATIAL ANALYSIS OF ANALYTES USING FIDUCIAL ALIGNMENT

(71) Applicant: 10X Genomics, Inc., Pleasanton, CA (US)

(72) Inventors: Neil Ira Weisenfeld, Lynnfield, MA (US); Narek Dshkhunyan, Pleasanton, CA (US); Preyas Shah, Pleasanton, CA (US)

(73) Assignee: 10X GENOMICS, INC., Pleasonton, CA (US)

( * ) Notice: Subject to any disclaimer, the term of this patent is extended or adjusted under 35 U.S.C. 154(b) by 134 days.

This patent is subject to a terminal disclaimer.

(21) Appl. No.: 16/951,843

(22) Filed: Nov. 18, 2020

(65) Prior Publication Data
US 2021/0158522 A1 May 27, 2021

Related U.S. Application Data

(60) Provisional application No. 62/938,967, filed on Nov. 22, 2019.

(51) Int. Cl.
*G06T 7/00* (2017.01)
*G06T 7/136* (2017.01)
(Continued)

(52) U.S. Cl.
CPC .......... *G06T 7/0014* (2013.01); *G06K 9/6215* (2013.01); *G06T 3/0075* (2013.01);
(Continued)

(58) Field of Classification Search
CPC ........ G06K 9/6215; G06T 2207/10056; G06T 2207/10064; G06T 2207/30024;
(Continued)

(56) References Cited

U.S. PATENT DOCUMENTS 5,472,881 A 12/1995 Beebe et al.
5,610,287 A 3/1997 Nikiforov et al.
(Continued)

FOREIGN PATENT DOCUMENTS

EP 1 336 662 A2 8/2003
JP 1336662 * 2/2003 ............... C12Q 1/68
(Continued)

OTHER PUBLICATIONS

Rao, "Discover the genes that matter while preserving spatial information: The Visium Gene Expression Solution", Sep. 26, 2019, https://www.labroots.com/webinar/discover-genes-matter-preserving-spatial-information-visium-gene-expression-solution (Year: 2019).*
(Continued)

*Primary Examiner* — Zhiyu Lu

(57) ABSTRACT

Systems and methods for spatial analysis of analytes are provided. A data structure is obtained comprising an image, as an array of pixel values, of a sample on a substrate having a identifier, fiducial markers and a set of capture spots. The pixel values are used to identify derived fiducial spots. The substrate identifier identifies a template having reference positions for reference fiducial spots and a corresponding coordinate system. The derived fiducial spots are aligned with the reference fiducial spots using an alignment algorithm to obtain a transformation between the derived and reference fiducial spots. The transformation and the template corresponding coordinate system are used to register the image to the set of capture spots. The registered image is then analyzed in conjunction with spatial analyte data associated with each capture spot, thereby performing spatial analysis of analytes.

31 Claims, 47 Drawing Sheets
(22 of 47 Drawing Sheet(s) Filed in Color)

Specification includes a Sequence Listing.

(51) Int. Cl.
| | |
|---|---|
| *G16B 25/00* | (2019.01) |
| *G06K 9/62* | (2022.01) |
| *G06T 3/00* | (2006.01) |
| *G06T 3/60* | (2006.01) |

(52) U.S. Cl.
CPC ............ *G06T 3/608* (2013.01); *G06T 7/136* (2017.01); *G16B 25/00* (2019.02); *G06T 2207/10056* (2013.01); *G06T 2207/30072* (2013.01)

(58) Field of Classification Search
CPC . G06T 2207/30072; G06T 2207/30204; G06T 3/0075; G06T 3/608; G06T 7/0014; G06T 7/11; G06T 7/136; G06T 7/33; G06V 20/695; G16B 25/00
See application file for complete search history.

(56) References Cited

U.S. PATENT DOCUMENTS

| | | | |
|---|---|---|---|
| 5,807,522 | A | 9/1998 | Brown et al. |
| 5,837,860 | A | 11/1998 | Anderson et al. |
| 5,919,626 | A | 7/1999 | Shi et al. |
| 6,210,891 | B1 | 4/2001 | Nyren et al. |
| 6,258,568 | B1 | 6/2001 | Nyren |
| 6,265,552 | B1 | 7/2001 | Schatz |
| 6,266,459 | B1 | 7/2001 | Walt et al. |
| 6,274,320 | B1 | 8/2001 | Rothburg et al. |
| 6,355,431 | B1 | 3/2002 | Chee et al. |
| 6,391,937 | B1 | 5/2002 | Beuhler et al. |
| 6,737,236 | B1 | 5/2004 | Pieken et al. |
| 6,770,441 | B2 | 8/2004 | Dickinson et al. |
| 6,859,570 | B2 | 2/2005 | Walt et al. |
| 6,867,028 | B2 | 3/2005 | Janulaitis et al. |
| 7,259,258 | B2 | 8/2007 | Koslov et al. |
| 7,282,328 | B2 | 10/2007 | Kong et al. |
| 7,375,234 | B2 | 5/2008 | Sharpless et al. |
| 7,427,678 | B2 | 9/2008 | Pieken et al. |
| 7,709,198 | B2 | 5/2010 | Luo et al. |
| 7,785,869 | B2 | 8/2010 | Belgrader et al. |
| 8,604,182 | B2 | 12/2013 | Luo et al. |
| 8,774,494 | B2 | 7/2014 | Staker |
| 8,951,726 | B2 | 2/2015 | Luo et al. |
| 9,012,022 | B2 | 4/2015 | George et al. |
| 9,359,641 | B2 | 6/2016 | Staker |
| 9,460,904 | B1* | 10/2016 | Greving .............. H01J 49/0409 |
| 9,512,422 | B2 | 12/2016 | Barnard et al. |
| 9,593,365 | B2 | 3/2017 | Frisen et al. |
| 9,727,810 | B2 | 4/2017 | Fodor et al. |
| 9,783,841 | B2 | 10/2017 | Nolan et al. |
| 9,889,422 | B2 | 2/2018 | Smith et al. |
| 10,002,316 | B2 | 6/2018 | Fodor et al. |
| 10,041,949 | B2 | 8/2018 | Bendall et al. |
| 10,059,990 | B2 | 8/2018 | Boyden et al. |
| 10,068,200 | B1* | 9/2018 | Greving .............. G06Q 10/087 |
| 2007/0174007 | A1* | 7/2007 | Ghosh .................... G16B 25/30 |
| | | | 702/19 |
| 2008/0280773 | A1 | 11/2008 | Fedurco et al. |
| 2009/0026082 | A1 | 1/2009 | Rothburg et al. |
| 2009/0127589 | A1 | 5/2009 | Rothburg et al. |
| 2010/0137143 | A1 | 6/2010 | Rothburg et al. |
| 2010/0282617 | A1 | 11/2010 | Rothburg et al. |
| 2011/0059865 | A1 | 3/2011 | Smith et al. |
| 2017/0016053 | A1 | 1/2017 | Beechem et al. |
| 2017/0253918 | A1 | 9/2017 | Kohman et al. |
| 2018/0052081 | A1 | 2/2018 | Kohman et al. |
| 2018/0105808 | A1 | 4/2018 | Mikkelsen et al. |
| 2018/0156784 | A1 | 6/2018 | Usmani et al. |
| 2018/0245142 | A1 | 8/2018 | So et al. |
| 2018/0312822 | A1 | 11/2018 | Lee et al. |
| 2019/0087948 | A1* | 3/2019 | Langlois .............. H04N 1/401 |
| 2019/0203275 | A1 | 7/2019 | Frisen et al. |
| 2021/0062272 | A1 | 3/2021 | Williams et al. |
| 2021/0097684 | A1 | 4/2021 | Melllen et al. |
| 2021/0155982 | A1* | 5/2021 | Yin ....................... G06V 20/695 |
| 2021/0317524 | A1* | 10/2021 | Lucero ................ C12Q 1/6841 |
| 2021/0324457 | A1* | 10/2021 | Ramachandran Iyer .................... C12Q 1/6841 |
| 2021/0332425 | A1* | 10/2021 | Pfeiffer ............... C12Q 1/6874 |

FOREIGN PATENT DOCUMENTS

| | | |
|---|---|---|
| WO | WO 2000/063437 | 10/2000 |
| WO | WO 2005/065814 | 7/2005 |
| WO | WO 2011/094669 | 8/2011 |
| WO | WO 2011/127099 | 10/2011 |
| WO | WO 2012/140224 | 10/2012 |
| WO | WO 2012/168003 | 12/2012 |
| WO | WO 2014/060483 | 4/2014 |
| WO | WO 2014/163886 A1 | 10/2014 |
| WO | WO 2014/210225 | 12/2014 |
| WO | WO 2014/210233 | 12/2014 |
| WO | WO 2015/161173 | 10/2015 |
| WO | WO 2016/007839 A1 | 1/2016 |
| WO | WO 2016/057552 | 4/2016 |
| WO | WO 2016/162309 | 10/2016 |
| WO | WO 2016/166128 | 10/2016 |
| WO | WO 2017/019456 A2 | 2/2017 |
| WO | WO 2017/027367 A1 | 2/2017 |
| WO | WO 2017/027368 | 2/2017 |
| WO | WO 2017/144338 A1 | 8/2017 |
| WO | WO 2017/147483 | 8/2017 |
| WO | WO 2017/222453 A1 | 12/2017 |
| WO | WO 2018/022809 A1 | 2/2018 |
| WO | WO 2018/045181 A1 | 3/2018 |
| WO | WO 2018/045186 A1 | 3/2018 |
| WO | WO 2018/057999 A1 | 3/2018 |
| WO | WO 2018/075693 A1 | 4/2018 |
| WO | WO 2018/091676 A1 | 5/2018 |
| WO | WO 2018/107054 A1 | 6/2018 |
| WO | WO 2018/136856 A1 | 7/2018 |
| WO | WO 2019/068880 A1 | 4/2019 |
| WO | WO 2019/075091 A1 | 4/2019 |
| WO | WO 2020/176788 A1 | 9/2020 |
| WO | WO 2021/092433 A2 | 5/2021 |

OTHER PUBLICATIONS

Inside Visium Spatial Technology—10x Genomics, The Power of Two: Mapping and Measuring Gene Expression, pp. 1-4 (2021).
Inside Visium Spatial Technology—Introduction and How to Prepare, 10X Genomics,Visium, Spatial Gene Expression (2019).
10X, 2019, Visium Spatial Gene Expression Solution.
Achim et al., 2015, "High-throughput spatial mapping of single-cell RNA-seq data to tissue of origin," Nature Biotechnology 33: 503-509, doi:10.1038/nbt.3209.
Adiconis, et al., Nat Methods, 2013, 10(7), p. 623-629.
Algayer et al., 2019, *Molecules*. 24(11). pii: E2079.
Andresen et al., 2009, Helicase-dependent amplification: use in OnChip amplification and potential for point-of-care diagnostics, Expert Rev Mol Diagn. 9, 645-650, doi: 10.1586/erm.09.46.
Andrew, 1979, "Another efficient algorithm for convex hulls in two dimensions," Information Processing Letters 9 (5), pp. 216-219.
Archer et al, 2014, Selective and flexible depletion of problematic sequences from RNA-seq libraries at the cDNA stage, BMC Genomics 15 401.
Asano et al., 2018, Current Protocols 80:1, doi:10.1002/cpcb.56.
Beattie et al. (1995) Clin. Chem. 45, 700-706.
Beier et al. (1999) Nucleic Acids Research 27, 1970-1977.
Bolognesi et al., 2017, J. Histochem. Cytochem. 65(8): 431-444.
Brown, 1979, "Voronoi diagrams from convex hulls," Information Processing Letters 9(5), pp. 223-228.
Carter et al., 2007, Applied Optics 46:421-427).
Chen et al., *Science* 348(6233):aaa6090, 2015.
Chen et al., 2015, *Science* 347(6221):543-548.
Chen et al., Nat. Methods 13:679-684, 2016.
Chetverikov et al., 2002, "The Trimmed Iterative Closest Point Algorithm," Object recognition supported by user interaction for service robots, Quebec City, Quebec, Canada, ISSN: 1051-4651.

(56) References Cited

OTHER PUBLICATIONS

Chetverikov et al., 2005, "Robust Euclidean alignment of 3D point sets; the trimmed iterative closest point algorithm," Image and Vision Computing 23(3), pp. 299-309.
Chiang et al., 2000, *J Biochem. Biophys. Methods*. 20;46(1-2):53-68.
Chrisey et al. (1996) Nucleic Acids Research 24, 3031-3039.
Chui and Rangarajanb, 2003, "A new point matching algorithm for non-rigid registration," Computer Vision and Image Understanding 89(2-3), pp. 114-141.
Cox and Emili., 2006, *Nat Protoc*. 1(4):1872-8.
Duda and Hart, *Pattern Classification and Scene Analysis*, 1973, John Wiley & Sons, Inc., New York, p. 211-256.
Duda and Hart, *Pattern Classification and Scene Analysis*, 1973, John Wiley & Sons, Inc., New York, p. 217.
Duda and Hart, *Pattern Classification and Scene Analysis*, 1973, John Wiley & Sons, Inc., New York, p. 537-563.
Fahy et al. (1993) Nucleic Acids Research 21, 1819-1826.
Fang et al., 2003, *Nucleic Acids Res*. 31(2): 708-715.
Gao et al., 2017, BMC Biology 15:50, doi:10.1186/s12915-017-0393-3.
Gill and Ghaemi, Nucleic acid isothermal amplification technologies: a review, Nucleosides, Nucleotides, & Nucleic Acids, 27(3), 224-43, doi: 10.1080/15257770701845204 (2008).
Glass et al., 2009, J. Histochem. Cytochem. 57:899-905.
Gould et al., 2018 Oncotarget. 20; 9(21): 15606-15615.
Govan et al., 2013, *Nucleic Acids Research* 41; 22, 10518-10528.
Grokhovsky, 2006, Specificity of DNA cleavage by ultrasound, Molecular Biology, 40(2), 276-283.
Guo et al. (1994) Nucleic Acids Research 22, 5456-5465.
Gupta et al., *Nature Biotechnol*. 36:1197-1202, 2018.
Han et al., 2019, *Microsyst Nanoeng*. 5:30.
Hipp et al. 2017, *Leukemia* 10, 2278.
Holmstrøm et al. (1993) Analytical Biochemistry 209, 278-283.
ILLUMINA, Indexed Sequencing Overview Guides, Feb. 2018, Document 15057455v04.
ILLUMINA Adapter Sequences, May 2019, Document #1000000002694v11.
Jamur et al., 2010, *Method Mol. Biol*. 588:63-66, 2010.
Joos et al. (1997) Analytical Biochemistry 247, 96-101.
Khallaghi, "PyCPD: Turorial on the Coherent Point Drift Algorithm", siavashk.github.io/2017/05/14/coherent-point-drift/ (May 14, 2017).
Koch et al., 2000, Bioconjugate Chem. 11, 474-483.
Lamture et al. (1994) Nucleic Acids Research 22, 2121-2125.
Lee et al., *Nat. Protoc*. 10(3):442-458, 2015.
Li et al., 2019, Review: a comprehensive summary of a decade development of the recombinase polymerase amplification, Analyst 144, 31-67, doi: 10.1039/C8AN01621F (2019).
Lin et al., 2015, Nat Commun. 6:8390.
Liu et al., 2014, *Acc. Chem. Res*., 47(1): 45-55 (2014).
Lu et al. *Lab Chip*. Jan. 2005;5(1):23-9.
Macosko et al., 2015 Cell 161, 1202-1214.
Miller et al., 2009, "Basic concepts of microarrays and potential applications in clinical microbiology." Clinical microbiology reviews 22.4, 611-633.
Myronenko, Andriy, et al. "Non-rigid point set registration: Coherent Point Drift", Department of Computer Science and Electrical Engineering, OGI School of Science and Engineering, Beaverton, OR, pp. 1-8 (2006).
Myronenko, Andriy, et al. "Point Set Registration: Coherent Point Drift", Department of Science and Engineering, School of Medicine, Oregon Health and Science University, Porland, OR, May 15, 2009, pp. 1-14.
Nikiforov et al. (1995) Analytical Biochemistry 227, 201-209.
Niklas et al., 2011, *Anal Biochem* 416(2):218-27.
Petrick et al., 2009, Measurement 2009, Proceedings of the 7th International Conference, Smolenice, Slovakia, pp. 352-355.
Piepenburg et al., 2006, DNA Detection Using Recombinant Proteins, PLoS Biol. 4, 7 e204.
Pirici et al., 2009, J. Histochem. Cytochem. 57:567-75.
Rao, Nikhil, "Discover the genes that matter while preserving spatial information: The Visium Gene Expression Solution" Sep. 26, 2019, XP054981474, p. 1.
Rodriques et al., *Science* 363(6434):1463-1467, 2019.
Ronaghi et al., Science, Jul. 17, 1998, v. 281, n. 5375, p. 363-365.
Satija et al., 2015, "Spatial reconstruction of single-cell gene expression data," Nature Biotechnology. 33, 495-502, doi:10.1038.nbt.3192.
Shalon et al. (1996) Genome Research, 639-645.
Stimpson et al. (1995) Proc. Natl. Acad. Sci. USA 92, 6379-6383.
Timofeev et al. (1996) Nucleic Acids Research 24, 3142-3148.
Trejo et al., *PLoS ONE* 14(2):e0212031, 2019.
Uchida, 2013, "Image processing and recognition for biological images," Develop. Growth Differ. 55, 523-549, doi:10.1111/dgd.12054.
Vandernoot, 2012, "cDNA normalization by hydroxyapatite chromatography to enrich transcriptome diversity in RNA-seq applications," Biotechniques, 53(6) 373-80.
Vincent et. al., 2004, Helicase-dependent isothermal DNA amplification, EMBO Rep., 795-800.
Wassie et al, 2018, Expansion microscopy: principles and uses in biological research, Nature Methods 16(1): 33-41.
Yamauchi and Herr et al., 2017, *Microsyst. Nanoeng*. 3. pii: 16079.
Yang, 2011, "The thin plate spline robust point matching (TPS-RPM) algorithm: A revisit," Pattern Recognition Letters 32(7), pp. 910-918.
Yershov et al. (1996) Proc. Natl. Acad. Sci. USA 93, 4913-4918.
Uytingco et al., Spatially Resolved Transcriptomics and Poteomic Cell-Types in the Human Central Nervous System, 10X Genomics, Inc., 2020.
Zhai, Jack Ye "Making GenePix Array List (GAL) Files", Molecular Devices, Application Note, Jul. 5, 2001, pp. 1-9.
Zhang et al. (1991) 19, 3929-3933.
Zhang, 2011, "Optimal multi-level Thresholding based on Maximum Tsallis Entropy via an Artificial Bee Colony Approach," Entropy 13(4): pp. 841-859.

\* cited by examiner

Contact sample with array of spatially-barcoded capture probes
(101)

Capture analytes using capture probes
(102)

Analyze capture probes to obtain spatially-resolved analyte information
(103)

Figure 1

Contact sample with array of spatially-barcoded capture probes
(201)

Optionally cleave capture probes from array and capture analyte on/in sample
(202)

Analyze capture probes to obtain spatially-resolved information about an analyte
(203)

1002 Systems and method for spatial analysis of analytes are provided.

1004 Obtain a data structure 1122 in electronic form comprising (i) an image 1124 of a biological sample (e.g., sectioned tissue sample) on a substrate and (ii) a substrate identifier 1128 unique to the substrate, where the substrate includes a plurality of fiducial markers and a set of capture spots and where the image comprises an array of pixel values.

1006 The biological sample is sectioned tissue having a depth of 100 microns or less.

1008 Each respective capture spot in the set of capture spots is (i) at a different position in a two-dimensional array and (ii) associates with one or more analytes from the sectioned tissue sample. Each respective capture spot in the set of capture spots is characterized by at least one unique spatial barcode in a plurality of spatial barcodes.

1010 The one or more analytes comprise five or more analytes, ten or more analytes, fifty or more analytes, one hundred or more analytes, five hundred or more analytes, 1000 or more analytes, 2000 or more analytes, or between 2000 and 10,000 analytes.

1012 The unique spatial barcode encodes a unique predetermined value selected from the set $\{1, ..., 1024\}$, $\{1, ..., 4096\}$, $\{1, ..., 16384\}$, $\{1, ..., 65536\}$, $\{1, ..., 262144\}$, $\{1, ..., 1048576\}$, $\{1, ..., 4194304\}$, $\{1, ..., 16777216\}$, $\{1, ..., 67108864\}$, or $\{1, ..., 1 \times 10^{12}\}$.

1014 The one or more analytes is a plurality of analytes. A respective capture spot in the set of capture spots includes a plurality of probes, each probe in the plurality of probes including a capture domain that is characterized by a capture domain type in a plurality of capture domain types. Each respective capture domain type in the plurality of capture domain types is configured to bind to a different analyte in the plurality of analytes.

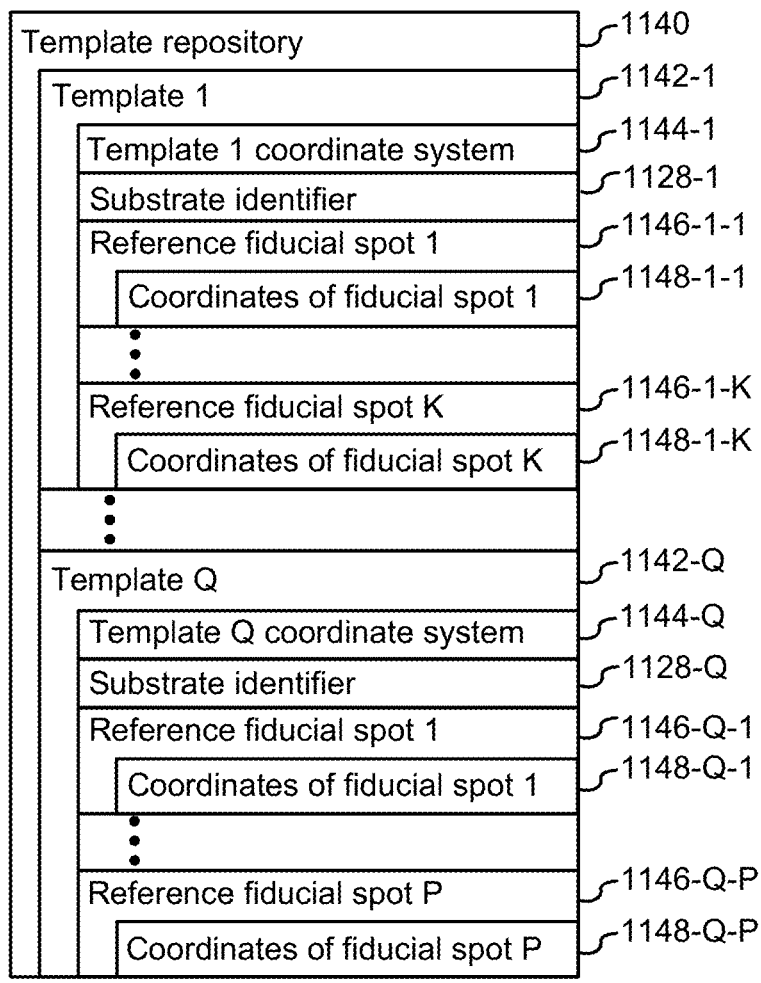
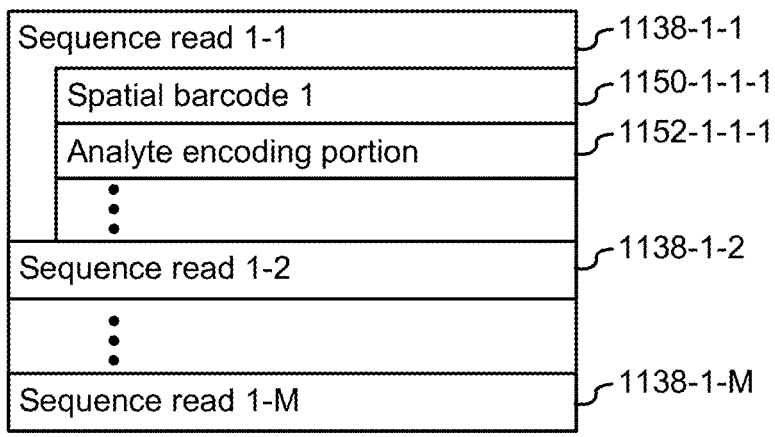
Figure 11B

```
ATF      1
20       5
"Type=GenePix ArrayList V1.0"
"BlockCount=16"
"BlockType=2"
"ArrayRevision=A"
"Block1=  4288, 29652, 105, 100, 75, 30, 260"
"Block2=  4825, 30073,  70, 128, 50, 39, 174"
"Block3= 13288, 29652, 105, 100, 75, 30, 260"
"Block4= 13825, 30073,  70, 128, 50, 39, 174"
"Block5=  4288, 38652, 105, 100, 75, 30, 260"
"Block6=  4825, 39073,  70, 128, 50, 39, 174"
"Block7= 13288, 38652, 105, 100, 75, 30, 260"
"Block8= 13825, 39073,  70, 128, 50, 39, 174"
"Block9=  4288, 47652, 105, 100, 75, 30, 260"
"Block10= 4825, 48073,  70, 128, 50, 39, 174"
"Block11=13288, 47652, 105, 100, 75, 30, 260"
"Block12=13825, 48073,  70, 128, 50, 39, 174"
"Block13= 4288, 56652, 105, 100, 75, 30, 260"
"Block14= 4825, 57073,  70, 128, 50, 39, 174"
"Block15=13288, 56652, 105, 100, 75, 30, 260"
"Block16=13825, 57073,  70, 128, 50, 39, 174"
Block  Column  Row  ID      Name
1         1     1    F      FRAME
1         2     1    F      FRAME
1         3     1    F      FRAME
1         4     1    F      FRAME
1         5     1    F      FRAME
1         6     1    EMPTY  EMPTY
```

1142

• Bright field image contains the location of the tissue in relation to the fiducial frame

• The slide design file (template) contains the location of the capture spots in relation to the fiducial frame

Align Spots
Identify Spots under Tissue
Extract Barcode, UMI
Align Reads
Correct Barcodes
Filter UMIs
Count UMIs
Secondary Analysis

Figure 18

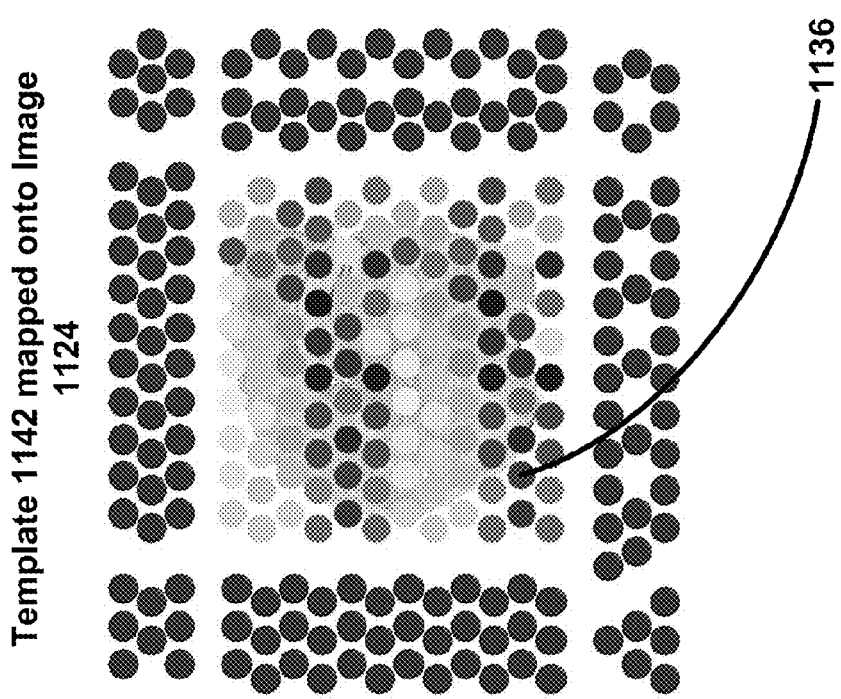

- Bright field image contains the location of the tissue in relation to the fiducial frame
- The slide design file contains the location of the active spots in relation to the fiducial frame
- Using the fiducial frame that is common to both inputs the pipeline can overlay the exact location of the active spots on the tissue
  — I.E Space Ranger uses the slide design to draw the active spots on the tissue

Figure 21

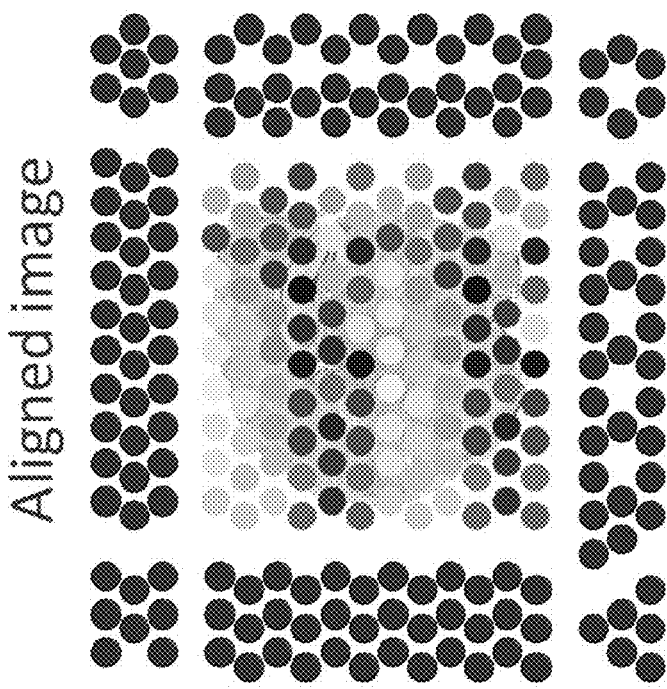
Aligned image
- After the capture spots are overlaid on the tissue, the pipeline identifies the spots that are under the tissue
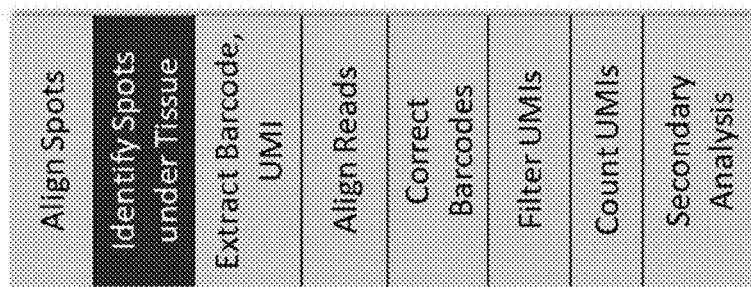
Align Spots | Identify Spots under Tissue | Extract Barcode, UMI | Align Reads | Correct Barcodes | Filter UMIs | Count UMIs | Secondary Analysis
Figure 22

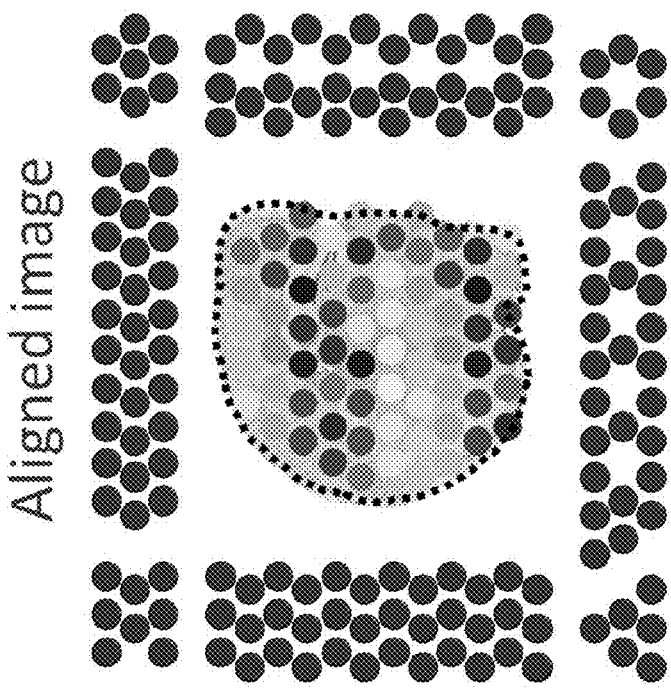

- After the capture spots are overlaid on the tissue, the pipeline identifies the spots that are under the tissue
- Once identified the spots outside of the tissue are excluded from further analysis
- The spots under the tissue are used to generate a filtered barcode matrix used in secondary analysis
- The input image is then broken into tiles for rapid viewing (similar to indexing a large text file)

Figure 23

SYSTEMS AND METHODS FOR SPATIAL ANALYSIS OF ANALYTES USING FIDUCIAL ALIGNMENT

CROSS REFERENCE TO RELATED APPLICATION

This application claims priority to U.S. Provisional Patent Application No. 62/938,967, entitled "Systems and Methods for Spatial Analysis Using Fiducial Alignment," filed Nov. 22, 2019, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 17, 2020, is named 104371-5029_ST25.txt and is 2 kilobytes in size.

TECHNICAL FIELD

This specification describes technologies relating to processing observed analyte data in large, complex datasets, such as spatially arranged next generation sequencing data.

BACKGROUND

Spatial resolution of analytes in complex tissues provides new insights into the processes underlying biological function and morphology, such as cell fate and development, disease progression and detection, and cellular and tissue-level regulatory networks. See, Satija et al., 2015, "Spatial reconstruction of single-cell gene expression data," Nature Biotechnology. 33, 495-502, doi:10.1038.nbt.3192 and Achim et al., 2015, "High-throughput spatial mapping of single-cell RNA-seq data to tissue of origin," Nature Biotechnology 33: 503-509, doi:10.1038/nbt.3209, each of which is hereby incorporated herein by reference in its entirety.

An understanding of the spatial patterns or other forms of relationships between analytes can provide information on differential cell behavior. This in turn, can help to elucidate complex conditions such as complex diseases. For example, the determination that the abundance of an analyte (e.g., a gene) is associated with a tissue subpopulation of a particular tissue class (e.g., disease tissue, healthy tissue, the boundary of disease and healthy tissue, etc.) provides inferential evidence of the association of the analyte with a condition such as complex disease. Likewise, the determination that the abundance of an analyte is associated with a particular subpopulation of a heterogeneous cell population in a complex 2-dimensional or 3-dimensional tissue (e.g., a mammalian brain, liver, kidney, heart, a tumor, or a developing embryo of a model organism) provides inferential evidence of the association of the analyte to the particular subpopulation.

Thus, spatial analysis of analytes can provide information for the early detection of disease by identifying at-risk regions in complex tissues and characterizing the analyte profiles present in these regions through spatial reconstruction (e.g., of gene expression, protein expression, DNA methylation, and/or single nucleotide polymorphisms, among others). A high-resolution spatial mapping of analytes to their specific location within a region or subregion reveals spatial expression patterns of analytes, provides relational data, and further implicates analyte network interactions relating to disease or other morphologies or phenotypes of interest, resulting in a holistic understanding of cells in their morphological context. See, 10×, 2019, "Spatially-Resolved Transcriptomics," 10×, 2019, "Inside Visium Spatial Technology," and 10×, 2019, "Visium Spatial Gene Expression Solution," each of which is hereby incorporated herein by reference in its entirety.

Spatial analysis of analytes can be performed by capturing analytes and/or analyte capture agents or analyte binding domains and mapping them to known locations (e.g., using barcoded capture probes attached to a substrate) using a reference image indicating the tissues or regions of interest that correspond to the known locations. For example, in some implementations of spatial analysis, a sample is prepared (e.g., fresh-frozen tissue is sectioned, placed onto a slide, fixed, and/or stained for imaging). The imaging of the sample provides the reference image to be used for spatial analysis. Analyte detection is then performed using, e.g., analyte or analyte ligand capture via barcoded capture probes, library construction, and/or sequencing. The resulting barcoded analyte data and the reference image can be combined during data visualization for spatial analysis. See, 10×, 2019, "Inside Visium Spatial Technology," which is hereby incorporated by reference.

One difficulty with such analysis is ensuring that a sample or an image of a sample (e.g., a tissue section or an image of a tissue section) is properly aligned with the barcoded capture probes (e.g., using fiducial alignment). Technical limitations in the field are further compounded by the frequent introduction of imperfections in sample quality during conventional wet-lab methods for tissue sample preparation and sectioning. These issues arise either due to the nature of the tissue sample itself (including, inter alia, interstitial regions, vacuoles and/or general granularity that is often difficult to interpret after imaging) or from improper handling or sample degradation resulting in gaps or holes in the sample (e.g., tearing samples or obtaining only a partial sample such as from a biopsy). Additionally, wet-lab methods for imaging result in further imperfections, including but not limited to air bubbles, debris, crystalline stain particles deposited on the substrate or tissue, inconsistent or poor-contrast staining, and/or microscopy limitations that produce image blur, over- or under-exposure, and/or poor resolution. See, Uchida, 2013, "Image processing and recognition for biological images," Develop. Growth Differ. 55, 523-549, doi:10.1111/dgd.12054, which is hereby incorporated herein by reference in its entirety. Such imperfections make the alignment more difficult.

Therefore, there is a need in the art for systems and methods that provide improved alignment. Such systems and methods would allow reproducible identification and alignment of tissue samples in images without the need for extensive training and labor costs, and would further improve the accuracy of identification by removing human error due to subjective alignment. Such systems and methods would further provide a cost-effective, user-friendly tool for a practitioner to reliably perform spatial reconstruction of analytes in tissue sections without the need for additional user input during the spatial mapping step beyond providing the image.

SUMMARY

Technical solutions (e.g., computing systems, methods, and non-transitory computer readable storage mediums) for addressing the above-identified problems with spatial alignment are provided in the present disclosure.

The following presents a summary of the present disclosure in order to provide a basic understanding of some of the aspects of the present disclosure. This summary is not an extensive overview of the present disclosure. It is not intended to identify key/critical elements of the present disclosure or to delineate the scope of the present disclosure. Its sole purpose is to present some of the concepts of the present disclosure in a simplified form as a prelude to the more detailed description that is presented later.

Systems and methods are disclosed for spatial analysis of analytes in which a data structure is obtained in electronic form comprising (i) an image of a sample (e.g., sectioned tissue sample) on a substrate and (ii) a substrate identifier unique to the substrate (e.g., chip). The substrate includes a plurality of fiducial markers and a set of capture spots. In some embodiments the set of capture spots comprises at least 1000, 2000, 5000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000 or 100,000 capture spots. The image comprises an array of pixel values. In some embodiments the array of pixel values comprises at least a least 100, 10,000, 100,000, $1\times10^6$, $2\times10^6$, $3\times10^6$, $5\times10^6$, $8\times10^6$, $10\times10^6$, or $15\times10^6$ pixel values. In some embodiments, the image is acquired using fluorescent microscopy or transmission light microscopy. In some embodiments, fiducial markers do not bind to analytes, either directly or indirectly. Rather, fiducial markers serve to provide a reference frame for a substrate. In some embodiments there are more than 5, 10, 15, 20, 25, 30, 35, 40, 45, 50, 55, 60, 65, 70, 75, 80, 85, 90, 95, 100, 200, 500, or 1000 fiducial markers. In some embodiments there are less than 1000 fiducial markers.

The array of pixel values is analyzed to identify a plurality of derived fiducial spots of the image.

The substrate identifier of the data structure is used to select a first template in a plurality of templates. Each template in the plurality of templates comprises reference positions for a corresponding plurality of reference fiducial spots and a corresponding coordinate system. The plurality of derived fiducial spots of the image is aligned with the corresponding plurality of reference fiducial spots of the first template using an alignment algorithm to obtain a transformation between the plurality of derived fiducial spots of the image and the corresponding plurality of reference fiducial spots of the first template.

The transformation and the coordinate system of the first template is used to register the image to the set of capture spots. Then, the image is analyzed in conjunction with spatial analyte data associated with each capture spot, thereby performing spatial analysis of analytes.

In some such embodiments, the plurality of derived fiducial spots of the image is determined by first identifying a plurality of candidate derived fiducial spots. The candidate derived fiducial spots are determined by thresholding the array of pixel values into a plurality of threshold images and identifying, within the plurality of threshold images, groups of pixels having white values. The plurality of candidate derived fiducial spots are clustered based on spot size are, thereby distributing the plurality of candidate derived fiducial spots into a plurality of subsets of candidate derived fiducial spots, with each respective subset of candidate derived fiducial spots in the plurality of subsets of candidate derived fiducial spots having a characteristic size. The subset of candidate derived fiducial spots in the plurality of subsets of candidate derived fiducial spots having the largest characteristic size is then selected as the plurality of derived fiducial spots of the image. In some such embodiments, respective pairs of candidate derived fiducial spots that are within a threshold distance of each other prior to the clustering. In some such embodiments, respective candidate derived fiducial spots that fail to satisfy a maximum or minimum size criterion are filtered out prior to the clustering. In some such embodiments, respective candidate derived fiducial spots that fail to satisfy a circularity criterion are filtered out, where the circularity of a respective derived fiducial spot is defined by:

$$\frac{4\pi \text{Area}}{(\text{perimeter})^2}$$

where "Area" is the area of the respective derived fiducial spot, and "perimeter" is the perimeter of the respective derived fiducial spot. In some embodiments, respective candidate derived fiducial spots are filtered out that fail to satisfy a convexity criterion or an inertia ratio criterion.

In some embodiments, the transformation is a similarity transform that comprises rotation, translation, and isotropic scaling of the plurality of derived fiducial spots of the image to minimize a residual error between the plurality of derived fiducial spots and the corresponding plurality of reference fiducial spots.

In some embodiments, the transformation is a non-rigid transform (e.g., an affline transformation) that comprises anisotropic scaling and skewing of the plurality of derived fiducial spots of the image to minimize a residual error between the plurality of derived fiducial spots and the corresponding plurality of reference fiducial spots.

In some embodiments, the alignment algorithm is a coherent point drift algorithm or an Iterative Closest Point algorithm. In some embodiments, the alignment algorithm is a Robust Point Matching algorithm or a Thin-Plate-Spline Robust Point Matching algorithm.

In some embodiments, the corresponding plurality of reference fiducial spots of the first template consists of between 100 spots and 1000 spots.

In some embodiments, the sample is a sectioned tissue sample, and each respective capture spot in the set of capture spots is (i) at a different position in a two-dimensional array and (ii) associates with one or more analytes from the sectioned tissue sample, and each respective capture spot in the set of capture spots is characterized by at least one unique spatial barcode in a plurality of spatial barcodes.

In some embodiments, a substrate may have two or more capture spots that have the same spatial barcodes. That is, between the two capture spots, neither has a unique spatial barcode. In some such embodiments, these capture spots with duplicate spatial barcodes are considered to be a single capture spot. In other embodiments, capture spots that do not have a unique spatial barcode are not considered to be part of the set of capture spots that is used for localizing respective sequence reads to capture spots of a particular set of capture spots.

In some embodiments at least one percent, at least five percent, at least 10 percent, at least 20 percent, at least 30 percent, or at least 40 percent of the capture spots on a substrate may not have a unique spatial barcode across the capture spots on the substrate. That is, for each respective spatial barcode of each such capture spot, there is at least one other capture spot on the substrate that has the respective spatial barcode. In some such embodiments, these capture spots without a unique spatial barcode are not considered to be part of the set of capture spots that is used for localizing respective sequence reads to capture spots of a particular set of capture spots.

In some embodiments at least ten, at least 100, at least 1000, at least 10,000, at least 100,000, or at least 1,000,000 of the capture spots on a substrate may not have a unique spatial barcode across the capture spots on the substrate. That is, for each respective spatial barcode of each such capture spot, there is at least one other capture spot on the substrate that has the respective spatial barcode. In some such embodiments, these capture spots without a unique spatial barcode are not considered to be part of the set of capture spots that is used for localizing respective sequence reads to capture spots of a particular set of capture spots.

In some embodiments, a capture spot in the set of capture spots comprises a capture domain. In some embodiments, a capture spot in the set of capture spots comprises a cleavage domain. In some embodiments, each capture spot in the set of capture spots is attached directly or attached indirectly to the substrate. In some embodiments, the one or more analytes comprise five or more analytes, ten or more analytes, fifty or more analytes, one hundred or more analytes, five hundred or more analytes, 1000 or more analytes, 2000 or more analytes, or between 2000 and 10,000 analytes.

In some embodiments, the unique spatial barcode encodes a unique predetermined value selected from the set $\{1, \ldots, 1024\}$, $\{1, \ldots, 4096\}$, $\{1, \ldots, 16384\}$, $\{1, \ldots, 65536\}$, $\{1, \ldots, 262144\}$, $\{1, \ldots, 1048576\}$, $\{1, \ldots, 4194304\}$, $\{1, \ldots, 16777216\}$, $\{1, \ldots, 67108864\}$, or $\{1, \ldots, 1 \times 10^{12}\}$.

In some embodiments, each respective capture spot in the set of capture spots includes 1000 or more capture probes, 2000 or more capture probes, 10,000 or more capture probes, 100,000 or more capture probes, $1 \times 10^6$ or more capture probes, $2 \times 10^6$ or more capture probes, or $5 \times 10^6$ or more capture probes. In some embodiments, each capture probe in the respective capture spot includes a poly-A sequence or a poly-T sequence and a unique spatial barcode that characterizes the respective capture spot. In some embodiments, each capture probe in the respective capture spot includes the same spatial barcode from the plurality of spatial barcodes. In some embodiments, each capture probe in the respective capture spot includes a different spatial barcode from the plurality of spatial barcodes.

In some embodiments, the sample is a sectioned tissue sample that has a depth of 100 microns or less.

In some embodiments, the one or more analytes is a plurality of analytes, and a respective capture spot in the set of capture spots includes a plurality of capture probes. In some such embodiments, each capture probe in the plurality of capture probes includes a capture domain that is characterized by a capture domain type in a plurality of capture domain types, and each respective capture domain type in the plurality of capture domain types is configured to bind to a different analyte in the plurality of analytes.

In some embodiments, the plurality of capture domain types comprises between 5 and 15,000 capture domain types and the respective capture spot includes at least five, at least 10, at least 100, or at least 1000 capture probes for each capture domain type in the plurality of capture domain types.

In some embodiments, the one or more analytes is a plurality of analytes, and a respective capture spot in the set of capture spots includes a plurality of capture probes. Further, each capture probe in the plurality of capture probes including a capture domain that is characterized by a single capture domain type configured to bind to each analyte in the plurality of analytes in an unbiased manner.

In some embodiments, each respective capture spot in the set of capture spots is contained within a 100 micron by 100 micron square on the substrate. In some embodiments, each respective capture spot in the set of capture spots is contained within a 50 micron by 50 micron square on the substrate. In some embodiments, each respective capture spot in the set of capture spots is contained within a 10 micron by 10 micron square on the substrate. In some embodiments, each respective capture spot in the set of capture spots is contained within a 1 micron by 1 micron square on the substrate. In some embodiments, each respective capture spot in the set of capture spots is contained within a 0.5 micron by 0.5 micron square on the substrate. In some embodiments, each respective capture spot in the set of capture spots is contained within a 0.3 micron by 0.3 micron square on the substrate. In some embodiments, each respective capture spot in the set of capture spots is contained within a 0.2 micron by 0.2 micron square on the substrate.

In some embodiments, a distance between a center of each respective spot to a neighboring capture spot in the set of capture spots on the substrate is between 300 nanometers and 300 microns. In some embodiments, a distance between a center of each respective spot to a neighboring capture spot in the set of capture spots on the substrate is between 700 nanometers and 10 microns. In some embodiments, a distance between a center of each respective spot to a neighboring capture spot in the set of capture spots on the substrate is between 800 nanometers and 3 microns.

In some embodiments, a shape of each capture spot in the set of capture spots on the substrate is a closed-form shape. In some embodiments, the closed-form shape is circular, elliptical, or an N-gon, where N is a value between 1 and 20. In some embodiments, the closed-form shape is hexagonal. In some embodiments, the closed-form shape is circular and each capture spot in the set of capture spots has a diameter of 80 microns or less. In some embodiments, the closed-form shape is circular and each capture spot in the set of capture spots has a diameter of between 0.3 microns and 65 microns.

In some embodiments, a distance between a center of each respective capture spot to a neighboring capture spot in the set of capture spots on the substrate is between 0.5 microns and 2 microns. In some embodiments, a distance between a center of each respective capture spot to a neighboring capture spot in the set of capture spots on the substrate is between 2 microns and 7 microns. In some embodiments, a distance between a center of each respective capture spot to a neighboring capture spot in the set of capture spots on the substrate is between 5 microns and 50 microns.

In some embodiments, the first template is obtained from a remote computer system, from among the plurality of templates, responsive to sending the substrate identifier to the remote computer system.

Another aspect of the present disclosure provides a computer system comprising one or more processors, memory, and one or more programs. The one or more programs are stored in the memory and are configured to be executed by the one or more processors. The one or more programs are for spatial analysis of analytes. The one or more programs include instructions for obtaining a data structure in electronic form comprising (i) an image of a sample (e.g., a sectioned tissue sample) on a substrate (e.g., from a subject), and (ii) a substrate identifier unique to the substrate.

The substrate includes a plurality of fiducial markers and a set of capture spots.

In some embodiments the set of capture spots comprises at least 1000, 2000, 5000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000 or 100,000 capture spots.

Fiducial markers do not bind to analytes, either directly or indirectly. Rather, fiducial markers serve to provide a reference frame for a substrate. In some embodiments, the plurality of fiducial markers comprises 5, 10, 15, 20, 25, 30, 35, 40, 45, 50, 55, 60, 65, 70, 75, 80, 85, 90, 95, 100, 200, 500, or 1000 fiducial markers. In some embodiments there are less than 1000 fiducial markers in the plurality of fiducial markers.

The image comprises an array of pixel values. In some embodiments the array of pixel values comprises at least a least 100, 10,000, 100,000, $1\times10^6$, $2\times10^6$, $3\times10^6$, $5\times10^6$, $8\times10^6$, $10\times10^6$, or $15\times10^6$ pixel values.

The array of pixel values is analyzed to identify a plurality of derived fiducial spots of the image. The substrate identifier of the data structure is used to select a first template in a plurality of templates, where each template in the plurality of templates comprises reference positions for a corresponding plurality of reference fiducial spots and a corresponding coordinate system. The plurality of derived fiducial spots of the image is aligned with the corresponding plurality of reference fiducial spots of the first template using an alignment algorithm to obtain a transformation between the plurality of derived fiducial spots of the image and the corresponding plurality of reference fiducial spots of the first template. The transformation and the coordinate system of the first template is used to register the image to the set of capture spots. Then, the image is analyzed in conjunction with spatial analysis data associated with each capture spot, thereby performing analysis of analytes.

Still another aspect of the present disclosure provides a computer readable storage medium storing one or more programs. The one or more programs comprise instructions, which when executed by an electronic device with one or more processors and a memory, cause the electronic device to perform spatial analysis of analytes. The spatial analysis of analytes comprises obtaining a data structure in electronic form comprising (i) an image of a biological tissue sample (e.g., sectioned tissue sample) on a substrate (e.g., from a subject), and (ii) a substrate identifier unique to the substrate.

The substrate includes a plurality of fiducial markers and a set of capture spots.

In some embodiments the set of capture spots comprises at least 1000, 2000, 5000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000 or 100,000 capture spots.

Fiducial markers do not bind to analytes, either directly or indirectly. Rather, fiducial markers serve to provide a reference frame for a substrate. In some embodiments, the plurality of fiducial markers comprises 5, 10, 15, 20, 25, 30, 35, 40, 45, 50, 55, 60, 65, 70, 75, 80, 85, 90, 95, 100, 200, 500, or 1000 fiducial markers. In some embodiments there are less than 1000 fiducial markers in the plurality of fiducial markers.

The image comprises an array of pixel values. In some embodiments the array of pixel values comprises at least a least 100, 10,000, 100,000, $1\times10^6$, $2\times10^6$, $3\times10^6$, $5\times10^6$, $8\times10^6$, $10\times10^6$, or $15\times10^6$ pixel values.

The array of pixel values is analyzed to identify a plurality of derived fiducial spots of the image. The substrate identifier of the data structure is used to select a first template in a plurality of templates. Each template in the plurality of templates comprises reference positions for a corresponding plurality of reference fiducial spots and a corresponding coordinate system. The plurality of derived fiducial spots of the image is aligned with the corresponding plurality of reference fiducial spots of the first template using an alignment algorithm to obtain a transformation between the plurality of derived fiducial spots of the image and the corresponding plurality of reference fiducial spots of the first template. The transformation and the coordinate system of the first template is used to register the image to the set of capture spots. Then the image is analyzed in conjunction with spatial analyte data associated with each capture spot, thereby performing spatial analysis of analytes.

Another aspect of the present disclosure provides a computing system including one or more processors and memory storing one or more programs for spatial nucleic analysis. It will be appreciated that this memory can be on a single computer, a network of computers, one or more virtual machines, or in a cloud computing architecture. The one or more programs are configured for execution by the one or more processors. The one or more programs include instructions for performing any of the methods disclosed herein.

Still another aspect of the present disclosure provides a computer readable storage medium storing one or more programs to be executed by an electronic device. The one or more programs include instructions for the electronic device to perform spatial analysis of analytes by any of the methods disclosed herein. It will be appreciated that the computer readable storage medium can exist as a single computer readable storage medium or any number of component computer readable storage mediums that are physically separated from each other.

Other embodiments are directed to systems, portable consumer devices, and computer readable media associated with methods described herein.

As disclosed herein, any embodiment disclosed herein when applicable can be applied to any aspect.

Various embodiments of systems, methods, and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, patent applications, and information available on the Internet and mentioned in this specification are herein incorporated by reference to the same extent as if each individual publication, patent, patent application, or item of information was specifically and individually indicated to be incorporated by reference. To the extent publications, patents, patent applications, or item of information available on the Internet incorporated by reference contradict the disclosure contained in the specification, the specification is intended to supersede and/or take precedence over any such contradictory material.

DESCRIPTION OF DRAWINGS

The patent or application file contains at least one drawing executed in color. Copies of this patent or patent application publication with color drawing(s) will be provided by the Office upon request and payment of the necessary fee.

The following drawings illustrate certain embodiments of the features and advantages of this disclosure. These embodiments are not intended to limit the scope of the appended claims in any manner. Like reference symbols in the drawings indicate like elements.

FIG. 1 shows an exemplary spatial analysis workflow in accordance with an embodiment of the present disclosure.

FIG. 2 shows an exemplary spatial analysis workflow in which optional steps are indicated by dashed boxes in accordance with an embodiment of the present disclosure.

FIGS. 10A, 10B, 10C, 10D, and 10E illustrate non-limiting methods for spatial analysis of analytes in accordance with some embodiments of the present disclosure, in which optional steps are illustrated by dashed line boxes.

FIGS. 11A and 11B are example block diagrams illustrating a computing device in accordance with some embodiments of the present disclosure.

FIG. 18 illustrates a template that comprises reference positions for a corresponding plurality of reference fiducial spots and a corresponding coordinate system in accordance with an embodiment of the present disclosure.

FIG. 21 illustrates the registration of the image with the substrate using a transformation and the coordinate system of the template to register the image to the set of capture spots of the substrate, in accordance with an embodiment of the present disclosure.

FIG. 22 illustrates the analysis of the image after the registration of the image with the substrate, using a transformation and the coordinate system of the template to register the image to the set of capture spots of the substrate, thereby identifying capture spots on the substrate that have been overlaid by tissue in accordance with an embodiment of the present disclosure.

FIG. 23 illustrates the capture spots on a substrate that have been overlaid by tissue in accordance with an embodiment of the present disclosure.

DETAILED DESCRIPTION

I. Introduction

Figure 3A:
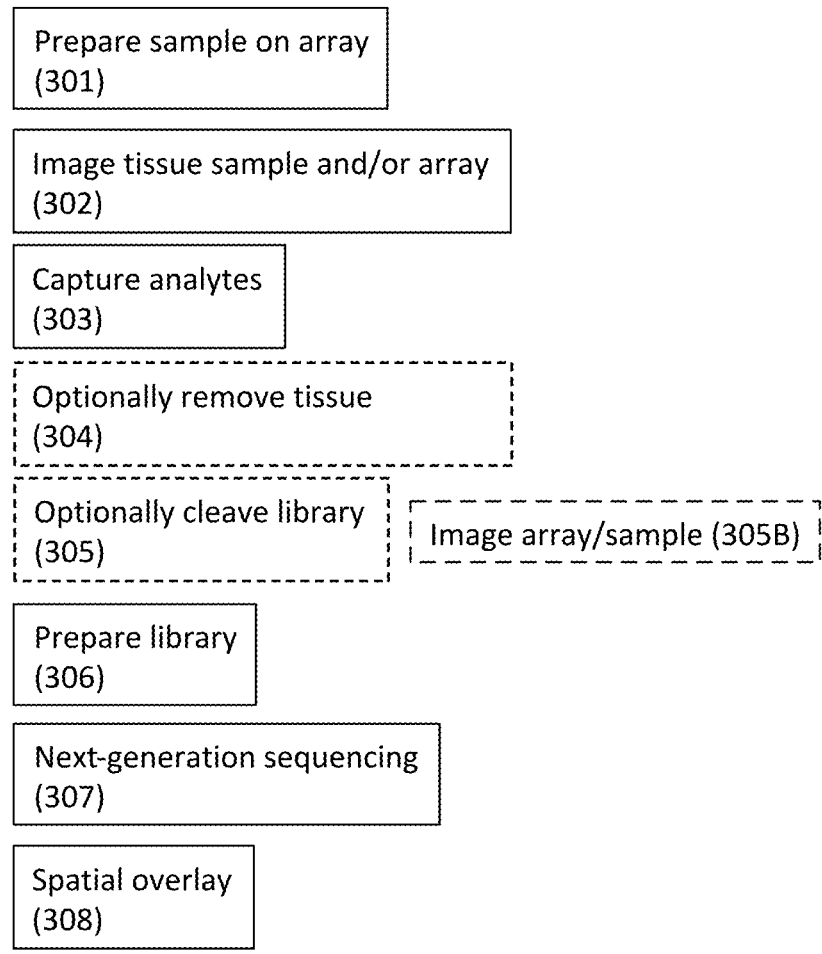
FIGS. 3A and 3B shows exemplary spatial analysis workflows in which, in FIG. 3A, optional steps are indicated by dashed boxes in accordance with an embodiment of the present disclosure.

This disclosure describes apparatus, systems, methods, and compositions for spatial analysis of samples. This section in particular describes certain general terminology, analytes, sample types, and preparative steps that are referred to in later sections of the disclosure.

(a) Spatial Analysis

Tissues and cells can be obtained from any source. For example, tissues and/or cells can be obtained from single-cell or multicellular organisms (e.g., a mammal). Tissues and cells obtained from a mammal (e.g., a human) often have varied analyte levels (e.g., gene and/or protein expression) that can result in differences in cell morphology and/or function. The position of a cell or subset of cells (e.g., neighboring cells and/or non-neighboring cells) within a tissue can affect, for example, the cell's fate, behavior, morphology, signaling and cross-talk with other cells in the tissue. Information regarding the differences in analyte levels (e.g., gene and/or protein expression) within different cells in a tissue of a mammal can also help physicians select or administer a treatment that will be effective and can allow researchers to identify and elucidate differences in cell morphology and/or cell function in single-cell or multicellular organisms (e.g., a mammal) based on the detected differences in analyte levels within different cells in the tissue. Differences in analyte levels within different cells in a tissue of a mammal can also provide information on how tissues (e.g., healthy and diseased tissues) function and/or develop. Differences in analyte levels within difference cells in a tissue of a mammal can also provide information on different mechanisms of disease pathogenesis in a tissue, and mechanism of action of a therapeutic treatment within a tissue. Differences in analyte levels within different cells in a tissue of a mammal can also provide information on the drug resistance mechanisms and the development of the same in mammalian tissues. Differences in the presence or absence of analytes within difference cells in a tissue of a multicellular organism (e.g., a mammal) can provide information on drug resistance mechanisms and the development of the same in a tissue of a multicellular organism.

The spatial analysis methodologies herein provide for the detection of differences in an analyte level (e.g., gene and/or protein expression) within different cells in a tissue of a mammal or within a single cell from a mammal. For example, spatial analysis methodologies can be used to detect the differences in analyte levels (e.g., gene and/or protein expression) within different cells in histological slide samples, the data from which can be reassembled to generate a three-dimensional map of analyte levels (e.g., gene and/or protein expression) of a sample (e.g., tissue sample) obtained from a mammal, with a degree of spatial resolution such as single-cell resolution.

Spatial heterogeneity in developing systems has typically been studied using RNA hybridization, immunohistochemistry, fluorescent reporters, or purification or induction of pre-defined subpopulations and subsequent genomic profiling (e.g., RNA-seq). Such approaches, however, rely on a relatively small set of pre-defined markers, therefore introducing selection bias that limits discovery. These prior approaches also rely on a priori knowledge. Spatial RNA assays traditionally relied on staining for a limited number of RNA species. In contrast, single-cell RNA-sequencing allows for deep profiling of cellular gene expression (including non-coding RNA), but the established methods separate cells from their native spatial context.

Spatial analysis methodologies described herein provide a vast amount of data on analyte level and/or expression data for a variety of multiple analytes within a sample at high spatial resolution, e.g., while retaining the native spatial context. Spatial analysis methods include, for example, the use of a capture probe including a spatial barcode (e.g., a nucleic acid sequence) that provides information as to the position of the capture probe within a cell or a tissue sample (e.g., mammalian cell or a mammalian tissue sample) and a capture domain that is capable of binding to an analyte (e.g., a protein and/or nucleic acid) produced by and/or present in a cell. As described herein, the spatial barcode can be a nucleic acid that has a unique sequence, a unique fluorophore, a unique combination of fluorophores, a unique amino acid sequence, a unique heavy metal or a unique combination of heavy metals, or any other unique detectable agent. The capture domain can be any agent that is capable of binding to an analyte produced by and/or present in a cell (e.g., a nucleic acid that is capable of hybridizing to a nucleic acid from a cell (e.g., an mRNA, genomic DNA, mitochondrial DNA, or miRNA), a substrate including an analytes, a binding partner of an analyte, or an antibody that binds specifically to an analyte). A capture probe can also include a nucleic acid sequence that is complementary to a sequence of a universal forward and/or universal reverse primer. A capture probe can also include a cleavage site (e.g., a cleavage recognition site of a restriction endonuclease), or a photolabile or thermosensitive bond.

The binding of an analyte to a capture probe can be detected using a number of different methods, e.g., nucleic acid sequencing, fluorophore detection, nucleic acid amplification, detection of nucleic acid ligation, and/or detection of nucleic acid cleavage products. In some examples, the detection is used to associate a specific spatial barcode with a specific analyte produced by and/or present in a cell (e.g., a mammalian cell).

Capture probes can be, e.g., attached to a surface, e.g., a solid array, a bead, or a coverslip. In some examples, capture probes are not attached to a surface. In some examples, capture probes are encapsulated within, embedded within, or layered on a surface of a permeable composition (e.g., any of the substrates described herein). For example, capture probes can be encapsulated or disposed within a permeable bead (e.g., a gel bead). In some examples, capture probes are encapsulated within, embedded within, or layered on a surface of a substrate (e.g., any of the exemplary substrates described herein, such as a hydrogel or a porous membrane).

In some examples, a cell or a tissue sample including a cell are contacted with capture probes attached to a substrate (e.g., a surface of a substrate), and the cell or tissue sample is permeabilized to allow analytes to be released from the cell and bind to the capture probes attached to the substrate. In some examples, analytes released from a cell can be actively directed to the capture probes attached to a substrate using a variety of methods, e.g., electrophoresis, chemical gradient, pressure gradient, fluid flow, or magnetic field.

In other examples, a capture probe is directed to interact with a cell or a tissue sample using a variety of methods, e.g., inclusion of a lipid anchoring agent in the capture probe, inclusion of an agent that binds specifically to, or forms a covalent bond with, a membrane protein in the capture probe, fluid flow, pressure gradient, chemical gradient, or magnetic field.

Non-limiting aspects of spatial analysis methodologies are described in WO 2011/127099, WO 2014/210233, WO 2014/210225, WO 2016/162309, WO 2018/091676, WO 2012/140224, WO 2014/060483, U.S. Pat. Nos. 10,002,316, 9,727,810, U.S. Patent Application Publication No. 2017/0016053, Rodrigues et al., *Science* 363(6434):1463-1467, 2019; WO 2018/045186, Lee et al., *Nat. Protoc.* 10(3):442-458, 2015; WO 2016/007839, WO 2018/045181, WO 2014/163886, Trejo et al., *PLoS ONE* 14(2):e0212031, 2019, U.S. Patent Application Publication No. 2018/0245142, Chen et al., *Science* 348(6233):aaa6090, 2015, Gao et al., *BMC Biol.* 15:50, 2017, WO 2017/144338, WO 2018/107054, WO 2017/222453, WO 2019/068880, WO 2011/094669, U.S. Pat. Nos. 7,709,198, 8,604,182, 8,951,726, 9,783,841, 10,041,949, WO 2016/057552, WO 2017/147483, WO 2018/022809, WO 2016/166128, WO 2017/027367, WO 2017/027368, WO 2018/136856, WO 2019/075091, U.S. Pat. No. 10,059,990, WO 2018/057999, WO 2015/161173, Gupta et al., *Nature Biotechnol.* 36:1197-1202, 2018, and U.S. patent application Ser. No. 16/992,569 entitled "Systems and Methods for Using Spatial Distribution of Haplotypes to Determine a Biological Condition," filed Aug. 13, 2020, and can be used herein in any combination. Further non-limiting aspects of spatial analysis methodologies are described herein.

(b) General Terminology

Specific terminology is used throughout this disclosure to explain various aspects of the apparatus, systems, methods, and compositions that are described. This sub-section includes explanations of certain terms that appear in later sections of the disclosure. To the extent that the descriptions in this section are in apparent conflict with usage in other sections of this disclosure, the definitions in this section will control.

(i) Subject

A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (e.g. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii*, *Takifugu rubripes*, yeast, *Saccharamoyces cerevisiae* or *Schizosaccharomyces pombe*; or a *Plasmodium falciparum*.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of nucleic acids, is intended as a semantic identifier for the nucleic acid or sequence in the context of a method or composition, and does not limit the structure or function of the nucleic acid or sequence beyond what is expressly indicated.

(iv) Barcode

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include non-random, semi-random, and/or random nucleic acid and/or amino acid sequences, and synthetic nucleic acid and/or amino acid sequences.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. In some embodiments, a barcode includes both a UMI and a spatial barcode. In some embodiments, a barcode includes two or more sub-barcodes that together function as a single barcode (e.g., a polynucleotide barcode). For example, a polynucleotide barcode can include two or more polynucleotide sequences (e.g., sub-barcodes) that are separated by one or more non-barcode sequences.

(v) Capture Spot

A "capture spot" (alternately, "feature" or "capture probe plurality") is used herein to describe an entity that acts as a support or repository for various molecular entities used in sample analysis. Examples of capture spots include, but are not limited to, a bead, a spot of any two- or three-dimensional geometry (e.g., an ink jet spot, a masked spot, a square on a grid), a well, and a hydrogel pad. In some embodiments, a capture spot is an area on a substrate at which capture probes labelled with spatial barcodes are clustered. Specific non-limiting embodiments of capture spots and substrates are further described below in the present disclosure.

Additional definitions relating generally to spatial analysis of analytes can be found in U.S. patent application Ser. No. 16/992,569 entitled "Systems and Methods for Using the Spatial Distribution of Haplotypes to Determine a Biological Condition," filed Aug. 13, 2020, which is hereby incorporated herein by reference.

(vi) Substrate

As used herein, a "substrate" is any surface onto which capture probes can be affixed (e.g., chip, a solid array, a bead, a slide, a substrate, a coverslip, etc.

(vii) Antibody

An "antibody" is a polypeptide molecule that recognizes and binds to a complementary target antigen. Antibodies typically have a molecular structure shape that resembles a Y shape, or polymers thereof. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site. Antibodies can also include single domain antibodies (VHH domains and VNAR domains), scFvs, and Fab fragments.

(c) Analytes

The apparatus, systems, methods, and compositions described in this disclosure can be used to detect and analyze a wide variety of different analytes. For the purpose of this disclosure, an "analyte" can include any biological substance, structure, moiety, or component to be analyzed. The term "target" can be similarly used to refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is an organelle (e.g., nuclei or mitochondria).

Cell surface features corresponding to analytes can include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis.

Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids.

Examples of nucleic acid analytes also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

Additional examples of analytes include mRNA and cell surface features (e.g., using the labelling agents described herein), mRNA and intracellular proteins (e.g., transcription factors), mRNA and cell methylation status, mRNA and accessible chromatin (e.g., ATAC-seq, DNase-seq, and/or MNase-seq), mRNA and metabolites (e.g., using the labelling agents described herein), a barcoded labelling agent (e.g., the oligonucleotide tagged antibodies described herein) and a V(D)J sequence of an immune cell receptor (e.g., T-cell receptor), mRNA and a perturbation agent (e.g., a CRISPR crRNA/sgRNA, TALEN, zinc finger nuclease, and/or antisense oligonucleotide as described herein). In some embodiments, a perturbation agent is a small molecule, an antibody, a drug, an aptamer, a miRNA, a physical environmental (e.g., temperature change), or any other known perturbation agents.

Analytes can include a nucleic acid molecule with a nucleic acid sequence encoding at least a portion of a V(D)J sequence of an immune cell receptor (e.g., a TCR or BCR). In some embodiments, the nucleic acid molecule is cDNA first generated from reverse transcription of the corresponding mRNA, using a poly(T) containing primer. The generated cDNA can then be barcoded using a capture probe, featuring a barcode sequence (and optionally, a UMI sequence) that hybridizes with at least a portion of the generated cDNA. In some embodiments, a template switching oligonucleotide hybridizes to a poly(C) tail added to a 3' end of the cDNA by a reverse transcriptase enzyme. The original mRNA template and template switching oligonucleotide can then be denatured from the cDNA and the barcoded capture probe can then hybridize with the cDNA and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described in PCT Patent Application PCT/US2017/057269, filed Oct. 18, 2017, and U.S. patent application Ser. No. 15/825,740, filed Nov. 29, 2017, both of which are incorporated herein by reference in their entireties. V(D)J analysis can also be completed with the use of one or more labelling agents that bind to particular surface features of immune cells and associated with barcode sequences. The one or more labelling agents can include an MHC or MHC multimer.

As described above, the analyte can include a nucleic acid capable of functioning as a component of a gene editing reaction, such as, for example, clustered regularly interspaced short palindromic repeats (CRISPR)-based gene editing. Accordingly, the capture probe can include a nucleic acid sequence that is complementary to the analyte (e.g., a sequence that can hybridize to the CRISPR RNA (crRNA), single guide RNA (sgRNA), or an adapter sequence engineered into a crRNA or sgRNA).

In certain embodiments, an analyte is extracted from a live cell. Processing conditions can be adjusted to ensure that a sample remains live during analysis, and analytes are extracted from (or released from) live cells of the sample. Live cell-derived analytes can be obtained only once from the sample, or can be obtained at intervals from a sample that continues to remain in viable condition.

In general, the systems, apparatus, methods, and compositions can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual capture spot of the substrate. Methods for performing multiplexed assays to analyze two or more different analytes will be discussed in a subsequent section of this disclosure.

(d) Samples (i) Types of Samples

The present disclosure allows for analysis of both biological and nonbiological samples. A "biological sample" is obtained from the subject for analysis using any of a variety of techniques including, but not limited to, biopsy, surgery, and laser capture microscopy (LCM), and generally includes cells and/or other biological material from the subject. In addition to the subjects described above, a biological sample can also be obtained from non-mammalian organisms (e.g., plants, insects, aracnids, nematodes, fungi, amphibians, and fish. A biological sample can also be obtained from a prokaryote such as a bacterium, e.g., *Escherichia coli*, Staphylococci or *Mycoplasma pneumoniae*; an archae; a virus such as Hepatitis C virus or human immunodeficiency virus; or a viroid. A biological sample can also be obtained from a eukaryote, such as a patient derived organoid (PDO) or patient derived xenograft (PDX). The biological sample can include organoids, a miniaturized and simplified version of an organ produced in vitro in three dimensions that shows realistic micro-anatomy. Organoids can be generated from one or more cells from a tissue, embryonic stem cells, and/or induced pluripotent stem cells, which can self-organize in three-dimensional culture owing to their self-renewal and differentiation capacities. In some embodiments, an organoid is a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, or a retinal organoid. Subjects from which biological samples can be obtained can be healthy or asymptomatic individuals, individuals that have or are suspected of having a disease (e.g., cancer) or a pre-disposition to a disease, and/or individuals that are in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

Biological samples can also include fetal cells. For example, a procedure such as amniocentesis can be performed to obtain a fetal cell sample from maternal circulation. Sequencing of fetal cells can be used to identify any of a number of genetic disorders, including, e.g., aneuploidy such as Down's syndrome, Edwards syndrome, and Patau syndrome. Further, cell surface features of fetal cells can be used to identify any of a number of disorders or diseases.

Biological samples can also include immune cells. Sequence analysis of the immune repertoire of such cells, including genomic, proteomic, and cell surface features, can provide a wealth of information to facilitate an understanding the status and function of the immune system. By way of example, determining the status (e.g., negative or positive) of minimal residue disease (MRD) in a multiple myeloma (MM) patient following autologous stem cell transplantation is considered a predictor of MRD in the MM patient (see, e.g., U.S. Patent Publication No. 2018/0156784, the entire contents of which are incorporated herein by reference).

Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cells, thrombocytes/megakaryocytes, and dendritic cells.

As discussed above, a biological sample can include a single analyte of interest, or more than one analyte of interest. Methods for performing multiplexed assays to analyze two or more different analytes in a single biological sample will be discussed in a subsequent section of this disclosure.

(ii) Preparation of Samples

A variety of steps can be performed to prepare a sample for analysis. Except where indicated otherwise, the preparative steps described below can generally be combined in any manner to appropriately prepare a particular sample for analysis.

(1) Tissue Sectioning

A sample can be harvested from a subject (e.g., via surgical biopsy, whole subject sectioning) or grown in vitro on a growth substrate or culture dish as a population of cells, or prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 micrometers thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 11, 12, 13, 14, 15, 20, 30, 40, or 50 micrometers. Thicker sections can also be used if desired or convenient, e.g., at least 70, 80, 90, or 100 micrometers or more. Typically, the thickness of a tissue section is between 1-100 micrometers, 1-50 micrometers, 1-30 micrometers, 1-25 micrometers, 1-20 micrometers, 1-15 micrometers, 1-10 micrometers, 2-8 micrometers, 3-7 micrometers, or 4-6 micrometers, but as mentioned above, sections with thicknesses larger or smaller than these ranges can also be analysed.

Multiple sections can also be obtained from a single sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the sample.

(2) Freezing

In some embodiments, the sample (e.g., a tissue section as described above) can be prepared by deep freezing at a temperature suitable to maintain or preserve the integrity (e.g., the physical characteristics) of the tissue structure. Such a temperature can be, e.g., less than −20° C., or less than −25° C., −30° C., −40° C., −50° C., −60° C., −70° C., −80° C., −90° C., −100° C., −110° C., −120° C., −130° C., −140° C., −150° C., −160° C., −170° C., −180° C., −190° C., or −200° C. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C. A sample can be snap frozen in isopentane and liquid nitrogen. Frozen samples can be stored in a sealed container prior to embedding.

(3) Formalin Fixation and Paraffin Embedding

In some embodiments, the sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

(4) Fixation

As an alternative to formalin fixation described above, a sample can be fixed in any of a variety of other fixatives to preserve the biological structure of the sample prior to analysis. For example, a sample can be fixed via immersion in ethanol, methanol, acetone, formaldehyde (e.g., 2% formaldehyde) paraformaldehyde-Triton, glutaraldehyde, or combinations thereof.

In some embodiments, acetone fixation is used with fresh frozen samples, which can include, but are not limited to, cortex tissue, mouse olfactory bulb, human brain tumor, human post-mortem brain, and breast cancer samples. In some embodiments, a compatible fixation method is chosen and/or optimized based on a desired workflow. For example, formaldehyde fixation may be chosen as compatible for workflows using IHC/IF protocols for protein visualization. As another example, methanol fixation may be chosen for workflows emphasizing RNA/DNA library quality. Acetone fixation may be chosen in some applications to permeabilize the tissue. When acetone fixation is performed, pre-permeabilization steps (described below) may not be performed. Alternatively, acetone fixation can be performed in conjunction with permeabilization steps.

(5) Embedding

As an alternative to paraffin embedding described above, a sample can be embedded in any of a variety of other embedding materials to provide structural substrate to the sample prior to sectioning and other handling steps. In general, the embedding material is removed prior to analysis of tissue sections obtained from the sample. Suitable embedding materials include, but are not limited to, waxes, resins (e.g., methacrylate resins), epoxies, and agar.

(6) Staining

To facilitate visualization, samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin.

The sample can be stained using known staining techniques, including Can-Grunwald, Giemsa, hematoxylin and eosin (H&E), Jenner's, Leishman, Masson's trichrome, Papauicolaou, Romanowsky, silver, Sudan, Wright's, and/or Periodic Acid Schiff (PAS) staining techniques. PAS staining is typically performed after formalin or acetone fixation.

In some embodiments, the sample is stained using a detectable label (e.g., radioisotopes, fluorophores, chemiluminescent compounds, bioluminescent compounds, and dyes) as described elsewhere herein. In some embodiments, a sample is stained using only one type of stain or one technique. In some embodiments, staining includes biological staining techniques such as H&E staining. In some embodiments, staining includes identifying analytes using fluorescently-conjugated antibodies. In some embodiments, a sample is stained using two or more different types of stains, or two or more different staining techniques. For example, a sample can be prepared by staining and imaging using one technique (e.g., H&E staining and brightfield imaging), followed by staining and imaging using another technique (e.g., IHC/IF staining and fluorescence microscopy) for the same sample.

In some embodiments, samples can be destained. Methods of destaining or discoloring a sample are known in the art, and generally depend on the nature of the stain(s) applied to the sample. For example, H&E staining can be destained by washing the sample in HCl, or any other low pH acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in a low pH acid (e.g., HCl). In some embodiments, destaining can include adding HCl to a downstream solution (e.g., permeabilization solution). In some embodiments, destaining can include dissolving an enzyme used in the disclosed methods (e.g., pepsin) in a low pH acid (e.g., HCl) solution. In some embodiments, after destaining hematoxylin with a low pH acid, other reagents can be added to the destaining solution to raise the pH for use in other applications. For example, SDS can be added to a low pH acid destaining solution in order to raise the pH as compared to the low pH acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., 2017, J. Histochem. Cytochem. 65(8): 431-444, Lin et al., 2015, Nat Commun. 6:8390, Pirici et al., 2009, J. Histochem. Cytochem. 57:567-75, and Glass et al., 2009, J. Histochem. Cytochem. 57:899-905, the entire contents of each of which are incorporated herein by reference.

(7) Hydrogel Embedding

In some embodiments, hydrogel formation occurs within a sample. In some embodiments, a sample (e.g., tissue section) is embedded in a hydrogel. In some embodiments, hydrogel subunits are infused into the sample, and polymerization of the hydrogel is initiated by an external or internal stimulus. A "hydrogel" as described herein can include a cross-linked 3D network of hydrophilic polymer chains. A "hydrogel subunit" can be a hydrophilic monomer, a molecular precursor, or a polymer that can be polymerized (e.g., cross-linked) to form a three-dimensional (3D) hydrogel network.

A hydrogel can swell in the presence of water. In some embodiments, a hydrogel comprises a natural material. In some embodiments, a hydrogel includes a synthetic material. In some embodiments, a hydrogel includes a hybrid material, e.g., the hydrogel material comprises elements of both synthetic and natural polymers. Any of the materials used in hydrogels or hydrogels comprising a polypeptide-based material described herein can be used. Embedding the sample in this manner typically involves contacting the sample with a hydrogel such that the sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the sample.

In some embodiments, the sample is immobilized in the hydrogel via cross-linking of the polymer material that forms the hydrogel. Cross-linking can be performed chemically and/or photochemically, or alternatively by any other hydrogel-formation method known in the art. For example, the sample can be immobilized in the hydrogel by polyacrylamide crosslinking. Further, analytes of a sample can be immobilized in a hydrogel by crosslinking (e.g., polyacrylamide crosslinking).

The composition and application of the hydrogel-matrix to a sample typically depends on the nature and preparation of the sample (e.g., sectioned, non-sectioned, fresh-frozen, type of fixation). A hydrogel can be any appropriate hydrogel where, upon formation of the hydrogel on the sample, the sample becomes anchored to or embedded in the hydrogel. Non-limiting examples of hydrogels are described herein or are known in the art. As one example, where the sample is a tissue section, the hydrogel can include a monomer solution and an ammonium persulfate (APS) initiator/tetramethylethylenediamine (TEMED) accelerator solution. As another example, where the sample consists of cells (e.g., cultured cells or cells disassociated from a tissue sample), the cells can be incubated with the monomer solution and APS/TEMED solutions. For cells, hydrogel is formed in compartments, including but not limited to devices used to culture, maintain, or transport the cells. For example, hydrogels can be formed with monomer solution plus APS/TEMED added to the compartment to a depth ranging from about 0.1 µm to about 2 mm.

Additional methods and aspects of hydrogel embedding of samples are described for example in Chen et al., 2015, Science 347(6221):543-548, and PCT publication 202020176788A1 entitled "Profiling of biological analytes with spatially barcoded oligonucleotide arrays," the entire contents of each of which are incorporated herein by reference.

(8) Sample Transfer

In some embodiments, a sample immobilized on a substrate (e.g., a biological sample prepared using methanol fixation or formalin-fixation and paraffin-embedding (FFPE)) is transferred to a spatial array using a hydrogel. In some embodiments, a hydrogel is formed on top of a sample on a substrate (e.g., glass slide). For example, hydrogel formation can occur in a manner sufficient to anchor (e.g., embed) the sample to the hydrogel. After hydrogel formation, the sample is anchored to (e.g., embedded in) the hydrogel where separating the hydrogel from the substrate results in the sample separating from the substrate along with the hydrogel. The sample can then be contacted with a spatial array, thereby allowing spatial profiling of the sample. In some embodiments, the hydrogel is removed after contacting the sample with the spatial array. For example, methods described herein can include an event-dependent (e.g., light or chemical) depolymerizing hydrogel, where upon application of the event (e.g., external stimuli) the hydrogel depolymerizes. In one example, a sample can be anchored to a DTT-sensitive hydrogel, where addition of DTT can cause the hydrogel to depolymerize and release the anchored sample. A hydrogel can be any appropriate hydrogel where upon formation of the hydrogel on the sample the sample becomes anchored to or embedded in the hydrogel. Non-limiting examples of hydrogels are described herein or are known in the art. In some embodiments, a hydrogel includes a linker that allows anchoring of the sample to the hydrogel. In some embodiments, a hydrogel includes linkers that allow anchoring of analytes to the hydrogel. In such cases, the linker can be added to the hydrogel before, contemporaneously with, or after hydrogel formation. Non-limiting examples of linkers that anchor nucleic acids to the hydrogel can include 6-((Acryloyl) amino) hexanoic acid (Acryloyl-X SE) (available from ThermoFisher, Waltham, Mass.), Label-IT Amine (available from MirusBio, Madison, Wis.) and Label X (Chen et al., Nat. Methods 13:679-684, 2016). Any variety of characteristics can determine the transfer conditions required for a given sample. Non-limiting examples of characteristics likely to impact transfer conditions include the sample (e.g., thickness, fixation, and cross-linking) and/or the analyte of interest (different conditions to preserve and/or transfer different analytes (e.g., DNA, RNA, and protein)). In some embodiments, hydrogel formation can occur in a manner sufficient to anchor the analytes (e.g., embed) in the sample to the hydrogel. In some embodiments, the hydrogel can be imploded (e.g., shrunk) with the anchored analytes (e.g., embedded in the hydrogel) present in the sample. In some embodiments, the hydrogel can be expanded (e.g., isometric expansion) with the anchored analytes (e.g., embedded in the hydrogel) present in the sample. In some embodiments, the hydrogel can be imploded (e.g., shrunk) and subsequently expanded with anchored analytes (e.g., embedded in the hydrogel) present in the sample.

(9) Isometric Expansion

In some embodiments, a sample embedded in a hydrogel can be isometrically expanded. Isometric expansion methods that can be used include hydration, a preparative step in expansion microscopy, as described in Chen et al., 2015, Science 347(6221) 543-548, Asano et al., 2018, Current Protocols 80:1, doi:10.1002/cpcb.56; Gao et al., 2017, BMC Biology 15:50, doi:10.1186/s12915-017-0393-3, and Wassie et al, 2018, Expansion microscopy: principles and uses in biological research, Nature Methods 16(1): 33-41, each of which is incorporated by reference in its entirety.

In general, the steps used to perform isometric expansion of the sample can depend on the characteristics of the sample (e.g., thickness of tissue section, fixation, cross-linking), and/or the analyte of interest (e.g., different conditions to anchor RNA, DNA, and protein to a gel).

Isometric expansion can be performed by anchoring one or more components of a sample to a gel, followed by gel formation, proteolysis, and swelling. Isometric expansion of the sample can occur prior to immobilization of the sample on a substrate, or after the sample is immobilized to a substrate. In some embodiments, the isometrically expanded sample can be removed from the substrate prior to contacting expanded sample with a spatially barcoded array (e.g., spatially barcoded capture probes on a substrate).

In some embodiments, proteins in the sample are anchored to a swellable gel such as a polyelectrolyte gel. An antibody can be directed to the protein before, after, or in conjunction with being anchored to the swellable gel. DNA and/or RNA in a sample can also be anchored to the swellable gel via a suitable linker. Examples of such linkers include, but are not limited to, 6-((Acryloyl)amino) hexanoic acid (Acryloyl-X SE) (available from ThermoFisher, Waltham, Mass.), Label-IT Amine (available from MirusBio, Madison, Wis.) and Label X (described for example in Chen et al., Nat. Methods 13:679-684, 2016, the entire contents of which are incorporated herein by reference).

Isometric expansion of the sample can increase the spatial resolution of the subsequent analysis of the sample. For example, isometric expansion of the sample can result in increased resolution in spatial profiling (e.g., single-cell profiling). The increased resolution in spatial profiling can be determined by comparison of an isometrically expanded sample with a sample that has not been isometrically expanded.

Isometric expansion can enable three-dimensional spatial resolution of the subsequent analysis of the sample. In some embodiments, isometric expansion of the sample can occur in the presence of spatial profiling reagents (e.g., analyte capture agents or capture probes). For example, the swellable gel can include analyte capture agents or capture probes anchored to the swellable gel via a suitable linker. In some embodiments, spatial profiling reagents can be delivered to particular locations in an isometrically expanded sample.

In some embodiments, a sample is isometrically expanded to a volume at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded volume. In some embodiments, the sample is isometrically expanded to at least 2× and less than 20× of its non-expanded volume.

In some embodiments, a sample embedded in a hydrogel is isometrically expanded to a volume at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded volume. In some embodiments, the sample embedded in a hydrogel is isometrically expanded to at least 2× and less than 20× of its non-expanded volume.

(10) Substrate Attachment

In some embodiments, the sample can be attached to a substrate (e.g., a chip). Examples of substrates suitable for this purpose are described in detail below. Attachment of the sample can be irreversible or reversible, depending upon the nature of the sample and subsequent steps in the analytical method.

In certain embodiments, the sample can be attached to the substrate reversibly by applying a suitable polymer coating to the substrate, and contacting the sample to the polymer coating. The sample can then be detached from the substrate using an organic solvent that at least partially dissolves the polymer coating. Hydrogels are examples of polymers that are suitable for this purpose.

More generally, in some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

(11) Disaggregation of Cells

In some embodiments, the sample corresponds to cells (e.g., derived from a cell culture or a tissue sample). In a cell sample with a plurality of cells, individual cells can be naturally unaggregated. For example, the cells can be derived from a suspension of cells and/or disassociated or disaggregated cells from a tissue or tissue section.

Alternatively, the cells in the sample may be aggregated, and may be disaggregated into individual cells using, for example, enzymatic or mechanical techniques. Examples of enzymes used in enzymatic disaggregation include, but are not limited to, dispase, collagenase, trypsin, and combinations thereof. Mechanical disaggregation can be performed, for example, using a tissue homogenizer.

In some embodiments of unaggregated cells or disaggregated cells, the cells are distributed onto the substrate such that at least one cell occupies a distinct spatial feature on the substrate. The cells can be immobilized on the substrate (e.g., to prevent lateral diffusion of the cells). In some embodiments, a cell immobilization agent can be used to immobilize a non-aggregated or disaggregated sample on a spatially-barcoded array prior to analyte capture. A "cell immobilization agent" can refer to an antibody, attached to a substrate, which can bind to a cell surface marker. In some embodiments, the distribution of the plurality of cells on the substrate follows Poisson statistics.

In some embodiments, cells from a plurality of cells are immobilized on a substrate. In some embodiments, the cells are immobilized to prevent lateral diffusion, for example, by adding a hydrogel and/or by the application of an electric field.

(12) Suspended and Adherent Cells

In some embodiments, the sample can be derived from a cell culture grown in vitro. Samples derived from a cell culture can include one or more suspension cells which are anchorage-independent within the cell culture. Examples of such cells include, but are not limited to, cell lines derived from hematopoietic cells, and from the following cell lines: Colo205, CCRF-CEM, HL-60, K562, MOLT-4, RPMI-8226, SR, HOP-92, NCI-H322M, and MALME-3M.

Samples derived from a cell culture can include one or more adherent cells that grow on the surface of the vessel that contains the culture medium. Additional non-limiting examples of suspended and adherent cells is found in U.S. patent application Ser. No. 16/992,569 entitled "Systems and Methods for Using the Spatial Distributions on Haplotypes to Determine a Biological Condition," filed Aug. 13, 2020, and PCT publication No. 202020176788A1 entitled "Profiling of biological analytes with spatially barcoded oligonucleotide arrays" the entire contents of each of which are incorporated herein by reference.

In some embodiments, a sample can be permeabilized to facilitate transfer of analytes out of the sample, and/or to facilitate transfer of species (such as capture probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution). In some embodiments, the sample can be permeabilized using any of the methods described herein (e.g., using any of the detergents described herein, e.g., SDS and/or N-lauroylsarcosine sodium salt solution) before or after enzymatic treatment (e.g., treatment with any of the enzymes described herein, e.g., trypin, proteases (e.g., pepsin and/or proteinase K)).

In some embodiments, a sample can be permeabilized by exposing the sample to greater than about 1.0 w/v % (e.g., greater than about 2.0 w/v %, greater than about 3.0 w/v %, greater than about 4.0 w/v %, greater than about 5.0 w/v %, greater than about 6.0 w/v %, greater than about 7.0 w/v %, greater than about 8.0 w/v %, greater than about 9.0 w/v %, greater than about 10.0 w/v %, greater than about 11.0 w/v %, greater than about 12.0 w/v %, or greater than about 13.0 w/v %) sodium dodecyl sulfate (SDS) and/or N-lauroylsarcosine or N-lauroylsarcosine sodium salt. In some embodiments, a sample can be permeabilized by exposing the sample (e.g., for about 5 minutes to about 1 hour, about 5 minutes to about 40 minutes, about 5 minutes to about 30 minutes, about 5 minutes to about 20 minutes, or about 5 minutes to about 10 minutes) to about 1.0 w/v % to about 14.0 w/v % (e.g., about 2.0 w/v % to about 14.0 w/v %, about 2.0 w/v % to about 12.0 w/v %, about 2.0 w/v % to about 10.0 w/v %, about 4.0 w/v % to about 14.0 w/v %, about 4.0 w/v % to about 12.0 w/v %, about 4.0 w/v % to about 10.0 w/v %, about 6.0 w/v % to about 14.0 w/v %, about 6.0 w/v % to about 12.0 w/v %, about 6.0 w/v % to about 10.0 w/v %, about 8.0 w/v % to about 14.0 w/v %, about 8.0 w/v % to about 12.0 w/v %, about 8.0 w/v % to about 10.0 w/v %, about 10.0% w/v % to about 14.0 w/v %, about 10.0 w/v % to about 12.0 w/v %, or about 12.0 w/v % to about 14.0 w/v %) SDS and/or N-lauroylsarcosine salt solution and/or proteinase K (e.g., at a temperature of about 4% to about 35° C., about 4° C. to about 25° C., about 4° C. to about 20° C., about 4° C. to about 10° C., about 10° C. to about 25° C., about 10° C. to about 20° C., about 10° C. to about 15° C., about 35° C. to about 50° C., about 35° C. to about 45° C., about 35° C. to about 40° C., about 40° C. to about 50° C., about 40° C. to about 45° C., or about 45° C. to about 50° C.).

In some embodiments, the sample can be incubated with a permeabilizing agent to facilitate permeabilization of the sample. Additional methods for sample permeabilization are described, for example, in Jamur et al., 2010, *Method Mol. Biol.* 588:63-66, 2010, the entire contents of which are incorporated herein by reference.

Lysis Reagents

In some embodiments, the sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Proteases

In some embodiments, a medium, solution, or permeabilization solution may contain one or more proteases. In some embodiments, a sample treated with a protease capable of degrading histone proteins can result in the generation of fragmented genomic DNA. The fragmented genomic DNA can be captured using the same capture domain (e.g., capture domain having a poly(T) sequence) used to capture mRNA. In some embodiments, a sample is treated with a protease capable of degrading histone proteins and an RNA protectant prior to spatial profiling in order to facilitate the capture of both genomic DNA and mRNA.

In some embodiments, a sample is permeabilized by exposing the sample to a protease capable of degrading histone proteins. As used herein, the term "histone protein" typically refers to a linker histone protein (e.g., H1) and/or a core histone protein (e.g., H2A, H2B, H3, and H4). In some embodiments, a protease degrades linker histone proteins, core histone proteins, or linker histone proteins and core histone proteins. Any suitable protease capable of degrading histone proteins in a sample can be used. Non-limiting examples of proteases capable of degrading histone proteins include proteases inhibited by leupeptin and TLCK (Tosyl-L-lysyl-chloromethane hydrochloride), a protease encoded by the EUO gene from *Chlamydia trachomatis* serovar A, granzyme A, a serine protease (e.g., trypsin or trypsin-like protease, neutral serine protease, elastase, cathepsin G), an aspartyl protease (e.g., cathepsin D), a peptidase family C1 enzyme (e.g., cathepsin L), pepsin, proteinase K, a protease that is inhibited by the diazomethane inhibitor Z-Phe-Phe-CHN(2) or the epoxide inhibitor E-64, a lysosomal protease, or an azurophilic enzyme (e.g., cathepsin G, elastase, proteinase 3, neutral serine protease). In some embodiments, a serine protease is a trypsin enzyme, trypsin-like enzyme or a functional variant or derivative thereof (e.g., P00761; C0HK48; Q8IYP2; Q8BW11; Q61E06; P35035; P00760; P06871; Q90627; P16049; P07477; P00762; P35031; P19799; P35036; Q29463; P06872; Q90628; P07478; P07146; P00763; P35032; P70059; P29786; P35037; Q90629; P35030; P08426; P35033; P35038; P12788; P29787; P35039; P35040; Q8NHM4; P35041; P35043; P35044; P54624; P04814; P35045; P32821; P54625; P35004; P35046; P32822; P35047; C0HKA5; C0HKA2; P54627; P35005; C0HKA6; C0HKA3; P52905; P83348; P00765; P35042; P81071; P35049; P51588; P35050; P35034; P35051; P24664; P35048; P00764; P00775; P54628; P42278; P54629; P42279; Q91041; P54630; P42280; C0HKA4) or a combination thereof. In some embodiments, a trypsin enzyme is P00761, P00760, Q29463, or a combination thereof. In some embodiments, a protease capable of degrading one or more histone proteins comprises an amino acid sequence with at least 80% sequence identity to P00761, P00760, or Q29463. In some embodiments, a protease capable of degrading one or more histone proteins comprises an amino acid sequence with at least 85%, 90%, 91%, 92%, 93%, 94%, 95%, 96%, 97%, 98%, or 99% identity to P00761, P00760, or Q29463. A protease may be considered a functional variant if it has at least 50% e.g., at least 60%, 70%, 80%, 90%, 95%, 96%, 97%, 98%, 99%, or 100% of the activity relative to the activity of the protease in condition optimum for the enzyme. In some embodiments, the enzymatic treatment with pepsin enzyme, or pepsin like enzyme, can include: P03954/PEPA1_MACFU; P28712/PEPA1_RABIT; P27677/PEPA2_MACFU; P27821/PEPA2_RABIT; PODJD8/PEPA3_HUMAN; P27822/PEPA3_RABIT; PODJD7/PEPA4_HUMAN; P27678/PEPA4_MACFU; P28713/PEPA4_RABIT; PODJD9/PEPA5_HUMAN; Q9D106/PEPA5_MOUSE; P27823/PEPAF_RABIT; P00792/PEPA_BOVIN; Q9N2D4/PEPA_CALJA; Q9GMY6/PEPA_CANLF; P00793/PEPA_CHICK; P11489/PEPA_MACMU; P00791/PEPA_PIG; Q9GMY7/PEPA_RHIFE; Q9GMY8/PEPA_SORUN; P81497/PEPA_SUNMU; P13636/PEPA_URSTH and functional variants and derivatives thereof, or a combination thereof. In some embodiments, the pepsin enzyme can include: P00791/PEPA_PIG; P00792/PEPA_BOVIN, functional variants, derivatives, or combinations thereof.

Additionally, the protease may be contained in a reaction mixture (solution), which also includes other components (e.g., buffer, salt, chelator (e.g., EDTA), and/or detergent (e.g., SDS, N-Lauroylsarcosine sodium salt solution)). The reaction mixture may be buffered, having a pH of about 6.5-8.5, e.g., about 7.0-8.0. Additionally, the reaction mixture may be used at any suitable temperature, such as about 10-50° C., e.g., about 10-44° C., 11-43° C., 12-42° C., 13-41° C., 14-40° C., 15-39° C., 16-38° C., 17-37° C., e.g., about 10° C., 12° C., 15° C., 18° C., 20° C., 22° C., 25° C., 28° C., 30° C., 33° C., 35° C. or 37° C., preferably about 35-45° C., e.g., about 37° C.

Other Reagents

In some embodiments, a permeabilization solution can contain additional reagents or a sample may be treated with additional reagents in order to optimize biological sample permeabilization. In some embodiments, an additional reagent is an RNA protectant. As used herein, the term "RNA protectant" typically refers to a reagent that protects RNA from RNA nucleases (e.g., RNases). Any appropriate RNA protectant that protects RNA from degradation can be used. A non-limiting example of a RNA protectant includes organic solvents (e.g., at least 60%, 65%, 70%, 75%, 80%, 85%, 90%, or 95% v/v organic solvent), which include, without limitation, ethanol, methanol, propan-2-ol, acetone, trichloroacetic acid, propanol, polyethylene glycol, acetic acid, or a combination thereof. In some embodiments, a RNA protectant includes ethanol, methanol and/or propan-2-ol, or a combination thereof. In some embodiments, a RNA protectant includes RNAlater ICE (ThermoFisher Scientific). In some embodiments, the RNA protectant comprises at least about 60% ethanol. In some embodiments, the RNA protectant comprises about 60-95% ethanol, about 0-35% methanol and about 0-35% propan-2-ol, where the total amount of organic solvent in the medium is not more than about 95%. In some embodiments, the RNA protectant comprises about 60-95% ethanol, about 5-20% methanol and about 5-20% propan-2-ol, where the total amount of organic solvent in the medium is not more than about 95%.

In some embodiments, the RNA protectant includes a salt. The salt may include ammonium sulfate, ammonium bisulfate, ammonium chloride, ammonium acetate, cesium sulfate, cadmium sulfate, cesium iron (II) sulfate, chromium (III) sulfate, cobalt (II) sulfate, copper (II) sulfate, lithium chloride, lithium acetate, lithium sulfate, magnesium sulfate, magnesium chloride, manganese sulfate, manganese chloride, potassium chloride, potassium sulfate, sodium chloride, sodium acetate, sodium sulfate, zinc chloride, zinc acetate and zinc sulfate. In some embodiments, the salt is a sulfate salt, for example, ammonium sulfate, ammonium bisulfate, cesium sulfate, cadmium sulfate, cesium iron (II) sulfate, chromium (III) sulfate, cobalt (II) sulfate, copper (II) sulfate, lithium sulfate, magnesium sulfate, manganese sulfate, potassium sulfate, sodium sulfate, or zinc sulfate. In some embodiments, the salt is ammonium sulfate. The salt may be present at a concentration of about 20 g/100 ml of medium or less, such as about 15 g/100 ml, 10 g/100 ml, 9 g/100 ml, 8 g/100 ml, 7 g/100 ml, 6 g/100 ml, 5 g/100 ml or less, e.g., about 4 g, 3 g, 2 g or 1 g/100 ml.

Additionally, the RNA protectant may be contained in a medium that further includes a chelator (e.g., EDTA), a buffer (e.g., sodium citrate, sodium acetate, potassium citrate, or potassium acetate, preferably sodium acetate), and/or buffered to a pH between about 4-8 (e.g., about 5).

In some embodiments, the sample is treated with one or more RNA protectants before, contemporaneously with, or after permeabilization. For example, a sample is treated with one or more RNA protectants prior to treatment with one or more permeabilization reagents (e.g., one or more proteases). In another example, a sample is treated with a solution including one or more RNA protectants and one or more permeabilization reagents (e.g., one or more proteases). In yet another example, a sample is treated with one or more RNA protectants after the sample has been treated with one or more permeabilization reagents (e.g., one or more proteases). In some embodiments, a sample is treated with one or more RNA protectants prior to fixation.

In some embodiments, identifying the location of the captured analyte in the sample includes a nucleic acid extension reaction. In some embodiments where a capture probe captures a fragmented genomic DNA molecule, a nucleic acid extension reaction includes DNA polymerase. For example, a nucleic acid extension reaction includes using a DNA polymerase to extend the capture probe that is hybridized to the captured analyte (e.g., fragmented genomic DNA) using the captured analyte (e.g., fragmented genomic DNA) as a template. The product of the extension reaction includes a spatially-barcoded analyte (e.g., spatially-barcoded fragmented genomic DNA). The spatially-barcoded analyte (e.g., spatially-barcoded fragmented genomic DNA) can be used to identify the spatial location of the analyte in the sample. Any DNA polymerase that is capable of extending the capture probe using the captured analyte as a template can be used for the methods described herein. Non-limiting examples of DNA polymerases include T7 DNA polymerase; Bsu DNA polymerase; and *E. coli* DNA Polymerase pol I.

Diffusion-Resistant Media

In some embodiments, a diffusion-resistant medium, typically used to limit diffusion of analytes, can include at least one permeabilization reagent. For example, the diffusion-resistant medium (e.g., a hydrogel) can include wells (e.g., micro-, nano-, or picowells or pores) containing a permeabilization buffer or reagents. In some embodiments, the diffusion-resistant medium (e.g., a hydrogel) is soaked in permeabilization buffer prior to contacting the hydrogel with a sample. In some embodiments, the hydrogel or other diffusion-resistant medium can contain dried reagents or monomers to deliver permeabilization reagents when the diffusion-resistant medium is applied to a sample. In some embodiments, the diffusion-resistant medium, (e.g., hydrogel) is covalently attached to a solid substrate (e.g., an acrylated glass slide).

In some embodiments, the hydrogel can be modified to both deliver permeabilization reagents and contain capture probes. For example, a hydrogel film can be modified to include spatially-barcoded capture probes. The spatially-barcoded hydrogel film is then soaked in permeabilization buffer before contacting the spatially-barcoded hydrogel film to the sample. In another example, a hydrogel can be modified to include spatially-barcoded capture probes and designed to serve as a porous membrane (e.g., a permeable hydrogel) when exposed to permeabilization buffer or any other sample preparation reagent. The permeabilization reagent diffuses through the spatially-barcoded permeable hydrogel and permeabilizes the sample on the other side of the hydrogel. The analytes then diffuse into the spatially-barcoded hydrogel after exposure to permeabilization reagents. In such cases, the spatially-barcoded hydrogel (e.g., porous membrane) is facilitating the diffusion of the analytes in the sample into the hydrogel. In some embodiments, analytes diffuse into the hydrogel before exposure to permeabilization reagents (e.g., when secreted analytes are present outside of the sample or in instances where a sample is lysed or permeabilized by other means prior to addition of permeabilization reagents). In some embodiments, the permeabilization reagent is flowed over the hydrogel at a variable flow rate (e.g., any flow rate that facilitates diffusion of the permeabilization reagent across the spatially-barcoded hydrogel). In some embodiments, the permeabilization reagents are flowed through a microfluidic chamber or channel over the spatially-barcoded hydrogel. In some embodiments, after using flow to introduce permeabilization reagents to the sample, sample preparation reagents can be flowed over the hydrogel to further facilitate diffusion of the analytes into the spatially-barcoded hydrogel. The spatially-barcoded hydrogel film thus delivers permeabilization reagents to a sample surface in contact with the spatially-barcoded hydrogel, enhancing analyte migration and capture. In some embodiments, the spatially-barcoded hydrogel is applied to a sample and placed in a permeabilization bulk solution. In some embodiments, the hydrogel film soaked in permeabilization reagents is sandwiched between a sample and a spatially-barcoded array. In some embodiments, target analytes are able to diffuse through the permeabilizing reagent soaked hydrogel and hybridize or bind the capture probes on the other side of the hydrogel. In some embodiments, the thickness of the hydrogel is proportional to the resolution loss. In some embodiments, wells (e.g., micro-, nano-, or picowells) can contain spatially-barcoded capture probes and permeabilization reagents and/or buffer. In some embodiments, spatially-barcoded capture probes and permeabilization reagents are held between spacers. In some embodiments, the sample is punch, cut, or transferred into the well, where a target analyte diffuses through the permeabilization reagent/buffer and to the spatially-barcoded capture probes. In some embodiments, resolution loss may be proportional to gap thickness (e.g., the amount of permeabilization buffer between the sample and the capture probes). In some embodiments, the diffusion-resistant medium (e.g., hydrogel) is between approximately 50-500 micrometers thick including 500, 450, 400, 350, 300, 250, 200, 150, 100, or 50 micrometers thick, or any thickness within 50 and 500 micrometers.

In some embodiments, a sample is exposed to a porous membrane (e.g., a permeable hydrogel) to aid in permeabilization and limit diffusive analyte losses, while allowing permeabilization reagents to reach a sample. Membrane chemistry and pore volume can be manipulated to minimize analyte loss. In some embodiments, the porous membrane may be made of glass, silicon, paper, hydrogel, polymer monoliths, or other material. In some embodiments, the material may be naturally porous. In some embodiments, the material may have pores or wells etched into solid material. In some embodiments, the permeabilization reagents are flowed through a microfluidic chamber or channel over the porous membrane. In some embodiments, the flow controls the sample's access to the permeabilization reagents. In some embodiments, the porous membrane is a permeable hydrogel. For example, a hydrogel is permeable when permeabilization reagents and/or sample preparation reagents can pass through the hydrogel using diffusion. Any suitable permeabilization reagents and/or sample preparation reagents described herein can be used under conditions sufficient to release analytes (e.g., nucleic acid, protein, metabolites, lipids, etc.) from the sample. In some embodiments, a hydrogel is exposed to the sample on one side and permeabilization reagent on the other side. The permeabilization reagent diffuses through the permeable hydrogel and permeabilizes the sample on the other side of the hydrogel. In some embodiments, permeabilization reagents are flowed over the hydrogel at a variable flow rate (e.g., any flow rate that facilitates diffusion of the permeabilization reagent across the hydrogel). In some embodiments, the permeabilization reagents are flowed through a microfluidic chamber or channel over the hydrogel. Flowing permeabilization reagents across the hydrogel enables control of the concentration of reagents. In some embodiments, hydrogel chemistry and pore volume can be tuned to enhance permeabilization and limit diffusive analyte losses.

In some embodiments, a porous membrane is sandwiched between a spatially-barcoded array and the sample, where permeabilization solution is applied over the porous membrane. The permeabilization reagents diffuse through the pores of the membrane and into the sample. In some embodiments, the sample can be placed on a substrate (e.g., a glass slide). Biological analytes then diffuse through the porous membrane and into to the space containing the capture probes. In some embodiments, the porous membrane is modified to include capture probes. For example, the capture probes can be attached to a surface of the porous membrane using any of the methods described herein. In another example, the capture probes can be embedded in the porous membrane at any depth that allows interaction with a biological analyte. In some embodiments, the porous membrane is placed onto a sample in a configuration that allows interaction between the capture probes on the porous membrane and the biological analytes from the sample. For example, the capture probes are located on the side of the porous membrane that is proximal to the sample. In such cases, permeabilization reagents on the other side of the porous membrane diffuse through the porous membrane into the location containing the sample and the capture probes in order to facilitate permeabilization of the sample (e.g., also facilitating capture of the biological analytes by the capture probes). In some embodiments, the porous membrane is located between the sample and the capture probes. In some embodiments, the permeabilization reagents are flowed through a microfluidic chamber or channel over the porous membrane.

Selective Permeabilization/Selective Lysis

In some embodiments, samples can be processed to selectively release an analyte from a subcellular region of a cell according to established methods. In some embodiments, a method provided herein can include detecting at least one analyte present in a subcellular region of a cell in a sample. As used herein, a "subcellular region" can refer to any subcellular region. For example, a subcellular region can refer to cytosol, a mitochondria, a nucleus, a nucleolus, an endoplasmic reticulum, a lysosome, a vesicle, a Golgi apparatus, a plastid, a vacuole, a ribosome, cytoskeleton, or combinations thereof. In some embodiments, the subcellular region comprises at least one of cytosol, a nucleus, a mitochondria, and a microsome. In some embodiments, the subcellular region is cytosol. In some embodiments, the subcellular region is a nucleus. In some embodiments, the subcellular region is a mitochondria. In some embodiments, the subcellular region is a microsome.

For example, a biological analyte can be selectively released from a subcellular region of a cell by selective permeabilization or selective lysing. In some embodiments, "selective permeabilization" can refer to a permeabilization method that can permeabilize a membrane of a subcellular region while leaving a different subcellular region substantially intact (e.g., biological analytes are not released from subcellular region due to the applied permeabilization method). Non-limiting examples of selective permeabilization methods include using electrophoresis and/or applying a permeabilization reagent. In some embodiments, "selective lysing" can refer to a lysis method that can lyse a membrane of a subcellular region while leaving a different subcellular region substantially intact (e.g., biological analytes are not released from subcellular region due to the applied lysis method). Several methods for selective permeabilization or lysis are known to one of skill in the art including the methods described in Lu et al. *Lab Chip*. 2005 January; 5(1):23-9; Niklas et al., 2011, *Anal Biochem* 416 (2):218-27; Cox and Emili., 2006, *Nat Protoc*. 1(4):1872-8; Chiang et al., 2000, *J Biochem. Biophys. Methods*. 20; 46(1-2):53-68; and Yamauchi and Herr et al., 2017, *Microsyst. Nanoeng*. 3. pii: 16079; each of which is incorporated herein by reference in its entirety.

In some embodiments, "selective permeabilization" or "selective lysis" refer to the selective permeabilization or selective lysis of a specific cell type. For example, "selective permeabilization" or "selective lysis" can refer to lysing one cell type while leaving a different cell type substantially intact (e.g., biological analytes are not released from the cell due to the applied permeabilization or lysis method). A cell that is a "different cell type" than another cell can refer to a cell from a different taxonomic kingdom, a prokaryotic cell versus a eukaryotic cell, a cell from a different tissue type, etc. Many methods are known to one of skill in the art for selectively permeabilizing or lysing different cell types. Non-limiting examples include applying a permeabilization reagent, electroporation, and/or sonication. See, e.g., International Application No. WO 2012/168003; Han et al., 2019, *Microsyst Nanoeng*. 5:30; Gould et al., 2018 *Oncotarget*. 20; 9(21): 15606-15615; Oren and Shai, 1997, *Biochemistry* 36(7), 1826-35; Algayer et al., 2019, *Molecules*. 24(11). pii: E2079; Hipp et al. 2017, *Leukemia* 10, 2278; International Application No. WO 2012/168003; and U.S. Pat. No. 7,785,869; all of which are incorporated by reference herein in their entireties.

In some embodiments, applying a selective permeabilization or lysis reagent comprises contacting the sample with a hydrogel comprising the permeabilization or lysis reagent.

In some embodiments, the sample is contacted with two or more arrays (e.g., flexible arrays, as described herein). For example, after a subcellular region is permeabilized and a biological analyte from the subcellular region is captured on a first array, the first array can be removed, and a biological analyte from a different subcellular region can be captured on a second array.

(13) Selective Enrichment of RNA Species

In some embodiments, where RNA is the analyte, one or more RNA analyte species of interest can be selectively enriched (e.g., Adiconis et. al., 2013, Comparative analysis of RNA sequencing methods for degraded and low-input samples, Nature 10, 623-632, herein incorporated by reference in its entirety). For example, one or more species of RNA of interest can be selected by addition of one or more oligonucleotides to the sample. In some embodiments, the additional oligonucleotide is a sequence used for priming a reaction by a polymerase. For example, one or more primer sequences with sequence complementarity to one or more RNAs of interest can be used to amplify the one or more RNAs of interest, thereby selectively enriching these RNAs. In some embodiments, an oligonucleotide with sequence complementarity to the complementary strand of captured RNA (e.g., cDNA) can bind to the cDNA. For example, biotinylated oligonucleotides with sequence complementary to one or more cDNAs of interest binds to the cDNA and can be selected using biotinylation-streptavidin affinity using any of a variety of methods known to the field (e.g., streptavidin beads).

Alternatively, one or more species of RNA (e.g., ribosomal and/or mitochondrial RNA) can be down-selected (e.g., removed, depleted) using any of a variety of methods. Non-limiting examples of a hybridization and capture method of ribosomal RNA depletion include RiboMinus™, RiboCop™, and Ribo-Zero™. Another non-limiting RNA depletion method involves hybridization of complementary DNA oligonucleotides to unwanted RNA followed by degradation of the RNA/DNA hybrids using RNase H. Non-limiting examples of a hybridization and degradation method include NEBNext® rRNA depletion, NuGEN AnyDeplete, or RiboZero Plus. Another non-limiting ribosomal RNA depletion method includes ZapR™ digestion, for example SMARTer. In the SMARTer method, random nucleic acid adapters are hybridized to RNA for first-strand synthesis and tailing by reverse transcriptase, followed by template switching and extension by reverse transcriptase. Additionally, first round PCR amplification adds full-length Illumina sequencing adapters (e.g., Illumina indexes). Ribosomal RNA is cleaved by ZapR v2 and R probes v2. A second round of PCR is performed, amplifying non-rRNA molecules (e.g., cDNA). Parts or steps of these ribosomal depletion protocols/kits can be further combined with the methods described herein to optimize protocols for a specific sample.

In depletion protocols, probes can be administered to a sample that selectively hybridize to ribosomal RNA (rRNA), thereby reducing the pool and concentration of rRNA in the sample. Probes can be administered to a sample that selectively hybridize to mitochondria RNA (mtRNA), thereby reducing the pool and concentration of mtRNA in the sample. In some embodiments, probes complementary to mitochondrial RNA can be added during cDNA synthesis, or probes complementary to both ribosomal and mitochondrial RNA can be added during cDNA synthesis. Subsequent application of capture probes to the sample can result in improved capture of other types of RNA due to a reduction in non-specific RNA (e.g. down-selected RNA) present in the sample. Additionally and alternatively, duplex-specific nuclease (DSN) treatment can remove rRNA (see, e.g., Archer et al, 2014, Selective and flexible depletion of problematic sequences from RNA-seq libraries at the cDNA stage, BMC Genomics 15 401, the entire contents of which are incorporated herein by reference). Furthermore, hydroxyapatite chromatography can remove abundant species (e.g., rRNA) (see, e.g., Vandernoot, 2012, "cDNA normalization by hydroxyapatite chromatography to enrich transcriptome diversity in RNA-seq applications," Biotechniques, 53(6) 373-80, the entire contents of which are incorporated herein by reference).

(14) Other Reagents

Additional reagents can be added to a sample to perform various functions prior to analysis of the sample. In some embodiments, nuclease inhibitors such as DNase and RNase inactivating agents or protease inhibitors such as proteinase K, and/or chelating agents such as EDTA, can be added to the sample. In other embodiments nucleases, such as DNase or RNAse, or proteases, such as pepsin or proteinase K, are added to the sample. In some embodiments, additional reagents may be dissolved in a solution or applied as a medium to the sample. In some embodiments, additional reagents (e.g., pepsin) may be dissolved in HCl prior to applying to the sample. For example, hematoxylin, from an H&E stain, can be optionally removed from the sample by washing in dilute HCl (0.001M to 0.1M) prior to further processing. In some embodiments, pepsin can be dissolved in dilute HCl (0.001M to 0.1M) prior to further processing. In some embodiments, samples can be washed additional times (e.g., 2, 3, 4, 5, or more times) in dilute HCl prior to incubation with a protease (e.g., pepsin), but after proteinase K treatment.

In some embodiments, the sample can be treated with one or more enzymes. For example, one or more endonucleases to fragment DNA, DNA polymerase enzymes, and dNTPs used to amplify nucleic acids can be added. Other enzymes that can also be added to the sample include, but are not limited to, polymerase, transposase, ligase, and DNAse, and RNAse.

Figure 37:
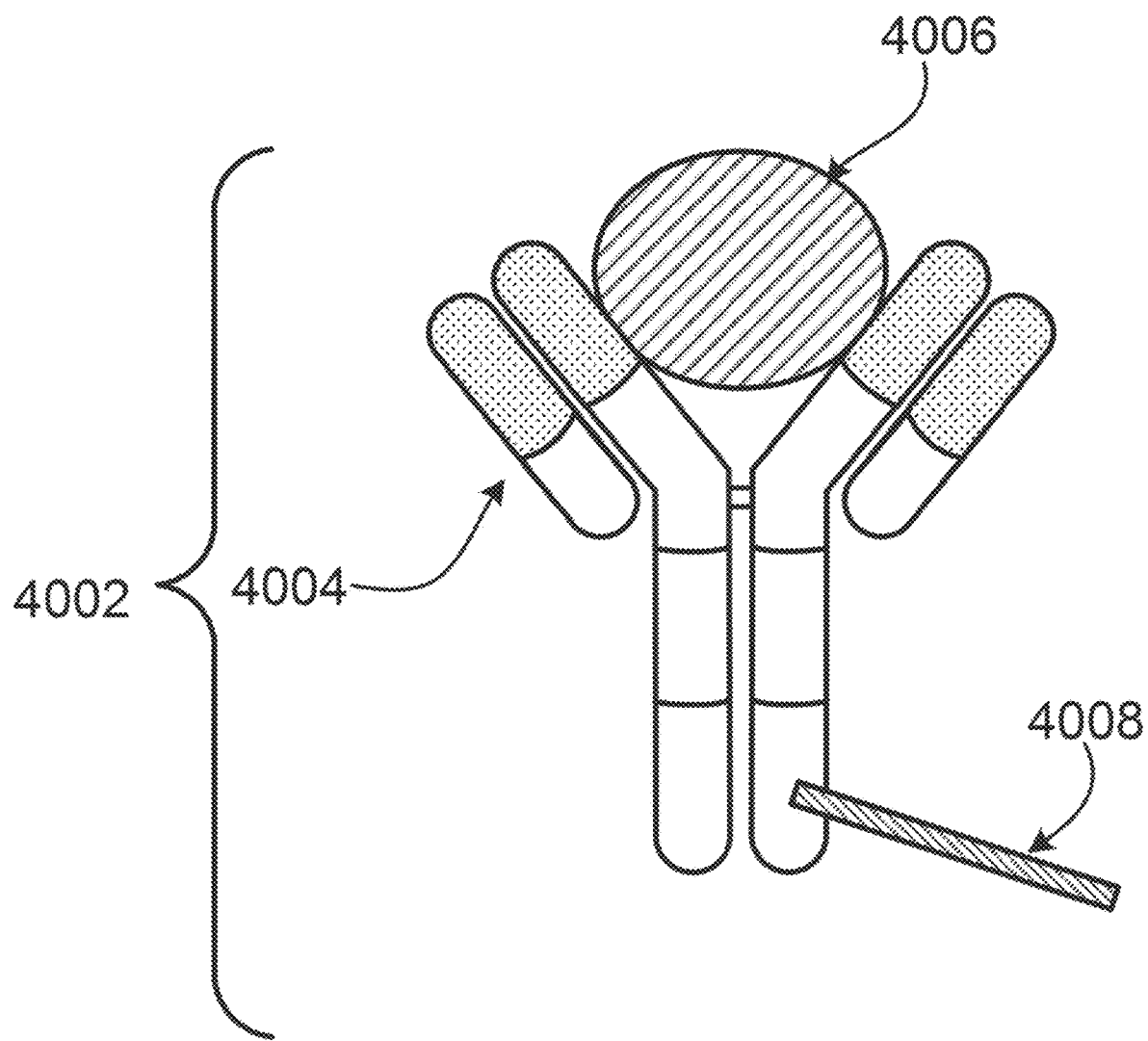
FIG. 37 is a schematic diagram of an exemplary analyte capture agent in accordance with some embodiments of the present disclosure.

In some embodiments, reverse transcriptase enzymes can be added to the sample, including enzymes with terminal transferase activity, primers, and template switch oligonucleotides (TSOs). Template switching can be used to increase the length of a cDNA, e.g., by appending a pre-defined nucleic acid sequence to the cDNA. Such a step of reverse transcription is illustrated in FIG. 37. In some embodiments, the appended nucleic acid sequence comprises one or more ribonucleotides.

In some embodiments, additional reagents can be added to improve the recovery of one or more target molecules (e.g., cDNA molecules, mRNA transcripts). For example, addition of carrier RNA to a RNA sample workflow process can increase the yield of extracted RNA/DNA hybrids from the sample. In some embodiments, carrier molecules are useful when the concentration of input or target molecules is low as compared to remaining molecules. Generally, single target molecules cannot form a precipitate, and addition of the carrier molecules can help in forming a precipitate. Some target molecule recovery protocols use carrier RNA to prevent small amounts of target nucleic acids present in the sample from being irretrievably bound. In some embodiments, carrier RNA can be added immediately prior to a second strand synthesis step. In some embodiments, carrier RNA can be added immediately prior to a second strand cDNA synthesis on oligonucleotides released from an array. In some embodiments, carrier RNA can be added immediately prior to a post in vitro transcription clean-up step. In some embodiments, carrier RNA can be added prior to amplified RNA purification and quantification. In some embodiments, carrier RNA can be added before RNA quantification. In some embodiments, carrier RNA can be added immediately prior to both a second strand cDNA synthesis and a post in vitro transcription clean-up step.

(15) Pre-Processing for Capture Probe Interaction

In some embodiments, analytes in a sample can be pre-processed prior to interaction with a capture probe. For example, prior to interaction with capture probes, polymerization reactions catalyzed by a polymerase (e.g., DNA polymerase or reverse transcriptase) are performed in the sample. In some embodiments, a primer for the polymerization reaction includes a functional group that enhances hybridization with the capture probe. The capture probes can include appropriate capture domains to capture biological analytes of interest (e.g., poly-dT sequence to capture poly (A) mRNA).

In some embodiments, biological analytes are pre-processed for library generation via next generation sequencing. For example, analytes can be pre-processed by addition of a modification (e.g., ligation of sequences that allow interaction with capture probes). In some embodiments, analytes (e.g., DNA or RNA) are fragmented using fragmentation techniques (e.g., using transposases and/or fragmentation buffers).

Fragmentation can be followed by a modification of the analyte. For example, a modification can be the addition through ligation of an adapter sequence that allows hybridization with the capture probe. In some embodiments, where the analyte of interest is RNA, poly(A) tailing is performed. Addition of a poly(A) tail to RNA that does not contain a poly(A) tail can facilitate hybridization with a capture probe that includes a capture domain with a functional amount of poly(dT) sequence.

In some embodiments, prior to interaction with capture probes, ligation reactions catalyzed by a ligase are performed in the sample. In some embodiments, ligation can be performed by chemical ligation. In some embodiments, the ligation can be performed using click chemistry as further described below. In some embodiments, the capture domain includes a DNA sequence that has complementarity to a RNA molecule, where the RNA molecule has complementarity to a second DNA sequence, and where the RNA-DNA sequence complementarity is used to ligate the second DNA sequence to the DNA sequence in the capture domain. In these embodiments, direct detection of RNA molecules is possible.

In some embodiments, prior to interaction with capture probes, target-specific reactions are performed in the sample. Examples of target specific reactions include, but are not limited to, ligation of target specific adaptors, probes and/or other oligonucleotides, target specific amplification using primers specific to one or more analytes, and target-specific detection using in situ hybridization, DNA microscopy, and/or antibody detection. In some embodiments, a capture probe includes capture domains targeted to target-specific products (e.g., amplification or ligation).

General Spatial Array-Based Analytical Methodology

This section of the disclosure describes methods, apparatus, systems, and compositions for spatial array-based analysis of samples.

(a) Spatial Analysis Methods

Array-based spatial analysis methods involve the transfer of one or more analytes from a sample to an array of capture spots on a substrate, each of which is associated with a unique spatial location on the array. Subsequent analysis of the transferred analytes includes determining the identity of the analytes and the spatial location of each analyte within the sample. The spatial location of each analyte within the sample is determined based on the capture spot to which each analyte is bound in the array, and the capture spot's relative spatial location within the array.

There are at least two general methods to associate a spatial barcode with one or more neighboring cells, such that the spatial barcode identifies the one or more cells, and/or contents of the one or more cells, as associated with a particular spatial location. One general method is to promote analytes out of a cell and towards the spatially-barcoded array. FIG. 1 depicts an exemplary embodiment of this general method. In FIG. 1, the spatially-barcoded array populated with capture probes (as described further herein) is contacted with a sample 101, and sample is permeabilized 102, allowing the target analyte to migrate away from the sample and toward the array 102. The target analyte interacts with a capture probe on the spatially-barcoded array. Once the target analyte hybridizes/is bound to the capture probe, the sample is optionally removed from the array and the capture probes are analyzed in order to obtain spatially-resolved analyte information 103.

Another general method is to cleave the spatially-barcoded capture probes from an array, and promote the spatially-barcoded capture probes towards and/or into or onto the sample. FIG. 2 depicts an exemplary embodiment of this general method, the spatially-barcoded array populated with capture probes (as described further herein) can be contacted with a sample 201. The spatially-barcoded capture probes are cleaved and then interact with cells within the provided sample 202. The interaction can be a covalent or non-covalent cell-surface interaction. The interaction can be an intracellular interaction facilitated by a delivery system or a cell penetration peptide. Once the spatially-barcoded capture probe is associated with a particular cell, the sample can be optionally removed for analysis. The sample can be optionally dissociated before analysis. Once the tagged cell is associated with the spatially-barcoded capture probe, the capture probes can be analyzed to obtain spatially-resolved information about the tagged cell 203.

Figure 3B:
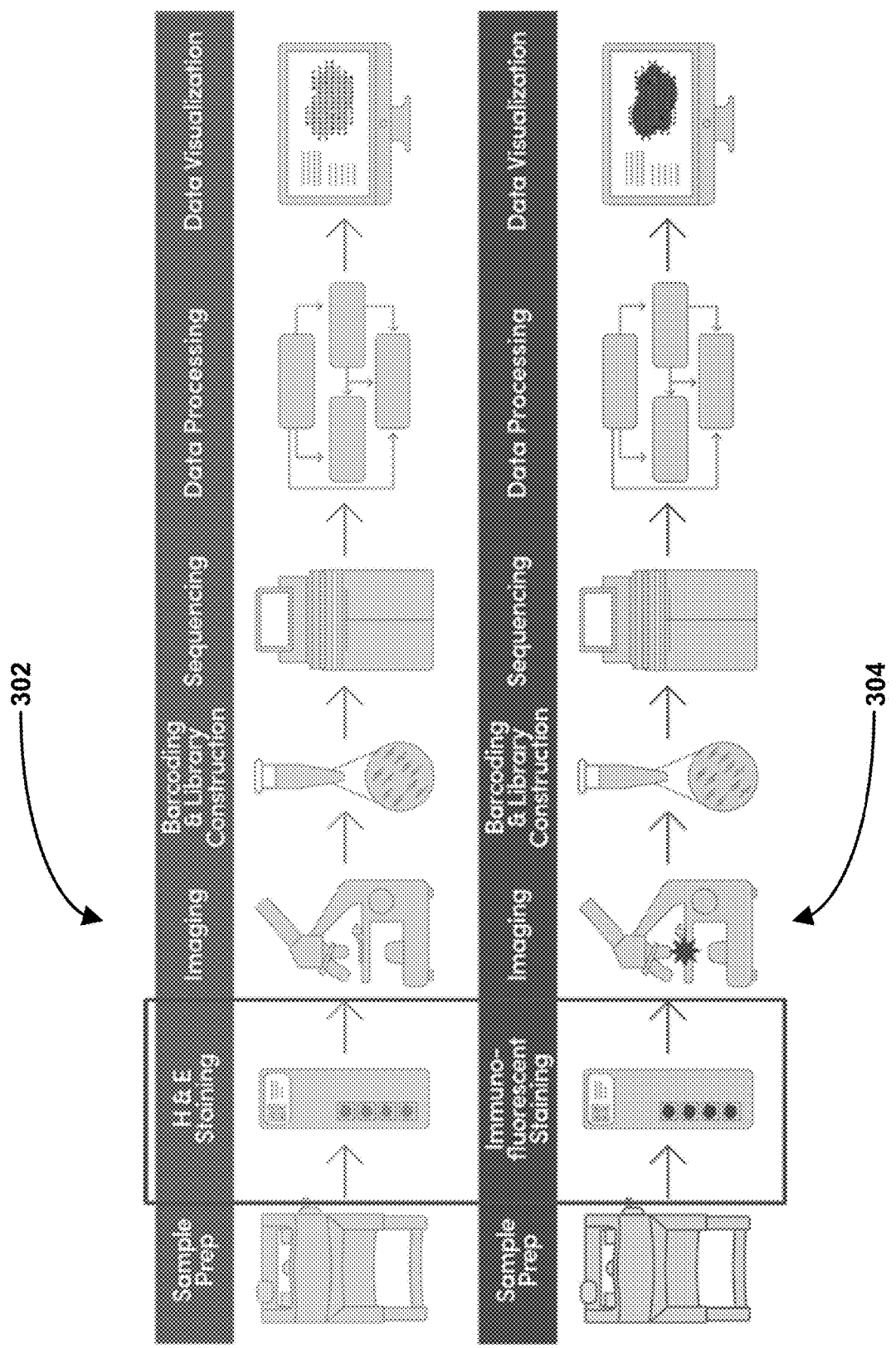

FIGS. 3A and 3B show exemplary workflows that include preparing a sample on a spatially-barcoded array 301. Sample preparation may include placing the sample on a substrate (e.g., chip, slide, etc.), fixing the sample, and/or staining the sample for imaging. The sample (stained or not stained) is then imaged on the array 302 using brightfield (to image the sample, e.g., using a hematoxylin and eosin stain) or fluorescence (to image capture spots) as illustrated in the upper panel 302 of FIG. 3B) and/or emission imaging modalities (as illustrated in the lower panel 304 of FIG. 3B).

Brightfield images are transmission microscopy images where broad-spectrum, white light is placed on one side of the sample mounted on a chip and the camera objective is placed on the other side and the sample itself filters the light in order to generate colors or grayscale intensity images 1124, akin to a stained glass window viewed from inside on a bright day.

In some embodiments, in addition to or instead of brightfield imaging, emission imaging, such as fluorescence imaging is used. In emission imaging approaches, the sample on the chip is exposed to light of a specific narrow band (first wavelength band) of light and then the light that is re-emitted from the sample at a slightly different wavelength (second wavelength band) is measured. This absorption and re-emission is due to the presence of a fluorophore that is sensitive to the excitation used and can be either a natural property of the sample or an agent the sample has been exposed to in preparation for the imaging. As one example, in an immunofluorescence experiment, an antibody that binds to a certain protein or class of proteins, and that is labeled with a certain fluorophore, is added to the sample. When this is done, the locations on the sample that include the protein or class of proteins will emit the second wavelength band. In fact, multiple antibodies with multiple fluorophores can be used to label multiple proteins in the sample. Each such fluorophore requires excitation with a different wavelength of light and further emits a different unique wavelength of light. In order to spatially resolve each of the different emitted wavelengths of light, the sample is subjected to the different wavelengths of light that will excite the multiple fluorophores on a serial basis and images for each of these light exposures is saved as an image thus generating a plurality of images. For instance, the image is subjected to a first wavelength that excites a first fluorophore to emit at a second wavelength and a first image of the sample is taken while the sample is being exposed to the first wavelength. Then the exposure of the sample to the first wavelength is discontinued and the sample is exposed to a third wavelength (different from the first wavelength) that excites a second fluorophore at a fourth wavelength (different from the second wavelength) and a second image of the sample is taken while the sample is being exposed to the third wavelength. Such a process is repeated for each different fluorophore in the multiple fluorophores (e.g., two or more fluorophores, three or more fluorophores, four or more fluorophores, five or more fluorophores). In this way, a series of images of the tissue, each depicting the spatial arrangement of some different parameter such as a particular protein or protein class, is obtained. In some embodiments, more than one fluorophore is imaged at the same time. In such an approach a combination of excitation wavelengths are used, each for one of the more than one fluorophore, and a single image is collected.

In some embodiments, each of the images collected through emission imaging is gray scaled. To differentiate such grey scaled images, in some embodiments each of the images are assigned a color (shades of red, shades of blue, etc.) and combined into one composite color image for viewing. Such fluorescence imaging allows for the spatial analysis of protein abundance (e.g., spatial proteomics) in the sample. In some embodiments, such spatial abundance is analyzed on its own. In other embodiments such spatial abundance is analyzed together with transcriptomics.

In some embodiments where the sample is analyzed with transcriptomics, along with the brightfield and/or emission imaging (e.g., fluorescence imaging), target analytes are released from the sample and capture probes forming a spatially-barcoded array hybridize or bind the released target analytes 303. The sample can be optionally removed from the array 304 and the capture probes can be optionally cleaved from the array 305. The sample and array are then optionally imaged a second time in both modalities 305B while the analytes are reverse transcribed into cDNA, and an amplicon library is prepared 306 and sequenced 307. The two sets of images are then spatially-overlaid in order to correlate spatially-identified sample information 308. When the sample and array are not imaged a second time, 305B, a spot coordinate file is supplied instead. The spot coordinate file replaces the second imaging step 305B. Further, amplicon library preparation 306 can be performed with a unique PCR adapter and sequenced 307.

Figure 4:
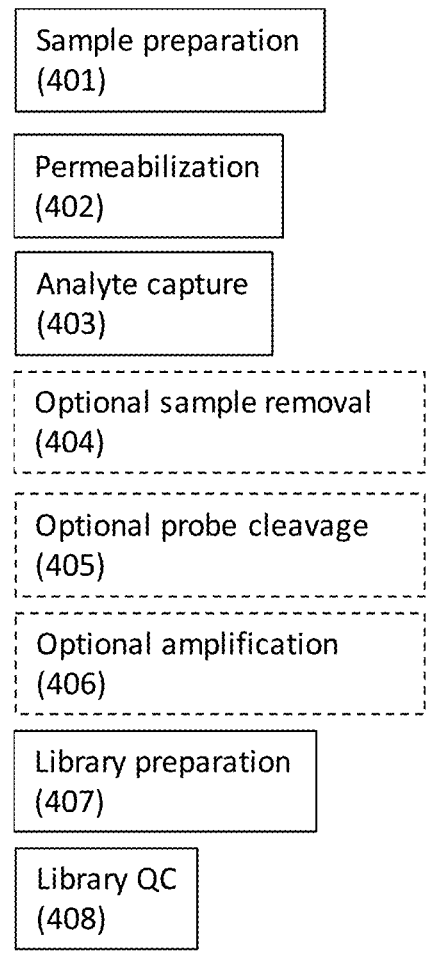
FIG. 4 shows an exemplary spatial analysis workflow in which optional steps are indicated by dashed boxes in accordance with an embodiment of the present disclosure.

FIG. 4 shows another exemplary workflow that utilizes a spatially-labelled array on a substrate (e.g., chip), where spatially-barcoded capture probes are clustered at areas called capture spots. The spatially-labelled capture probes can include a cleavage domain, one or more functional sequences, a spatial barcode, a unique molecular identifier, and a capture domain. The spatially-labelled capture probes can also include a 5' end modification for reversible attachment to the substrate. The spatially-barcoded array is contacted with a sample 401, and the sample is permeabilized through application of permeabilization reagents 402. Permeabilization reagents may be administered by placing the array/sample assembly within a bulk solution. Alternatively, permeabilization reagents may be administered to the sample via a diffusion-resistant medium and/or a physical barrier such as a lid, where the sample is sandwiched between the diffusion-resistant medium and/or barrier and the array-containing substrate. The analytes are migrated toward the spatially-barcoded capture array using any number of techniques disclosed herein. For example, analyte migration can occur using a diffusion-resistant medium lid and passive migration. As another example, analyte migration can be active migration, using an electrophoretic transfer system, for example. Once the analytes are in close proximity to the spatially-barcoded capture probes, the capture probes can hybridize or otherwise bind a target analyte 403. The sample can be optionally removed from the array 404.

The capture probes can be optionally cleaved from the array 405, and the captured analytes can be spatially-barcoded by performing a reverse transcriptase first strand cDNA reaction. A first strand cDNA reaction can be optionally performed using template switching oligonucleotides. For example, a template switching oligonucleotide can hybridize to a poly(C) tail added to a 3' end of the cDNA by a reverse transcriptase enzyme. The original mRNA template and template switching oligonucleotide can then be denatured from the cDNA and the spatially-barcoded capture probe can then hybridize with the cDNA and a complement of the cDNA can be generated. The first strand cDNA can then be purified and collected for downstream amplification steps. The first strand cDNA can be optionally amplified using PCR 406, where the forward and reverse primers flank the spatial barcode and target analyte regions of interest, generating a library associated with a particular spatial barcode 407. In some embodiments, the cDNA comprises a sequencing by synthesis (SBS) primer sequence. In some embodiments, the library preparation can be quantified and/or subjected to quality control to verify the success of the library preparation steps 408. The library amplicons are sequenced and analyzed to decode spatial information 407, with an additional library quality control (QC) step 408.

Using the methods, compositions, systems, kits, and devices described herein, RNA transcripts present in biological samples (e.g., tissue samples) can be used for spatial transcriptome analysis. In particular, in some cases, the barcoded oligonucleotides may be configured to prime, replicate, and consequently yield barcoded extension products from an RNA template, or derivatives thereof. For example, in some cases, the barcoded oligonucleotides may include mRNA specific priming sequences, e.g., poly-T primer segments that allow priming and replication of mRNA in a reverse transcription reaction or other targeted priming sequences. Alternatively or additionally, random RNA priming may be carried out using random N-mer primer segments of the barcoded oligonucleotides. Reverse transcriptases (RTs) can use an RNA template and a primer complementary to the 3' end of the RNA template to direct the synthesis of the first strand complementary DNA (cDNA). Many RTs can be used in this reverse transcription reactions, including, for example, avian myeloblastosis virus (AMV) reverse transcriptase, moloney murine leukemia virus (M-MuLV or MMLV), and other variants thereof. Some recombinant M-MuLV reverse transcriptase, such as, for example, PROTOSCRIPT® II reverse transcriptase, can have reduced RNase H activity and increased thermostability when compared to its wild type counterpart, and provide higher specificity, higher yield of cDNA and more full-length cDNA products with up to 12 kilobase (kb) in length. In some embodiments, the reverse transcriptase enzyme is a mutant reverse transcriptase enzyme such as, but not limited to, mutant MMLV reverse transcriptase. In another embodiment, the reverse transcriptase is a mutant MMLV reverse transcriptase such as, but not limited to, one or more variants described in U.S. Patent Publication No. 20180312822 and U.S. Provisional Patent Application No. 62/946,885 filed on Dec. 11, 2019, both of which are incorporated herein by reference in their entireties.

Figure 5:
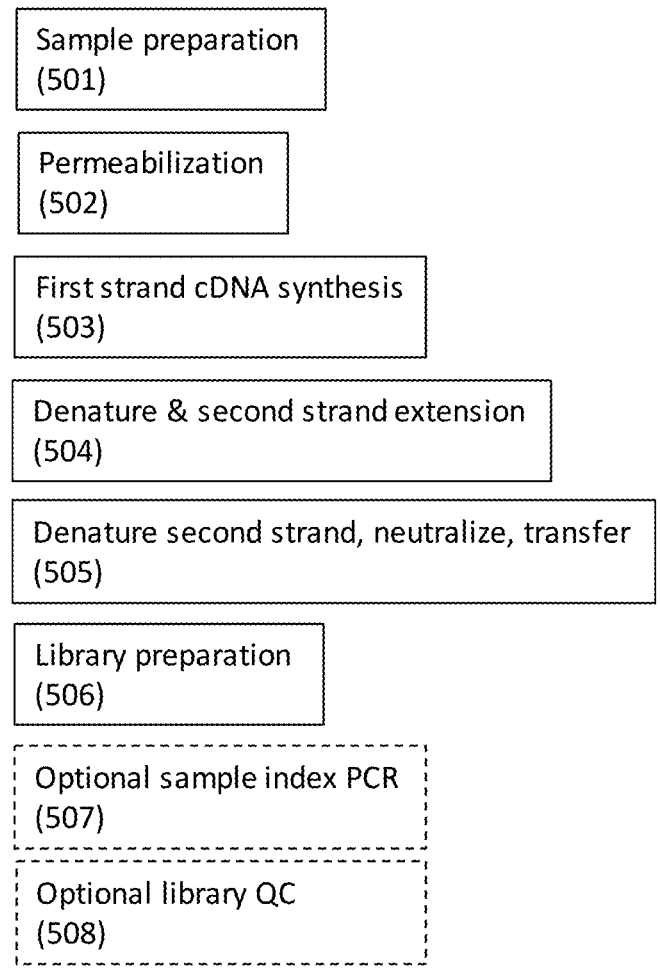
FIG. 5 shows an exemplary spatial analysis workflow in which optional steps are indicated by dashed boxes in accordance with an embodiment of the present disclosure.

FIG. 5 depicts an exemplary workflow where the sample is removed from the spatially-barcoded array and the spatially-barcoded capture probes are removed from the array for barcoded analyte amplification and library preparation. Another embodiment includes performing first strand synthesis using template switching oligonucleotides on the spatially-barcoded array without cleaving the capture probes. In this embodiment, sample preparation 501 and permeabilization 502 are performed as described elsewhere herein. Once the capture probes capture the target analyte(s), first strand cDNA created by template switching and reverse transcriptase 503 is then denatured and the second strand is then extended 504. The second strand cDNA is then denatured from the first strand cDNA, neutralized, and transferred to a tube 505. cDNA quantification and amplification can be performed using standard techniques discussed herein. The cDNA can then be subjected to library preparation 506 and indexing 507, including fragmentation, end-repair, and a-tailing, and indexing PCR steps. The library can also be optionally tested for quality control (QC) 508.

In a non-limiting example of the workflows described above, a sample (e.g. tissue section), can be fixed with methanol, stained with hematoxylin and eosin, and imaged. Optionally, the sample can be destained prior to permeabilization. The images can be used to map spatial analyte abundance (e.g., gene expression) patterns back to the sample. A permeabilization enzyme can be used to permeabilize the sample directly on the slide. Analytes (e.g., polyadenylated mRNA) released from the overlying cells of the sample can be captured by capture probes within a capture area on a substrate. Reverse transcription (RT) reagents can be added to permeabilized samples. Incubation with the RT reagents can produce spatially-barcoded full-length cDNA from the captured analytes (e.g., polyadenylated mRNA). Second strand reagents (e.g., second strand primers, enzymes) can be added to the sample on the slide to initiate second strand synthesis. The resulting cDNA can be denatured from the capture probe template and transferred (e.g., to a clean tube) for amplification, and/or library construction. The spatially-barcoded, full-length cDNA can be amplified via PCR prior to library construction. The cDNA can then be enzymatically fragmented and size-selected in order to optimize the cDNA amplicon size. P5, P7, i7, and i5 can be used as sample indexes, and TruSeq Read 2 can be added via End Repair, A-tailing, Adaptor Ligation, and PCR. The cDNA fragments can then be sequenced using paired-end sequencing using TruSeq Read 1 and TruSeq Read 2 as sequencing primer sites. See, Illumina, Indexed Sequencing Overview Guides, February 2018, Document 15057455v04; and Illumina Adapter Sequences, May 2019, Document #1000000002694v11, each of which is hereby incorporated by reference, for information on P5, P7, i7, i5, TruSeq Read 2, indexed sequencing, and other reagents described herein.

In some embodiments, performing correlative analysis of data produced by this workflow, and other workflows described herein, can yield over 95% correlation of genes expressed across two capture areas (e.g. 95% or greater, 96% or greater, 97% or greater, 98% or greater, or 99% or greater). When performing the described workflows using single cell RNA sequencing of nuclei, in some embodiments, correlative analysis of the data can yield over 90% (e.g. over 90%, 91%, 92%, 93%, 94%, 95%, 96%, 97%, 98%, or 99%) correlation of genes expressed across two capture areas.

In some embodiments, after cDNA is generated (e.g., by reverse transcription) the cDNA can be amplified directly on the substrate surface. Generating multiple copies of the cDNA (e.g., cDNA synthesized from captured analytes) via amplification directly on the substrate surface can improve final sequencing library complexity. Thus, in some embodiments, cDNA can be amplified directly on the substrate surface by isothermal nucleic acid amplification. In some embodiments, isothermal nucleic acid amplification can amplify RNA or DNA.

In some embodiments, isothermal amplification can be faster than a standard PCR reaction. In some embodiments, isothermal amplification can be linear amplification (e.g., asymmetrical with a single primer), or exponential amplification (e.g., with two primers). In some embodiments, isothermal nucleic acid amplification can be performed by a template-switching oligonucleotide primer. In some embodiments, the template switching oligonucleotide adds a common sequence onto the 5' end of the RNA being reverse transcribed. For example, after a capture probe interacts with an analyte (e.g., mRNA) and reverse transcription is performed such that additional nucleotides are added to the end of the cDNA creating a 3' overhang as described herein. In some embodiments, a template switching oligonucleotide hybridizes to untemplated poly(C) nucleotides added by a reverse transcriptase to continue replication to the 5' end of the template switching oligonucleotide, thereby generating full-length cDNA ready for further amplification. In some embodiments, the template switching oligonucleotide adds a common 5' sequence to full-length cDNA that is used for cDNA amplification (e.g., a reverse complement of the template switching oligonucleotide).

In some embodiments, once a full-length cDNA molecule is generated, the template switching oligonucleotide can serve as a primer in a cDNA amplification reaction (e.g., with a DNA polymerase). In some embodiments, double stranded cDNA (e.g., first strand cDNA and second strand reverse complement cDNA) can be amplified via isothermal amplification with either a helicase or recombinase, followed by a strand displacing DNA polymerase. The strand displacing DNA polymerase can generate a displaced second strand resulting in an amplified product.

In any of isothermal amplification methods described herein, barcode exchange (e.g., spatial barcode) can occur after the first amplification cycle where there are unused capture probes on the substrate surface. In some embodiments, the free 3' OH end of the unused capture probes can be blocked by any suitable 3'OH blocking method. In some embodiments, the 3'OH can be blocked by hairpin ligation.

Isothermal nucleic acid amplification can be used in addition to, or as an alternative to standard PCR reactions (e.g., a PCR reaction that requires heating to about 95° C. to denature double stranded DNA). Isothermal nucleic acid amplification generally does not require the use of a thermocycler, however in some embodiments, isothermal amplification can be performed in a thermocycler. In some embodiments, isothermal amplification can be performed from about 35° C. to about 75° C. In some embodiments, isothermal amplification can be performed from about 40° C., about 45° C., about 50° C., about 55° C., about 60° C., about 65° C., or about 70° C. or anywhere in between depending on the polymerase and auxiliary enzymes used.

Isothermal nucleic acid amplification techniques are known in the art, and can be used alone or in combination with any of the spatial methods described herein. For example, non-limiting examples of suitable isothermal nucleic acid amplification techniques include transcription mediated amplification, nucleic acid sequence-based amplification, signal mediated amplification of RNA technology, strand displacement amplification, rolling circle amplification, loop-mediated isothermal amplification of DNA (LAMP), isothermal multiple displacement amplification, recombinase polymerase amplification, helicase-dependent amplification, single primer isothermal amplification, and circular helicase-dependent amplification (See, e.g., Gill and Ghaemi, Nucleic acid isothermal amplification technologies: a review, Nucleosides, Nucleotides, & Nucleic Acids, 27(3), 224-43, doi: 10.1080/15257770701845204 (2008), which is incorporated herein by reference in its entirety).

In some embodiments, the isothermal nucleic acid amplification is helicase-dependent nucleic acid amplification. Helicase-dependent isothermal nucleic acid amplification is described in Vincent et. al., 2004, Helicase-dependent isothermal DNA amplification, EMBO Rep., 795-800 and U.S. Pat. No. 7,282,328, which are both incorporated herein by reference in their entireties. Further, helicase-dependent nucleic acid amplification on a substrate (e.g., on-chip) is described in Andresen et. al., 2009, Helicase-dependent amplification: use in OnChip amplification and potential for point-of-care diagnostics, Expert Rev Mol Diagn. 9, 645-650, doi: 10.1586/erm.09.46, which is incorporated herein by reference in its entirety. In some embodiments, the isothermal nucleic acid amplification is recombinase polymerase nucleic acid amplification. Recombinase polymerase nucleic acid amplification is described in Piepenburg et al., 2006, DNA Detection Using Recombinant Proteins, PLoS Biol. 4, 7 e204 and Li et. al., 2019, Review: a comprehensive summary of a decade development of the recombinase polymerase amplification, Analyst 144, 31-67, doi: 10.1039/C8AN01621F (2019), both of which are incorporated herein by reference in their entireties.

Generally, isothermal amplification techniques use standard PCR reagents (e.g., buffer, dNTPs etc.) known in the art. Some isothermal amplification techniques can require additional reagents. For example, helicase dependent nucleic acid amplification uses a single-strand binding protein and an accessory protein. In another example, recombinase polymerase nucleic acid amplification uses recombinase (e.g., T4 UvsX), recombinase loading factor (e.g., TF UvsY), single-strand binding protein (e.g., T4 gp32), crowding agent (e.g., PEG-35K), and ATP.

After isothermal nucleic acid amplification of the full-length cDNA described by any of the methods herein, the isothermally amplified cDNAs (e.g., single-stranded or double-stranded) can be recovered from the substrate, and optionally followed by amplification with typical cDNA PCR in microcentrifuge tubes. The sample can then be used with any of the spatial methods described herein.

Immunohistochemistry and Immunofluorescence

In some embodiments, immunofluorescence or immunohistochemistry protocols (direct and indirect staining techniques) is performed as a part of, or in addition to, the exemplary spatial workflows presented herein. For example, tissue sections can be fixed according to methods described herein. The biological sample can be transferred to an array (e.g., capture probe array), where analytes (e.g., proteins) are probed using immunofluorescence protocols. For example, the sample can be rehydrated, blocked, and permeabilized (3×SSC, 2% BSA, 0.1% Triton X, 1 U/µl RNAse inhibitor for 10 min at 4° C.) before being stained with fluorescent primary antibodies (1:100 in 3×SSC, 2% BSA, 0.1% Triton X, 1 U/µl RNAse inhibitor for 30 min at 4° C.). The biological sample can be washed, coverslipped (in glycerol+1 U/µl RNAse inhibitor), imaged (e.g., using a confocal microscope or other apparatus capable of fluorescent detection), washed, and processed according to analyte capture or spatial workflows described herein.

As used herein, an "antigen retrieval buffer" can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases unspecific binding of the antibodies to the array and/or biological sample (decreases background). Some embodiments provide for blocking buffers/blocking solutions that can be applied before and/or during application of the label, where the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

In some embodiments, additional steps or optimizations can be included in performing IF/IHC protocols in conjunction with spatial arrays. Additional steps or optimizations can be included in performing spatially-tagged analyte capture agent workflows discussed herein.

In some embodiments, provided herein are methods for spatially detecting an analyte (e.g., detecting the location of an analyte, e.g., a biological analyte) from a biological sample (e.g., an analyte present in a biological sample, such as a tissue section) that include: (a) providing a biological sample on a substrate; (b) staining the biological sample on the substrate, imaging the stained biological sample, and selecting the biological sample or subsection of the biological sample (e.g., region of interest) to subject to analysis; (c) providing an array comprising one or more pluralities of capture probes on a substrate; (d) contacting the biological sample with the array, thereby allowing a capture probe of the one or more pluralities of capture probes to capture the analyte of interest; and (e) analyzing the captured analyte, thereby spatially detecting the analyte of interest. Any variety of staining and imaging techniques as described herein or known in the art can be used in accordance with methods described herein. In some embodiments, the staining includes optical labels as described herein, including, but not limited to, fluorescent, radioactive, chemiluminescent, calorimetric, or colorimetric detectable labels. In some embodiments, the staining includes a fluorescent antibody directed to a target analyte (e.g., cell surface or intracellular proteins) in the biological sample. In some embodiments, the staining includes an immunohistochemistry stain directed to a target analyte (e.g., cell surface or intracellular proteins) in the biological sample. In some embodiments, the staining includes a chemical stain such as hematoxylin and eosin (H&E) or periodic acid-schiff (PAS). In some embodiments, significant time (e.g., days, months, or years) can elapse between staining and/or imaging the biological sample and performing analysis. In some embodiments, reagents for performing analysis are added to the biological sample before, contemporaneously with, or after the array is contacted to the biological sample. In some embodiments, step (d) includes placing the array onto the biological sample. In some embodiments, the array is a flexible array where the plurality of spatially-barcoded features (e.g., a substrate with capture probes, a bead with capture probes) are attached to a flexible substrate. In some embodiments, measures are taken to slow down a reaction (e.g., cooling the temperature of the biological sample or using enzymes that preferentially perform their primary function at lower or higher temperature as compared to their optimal functional temperature) before the array is contacted with the biological sample. In some embodiments, step (e) is performed without bringing the biological sample out of contact with the array. In some embodiments, step (e) is performed after the biological sample is no longer in contact with the array. In some embodiments, the biological sample is tagged with an analyte capture agent before, contemporaneously with, or after staining and/or imaging of the biological sample. In such cases, significant time (e.g., days, months, or years) can elapse between staining and/or imaging and performing analysis. In some embodiments, the array is adapted to facilitate biological analyte migration from the stained and/or imaged biological sample onto the array (e.g., using any of the materials or methods described herein). In some embodiments, a biological sample is permeabilized before being contacted with an array. In some embodiments, the rate of permeabilization is slowed prior to contacting a biological sample with an array (e.g., to limit diffusion of analytes away from their original locations in the biological sample). In some embodiments, modulating the rate of permeabilization (e.g., modulating the activity of a permeabilization reagent) can occur by modulating a condition that the biological sample is exposed to (e.g., modulating temperature, pH, and/or light). In some embodiments, modulating the rate of permeabilization includes use of external stimuli (e.g., small molecules, enzymes, and/or activating reagents) to modulate the rate of permeabilization. For example, a permeabilization reagent can be provided to a biological sample prior to contact with an array, which permeabilization reagent is inactive until a condition (e.g., temperature, pH, and/or light) is changed or an external stimulus (e.g., a small molecule, an enzyme, and/or an activating reagent) is provided.

In some embodiments, provided herein are methods for spatially detecting an analyte (e.g., detecting the location of an analyte, e.g., a biological analyte) from a biological sample (e.g., present in a biological sample such as a tissue section) that include: (a) providing a biological sample on a substrate; (b) staining the biological sample on the substrate, imaging the stained biological sample, and selecting the biological sample or subsection of the biological sample (e.g., a region of interest) to subject to spatial transcriptomic analysis; (c) providing an array comprising one or more pluralities of capture probes on a substrate; (d) contacting the biological sample with the array, thereby allowing a capture probe of the one or more pluralities of capture probes to capture the biological analyte of interest; and (e) analyzing the captured biological analyte, thereby spatially detecting the biological analyte of interest.

(b) Capture Probes

A "capture probe," also interchangeably referred to herein as a "probe," refers to any molecule capable of capturing (directly or indirectly) and/or labelling an analyte (e.g., an analyte of interest in a sample. In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain.

Figure 6:
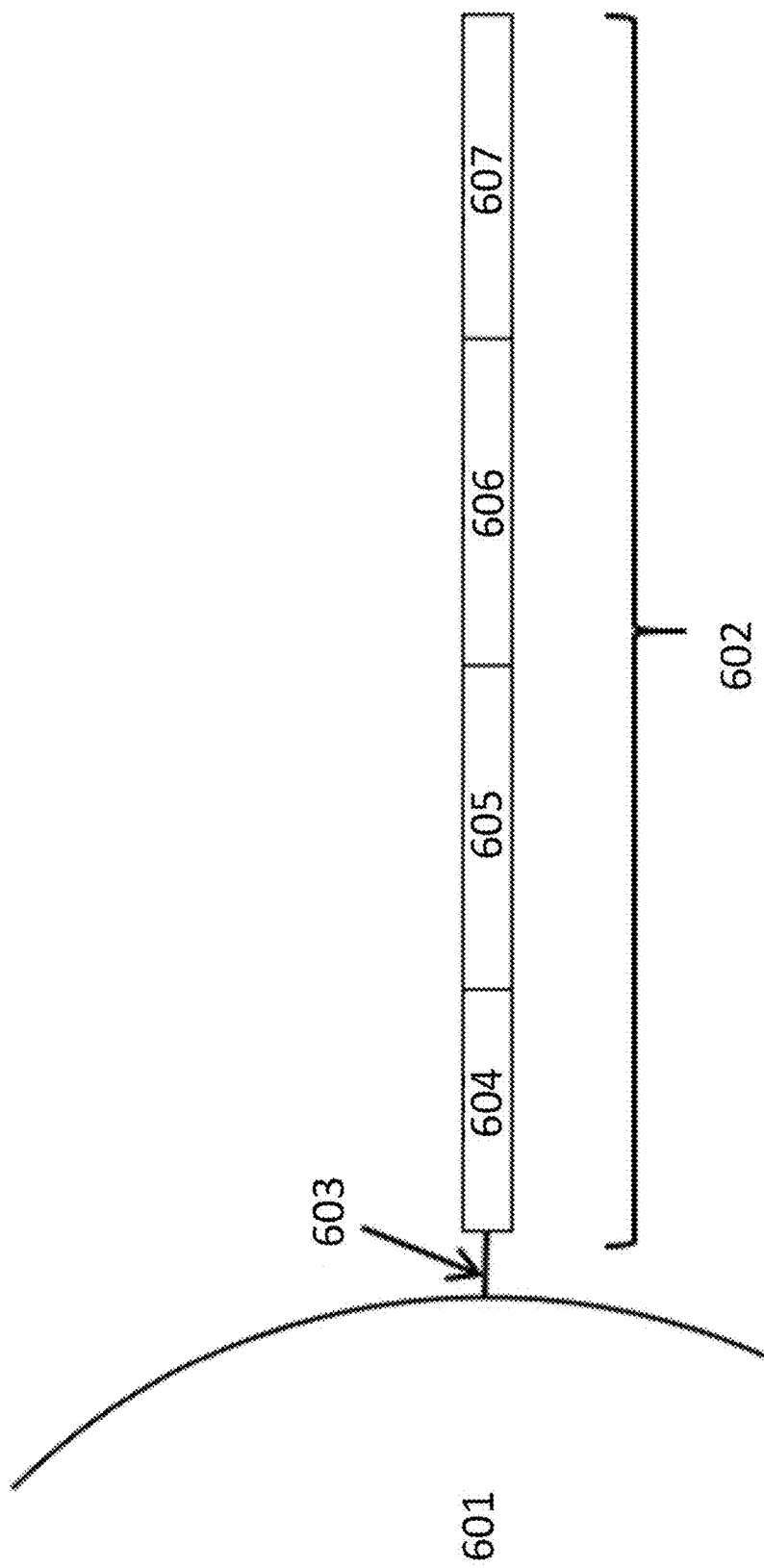
FIG. 6 is a schematic diagram showing an example of a barcoded capture probe, as described herein in accordance with an embodiment of the present disclosure.

FIG. 6 is a schematic diagram showing an example of a capture probe, as described herein. As shown, the capture probe 602 is optionally coupled to a capture spot 601 by a cleavage domain 603, such as a disulfide linker.

The capture probe 602 can include functional sequences that are useful for subsequent processing, such as functional sequence 604, which can include a sequencer specific flow cell attachment sequence, e.g., a P5 sequence, as well as functional sequence 606, which can include sequencing primer sequences, e.g., a R1 primer binding site, an R2 primer binding site. In some embodiments, sequence 604 is a P7 sequence and sequence 606 is a R2 primer binding site.

A spatial barcode 605 can be included within the capture probe for use in barcoding the target analyte. The functional sequences can be selected for compatibility with a variety of different sequencing systems, e.g., 454 Sequencing, Ion Torrent Proton or PGM, Illumina sequencing instrments, PacBio, Oxford Nanopute, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 605, functional sequences 604 (e.g., flow cell attachment sequence) and 606 (e.g., sequencing primer sequences) can be common to all of the probes attached to a given capture spot. The spatial barcode can also include a capture domain 607 to facilitate capture of a target analyte.

(i) Capture Domain

As discussed above, each capture probe includes at least one capture domain 607. The "capture domain" is an oligonucleotide, a polypeptide, a small molecule, or any combination thereof, that binds specifically to a desired analyte. In some embodiments, a capture domain can be used to capture or detect a desired analyte.

In some embodiments, the capture domain is a functional nucleic acid sequence configured to interact with one or more analytes, such as one or more different types of nucleic acids (e.g., RNA molecules and DNA molecules). In some embodiments, the functional nucleic acid sequence can include an N-mer sequence (e.g., a random N-mer sequence), which N-mer sequences are configured to interact with a plurality of DNA molecules. In some embodiments, the functional sequence can include a poly(T) sequence, which poly(T) sequences are configured to interact with messenger RNA (mRNA) molecules via the poly(A) tail of an mRNA transcript. In some embodiments, the functional nucleic acid sequence is the binding target of a protein (e.g., a transcription factor, a DNA binding protein, or a RNA binding protein), where the analyte of interest is a protein.

Capture probes can include ribonucleotides and/or deoxyribonucleotides as well as synthetic nucleotide residues that are capable of participating in Watson-Crick type or analogous base pair interactions. In some embodiments, the capture domain is capable of priming a reverse transcription reaction to generate cDNA that is complementary to the captured RNA molecules. In some embodiments, the capture domain of the capture probe can prime a DNA extension (polymerase) reaction to generate DNA that is complementary to the captured DNA molecules. In some embodiments, the capture domain can template a ligation reaction between the captured DNA molecules and a surface probe that is directly or indirectly immobilized on the substrate. In some embodiments, the capture domain can be ligated to one strand of the captured DNA molecules. For example, SplintR ligase along with RNA or DNA sequences (e.g., degenerate RNA) can be used to ligate a single stranded DNA or RNA to the capture domain. In some embodiments, ligases with RNA-templated ligase activity, e.g., SplintR ligase, T4 RNA ligase 2 or KOD ligase, can be used to ligate a single-stranded DNA or RNA to the capture domain. In some embodiments, a capture domain includes a splint oligonucleotide. In some embodiments, a capture domain captures a splint oligonucleotide.

In some embodiments, the capture domain is located at the 3' end of the capture probe and includes a free 3' end that can be extended, e.g., by template dependent polymerization, to form an extended capture probe as described herein. In some embodiments, the capture domain includes a nucleotide sequence that is capable of hybridizing to nucleic acid, e.g., RNA or other analyte, present in the cells of the tissue sample contacted with the array. In some embodiments, the capture domain can be selected or designed to bind selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, e.g., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly-U oligonucleotide or an oligonucleotide included of deoxythymidine analogues. In some embodiments, the capture domain includes at least 10, 11, 12, 13, 14, 15, 16, 17, 18, 19, or 20 nucleotides. In some embodiments, the capture domain includes at least 25, 30, or 35 nucleotides.

In some embodiments, a capture probe includes a capture domain having a sequence that is capable of binding to mRNA and/or genomic DNA. For example, the capture probe can include a capture domain that includes a nucleic acid sequence (e.g., a poly(T) sequence) capable of binding to a poly(A) tail of an mRNA and/or to a poly(A) homopolymeric sequence present in genomic DNA. In some embodiments, a homopolymeric sequence is added to an mRNA molecule or a genomic DNA molecule using a terminal transferase enzyme in order to produce an analyte that has a poly(A) or poly(T) sequence. For example, a poly(A) sequence can be added to an analyte (e.g., a fragment of genomic DNA) thereby making the analyte capable of capture by a poly(T) capture domain.

In some embodiments, random sequences, e.g., random hexamers or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" probe). This can, for example, be located 5' or 3' of the poly(T) sequence, e.g., at the 3' end of the capture domain. The poly(T)-random sequence probe can facilitate the capture of the mRNA poly(A) tail. In some embodiments, the capture domain can be an entirely random sequence. In some embodiments, degenerate capture domains can be used.

In some embodiments, a pool of two or more capture probes form a mixture, where the capture domain of one or more capture probes includes a poly(T) sequence and the capture domain of one or more capture probes includes random sequences. In some embodiments, a pool of two or more capture probes form a mixture where the capture domain of one or more capture probes includes poly(T)-like sequence and the capture domain of one or more capture probes includes random sequences. In some embodiments, a pool of two or more capture probes form a mixture where the capture domain of one or more capture probes includes a poly(T)-random sequences and the capture domain of one or more capture probes includes random sequences. In some embodiments, probes with degenerate capture domains can be added to any of the preceding combinations listed herein. In some embodiments, probes with degenerate capture domains can be substituted for one of the probes in each of the pairs described herein.

The capture domain can be based on a particular gene sequence or particular motif sequence or common/conserved sequence, that it is designed to capture (i.e., a sequence-specific capture domain). Thus, in some embodiments, the capture domain is capable of binding selectively to a desired sub-type or subset of nucleic acid, for example a particular type of RNA, such as mRNA, rRNA, tRNA, SRP RNA, tmRNA, snRNA, snoRNA, SmY RNA, scaRNA, gRNA, RNase P, RNase MRP, TERC, SL RNA, aRNA, cis-NAT, crRNA, lncRNA, miRNA, piRNA, siRNA, shRNA, tasiRNA, rasiRNA, 7SK, eRNA, ncRNA or other types of RNA. In a non-limiting example, the capture domain can be capable of binding selectively to a desired subset of ribonucleic acids, for example, microbiome RNA, such as 16S rRNA.

In some embodiments, a capture domain includes an "anchor" or "anchoring sequence", which is a sequence of nucleotides that is designed to ensure that the capture domain hybridizes to the intended biological analyte. In some embodiments, an anchor sequence includes a sequence of nucleotides, including a 1-mer, 2-mer, 3-mer or longer sequence. In some embodiments, the short sequence is random. For example, a capture domain including a poly(T) sequence can be designed to capture an mRNA. In such embodiments, an anchoring sequence can include a random 3-mer (e.g., GGG) that helps ensure that the poly(T) capture domain hybridizes to an mRNA. In some embodiments, an anchoring sequence can be VN, N, or NN. Alternatively, the sequence can be designed using a specific sequence of nucleotides. In some embodiments, the anchor sequence is at the 3' end of the capture domain. In some embodiments, the anchor sequence is at the 5' end of the capture domain.

In some embodiments, capture domains of capture probes are blocked prior to contacting the sample with the array, and blocking probes are used when the nucleic acid in the sample is modified prior to its capture on the array. In some embodiments, the blocking probe is used to block or modify the free 3' end of the capture domain. In some embodiments, blocking probes can be hybridized to the capture probes to mask the free 3' end of the capture domain, e.g., hairpin probes, partially double stranded probes or complementary sequences. In some embodiments, the free 3' end of the capture domain can be blocked by chemical modification, e.g., addition of an azidomethyl group as a chemically reversible capping moiety such that the capture probes do not include a free 3' end. Blocking or modifying the capture probes, particularly at the free 3' end of the capture domain, prior to contacting the sample with the array, prevents modification of the capture probes, e.g., prevents the addition of a poly(A) tail to the free 3' end of the capture probes.

Non-limiting examples of 3' modifications include dideoxy C-3' (3'-ddC), 3' inverted dT, 3' C3 spacer, 3'Amino, and 3' phosphorylation. In some embodiments, the nucleic acid in the sample can be modified such that it can be captured by the capture domain. For example, an adaptor sequence (including a binding domain capable of binding to the capture domain of the capture probe) can be added to the end of the nucleic acid, e.g., fragmented genomic DNA. In some embodiments, this is achieved by ligation of the adaptor sequence or extension of the nucleic acid. In some embodiments, an enzyme is used to incorporate additional nucleotides at the end of the nucleic acid sequence, e.g., a poly(A) tail. In some embodiments, the capture probes can be reversibly masked or modified such that the capture domain of the capture probe does not include a free 3' end. In some embodiments, the 3' end is removed, modified, or made inaccessible so that the capture domain is not susceptible to the process used to modify the nucleic acid of the sample, e.g., ligation or extension.

In some embodiments, the capture domain of the capture probe is modified to allow the removal of any modifications of the capture probe that occur during modification of the nucleic acid molecules of the sample. In some embodiments, the capture probes can include an additional sequence downstream of the capture domain, i.e., 3' to the capture domain, namely a blocking domain.

In some embodiments, the capture domain of the capture probe can be a non-nucleic acid domain. Examples of suitable capture domains that are not exclusively nucleic-acid based include, but are not limited to, proteins, peptides, aptamers, antigens, antibodies, and molecular analogs that mimic the functionality of any of the capture domains described herein.

(ii) Cleavage Domain

Each capture probe can optionally include at least one cleavage domain. The cleavage domain represents the portion of the probe that is used to reversibly attach the probe to an array capture spot, as will be described further below. Further, one or more segments or regions of the capture probe can optionally be released from the array capture spot by cleavage of the cleavage domain. As an example spatial barcodes and/or universal molecular identifiers (UMIs) can be released by cleavage of the cleavage domain.

Figure 7:
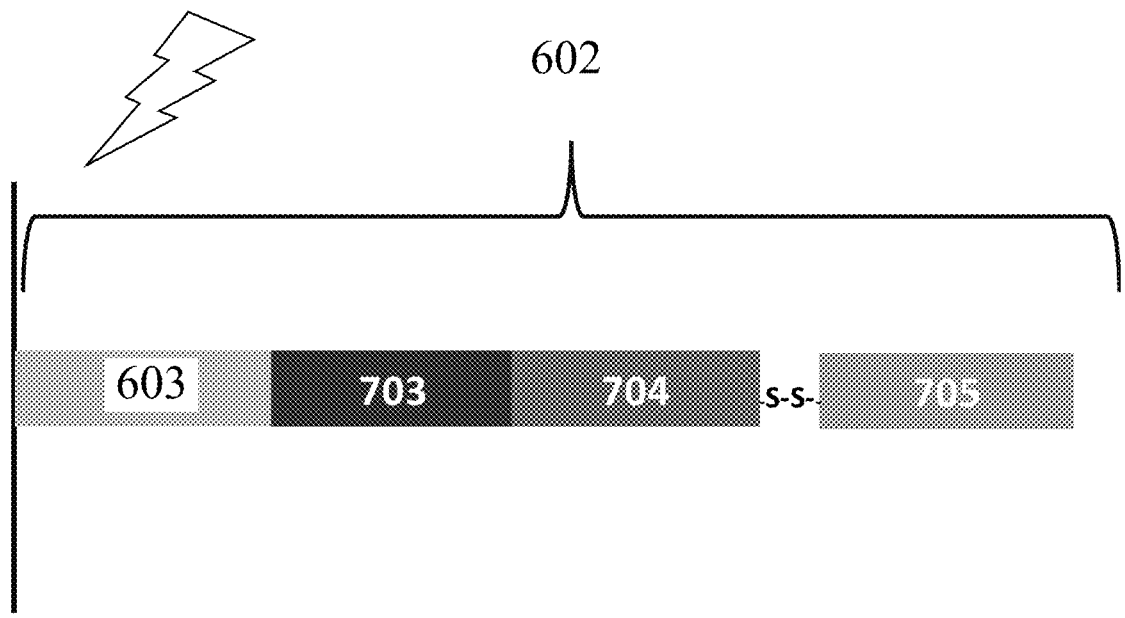
FIG. 7 is a schematic illustrating a cleavable capture probe in accordance with an embodiment of the present disclosure.

FIG. 7 is a schematic illustrating a cleavable capture probe, where the cleaved capture probe can enter into a non-permeabilized cell and bind to target analytes within the sample. The capture probe 602 contains a cleavage domain 603, a cell penetrating peptide 703, a reporter molecule 704, and a disulfide bond (—S—S—). 705 represents all other parts of a capture probe, for example a spatial barcode and a capture domain. The capture probe 1801 contains a cleavage domain 702, a cell penetrating peptide 703, a reporter molecule 704, and a disulfide bond (—S—S—). 705 represents all other parts of a capture probe, for example a spatial barcode and a capture domain.

In some embodiments, the cleavage domain 603 linking the capture probe to a capture spot is a covalent bond capable of cleavage by an enzyme. An enzyme can be added to cleave the cleavage domain 603, resulting in release of the capture probe from the capture spot. As another example, heating can also result in degradation of the cleavage domain and release of the attached capture probe from the array capture spot. In some embodiments, laser radiation is used to heat and degrade cleavage domains of capture probes at specific locations. In some embodiments, the cleavage domain is a photo-sensitive chemical bond (e.g., a chemical bond that dissociates when exposed to light such as ultraviolet light). In some embodiments, the cleavage domain can be an ultrasonic cleavage domain. For example, ultrasonic cleavage can depend on nucleotide sequence, length, pH, ionic strength, temperature, and the ultrasonic frequency (e.g., 22 kHz, 44 kHz) (Grokhovsky, 2006, Specificity of DNA cleavage by ultrasound, Molecular Biology, 40(2), 276-283).

Other examples of cleavage domains 603 include labile chemical bonds such as, but not limited to, ester linkages (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

In some embodiments, the cleavage domain includes a sequence that is recognized by one or more enzymes capable of cleaving a nucleic acid molecule, e.g., capable of breaking the phosphodiester linkage between two or more nucleotides. A bond can be cleavable via other nucleic acid molecule targeting enzymes, such as restriction enzymes (e.g., restriction endonucleases). For example, the cleavage domain can include a restriction endonuclease (restriction enzyme) recognition sequence. Restriction enzymes cut double-stranded or single stranded DNA at specific recognition nucleotide sequences known as restriction sites. In some embodiments, a rare-cutting restriction enzyme, i.e., enzymes with a long recognition site (at least 8 base pairs in length), is used to reduce the possibility of cleaving elsewhere in the capture probe.

Oligonucleotides with photo-sensitive chemical bonds (e.g., photo-cleavable linkers) have various advantages. They can be cleaved efficiently and rapidly (e.g., in nanoseconds and milliseconds). In some cases, photo-masks can be used such that only specific regions of the array are exposed to cleavable stimuli (e.g., exposure to UV light, exposure to light, exposure to heat induced by laser). When a photo-cleavable linker is used, the cleavable reaction is triggered by light, and can be highly selective to the linker and consequently biorthogonal. Typically, wavelength absorption for the photocleavable linker is located in the near-UV range of the spectrum. In some embodiments, $\lambda_{max}$ of the photocleavable linker is from about 300 nm to about 400 nm, or from about 310 nm to about 365 nm. In some embodiments, $\lambda_{max}$ of the photocleavable linker is about 300 nm, about 312 nm, about 325 nm, about 330 nm, about 340 nm, about 345 nm, about 355 nm, about 365 nm, or about 400 nm. Non-limiting examples of a photo-sensitive chemical bond that can be used in a cleavage domain are disclosed in PCT publication 202020176788A1 entitled "Profiling of biological analytes with spatially barcoded oligonucleotide arrays" the entire contents of which is incorporated herein by reference.

In some embodiments, the cleavage domain includes a poly-U sequence which can be cleaved by a mixture of Uracil DNA glycosylase (UDG) and the DNA glycosylase-lyase Endonuclease VIII, commercially known as the USER™ enzyme. Releasable capture probes can be available for reaction once released. Thus, for example, an activatable capture probe can be activated by releasing the capture probes from a capture spot.

In some embodiments, where the capture probe is attached indirectly to a substrate, e.g., via a surface probe, the cleavage domain includes one or more mismatch nucleotides, so that the complementary parts of the surface probe and the capture probe are not 100% complementary (for example, the number of mismatched base pairs can one, two, or three base pairs). Such a mismatch is recognized, e.g., by the MutY and T7 endonuclease I enzymes, which results in cleavage of the nucleic acid molecule at the position of the mismatch. As described herein a "surface probe" can be any moiety present on the surface of the substrate capable of attaching to an agent (e.g., a capture probe). In some embodiments, the surface probe is an oligonucleotide. In some embodiments, the surface probe is part of the capture probe.

In some embodiments, where the capture probe is attached to a capture spot indirectly (e.g., immobilized), e.g., via a surface probe, the cleavage domain includes a nickase recognition site or sequence. Nickases are endonucleases that cleave only a single strand of a DNA duplex. Thus, the cleavage domain can include a nickase recognition site close to the 5' end of the surface probe (and/or the 5' end of the capture probe) such that cleavage of the surface probe or capture probe destabilizes the duplex between the surface probe and capture probe thereby releasing the capture probe) from the capture spot.

Nickase enzymes can also be used in some embodiments where the capture probe is attached (e.g., immobilized) to the capture spot directly. For example, the substrate can be contacted with a nucleic acid molecule that hybridizes to the cleavage domain of the capture probe to provide or reconstitute a nickase recognition site, e.g., a cleavage helper probe. Thus, contact with a nickase enzyme will result in cleavage of the cleavage domain thereby releasing the capture probe from the capture spot. Such cleavage helper probes can also be used to provide or reconstitute cleavage recognition sites for other cleavage enzymes, e.g., restriction enzymes.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is incorporated herein by reference in its entirety. In general, any suitable nickase can be used to bind to a complementary nickase recognition site of a cleavage domain. Following use, the nickase enzyme can be removed from the assay or inactivated following release of the capture probes to prevent unwanted cleavage of the capture probes.

In some embodiments, a cleavage domain is absent from the capture probe. Examples of substrates with attached capture probes lacking a cleavage domain are described for example in Macosko et al., 2015 Cell 161, 1202-1214, the entire contents of which are incorporated herein by reference.

Examples of suitable capture domains that are not exclusively nucleic-acid based include, but are not limited to, proteins, peptides, aptamers, antigens, antibodies, and molecular analogs that mimic the functionality of any of the capture domains described herein.

In some embodiments, the region of the capture probe corresponding to the cleavage domain can be used for some other function. For example, an additional region for nucleic acid extension or amplification can be included where the cleavage domain would normally be positioned. In such embodiments, the region can supplement the functional domain or even exist as an additional functional domain. In some embodiments, the cleavage domain is present but its use is optional.

(iii) Functional Domain

Each capture probe can optionally include at least one functional domain. Each functional domain typically includes a functional nucleotide sequence for a downstream analytical step in the overall analysis procedure.

Further details of functional domains that can be used in conjunction with the present disclosure are described in U.S. patent application Ser. No. 16/992,569 entitled "Systems and Methods for Using the Spatial Distribution of Haplotypes to Determine a Biological Condition," filed Aug. 13, 2020, as well as PCT publication 202020176788A1 entitled "Profiling of biological analyes with spatially barcoded oligonucleotide arrays" each of which is hereby incorporated herein by reference.

(iv) Spatial Barcode

As discussed above, the capture probe can include one or more spatial barcodes (e.g., two or more, three or more, four or more, five or more) spatial barcodes. A "spatial barcode" is a contiguous nucleic acid segment or two or more non-contiguous nucleic acid segments that function as a label or identifier that conveys or is capable of conveying spatial information. In some embodiments, a capture probe includes a spatial barcode that possesses a spatial aspect, where the barcode is associated with a particular location within an array or a particular location on a substrate.

A spatial barcode can be part of an analyte, or independent from an analyte (e.g., part of the capture probe). A spatial barcode can be a tag attached to an analyte (e.g., a nucleic acid molecule) or a combination of a tag in addition to an endogenous characteristic of the analyte (e.g., size of the analyte or end sequence(s)). A spatial barcode can be unique.

In some embodiments where the spatial barcode is unique, the spatial barcode functions both as a spatial barcode and as a unique molecular identifier (UMI), associated with one particular capture probe.

Spatial barcodes can have a variety of different formats. For example, spatial barcodes can include polynucleotide spatial barcodes; random nucleic acid and/or amino acid sequences; and synthetic nucleic acid and/or amino acid sequences. In some embodiments, a spatial barcode is attached to an analyte in a reversible or irreversible manner. In some embodiments, a spatial barcode is added to, for example, a fragment of a DNA or RNA sample before, during, and/or after sequencing of the sample. In some embodiments, a spatial barcode allows for identification and/or quantification of individual sequencing-reads. In some embodiments, a spatial barcode is a used as a fluorescent barcode for which fluorescently labeled oligonucleotide probes hybridize to the spatial barcode.

In some embodiments, the spatial barcode is a nucleic acid sequence that does not substantially hybridize to analyte nucleic acid molecules in a sample. In some embodiments, the spatial barcode has less than 80% sequence identity (e.g., less than 70%, 60%, 50%, or less than 40% sequence identity) to the nucleic acid sequences across a substantial part (e.g., 80% or more) of the nucleic acid molecules in the sample.

The spatial barcode sequences can include from about 6 to about 20 or more nucleotides within the sequence of the capture probes. In some embodiments, the length of a spatial barcode sequence can be about 6, 7, 8, 9, 10, 11, 12, 13, 14, 15, 16, 17, 18, 19, 20 nucleotides or longer. In some embodiments, the length of a spatial barcode sequence can be at least about 6, 7, 8, 9, 10, 11, 12, 13, 14, 15, 16, 17, 18, 19, 20 nucleotides or longer. In some embodiments, the length of a spatial barcode sequence is at most about 6, 7, 8, 9, 10, 11, 12, 13, 14, 15, 16, 17, 18, 19, 20 nucleotides or shorter.

These nucleotides can be completely contiguous, i.e., in a single stretch of adjacent nucleotides, or they can be separated into two or more separate subsequences that are separated by 1 or more nucleotides. Separated spatial barcode subsequences can be from about 4 to about 16 nucleotides in length. In some embodiments, the spatial barcode subsequence can be about 4, 5, 6, 7, 8, 9, 10, 11, 12, 13, 14, 15, 16 nucleotides or longer. In some embodiments, the spatial barcode subsequence can be at least about 4, 5, 6, 7, 8, 9, 10, 11, 12, 13, 14, 15, 16 nucleotides or longer. In some embodiments, the spatial barcode subsequence can be at most about 4, 5, 6, 7, 8, 9, 10, 11, 12, 13, 14, 15, 16 nucleotides or shorter.

For multiple capture probes that are attached to a common array capture spot, the one or more spatial barcode sequences of the multiple capture probes can include sequences that are the same for all capture probes coupled to the capture spot, and/or sequences that are different across all capture probes coupled to the capture spot.

Figure 8:
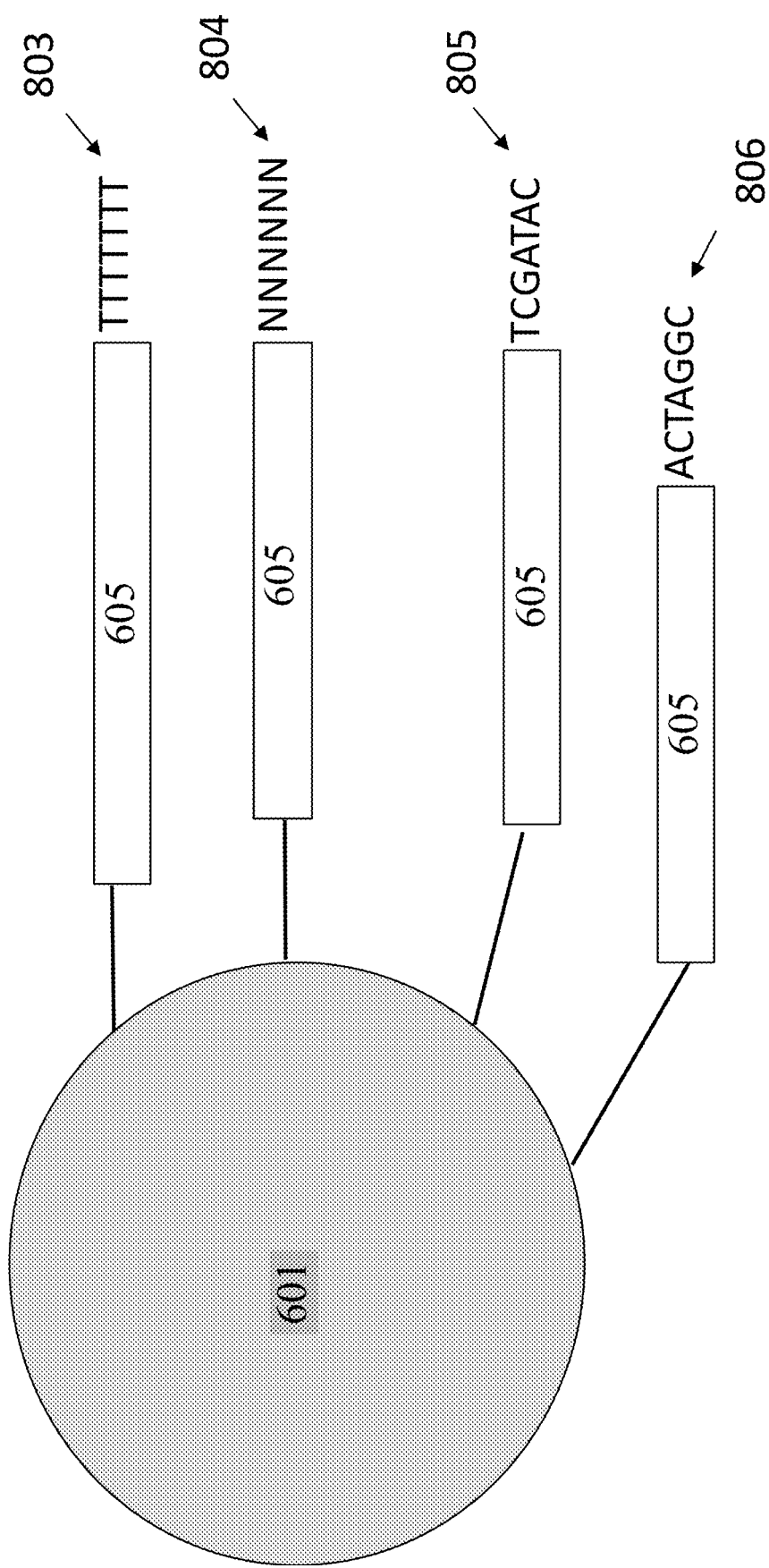
FIG. 8 is a schematic diagram of an exemplary multiplexed spatially-labelled capture spot in accordance with an embodiment of the present disclosure.

FIG. 8 is a schematic diagram of an exemplary multiplexed spatially-labelled capture spot. In FIG. 8, the capture spot 601 can be coupled to spatially-barcoded capture probes, where the spatially-barcoded probes of a particular capture spot can possess the same spatial barcode, but have different capture domains designed to associate the spatial barcode of the capture spot with more than one target analyte. For example, a capture spot may be coupled to four different types of spatially-barcoded capture probes, each type of spatially-barcoded capture probe possessing the spatial barcode 605. One type of capture probe associated with the capture spot includes the spatial barcode 605 in combination with a poly(T) capture domain 803, designed to capture mRNA target analytes. A second type of capture probe associated with the capture spot includes the spatial barcode 605 in combination with a random N-mer capture domain 804 for gDNA analysis. A third type of capture probe associated with the capture spot includes the spatial barcode 605 in combination with a capture domain complementary to the capture domain on an analyte capture agent 805. A fourth type of capture probe associated with the capture spot includes the spatial barcode 605 in combination with a capture probe that can specifically bind a nucleic acid molecule 806 that can function in a CRISPR assay (e.g., CRISPR/Cas9). While only four different capture probe-barcoded constructs are shown in FIG. 8, capture-probe barcoded constructs can be tailored for analyses of any given analyte associated with a nucleic acid and capable of binding with such a construct. For example, the schemes shown in FIG. 8 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MEW multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents.

Capture probes attached to a single array capture spot can include identical (or common) spatial barcode sequences, different spatial barcode sequences, or a combination of both. Capture probes attached to a capture spot can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

(v) Unique Molecular Identifier

The capture probe can include one or more (e.g., two or more, three or more, four or more, five or more) Unique Molecular Identifiers (UMIs). A unique molecular identifier is a contiguous nucleic acid segment or two or more non-contiguous nucleic acid segments that function as a label or identifier for a particular analyte, or for a capture probe that binds a particular analyte (e.g., via the capture domain).

Further details of UMIs that can be used with the systems and methods of the present disclosure are described in U.S. patent application Ser. No. 16/992,569 entitled "Systems and Methods for Using the Spatial Distribution of Haplotypes to Determine a Biological Condition," filed Aug. 13, 2020, and PCT publication 202020176788A1 entitled "Profiling of biological analyes with spatially barcoded oligonucleotide arrays," each of which is hereby incorporated herein by reference. (vi) Other aspects of capture probes.

For capture probes that are attached to an array capture spot, an individual array capture spot can include one or more capture probes. In some embodiments, an individual array capture spot includes hundreds or thousands of capture probes. In some embodiments, the capture probes are associated with a particular individual capture spot, where the individual capture spot contains a capture probe including a spatial barcode unique to a defined region or location on the array.

In some embodiments, a particular capture spot contains capture probes including more than one spatial barcode (e.g., one capture probe at a particular capture spot can include a spatial barcode that is different than the spatial barcode included in another capture probe at the same particular capture spot, while both capture probes include a second, common spatial barcode), where each spatial barcode corresponds to a particular defined region or location on the array. For example, multiple spatial barcode sequences associated with one particular capture spot on an array can provide a stronger address or attribution to a given location by providing duplicate or independent confirmation of the location. In some embodiments, the multiple spatial barcodes represent increasing specificity of the location of the particular array point. In a non-limiting example, a particular array point can be coded with two different spatial barcodes, where each spatial barcode identifies a particular defined region within the array, and an array point possessing both spatial barcodes identifies the sub-region where two defined regions overlap, e.g., such as the overlapping portion of a Venn diagram.

In another non-limiting example, a particular array point can be coded with three different spatial barcodes, where the first spatial barcode identifies a first region within the array, the second spatial barcode identifies a second region, where the second region is a subregion entirely within the first region, and the third spatial barcode identifies a third region, where the third region is a subregion entirely within the first and second subregions.

In some embodiments, capture probes attached to array capture spots are released from the array capture spots for sequencing. Alternatively, in some embodiments, capture probes remain attached to the array capture spots, and the probes are sequenced while remaining attached to the array capture spots (e.g., via in-situ sequencing). Further aspects of the sequencing of capture probes are described in subsequent sections of this disclosure.

In some embodiments, an array capture spot can include different types of capture probes attached to the capture spot. For example, the array capture spot can include a first type of capture probe with a capture domain designed to bind to one type of analyte, and a second type of capture probe with a capture domain designed to bind to a second type of analyte. In general, array capture spots can include one or more (e.g., two or more, three or more, four or more, five or more, six or more, eight or more, ten or more, 12 or more, 15 or more, 20 or more, 30 or more, 50 or more) different types of capture probes attached to a single array capture spot.

In some embodiments, the capture probe is nucleic acid. In some embodiments, the capture probe is attached to the array capture spot via its 5' end. In some embodiments, the capture probe includes from the 5' to 3' end: one or more barcodes (e.g., a spatial barcode and/or a UMI) and one or more capture domains. In some embodiments, the capture probe includes from the 5' to 3' end: one barcode (e.g., a spatial barcode or a UMI) and one capture domain. In some embodiments, the capture probe includes from the 5' to 3' end: a cleavage domain, a functional domain, one or more barcodes (e.g., a spatial barcode and/or a UMI), and a capture domain. In some embodiments, the capture probe includes from the 5' to 3' end: a cleavage domain, a functional domain, one or more barcodes (e.g., a spatial barcode and/or a UMI), a second functional domain, and a capture domain. In some embodiments, the capture probe includes from the 5' to 3' end: a cleavage domain, a functional domain, a spatial barcode, a UMI, and a capture domain. In some embodiments, the capture probe does not include a spatial barcode. In some embodiments, the capture probe does not include a UMI. In some embodiments, the capture probe includes a sequence for initiating a sequencing reaction.

In some embodiments, the capture probe is immobilized on a capture spot via its 3' end. In some embodiments, the capture probe includes from the 3' to 5' end: one or more barcodes (e.g., a spatial barcode and/or a UMI) and one or more capture domains. In some embodiments, the capture probe includes from the 3' to 5' end: one barcode (e.g., a spatial barcode or a UMI) and one capture domain. In some embodiments, the capture probe includes from the 3' to 5' end: a cleavage domain, a functional domain, one or more barcodes (e.g., a spatial barcode and/or a UMI), and a capture domain. In some embodiments, the capture probe includes from the 3' to 5' end: a cleavage domain, a functional domain, a spatial barcode, a UMI, and a capture domain.

In some embodiments, a capture probe includes an in situ synthesized oligonucleotide. The in situ synthesized oligonucleotide can be attached to a substrate, or to a feature on a substrate. In some embodiments, the in situ synthesized oligonucleotide includes one or more constant sequences, one or more of which serves as a priming sequence (e.g., a primer for amplifying target nucleic acids). The in situ synthesized oligonucleotide can, for example, include a constant sequence at the 3' end that is attached to a substrate, or attached to a feature on the substrate. Additionally or alternatively, the in situ synthesized oligonucleotide can include a constant sequence at the free 5' end. In some embodiments, the one or more constant sequences can be a cleavable sequence. In some embodiments, the in situ synthesized oligonucleotide includes a barcode sequence, e.g., a variable barcode sequence. The barcode can be any of the barcodes described herein. The length of the barcode can be approximately 8 to 16 nucleotides (e.g., 8, 9, 10, 11, 12, 13, 14, 15, or 16 nucleotides). The length of the in situ synthesized oligonucleotide can be less than 100 nucleotides (e.g., less than 90, 80, 75, 70, 60, 50, 45, 40, 35, 30, 25 or 20 nucleotides). In some instances, the length of the in situ synthesized oligonucleotide is about 20 to about 40 nucleotides. Exemplary in situ synthesized oligonucleotides are produced by Affymetrix. In some embodiments, the in situ synthesized oligonucleotide is attached to a capture spot of an array.

Additional oligonucleotides can be ligated to an in situ synthesized oligonucleotide to generate a capture probe. For example, a primer complementary to a portion of the in situ synthesized oligonucleotide (e.g., a constant sequence in the oligonucleotide) can be used to hybridize an additional oligonucleotide and extend (using the in situ synthesized oligonucleotide as a template e.g., a primer extension reaction) to form a double stranded oligonucleotide and to further create a 3' overhang. In some embodiments, the 3' overhang can be created by template-independent ligases (e.g., terminal deoxynucleotidyl transferase (TdT) or poly (A) polymerase). An additional oligonucleotide comprising one or more capture domains can be ligated to the 3' overhang using a suitable enzyme (e.g., a ligase) and a splint oligonucleotide, to generate a capture probe. Thus, in some embodiments, a capture probe is a product of two or more oligonucleotide sequences, (e.g., the in situ synthesized oligonucleotide and the additional oligonucleotide) that are ligated together. In some embodiments, one of the oligonucleotide sequences is an in situ synthesized oligonucleotide.

In some embodiments, the capture probe includes a splint oligonucleotide. Two or more oligonucleotides can be ligated together using a splint oligonucleotide and any variety of ligases known in the art or described herein (e.g., SplintR ligase).

In some embodiments, one of the oligonucleotides includes: a constant sequence (e.g., a sequence complementary to a portion of a splint oligonucleotide), a degenerate sequence, and a capture domain (e.g., as described herein). In some embodiments, the capture probe is generated by having an enzyme add polynucleotides at the end of an oligonucleotide sequence. The capture probe can include a degenerate sequence, which can function as a unique molecular identifier.

A capture probe can include a degenerate sequence, which is a sequence in which some positions of a nucleotide sequence contain a number of possible bases. A degenerate sequence can be a degenerate nucleotide sequence including about or at least 5, 6, 7, 8, 9, 10, 11, 12, 13, 14, 15, 16, 17, 18, 19, 20, 25, 30, 35, 40, 45, or 50 nucleotides. In some embodiments, a nucleotide sequence contains 1, 2, 3, 4, 5, 6, 7, 8, 9, 0, 10, 15, 20, 25, or more degenerate positions within the nucleotide sequence. In some embodiments, the degenerate sequence is used as a UMI.

In some embodiments, a capture probe includes a restriction endonuclease recognition sequence or a sequence of nucleotides cleavable by specific enzyme activities. For example, uracil sequences can be enzymatically cleaved from a nucleotide sequence using uracil DNA glycosylase (UDG) or Uracil Specific Excision Reagent (USER). As another example, other modified bases (e.g., modified by methylation) can be recognized and cleaved by specific endonucleases. The capture probes can be subjected to an enzymatic cleavage, which removes the blocking domain and any of the additional nucleotides that are added to the 3' end of the capture probe during the modification process. The removal of the blocking domain reveals and/or restores the free 3' end of the capture domain of the capture probe. In some embodiments, additional nucleotides can be removed to reveal and/or restore the 3' end of the capture domain of the capture probe.

In some embodiments, a blocking domain can be incorporated into the capture probe when it is synthesized, or after its synthesis. The terminal nucleotide of the capture domain is a reversible terminator nucleotide (e.g., 3'-O-blocked reversible terminator and 3'-unblocked reversible terminator), and can be included in the capture probe during or after probe synthesis.

(vii) Extended Capture Probes

An "extended capture probe" is a capture probe with an enlarged nucleic acid sequence. For example, where the capture probe includes nucleic acid, an "extended 3' end" indicates that further nucleotides were added to the most 3' nucleotide of the capture probe to extend the length of the capture probe, for example, by standard polymerization reactions utilized to extend nucleic acid molecules including templated polymerization catalyzed by a polymerase (e.g., a DNA polymerase or reverse transcriptase).

In some embodiments, extending the capture probe includes generating cDNA from the captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending the capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, the capture domain of the capture probe includes a primer for producing the complementary strand of the nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA, e.g., cDNA, molecule is generated. In some embodiments, a "full-length" DNA molecule refers to the whole of the captured nucleic acid molecule. However, if the nucleic acid, e.g., RNA, was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Lucigen, Middleton, Wis.). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended capture probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Lucigen, Middleton, Wis.), and SplintR (available from New England Biolabs, Ipswich, Mass.). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to an array feature specific for the affinity group. In some embodiments, the substrate can include an antibody or antibody fragment. In some embodiments, the array feature includes avidin or streptavidin and the affinity group includes biotin. In some embodiments, the array feature includes maltose and the affinity group includes maltose-binding protein. In some embodiments, the array feature includes maltose-binding protein and the affinity group includes maltose. In some embodiments, amplifying the extended capture probes can function to release the extended probes from the array feature, insofar as copies of the extended probes are not attached to the array feature.

In some embodiments, the extended capture probe or complement or amplicon thereof is released from an array feature. The step of releasing the extended capture probe or complement or amplicon thereof from an array feature can be achieved in a number of ways. In some embodiments, an extended capture probe or a complement thereof is released from the feature by nucleic acid cleavage and/or by denaturation (e.g., by heating to denature a double-stranded molecule).

In some embodiments, the extended capture probe or complement or amplicon thereof is released from the array feature by physical means. For example, methods for inducing physical release include denaturing double stranded nucleic acid molecules. Another method for releasing the extended capture probes is to use a solution that interferes with the hydrogen bonds of the double stranded molecules. In some embodiments, the extended capture probe is released by applying heated water such as water or buffer of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the array feature. In some embodiments, a formamide solution can be used to destabilize the interaction between nucleic acid molecules to release the extended capture probe from the array feature.

(viii) Amplification of Capture Probes

In some embodiments, methods are provided herein for amplifying a capture probe affixed to a spatial array, where amplification of the capture probe increases the number of capture domains and spatial barcodes on the spatial array. In some embodiments where a capture probe is amplified, the amplification is performed by rolling circle amplification. In some embodiments, the capture probe to be amplified includes sequences (e.g., docking sequences, functional sequences, and/or primer sequences) that enable rolling circle amplification. In one example, the capture probe can include a functional sequence that is capable of binding to a primer used for amplification. In another example, the capture probe can include one or more docking sequences (e.g., a first docking sequence and a second docking sequence) that can hybridize to one or more oligonucleotides (e.g., a padlock probe(s)) used for rolling circle amplification. In some embodiments, additional probes are affixed to the substrate, where the additional probes include sequences (e.g., a docking sequence(s), a functional sequence(s), and/or a primer sequence(s)) that enable rolling circle amplification. In some embodiments, the spatial array is contacted with an oligonucleotide (e.g., a padlock probe). As used herein, a "padlock probe" refers to an oligonucleotide that has, at its 5' and 3' ends, sequences that are complementary to adjacent or nearby target sequences (e.g., docking sequences) on a capture probe. Upon hybridization to the target sequences (e.g., docking sequences), the two ends of the padlock probe are either brought into contact or an end is extended until the two ends are brought into contact, allowing circularization of the padlock probe by ligation (e.g., ligation using any of the methods described herein). In some embodiments, after circularization of the oligonucleotide, rolling circle amplification can be used to amplify the ligation product, which includes at least a capture domain and a spatial barcode from the capture probe. In some embodiments, amplification of the capture probe using a padlock oligonucleotide and rolling circle amplification increases the number of capture domains and the number of spatial barcodes on the spatial array.

In some embodiments, a method of increasing capture efficiency of a spatial array includes amplifying all or part of a capture probe affixed to a substrate. For example, amplification of all or part of the capture probes affixed to the substrate can increase the capture efficiency of the spatial array by increasing the number of capture domains and spatial barcodes. In some embodiments, a method of determining a location of an analyte in a biological sample includes using a spatial array having increased capture efficiency (e.g., a spatial array where a capture probe has been amplified as described herein). For example, the capture efficiency of a spatial array can be increased by amplification of all or part of the capture probe prior to contact with a biological sample. The amplification results in an increased number of capture domains that enable capture of more analytes as compared to a spatial array where the capture probe was not amplified prior to contacting the biological sample. In some embodiments, a method of producing a spatial array that has increased capture efficiency includes amplifying all or part of a capture probe. In some embodiments where a spatial array having increased capture efficiency is produced by amplifying all or part of a capture probe, the amplification increases the number of capture domains and the number of spatial barcodes on the spatial array. In some embodiments, a method of determining the location of a capture probe (e.g., a capture probe on a feature) on a spatial array includes amplifying all or part of a capture probe. For example, amplification of the capture probe affixed to the substrate can increase the number of spatial barcodes used for direct decoding (e.g., direct decoding using any of the methods described herein including, without limitation, in situ sequencing) of the location of the capture probe.

(ix) Analyte Capture Agents

This disclosure also provides methods and materials for using analyte capture agents for spatial profiling of biological analytes (e.g., mRNA, genomic DNA, accessible chromatin, and cell surface or intracellular proteins and/or metabolites). As used herein, an "analyte capture agent" (also referred to previously at times as a "cell labelling" agent") refers to an agent that interacts with an analyte (e.g., an analyte in a sample) and with a capture probe (e.g., a capture probe attached to a substrate) to identify the analyte. In some embodiments, the analyte capture agent includes an analyte binding moiety and a capture agent barcode domain.

FIG. 37 is a schematic diagram of an exemplary analyte capture agent 4002 for capturing analytes. The analyte capture agent comprises an analyte binding moiety 4004 and a capture agent barcode domain 4008. An analyte binding moiety 4004 is a molecule capable of binding to an analyte 4006 and interacting with a spatially-barcoded capture probe. The analyte binding moiety can bind to the analyte 4006 with high affinity and/or with high specificity. The analyte capture 4002 agent can include a capture agent barcode domain 4008, a nucleotide sequence (e.g., an oligonucleotide), which can hybridize to at least a portion or an entirety of a capture domain of a capture probe. The analyte binding moiety 4004 can include a polypeptide and/or an aptamer (e.g., an oligonucleotide or peptide molecule that binds to a specific target analyte). The analyte binding moiety 4004 can include an antibody or antibody fragment (e.g., an antigen-binding fragment).

As used herein, the term "analyte binding moiety" refers to a molecule or moiety capable of binding to a macromolecular constituent (e.g., an analyte such as a biological analyte). In some embodiments of any of the spatial profiling methods described herein, the analyte binding moiety 4004 of the analyte capture agent 4002 that binds to a biological analyte 4006 can include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a probody, an aptamer, a monobody, an affimer, a darpin, and a protein scaffold, or any combination thereof. The analyte binding moiety 4004 can bind to the macromolecular constituent (e.g., analyte) with high affinity and/or with high specificity. The analyte binding moiety 4004 can include a nucleotide sequence (e.g., an oligonucleotide), which can correspond to at least a portion or an entirety of the analyte binding moiety. The analyte binding moiety 4004 can include a polypeptide and/or an aptamer (e.g., a polypeptide and/or an aptamer that binds to a specific target molecule, e.g., an analyte). The analyte binding moiety 4004 can include an antibody or antibody fragment (e.g., an antigen-binding fragment) that binds to a specific analyte (e.g., a polypeptide).

In some embodiments, an analyte binding moiety 4004 of an analyte capture agent 4002 includes one or more antibodies or antigen binding fragments thereof. The antibodies or antigen binding fragments including the analyte binding moiety 4004 can specifically bind to a target analyte. In some embodiments, the analyte 4006 is a protein (e.g., a protein on a surface of the biological sample, such as a cell, or an intracellular protein). In some embodiments, a plurality of analyte capture agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte capture agents are the same. In some embodiments in which the plurality of analytes includes a single species of analyte, the analyte binding moieties of the plurality of analyte capture agents are the different (e.g., members of the plurality of analyte capture agents can have two or more species of analyte binding moieties, where each of the two or more species of analyte binding moieties binds a single species of analyte, e.g., at different binding sites). In some embodiments, the plurality of analytes includes multiple different species of analyte (e.g., multiple different species of polypeptides).

An analyte capture agent 4002 can include an analyte binding moiety 4004. The analyte binding moiety 4004 can be an antibody. Exemplary, non-limiting antibodies that can be used as analyte binding moieties 4004 in an analyte capture agent 4002 or that can be used in the applications disclosed herein include any of the following including variations thereof: A-ACT, A-AT, ACTH, Actin-Muscle-specific, Actin-Smooth Muscle (SMA), AE1, AE1/AE3, AE3, AFP, AKT Phosphate, ALK-1, Amyloid A, Androgen Receptor, Annexin A1, B72.3, BCA-225, BCL-1 (Cyclin D1), BCL-1/CD20, BCL-2, BCL-2/BCL-6, BCL-6, Ber-EP4, Beta-amyloid, Beta-catenin, BG8 (Lewis Y), BOB-1, CA 19.9, CA 125, CAIX, Calcitonin, Caldesmon, Calponin, Calretinin, CAM 5.2, CAM 5.2/AE1, CD1a, CD2, CD3 (M), CD3 (P), CD3/CD20, CD4, CD5, CD7, CD8, CD10, CD14, CD15, CD20, CD21, CD22, CD23, CD25, CD30, CD31, CD33, CD34, CD35, CD43, CD45 (LCA), CD45RA, CD56, CD57, CD61, CD68, CD71, CD74, CD79a, CD99, CD117 (c-KIT), CD123, CD138, CD163, CDX-2, CDX-2/CK-7, CEA (M), CEA (P), Chromogranin A, Chymotrypsin, CK-5, CK-5/6, CK-7, CK-7/TTF-1, CK-14, CK-17, CK-18, CK-19, CK-20, CK-HMW, CK-LMW, COLL-IV, COX-2, D2-40, DBA44, Desmin, DOG1, EBER-ISH, EBV (LMP1), E-Cadherin, EGFR, EMA, ER, ERCC1, Factor VIII (vWF), Factor XIIIa, Fascin, FLI-1, FHS, Galectin-3, Gastrin, GCDFP-15, GFAP, Glucagon, Glycophorin A, Glypican-3, Granzyme B, Growth Hormone (GH), GST, HAM 56, HMBE-1, HBP, HCAg, HCG, Hemoglobin A, HEP B CORE (HBcAg), HEP B SURF, (HBsAg), HepPar1, HER2, Herpes I, Herpes II, HHV-8, HLA-DR, HMB 45, HPL, HPV-IHC, HPV (6/11)-ISH, HPV (16/18)-ISH, HPV (31/33)-ISH, HPV WSS-ISH, HPV High-ISH, HPV Low-ISH, HPV High & Low-ISH, IgA, IgD, IgG, IgG4, IgM, Inhibin, Insulin, JC Virus-ISH, Kappa-ISH, KER PAN, Ki-67, Lambda-IHC, Lambda-ISH, LH, Lipase, Lysozyme (MURA), Mammaglobin, MART-1, MBP, M-Cell Tryptase, MEL-5, Melan-A, Melan-A/Ki-67, Mesothelin, MiTF, MLH-1, MOC-31, MPO, MSH-2, MSH-6, MUC1, MUC2, MUC4, MUC5AC, MUM-1, MYO D1, Myogenin, Myoglobin, Myoin Heavy Chain, Napsin A, NB84a, NEW-N, NF, NK1-C3, NPM, NSE, OCT-2, OCT-3/4, OSCAR, p16, p21, p27/Kip1, p53, p57, p63, p120, P504S, Pan Melanoma, PANC.POLY, Parvovirus B19, PAX-2, PAX-5, PAX-5/CD43, PAX=5/CD5, PAX-8, PC, PD1, Perforin, PGP 9.5, PLAP, PMS-2, PR, Prolactin, PSA, PSAP, PSMA, PTEN, PTH, PTS, RB, RCC, S6, S100, Serotonin, Somatostatin, Surfactant (SP-A), Synaptophysin, Synuclein, TAU, TCL-1, TCR beta, TdT, Thrombomodulin, Thyroglobulin, TIA-1, TOXO, TRAP, TriView™ breast, TriView™ prostate, Trypsin, TS, TSH, TTF-1, Tyrosinase, Ubiqutin, Uroplakin, VEGF, Villin, Vimentin (VIM), VIP, VZV, WT1 (M)N-Terminus, WT1 (P)C-Terminus, and ZAP-70.

Further, exemplary, non-limiting antibodies that can be used as analyte binding moieties 4004 in an analyte capture agent 4002 or that can be used in the applications disclosed herein include any of the following antibodies (and variations thereof) to: cell surface proteins, intracellular proteins, kinases (e.g., AGC kinase family such as AKT1, AKT2, PDK1, Protein Kinase C, ROCK1, ROCK2, SGK3), CAMK kinase family (e.g., AMPK1, AMPK2, CAMK, Chk1, Chk2, Zip), CK1 kinase family, TK kinase family (e.g., Ab12, AXL, CD167, CD246/ALK, c-Met, CSK, c-Src, EGFR, ErbB2 (HER2/neu), ErbB3, ErbB4, FAK, Fyn, LCK, Lyn, PKT7, Syk, Zap70), STE kinase family (e.g., ASK1, MAPK, MEK1, MEK2, MEK3 MEK4, MEK5, PAK1, PAK2, PAK4, PAK6), CMGC kinase family (e.g., Cdk2, Cdk4, Cdk5, Cdk6, Cdk7, Cdk9, Erk1, GSK3, Jnk/MAPK8, Jnk2/MAPK9, JNK3/MAPK10, p38/MAPK), and TKL kinase family (e.g., ALK1, ILK1, IRAK1, IRAK2, IRAK3, IRAK4, LIMK1, LIMK2, M3K11, RAF1, RIP1, RIP3, VEGFR1, VEGFR2, VEGFR3), Aurora A kinase, Aurora B kinase, IKK, Nemo-like kinase, PINK, PLK3, ULK2, WEE1, transcription factors (e.g., FOXP3, ATF3, BACH1, EGR, ELF3, FOXA1, FOXA2, FOX01, GATA), growth factor receptors, and tumor suppressors (e.g., anti-p53, anti-BLM, anti-Cdk2, anti-Chk2, anti-BRCA-1, anti-NBS1, anti-BRCA-2, anti-WRN, anti-PTEN, anti-WT1, anti-p38).

In some embodiments, analyte capture agents 4002 are capable of binding to analytes 4006 present inside a cell. In some embodiments, analyte capture agents are capable of binding to cell surface analytes that can include, without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents 4002 are capable of binding to cell surface analytes that are post-translationally modified. In such embodiments, analyte capture agents can be specific for cell surface analytes based on a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some embodiments, the analyte capture agent 4002 includes a capture agent barcode domain 4008 that is conjugated or otherwise attached to the analyte binding moiety. In some embodiments, the capture agent barcode domain 4008 is covalently-linked to the analyte binding moiety 4004. In some embodiments, a capture agent barcode domain 4008 is a nucleic acid sequence. In some embodiments, a capture agent barcode domain 4008 includes, or is covalently bound to, an analyte binding moiety barcode and an analyte capture sequence 4114.

As used herein, the term "analyte binding moiety barcode" refers to a barcode that is associated with or otherwise identifies the analyte binding moiety 4004. In some embodiments, by identifying an analyte binding moiety 4004 and its associated analyte binding moiety barcode, the analyte 4006 to which the analyte binding moiety binds 4004 can also be identified. An analyte binding moiety barcode can be a nucleic acid sequence of a given length and/or sequence that is associated with the analyte binding moiety 4004. An analyte binding moiety barcode can generally include any of the variety of aspects of barcodes described herein. For example, an analyte capture agent 4002 that is specific to one type of analyte can have coupled thereto a first capture agent barcode domain (e.g., that includes a first analyte binding moiety barcode), while an analyte capture agent that is specific to a different analyte can have a different capture agent barcode domain (e.g., that includes a second barcode analyte binding moiety barcode) coupled thereto. In some aspects, such a capture agent barcode domain can include an analyte binding moiety barcode that permits identification of the analyte binding moiety 4004 to which the capture agent barcode domain is coupled. The selection of the capture agent barcode domain 4008 can allow significant diversity in terms of sequence, while also being readily attachable to most analyte binding moieties (e.g., antibodies or aptamers) as well as being readily detected, (e.g., using sequencing or array technologies).

In some embodiments, the capture agent barcode domain of an analyte capture agent 4002 includes an analyte capture sequence. As used herein, the term "analyte capture sequence" refers to a region or moiety configured to hybridize to, bind to, couple to, or otherwise interact with a capture domain of a capture probe. In some embodiments, an analyte capture sequence includes a nucleic acid sequence that is complementary to or substantially complementary to the capture domain of a capture probe such that the analyte capture sequence hybridizes to the capture domain of the capture probe. In some embodiments, an analyte capture sequence comprises a poly(A) nucleic acid sequence that hybridizes to a capture domain that comprises a poly(T) nucleic acid sequence. In some embodiments, an analyte capture sequence comprises a poly(T) nucleic acid sequence that hybridizes to a capture domain that comprises a poly(A) nucleic acid sequence. In some embodiments, an analyte capture sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the analyte capture region.

In some embodiments of any of the spatial analysis methods described herein that employ an analyte capture agent 4002, the capture agent barcode domain can be directly coupled to the analyte binding moiety 4004, or they can be attached to a bead, molecular lattice, e.g., a linear, globular, cross-slinked, or other polymer, or other framework that is attached or otherwise associated with the analyte binding moiety, which allows attachment of multiple capture agent barcode domains to a single analyte binding moiety. Attachment (coupling) of the capture agent barcode domains to the analyte binding moieties 4004 can be achieved through any of a variety of direct or indirect, covalent or non-covalent associations or attachments. For example, in the case of a capture agent barcode domain coupled to an analyte binding moiety 4004 that includes an antibody or antigen-binding fragment, such capture agent barcode domains can be covalently attached to a portion of the antibody or antigen-binding fragment using chemical conjugation techniques (e.g., LIGHTNING-LINK® antibody labelling kits available from Innova Biosciences). In some embodiments, a capture agent barcode domain can be coupled to an antibody or antigen-binding fragment using non-covalent attachment mechanisms (e.g., using biotinylated antibodies and oligonucleotides or beads that include one or more biotinylated linker(s), coupled to oligonucleotides with an avidin or streptavidin linker). Antibody and oligonucleotide biotinylation techniques can be used, and are described for example in Fang et al., 2003, Nucleic Acids Res. 31(2): 708-715, the entire contents of which are incorporated by reference herein. Likewise, protein and peptide biotinylation techniques have been developed and can be used, and are described for example in U.S. Pat. No. 6,265,552, the entire contents of which are incorporated by reference herein. Furthermore, click reaction chemistry such as a methyltetrazine-PEG5-NHS ester reaction, a TCO-PEG4-NHS ester reaction, or the like, can be used to couple capture agent barcode domains to analyte binding moieties 4004. The reactive moiety on the analyte binding moiety can also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., NH2). The reactive moiety on the analyte binding moiety 4004 can be a chemical compound or group bound to the reactive moiety. Exemplary strategies to conjugate the analyte binding moiety 4004 to the capture agent barcode domain include the use of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation. In the cases where the analyte binding moiety 4004 is an antibody, the antibody can be modified prior to or contemporaneously with conjugation of the oligonucleotide. For example, the antibody can be glycosylated with a chemical substrate-permissive mutant of β-1,4-galactosyltransferase, GalT (Y289L) and azide-bearing uridine diphosphate-N-acetylgalactosamine analog uridine diphosphate-GalNAz. The modified antibody can be conjugated to an oligonucleotide with a dibenzocyclooctyne-PEG4-NHS group. In some embodiments, certain steps (e.g., COOH activation such as EDC) and homobifunctional cross linkers) can be avoided to prevent the analyte binding moieties from conjugating to themselves. In some embodiments of any of the spatial profiling methods described herein, the analyte capture agent (e.g., analyte binding moiety 4004 coupled to an oligonucleotide) can be delivered into the cell, e.g., by transfection (e.g., using transfectamine, cationic polymers, calcium phosphate or electroporation), by transduction (e.g., using a bacteriophage or recombinant viral vector), by mechanical delivery (e.g., magnetic beads), by lipid (e.g., 1,2-dioleoyl-sn-glycero-3-phosphocholine (DOPC)), or by transporter proteins.

An analyte capture agent 4002 can be delivered into a cell using exosomes. For example, a first cell can be generated that releases exosomes comprising an analyte capture agent. An analyte capture agent can be attached to an exosome membrane. An analyte capture agent can be contained within the cytosol of an exosome. Released exosomes can be harvested and provided to a second cell, thereby delivering the analyte capture agent into the second cell. An analyte capture agent can be releasable from an exosome membrane before, during, or after delivery into a cell. In some embodiments, the cell is permeabilized to allow the analyte capture agent 4002 to couple with intracellular constituents (such as, without limitation, intracellular proteins, metabolites, and nuclear membrane proteins). Following intracellular delivery, analyte capture agents 4002 can be used to analyze intracellular constituents as described herein.

In some embodiments of any of the spatial profiling methods described herein, the capture agent barcode domain coupled to an analyte capture agent 4002 can include modifications that render it non-extendable by a polymerase. In some embodiments, when binding to a capture domain of a capture probe or nucleic acid in a sample for a primer extension reaction, the capture agent barcode domain can serve as a template, not a primer. When the capture agent barcode domain also includes a barcode (e.g., an analyte binding moiety barcode), such a design can increase the efficiency of molecular barcoding by increasing the affinity between the capture agent barcode domain and unbarcoded sample nucleic acids, and eliminate the potential formation of adaptor artifacts. In some embodiments, the capture agent barcode domain 4008 can include a random N-mer sequence that is capped with modifications that render it non-extendable by a polymerase. In some cases, the composition of the random N-mer sequence can be designed to maximize the binding efficiency to free, unbarcoded ssDNA molecules. The design can include a random sequence composition with a higher GC content, a partial random sequence with fixed G or C at specific positions, the use of guanosines, the use of locked nucleic acids, or any combination thereof.

A modification for blocking primer extension by a polymerase can be a carbon spacer group of different lengths or a dideoxynucleotide. In some embodiments, the modification can be an abasic site that has an apurine or apyrimidine structure, a base analog, or an analogue of a phosphate backbone, such as a backbone of N-(2-aminoethyl)-glycine linked by amide bonds, tetrahydrofuran, or 1', 2'-Dideoxyribose. The modification can also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer)), biotin, di-deoxynucleotide triphosphate, ethylene glycol, amine, or phosphate).

In some embodiments of any of the spatial profiling methods described herein, the capture agent barcode domain 4008 coupled to the analyte binding moiety 4004 includes a cleavable domain. For example, after the analyte capture agent binds to an analyte (e.g., a cell surface analyte), the capture agent barcode domain can be cleaved and collected for downstream analysis according to the methods as described herein. In some embodiments, the cleavable domain of the capture agent barcode domain includes a U-excising element that allows the species to release from the bead. In some embodiments, the U-excising element can include a single-stranded DNA (ssDNA) sequence that contains at least one uracil. The species can be attached to a bead via the ssDNA sequence. The species can be released by a combination of uracil-DNA glycosylase (e.g., to remove the uracil) and an endonuclease (e.g., to induce a ssDNA break). If the endonuclease generates a 5' phosphate group from the cleavage, then additional enzyme treatment can be included in downstream processing to eliminate the phosphate group, e.g., prior to ligation of additional sequencing handle elements, e.g., Illumina full P5 sequence, partial P5 sequence, full R1 sequence, and/or partial R1 sequence.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information, for example sequences of transcripts, or both). For example, a cell surface protein of a cell can be associated with one or more physical properties of the cell (e.g., a shape, size, activity, or a type of the cell). The one or more physical properties can be characterized by imaging the cell. The cell can be bound by an analyte capture agent comprising an analyte binding moiety that binds to the cell surface protein and an analyte binding moiety barcode that identifies that analyte binding moiety, and the cell can be subjected to spatial analysis (e.g., any of the variety of spatial analysis methods described herein). For example, the analyte capture agent 4002 bound to the cell surface protein can be bound to a capture probe (e.g., a capture probe on an array), which capture probe includes a capture domain that interacts with an analyte capture sequence present on the capture agent barcode domain of the analyte capture agent 902. All or part of the capture agent barcode domain (including the analyte binding moiety barcode) can be copied with a polymerase using a 3' end of the capture domain as a priming site, generating an extended capture probe that includes the all or part of complementary sequence that corresponds to the capture probe (including a spatial barcode present on the capture probe) and a copy of the analyte binding moiety barcode. In some embodiments, an analyte capture agent with an extended capture agent barcode domain that includes a sequence complementary to a spatial barcode of a capture probe is called a "spatially-tagged analyte capture agent."

In some embodiments, the spatial array with spatially-tagged analyte capture agents can be contacted with a sample, where the analyte capture agent(s) associated with the spatial array capture the target analyte(s). The analyte capture agent(s) containing the extended capture probe(s), which includes a sequence complementary to the spatial barcode(s) of the capture probe(s) and the analyte binding moiety barcode(s), can then be denatured from the capture probe(s) of the spatial array. This allows the spatial array to be reused. The sample can be dissociated into non-aggregated cells (e.g., single cells) and analyzed by the single cell/droplet methods described herein. The spatially-tagged analyte capture agent can be sequenced to obtain the nucleic acid sequence of the spatial barcode of the capture probe and the analyte binding moiety barcode of the analyte capture agent. The nucleic acid sequence of the extended capture probe can thus be associated with an analyte (e.g., cell surface protein), and in turn, with the one or more physical properties of the cell (e.g., a shape or cell type). In some embodiments, the nucleic acid sequence of the extended capture probe can be associated with an intracellular analyte of a nearby cell, where the intracellular analyte was released using any of the cell permeabilization or analyte migration techniques described herein.

In some embodiments of any of the spatial profiling methods described herein, the capture agent barcode domains released from the analyte capture agents can then be subjected to sequence analysis to identify which analyte capture agents were bound to analytes. Based upon the capture agent barcode domains that are associated with a capture spot (e.g., a capture spot at a particular location) on a spatial array and the presence of the analyte binding moiety barcode sequence, an analyte profile can be created for a biological sample. Profiles of individual cells or populations of cells can be compared to profiles from other cells, e.g., 'normal' cells, to identify variations in analytes, which can provide diagnostically relevant information. In some embodiments, these profiles can be useful in the diagnosis of a variety of disorders that are characterized by variations in cell surface receptors, such as cancer and other disorders.

Figure 38A:
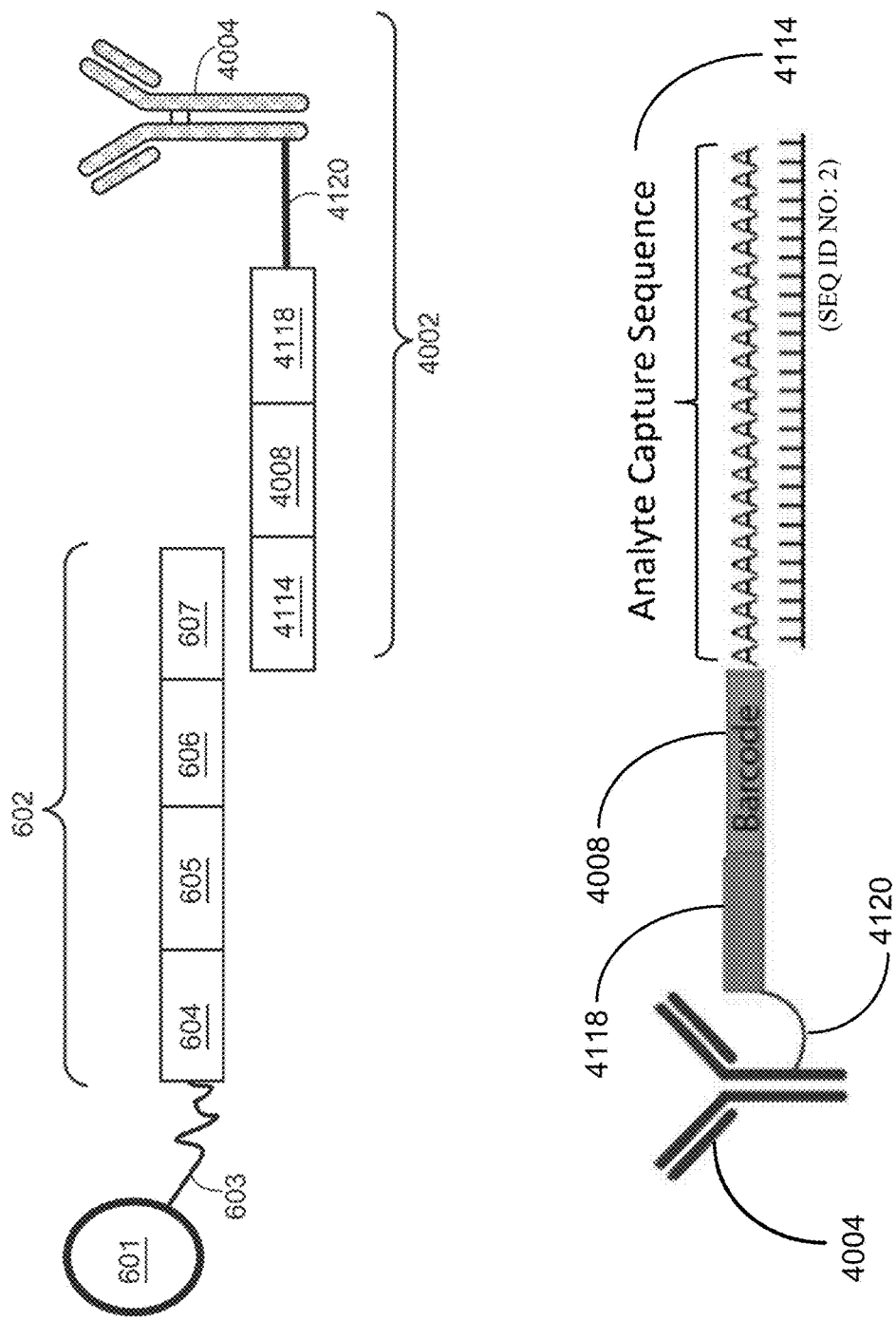
FIG. 38A is a schematic diagram depicting an exemplary interaction between a feature-immobilized capture probe and an analyte capture agent in accordance with some embodiments of the present disclosure.

FIG. 38A, top panel, is a schematic diagram depicting an exemplary interaction between a feature-immobilized capture probe 602 and an analyte capture agent 4002 (where the terms "feature" and "capture spot" are used interchangeably). The feature-immobilized capture probe 602 can include a spatial barcode 605 as well as one or more functional sequences 604 and 606, as described elsewhere herein. The capture probe 602 can also include a capture domain 607 that is capable of binding to an analyte capture agent 4002. In some embodiments, the analyte capture agent 4002 comprises a functional sequence 4118, capture agent barcode domain 4008, and an analyte capture sequence 4114. In some embodiments the analyte capture sequence 4114 is capable of binding to the capture domain 607 of the capture probe 602. The analyte capture agent 4002 can also include a linker 4120 that allows the capture agent barcode domain 4008 (4114/4008/4118) to couple to the analyte binding moiety 4004.

FIG. 38A, bottom panel, further illustrates a spatially-tagged analyte capture agent 4002 in which the analyte capture sequence 4114 (poly-A sequence) of the capture agent barcode domain 4118/4008/4114 can be blocked with a blocking probe (poly-T oligonucleotide).

Figure 38B:
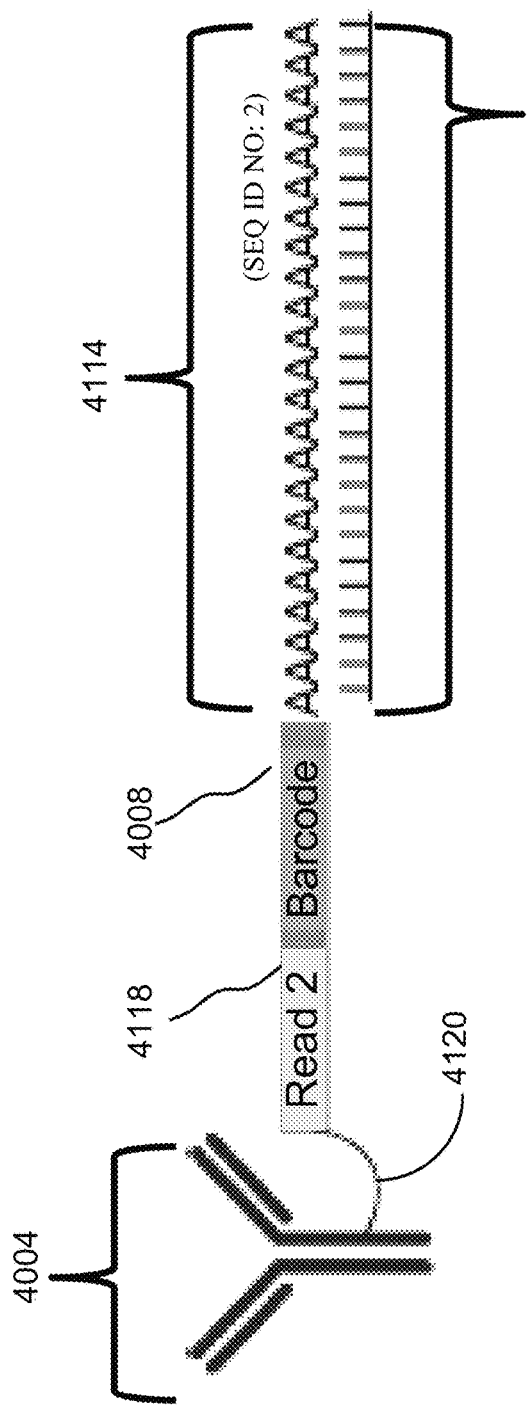
FIG. 38B is an exemplary schematic showing an analyte binding moiety comprising an oligonucleotide having a capture binding domain (indicated by a poly(A) sequence) that is hybridized to a blocking domain (indicated by a poly(T) sequence).

In some embodiments, the capture binding domain can include a sequence that is at least partially complementary to a sequence of a capture domain of a capture probe (e.g., any of the exemplary capture domains described herein). FIG. 38B shows an exemplary capture binding domain attached to an analyte-binding moiety used to detect a protein in a biological sample. As show in FIG. 38B, an analyte-binding moiety 4004 includes an oligonucleotide that includes a primer (e.g., a read2) sequence 4118, an analyte-binding-moiety barcode 4008, a capture binding domain having a first sequence (e.g., a capture binding domain) 4114 (e.g., an exemplary poly A), and a blocking probe or second sequence 4120 (e.g., poly T or poly U), where the blocking sequence blocks the capture binding domain from hybridizing to a capture domain on a capture probe. In some instances, the blocking sequence 4120 is called a blocking probe as disclosed herein. In some instances, the blocking probe is a poly T sequence as exemplified in FIG. 38B.

In some instances, as shown in FIG. 38A, the blocking probe sequence is not on a contiguous sequence with the capture binding domain. In other words, in some instances, the capture binding domain (also herein called a first sequence) and the blocking sequence are independent polynucleotides. In some instances, it will be apparent to one skilled in the art that the terms "capture binding domain" and "first sequence" are used interchangeably in this disclosure.

In a non-limiting example, the first sequence can be a poly(A) sequence when the capture domain sequence of the capture probe on the substrate is a poly(T) sequence. In some embodiments, the capture binding domain includes a capture binding domain substantially complementary to the capture domain of the capture probe. By substantially complementary, it is meant that the first sequence of the capture binding domain is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a sequence in the capture domain of the capture probe. In another example, the first sequence of the capture binding domain can be a random sequence (e.g., random hexamer) that is at least partially complementary to a capture domain sequence of the capture probe that is also a random sequence. In yet another example, a capture binding domain can be a mixture of a homopolymeric sequence (e.g., a poly(T) sequence) and a random sequence (e.g., random hexamer) when a capture domain sequence of the capture probe is also a sequence that includes a homopolymeric sequence (e.g., a poly(A) sequence) and a random sequence. In some embodiments, the capture binding domain includes ribonucleotides, deoxyribonucleotides, and/or synthetic nucleotides that are capable of participating in Watson-Crick type or analogous base pair interactions. In some embodiments, the first sequence of the capture binding domain sequence includes at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, or at least 24 nucleotides. In some embodiments, the first sequence of the capture binding domain includes at least 25 nucleotides, at least 30 nucleotides, or at least 35 nucleotides.

In some embodiments, the capture binding domain (e.g., the first sequence) and the blocking probe (e.g., the second sequence) of the capture binding domain are located on the same contiguous nucleic acid sequence. Where the capture binding domain and the blocking probe are located on the same contiguous nucleic acid sequence, the second sequence (e.g., a blocking probe) is located 3' of the first sequence. Where the first sequence and the second sequence (e.g., a blocking probe) of the capture binding domain are located on the same contiguous nucleic acid sequence, the second sequence (e.g., the blocking probe) is located 5' of the first sequence. As used herein, the terms second sequence and blocking probe are used interchangeably.

In some instances, the second sequence (e.g., the blocking probe) of the capture binding domain includes a nucleic acid sequence. In some instances, the second sequence is also called a blocking probe or blocking domain, and each term is used interchangeably. In some instances, the blocking domain is a DNA oligonucleotide. In some instances, the blocking domain is an RNA oligonucleotide. In some embodiments, a blocking probe of the capture binding domain includes a sequence that is complementary or substantially complementary to a first sequence of the capture binding domain. In some embodiments, the blocking probe prevents the first sequence of the capture binding domain from binding the capture domain of the capture probe when present. In some embodiments, the blocking probe is removed prior to binding the first sequence of the capture binding domain (e.g., present in a ligated probe) to a capture domain on a capture probe. In some embodiments, a blocking probe of the capture binding domain includes a poly-uridine sequence, a poly-thymidine sequence, or both. In some instances, the blocking probe (or the second sequence) is part of a hairpin structure that specifically binds to a capture binding domain and prevents the capture binding domain from hybridizing to a capture domain of a capture probe. See e.g., FIG. 38C.

In some embodiments, the second sequence (e.g., the blocking probe) of the capture binding domain includes a sequence configured to hybridize to the first sequence of the capture binding domain. When the blocking probe is hybridized to the first sequence, the first sequence is blocked from hybridizing with a capture domain of a capture probe. In some embodiments, the blocking probe includes a sequence that is complementary to the first sequence. In some embodiments, the blocking probe includes a sequence that is substantially complementary to the first sequence. In some embodiments, the blocking probe includes a sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the first sequence of the capture binding domain.

In some embodiments, the blocking probe of the capture binding domain includes a homopolymeric sequence that is substantially complementary to the first sequence of the capture binding domain. In some embodiments, the blocking probe is configured to hybridize to a poly(A), poly(T), or a poly-rU sequence. In some embodiments, the blocking probe includes a poly(A), poly(T), or a poly(U) sequence. In some embodiments, the first sequence includes a homopolymeric sequence. In some embodiments, the first sequence includes a poly(A), poly(U), or a poly(T) sequence.

Figure 38C:
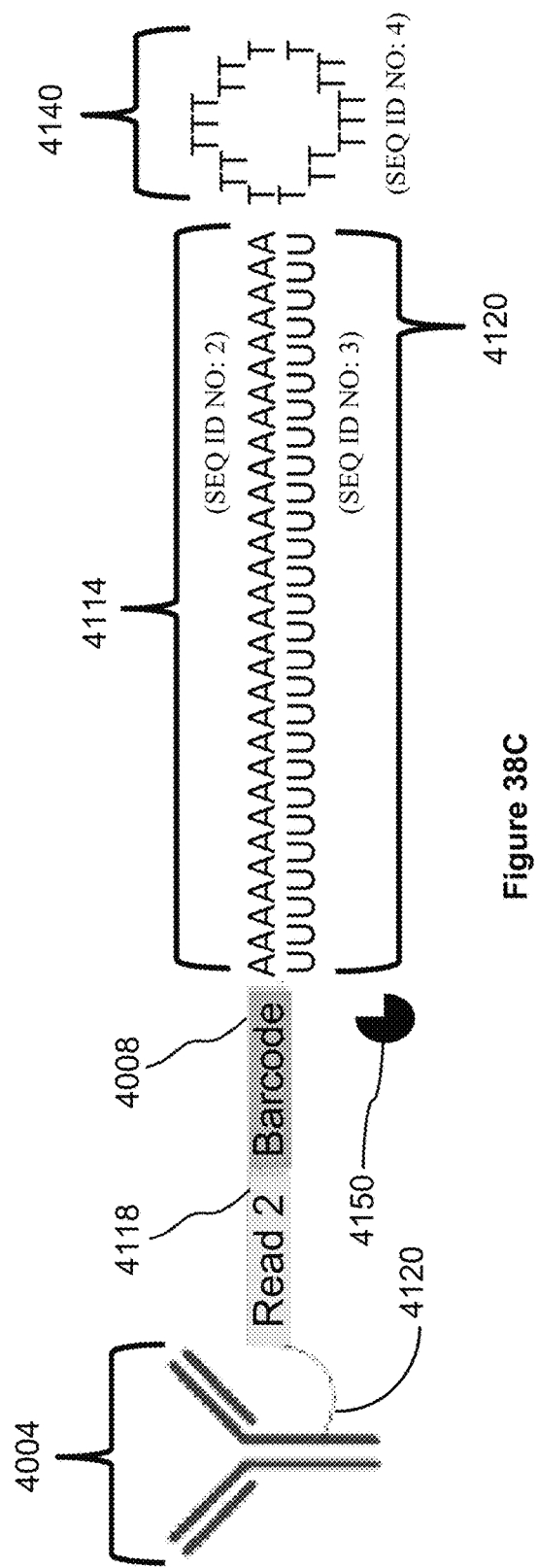
FIG. 38C is an exemplary schematic showing an analyte binding moiety that includes an oligonucleotide comprising a hairpin sequence disposed between a blocking domain (indicated by a poly(U) sequence) and a capture binding domain (indicated by a poly(A) sequence). As shown, the blocking domain hybridizes to the capture binding domain.

In some embodiments, the capture binding domain further includes a hairpin sequence (as shown in FIG. 38C). FIG. 38C shows an exemplary capture binding domain attached to an analyte-binding moiety used to detect a protein in a biological sample. As shown in FIG. 38C, an analyte-binding moiety 4004 includes an oligonucleotide that includes a primer (e.g., a read2) sequence 4118, an analyte-binding-moiety barcode 4008, a capture binding domain having a first sequence 4114 (e.g., an exemplary poly A), a blocking probe 4120 and a third sequence 4140, where the second and/or third sequence can be poly T or poly U or a combination thereof, where the blocking probe creates a hairpin type structure and the third sequence blocks the first sequence from hybridizing to a capture domain on a capture probe. In some instances, the third sequence 4140 is called a blocking sequence. Further, 4150 exemplifies a nuclease capable of digesting the blocking sequencing. In this example, 4150 could be an endonuclease or mixture of nucleases capable of digesting uracils, such as UDG or a uracil specific excision mix such as USER (NEB).

Figure 38D:
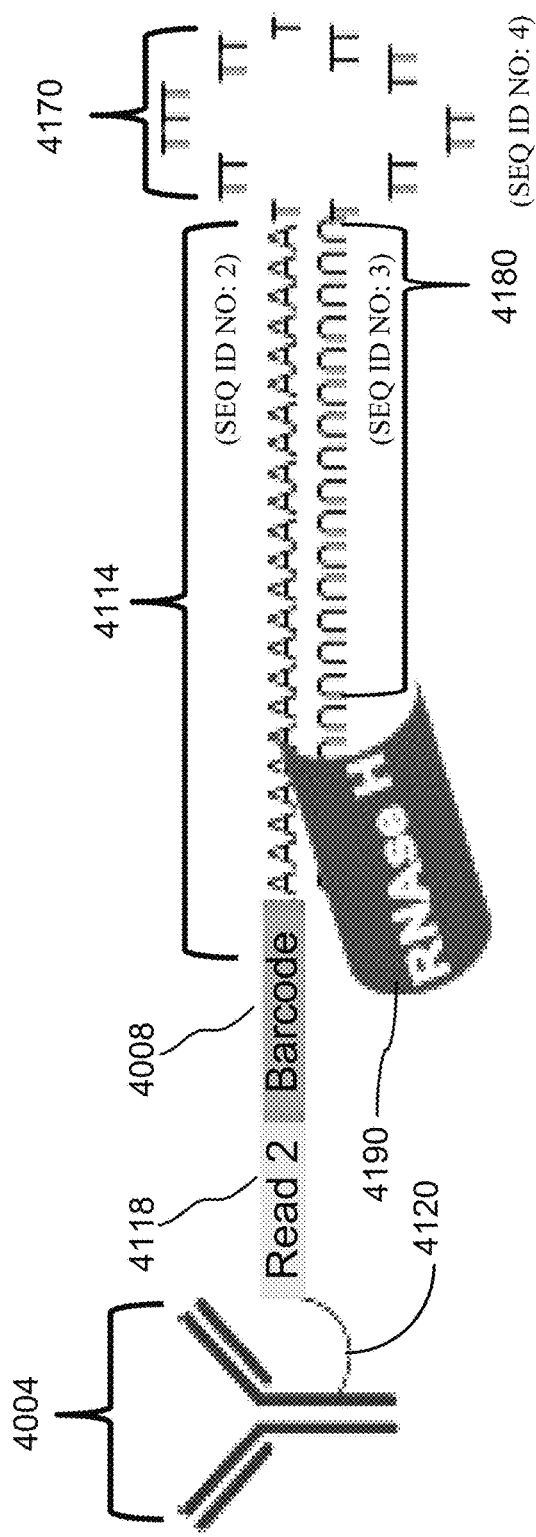
FIG. 38D is an exemplary schematic showing a blocking domain released by RNAse H.

Another embodiment of a hairpin blocker scenario is exemplified in FIG. 38D. As exemplified in FIG. 38D, an analyte-binding moiety 4004 includes an oligonucleotide that includes a primer (e.g., a read2) sequence 4118, an analyte-binding-moiety barcode 4008, a capture binding domain having a first sequence (e.g., a capture binding domain) 4114 (e.g., an exemplary poly A), a second hairpin sequence 4170 and a third sequence 4180, where the third sequence (e.g., a blocking probe) blocks the first sequence from hybridizing to a capture domain on a capture probe. In this example, 4190 exemplifies an RNase H nuclease capable of digesting the uracil blocking sequencing from the DNA:RNA hybrid that is formed by blocking of the first sequence with a uracil containing third sequence.

In some embodiments, the hairpin sequence 4170 is located 5' of the blocking probe in the capture binding domain. In some embodiments, the hairpin sequence 4170 is located 5' of the first sequence in the capture binding domain. In some embodiments, the capture binding domain includes from 5' to 3' a first sequence substantially complementary to the capture domain of a capture probe, a hairpin sequence, and a blocking probe substantially complementary to the first sequence. Alternatively, the capture binding domain includes from 3' to 5' a first sequence substantially complementary to the capture domain of a capture probe, a hairpin sequence, and a blocking probe substantially complementary to the first sequence.

In some embodiments, the hairpin sequence 4170 includes a sequence of about three nucleotides, about four nucleotides, about five nucleotides, about six nucleotides, about seven nucleotides, about eight nucleotides, about nine nucleotides or about 10 or more nucleotides. In some instances, the hairpin is at least about 15 nucleotides, at least about 20 nucleotides, at least about 25 nucleotides, at least about 30 nucleotides, or more nucleotides.

In some embodiments, the hairpin sequence includes DNA, RNA, DNA-RNA hybrid, or includes modified nucleotides. In some instances, the hairpin is a poly(U) sequence. In some instances, the RNA hairpin sequence is digested by USER and/or RNAse H using methods disclosed herein. In some instances, the poly(U) hairpin sequence is digested by USER and/or RNAse H using methods disclosed herein. In some instances, the hairpin is a poly(T) sequence. It is appreciated that the sequence of the hairpin (whether it includes DNA, RNA, DNA-RNA hybrid, or includes modified nucleotides) can be nearly any nucleotide sequence so long as it forms a hairpin, and in some instances, so long as it is digested by USER and/or RNAse H.

In some embodiments, methods provided herein require that the second sequence (e.g., the blocking probe) of the capture binding domain that is hybridized to the first sequence of the capture binding domain is released from the first sequence. In some embodiments, releasing the blocking probe (or second sequence) from the first sequence is performed under conditions where the blocking probe de-hybridizes from the first sequence.

In some embodiments, releasing the blocking probe from the first sequence includes cleaving the hairpin sequence. In some embodiments, the hairpin sequence includes a cleavable linker. For example, the cleavable linker can be a photocleavable linker, UV-cleavable linker, or an enzyme-cleavable linker. In some embodiments, the enzyme that cleaves that enzymatic-cleavable domain is an endonuclease. In some embodiments, the hairpin sequence includes a target sequence for a restriction endonuclease.

In some embodiments, releasing the blocking probe (or the second sequence) of the capture binding domain that is hybridized to the first sequence of the capture binding domain includes contacting the blocking probe with a restriction endonuclease. In some embodiments, releasing the blocking probe from the first sequence includes contacting the blocking probe with an endoribonuclease. In some embodiments, when the blocking probe is an RNA sequence (e.g., a sequence comprising uracils) the endoribonuclease is one or more of RNase H, RNase A, RNase C, or RNase I. In some embodiments, where the endoribonuclease is RNase H. In some embodiments, the RNase H includes RNase H1, RNase H2, or RNase H1 and RNase H2.

In some embodiments, the hairpin sequence includes a homopolymeric sequence. In some embodiments, the hairpin sequence 4170 includes a poly(T) or poly(U) sequence. For example, the hairpin sequence includes a poly(U) sequence. In some embodiments, provided herein are methods for releasing the blocking probe by contacting the hairpin sequence with a Uracil-Specific Excision Reagent (USER) enzyme.

In some embodiments, releasing the blocking probe from the first sequence includes denaturing the blocking probe under conditions where the blocking probe de-hybridizes from the first sequence. In some embodiments, denaturing comprises using chemical denaturation or physical denaturation. For example, where physical denaturation (e.g., temperature) is used to release the blocking probe. In some embodiments, denaturing includes temperature modulation. For example, a first sequence and a blocking probe have predetermined annealing temperatures based on the composition (A, G, C, or T) within the known sequences. In some embodiments, the temperature is modulate up to 5° C., up to 10° C., up to 15° C., up to 20° C., up to 25° C., up to 30° C., or up to 35° C. above the predetermined annealing temperature. In some embodiments, the temperature is modulated at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35° C. above the predetermined annealing temperature. In some embodiments, once the temperature is modulated to a temperature above the predetermined annealing temperature, the temperature is cooled down to the predetermined annealing temperature at a ramp rate of about 0.1° C./second to about 1.0° C./second (e.g., about 0.1° C./second to about 0.9° C./second, about 0.1° C./second to about 0.8° C./second, about 0.1° C./second to about 0.7° C./second, about 0.1° C./second to about 0.6° C./second, about 0.1° C./second to about 0.5° C./second, about 0.1° C./second to about 0.4° C./second, about 0.1° C./second to about 0.3° C./second, about 0.1° C./second to about 0.2° C./second, about 0.2° C./second to about 1.0° C./second, about 0.2° C./second to about 0.9° C./second, about 0.2° C./second to about 0.8° C./second, about 0.2° C./second to about 0.7° C./second, about 0.2° C./second to about 0.6° C./second, about 0.2° C./second to about 0.5° C./second, about 0.2° C./second to about 0.4° C./second, about 0.2° C./second to about 0.3° C./second, about 0.3 to about 1.0° C./second, about 0.3° C./second to about 0.9° C./second, about 0.3° C./second to about 0.8° C./second, about 0.3° C./second to about 0.7° C./second, about 0.3° C./second to about 0.6° C./second, about 0.3° C./second to about 0.5° C./second, about 0.3° C./second to about 0.4° C./second, about 0.4° C./second to about 1.0° C./second, about 0.4° C./second to about 0.9° C./second, about 0.4° C./second to about 0.8° C./second, about 0.4° C./second to about 0.7° C./second, about 0.4° C./second to about 0.6° C./second, about 0.4° C./second to about 0.5° C./second, about 0.5° C./second to about 1.0° C./second, about 0.5° C./second to about 0.9° C./second, about 0.5° C./second to about 0.8° C./second, about 0.5° C./second to about 0.7° C./second, about 0.5° C./second to about 0.6° C./second, about 0.6° C./second to about 1.0° C./second, about 0.6° C./second to about 0.9° C./second, about 0.6° C./second to about 0.8° C./second, about 0.6° C./second to about 0.7° C./second, about 0.7° C./second to about 1.0° C./second, about 0.7° C./second to about 0.9° C./second, about 0.7° C./second to about 0.8° C./second, about 0.8° C./second to about 1.0° C./second, about 0.8° C./second to about 0.9° C./second, or about 0.9° C./second to about 1.0° C./second). In some embodiments, denaturing includes temperature cycling. In some embodiments, denaturing includes alternating between denaturing conditions (e.g., a denaturing temperature) and non-denaturing conditions (e.g., annealing temperature).

It is appreciated that, notwithstanding any particular function in an embodiment, the hairpin sequence can be any sequence configuration, so long as a hairpin is formed. Thus, in some instances, it could be, for example, a degenerate sequence, a random sequence, or otherwise (comprising any sequence of polynucleotides).

In some embodiments, the hairpin sequence 4170 further includes a sequence that is capable of binding to a capture domain of a capture probe. For example, releasing the hairpin sequence from the capture binding domain can require that the hairpin sequence is cleaved, where the portion of the hairpin sequence that is left following cleavage includes a sequence that is capable of binding to a capture domain of a capture probe. In some embodiments, all or a portion of the hairpin sequence is substantially complementary to a capture domain of a capture probe. In some embodiments, the sequence that is substantially complementary to a capture domain of a capture probe is located on the free 5' or free 3' end following cleavage of the hairpin sequence. In some embodiments, the cleavage of the hairpin results in a single stranded sequence that is capable of binding to a capture domain of a capture probe on a spatial array. While the release of a hairpin sequence may enable hybridization to a capture domain of a capture probe, it is contemplated that release of the hairpin would not significantly affect the capture of the target analyte by an analyte-binding moiety or a probe oligonucleotide (e.g., a second probe oligonucleotide).

In some instances, the one or more blocking methods disclosed herein include a plurality of caged nucleotides. In some embodiments, provided herein are methods where a capture binding domain includes a plurality of caged nucleotides. The caged nucleotides prevent the capture binding domain from interacting with the capture domain of the capture probe. The caged nucleotides include caged moieties that block Watson-Crick hydrogen bonding, thereby preventing interaction until activation, for example, through photolysis of the caged moiety that releases the caged moiety and restores the caged nucleotides ability to engage in Watson-Crick base pairing with a complement nucleotide.

Figure 38E:
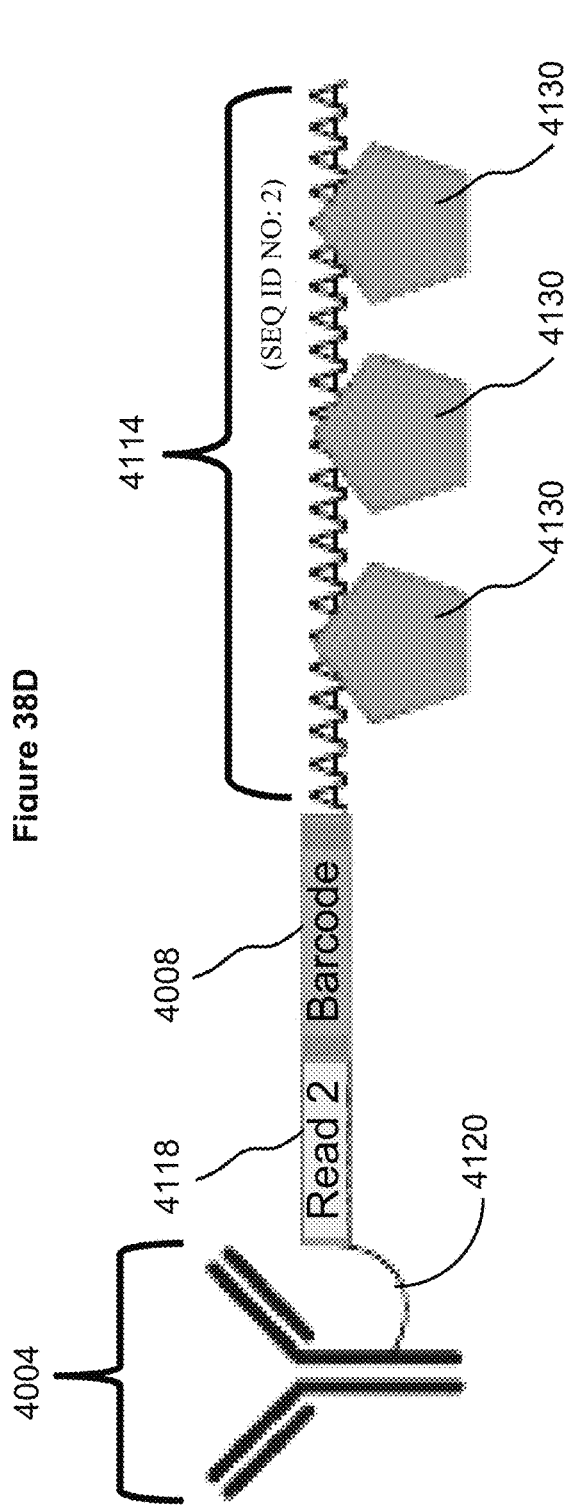
FIG. 38E is an exemplary schematic showing an analyte binding moiety that includes an oligonucleotide comprising a capture binding domain that is blocked using caged nucleotides (indicated by pentagons).

FIG. 38E is demonstrative of blocking a capture binding domain with caged nucleotides. As exemplified in FIG. 38E, an analyte-binding moiety 4004 includes an oligonucleotide that includes a primer (e.g., a read2) sequence 4118, an analyte-binding-moiety barcode 4008 and a capture binding domain having a sequence 4114 (e.g., an exemplary polyA). Caged nucleotides 4130 block the sequence 4114, thereby blocking the interaction between the capture binding domain and the capture domain of the capture probe. In some embodiments, the capture binding domain includes a plurality of caged nucleotides, where a caged nucleotide of the plurality of caged nucleotides includes a caged moiety that is capable of preventing interaction between the capture binding domain and the capture domain of the capture probe. Non-limiting examples of caged nucleotides, also known as light-sensitive oligonucleotides, are described in Liu et al., 2014, Acc. Chem. Res., 47(1): 45-55 (2014), which is incorporated by reference in its entirety. In some embodiments, the caged nucleotides include a caged moiety selected from the group of 6-nitropiperonyloxymethy (NPOM), 1-(ortho-nitrophenyl)-ethyl (NPE), 2-(ortho-nitrophenyl)propyl (NPP), diethylaminocoumarin (DEACM), and nitrodibenzofuran (NDBF).

In some embodiments, a caged nucleotide includes a non-naturally-occurring nucleotide selected from the group consisting of 6-nitropiperonyloxymethy (NPOM)-caged adenosine, 6-nitropiperonyloxymethy (NPOM)-caged guanosine, 6-nitropiperonyloxymethy (NPOM)-caged uridine, and 6-nitropiperonyloxymethy (NPOM)-caged thymidine. For example, the capture binding domain includes one or more caged nucleotides where the cage nucleotides include one or more 6-nitropiperonyloxymethy (NPOM)-caged guanosine. In another example, the capture binding domain includes one or more caged nucleotides where the cage nucleotides include one or more nitropiperonyloxymethy (NPOM)-caged uridine. In yet another example, the capture binding domain includes one or more caged nucleotides where the caged nucleotide includes one or more 6-nitropiperonyloxymethy (NPOM)-caged thymidine.

In some embodiments, the capture binding domain includes a combination of at least two or more of any of the caged nucleotides described herein. For example, the capture binding domain can include one or more 6-nitropiperonyloxymethy (NPOM)-caged guanosine and one or more nitropiperonyloxymethy (NPOM)-caged uridine. It is appreciated that a capture binding domain can include any combination of any of the caged nucleotides described herein.

In some embodiments, the capture binding domain includes one caged nucleotide, two caged nucleotides, three caged nucleotides, four caged nucleotides, five caged nucleotides, six caged nucleotides, seven caged nucleotides, eight caged nucleotides, nine caged nucleotides, or ten or more caged nucleotides.

In some embodiments, the capture binding domain includes a caged nucleotide at the 3' end. In some embodiments, the capture binding domain includes two caged nucleotides at the 3' end. In some embodiments, the capture binding domain includes at least three caged nucleotides at the 3' end.

In some embodiments, the capture binding domain includes a caged nucleotide at the 5' end. In some embodiments, the capture binding domain includes two caged nucleotides at the 5' end. In some embodiments, the capture binding domain includes at least three caged nucleotides at the 5' end.

In some embodiments, the capture binding domain includes a caged nucleotide at every odd position starting at the 3' end of the capture binding domain. In some embodiments, the capture binding domain includes a caged nucleotide at every odd position starting at the 5' end of the capture binding domain. In some embodiments, the capture binding domain includes a caged nucleotide at every even position starting at the 3' end of the capture binding domain. In some embodiments, the capture binding domain includes a caged nucleotide at every even position starting at the 5' end of the capture binding domain.

In some embodiments, the capture binding domain includes a sequence including at least 10%, at least, 20%, or at least 30% caged nucleotides. In some instances, the percentage of caged nucleotides in the capture binding domain is about 40%, about 50%, about 60%, about 70%, about 80% or higher. In some embodiments, the capture binding domain includes a sequence where every nucleotide is a caged nucleotide. It is understood that the limit of caged nucleotides is based on the sequence of the capture binding domain and on steric limitations of creating caged nucleotides in proximity to one another. Thus, in some instances, particular nucleotides (e.g., guanines) are replaced with caged nucleotides. In some instances, all guanines in a capture binding domain are replaced with caged nucleotides. In some instances, a fraction (e.g., about 10%, about 20%, about 30%, about 40%, about 50%, about 60%, about 70%, about 80%, about 90%, or about 95%) of guanines in a capture binding domain are replaced with caged nucleotides. In some instances, particular nucleotides (e.g., uridines or thymines) are replaced with caged nucleotides. In some instances, all uridines or thymines in a capture binding domain are replaced with caged nucleotides. In some instances, a fraction (e.g., about 10%, about 20%, about 30%, about 40%, about 50%, about 60%, about 70%, about 80%, about 90%, or about 95%) of uridines or thymines in a capture binding domain are replaced with caged nucleotides. Caged nucleotides are disclosed in Govan et al., 2013, *Nucleic Acids Research* 41; 22, 10518-10528, which is incorporated by reference in its entirety.

In some embodiments, the capture binding domain includes caged nucleotides that are evenly distributed throughout the capture binding domain. For example, a capture binding domain can include a sequence that includes at least 10% caged nucleotides where the caged nucleotides are evenly distributed throughout the capture binding domain. In some embodiments, the capture binding domain includes a sequence that is at least 10% caged nucleotides and where the 10% caged nucleotides are positioned at the 3' of the capture binding domain. In some embodiments, the capture binding domain includes a sequence that is at least 10% caged nucleotides and where the 10% caged nucleotides are positioned at the 5' end of the capture binding domain. In some embodiments, the caged nucleotides are included at every third, at every fourth, at every fifth, at every sixth nucleotide, or a combination thereof, of the capture binding domain sequence.

In some embodiments, provided herein are methods for releasing the caged moiety from the caged nucleotide. In some embodiments, releasing the caged moiety from the caged nucleotide includes activating the caged moiety. In some embodiments, releasing the caged moiety from the caged nucleotide restores the caged nucleotides ability to hybridize to a complementary nucleotide through Watson-Crick hydrogen bonding. For example, restoring the caged nucleotides ability to hybridize with a complementary nucleotide enables/restores the capture binding domain's ability to interact with the capture domain. Upon releasing the caged moiety from the caged nucleotide, the caged nucleotide is no longer "caged" in that the caged moiety is no longer linked (e.g., either covalently or non-covalently) to the caged nucleotide. As used herein, the term "caged nucleotide" can refer to a nucleotide that is linked to a caged moiety or a nucleotide that was linked to a caged moiety but is no longer linked as a result of activation of the caged moiety.

In some embodiments, provided herein are methods for activating the caged moiety thereby releasing the caged moiety from the caged nucleotide. In some embodiments, activating the caged moiety includes photolysis of the caged moiety from the nucleotide. As used herein, "photolysis" can refer to the process of removing or separating a caged moiety from a caged nucleotide using light. In some embodiments, activating (e.g., photolysis) the caged moiety includes exposing the caged moiety to light pulses (e.g., two or more, three or more, four or more, or five or more pulses of light) that in total are sufficient to release the caged moiety from the caged nucleotide. In some embodiments, activating the caged moiety includes exposing the caged moiety to a light pulse (e.g., a single light pulse) that is sufficient to release the caged moiety from the caged nucleotide. In some embodiments, activating the caged moiety includes exposing the caged moiety to a plurality of pulses (e.g., one, or two or more pulses of light) where the light is at a wavelength of about less than about 360 nm. In some embodiments, the source of the light that is at a wavelength of about less than 360 nm is a UV light. The UV light can originate from a fluorescence microscope, a UV laser or a UV flashlamp, or any source of UV light known in the art.

In some embodiments, once the caged moiety is released from the capture binding domain, the oligonucleotide, probe oligonucleotide, or ligation product that includes the capture binding domain, is able to hybridize to the capture domain of the capture probe. Finally, to identify the location of the analyte or determine the interaction between two or more analyte-binding moieties, all or part of the sequence of the oligonucleotide, probe oligonucleotide, or ligation product, or a complement thereof, can be determined.

For more disclosure on embodiments in which the analyte capture sequence is blocked, see International Patent Application No PCT/US2020/059472 entitled "Enhancing Specificity of Analyte Binding," filed Nov. 6, 2020, which is hereby incorporated by reference.

Figure 39:
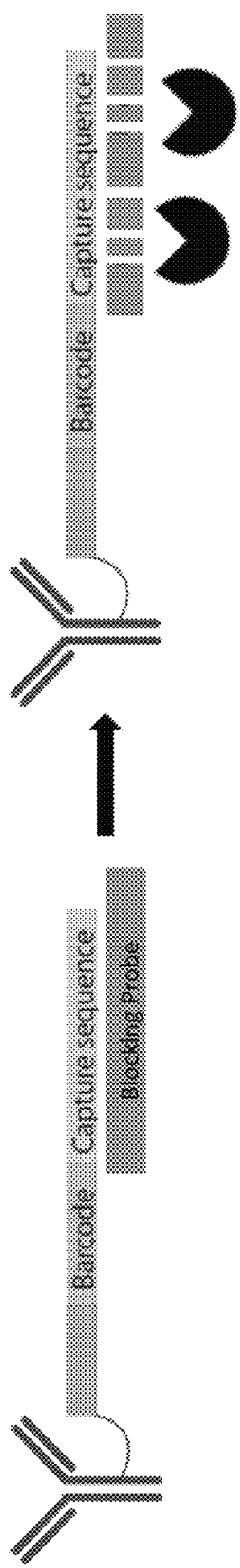
FIG. 39 is an exemplary schematic illustrating a spatially-tagged analyte capture agent where the analyte capture sequence is blocked via a blocking probe, and in which the blocking probe can be removed, for example with an RNAse treatment, in accordance with some embodiments of the present disclosure.

FIG. 39 illustrates how blocking probes are added to the spatially-tagged analyte capture agent 4002 to prevent non-specific binding to capture domain on the array. In some embodiments, blocking oligonucleotides and antibodies are delivered to tissue where, after binding to tissue target, the blocking oligonucleotides can be subsequently removed (e.g., digested by RNase). In the example illustrated in FIG. 39, cleavage of the linker between the oligonucleotide and antibody allows the oligonucleotide to migrate to the capture domain on the array. See Examples 3 and 4 below.

In some embodiments of any of the spatial profiling methods described herein, the methods are used to identify immune cell profiles. Immune cells express various adaptive immunological receptors relating to immune function, such as T cell receptors (TCRs) and B cell receptors (BCRs). T cell receptors and B cell receptors play a part in the immune response by specifically recognizing and binding to antigens and aiding in their destruction. More information on such applications of the disclosed methods is provided in PCT publication 202020176788A1 entitled "Profiling of biological analyes with spatially barcoded oligonucleotide arrays" the entire contents of each of which are incorporated herein by reference.

(c) Substrate

For the spatial array-based analytical methods described in this section, the substrate (e.g., chip) functions as a support for direct or indirect attachment of capture probes to capture spots of the array. In addition, in some embodiments, a substrate (e.g., the same substrate or a different substrate) is used to provide support to a sample, particularly, for example, a thin tissue section. Accordingly, a "substrate" is a support that is insoluble in aqueous liquid and that allows for positioning of biological samples, analytes, capture spots, and/or capture probes on the substrate.

A wide variety of different substrates can be used for the foregoing purposes. In general, a substrate can be any suitable support material. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate.

The substrate can also correspond to a flow cell. Flow cells can be formed of any of the foregoing materials, and can include channels that permit reagents, solvents, capture spots, and molecules to pass through the flow cell.

Among the examples of substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In some embodiments, a substrate is coated with a surface treatment such as poly-L-lysine. Additionally or alternatively, the substrate can be treated by silanation, e.g., with epoxy-silane, amino-silane, and/or by a treatment with polyacrylamide.

The substrate can generally have any suitable form or format. For example, the substrate can be flat, curved, e.g., convexly or concavely curved towards the area where the interaction between a sample, e.g., tissue sample, and the substrate takes place. In some embodiments, the substrate is a flat, e.g., planar, chip or slide. The substrate can contain one or more patterned surfaces within the substrate (e.g., channels, wells, projections, ridges, divots, etc.).

A substrate can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or cross-table). In some embodiments, where a substrate structure is flat, the substrate structure can be any appropriate type of support having a flat surface (e.g., a chip or a slide such as a microscope slide).

Substrates can optionally include various structures such as, but not limited to, projections, ridges, and channels. A substrate can be micropatterned to limit lateral diffusion (e.g., to prevent overlap of spatial barcodes). A substrate modified with such structures can be modified to allow association of analytes, capture spots (e.g., beads), or probes at individual sites. For example, the sites where a substrate is modified with various structures can be contiguous or non-contiguous with other sites.

In some embodiments, the surface of a substrate can be modified so that discrete sites are formed that can only have or accommodate a single capture spot. In some embodiments, the surface of a substrate can be modified so that capture spots adhere to random sites.

In some embodiments, the surface of a substrate is modified to contain one or more wells, using techniques such as (but not limited to) stamping techniques, microetching techniques, and molding techniques. In some embodiments in which a substrate includes one or more wells, the substrate can be a concavity slide or cavity slide. For example, wells can be formed by one or more shallow depressions on the surface of the substrate. In some embodiments, where a substrate includes one or more wells, the wells can be formed by attaching a cassette (e.g., a cassette containing one or more chambers) to a surface of the substrate structure.

In some embodiments, the structures of a substrate (e.g., wells) can each bear a different capture probe. Different capture probes attached to each structure can be identified according to the locations of the structures in or on the surface of the substrate. Exemplary substrates include arrays in which separate structures are located on the substrate including, for example, those having wells that accommodate capture spots.

In some embodiments, a substrate includes one or more markings on a surface of the substrate, e.g., to provide guidance for correlating spatial information with the characterization of the analyte of interest. For example, a substrate can be marked with a grid of lines (e.g., to allow the size of objects seen under magnification to be easily estimated and/or to provide reference areas for counting objects). In some embodiments, fiducial markers can be included on the substrate. Such markings can be made using techniques including, but not limited to, printing, sandblasting, and depositing on the surface.

In some embodiments where the substrate is modified to contain one or more structures, including but not limited to wells, projections, ridges, or markings, the structures can include physically altered sites. For example, a substrate modified with various structures can include physical properties, including, but not limited to, physical configurations, magnetic or compressive forces, chemically functionalized sites, chemically altered sites, and/or electrostatically altered sites.

In some embodiments where the substrate is modified to contain various structures, including but not limited to wells, projections, ridges, or markings, the structures are applied in a pattern. Alternatively, the structures can be randomly distributed.

In some embodiments, a substrate is treated in order to minimize or reduce non-specific analyte hybridization within or between capture spots. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Application Publication Nos. U.S. 2017/0253918 and U.S. 2018/0052081, can be used. The entire contents of each of the foregoing documents are incorporated herein by reference.

Treatment can include adding a functional group that is reactive or capable of being activated such that it becomes reactive after receiving a stimulus (e.g., photoreactive). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

The substrate (e.g., or a bead or a capture spot on an array) can include tens to hundreds of thousands or millions of individual oligonucleotide molecules (e.g., at least about 10,000, 50,000, 100,000, 500,000, 1,000,000, 10,000,000, 100,000,000, 1,000,000,000 or 10,000,000,000 oligonucleotide molecules).

In some embodiments, the surface of the substrate is coated with a cell permissive coating to allow adherence of live cells. A "cell-permissive coating" is a coating that allows or helps cells to maintain cell viability (e.g., remain viable) on the substrate. For example, a cell-permissive coating can enhance cell attachment, cell growth, and/or cell differentiation, e.g., a cell-permissive coating can provide nutrients to the live cells. A cell-permissive coating can include a biological material and/or a synthetic material. Non-limiting examples of a cell-permissive coating include coatings that feature one or more extracellular matrix (ECM) components (e.g., proteoglycans and fibrous proteins such as collagen, elastin, fibronectin and laminin), poly-lysine, poly-L-ornithine, and/or a biocompatible silicone (e.g., CYTOSOFT®). For example, a cell-permissive coating that includes one or more extracellular matrix components can include collagen Type I, collagen Type II, collagen Type IV, elastin, fibronectin, laminin, and/or vitronectin. In some embodiments, the cell-permissive coating includes a solubilized basement membrane preparation extracted from the Engelbreth-Holm-Swarm (EHS) mouse sarcoma (e.g., MATRIGEL®). In some embodiments, the cell-permissive coating includes collagen.

Where the substrate includes a gel (e.g., a hydrogel or gel matrix), oligonucleotides within the gel can attach to the substrate. The terms "hydrogel" and "hydrogel matrix" are used interchangeably herein to refer to a macromolecular polymer gel including a network. Within the network, some polymer chains can optionally be cross-linked, although cross-linking does not always occur.

Further details and non-limiting embodiments relating to hydrogels and hydrogel subunits that can be used in the present disclosure are described in U.S. patent application Ser. No. 16/992,569 entitled "Systems and Methods for Using the Spatial Distribution of Haplotypes to Determine a Biological Condition," filed Aug. 13, 2020, which is hereby incorporated herein by reference.

Further examples of substrates, including for example fiducial markers on such substrates, are disclosed in PCT publication 202020176788A1 entitled "Profiling of biological analyes with spatially barcoded oligonucleotide arrays" which is hereby incorporated by reference.

(d) Arrays

In many of the methods disclosed herein, capture spots are collectively positioned on a substrate in an array. An "array" is a specific arrangement of a plurality of capture spots (also termed "features") that is either irregular or forms a regular pattern. Individual capture spots in the array differ from one another based on their relative spatial locations. In general, at least two of the plurality of capture spots in the array include a distinct capture probe (e.g., any of the examples of capture probes described herein).

Arrays can be used to measure large numbers of analytes simultaneously. In some embodiments, oligonucleotides are used, at least in part, to create an array. For example, one or more copies of a single species of oligonucleotide (e.g., capture probe) can correspond to or be directly or indirectly attached to a given capture spot in the array. In some embodiments, a given capture spot in the array includes two or more species of oligonucleotides (e.g., capture probes). In some embodiments, the two or more species of oligonucleotides (e.g., capture probes) attached directly or indirectly to a given capture spot on the array include a common (e.g., identical) spatial barcode.

As defined above, a "capture spot" is an entity that acts as a support or repository for various molecular entities used in sample analysis. Examples of capture spots include, but are not limited to, a bead, a spot of any two- or three-dimensional geometry (e.g., an ink jet spot, a masked spot, a square on a grid), a well, and a hydrogel pad. In some embodiments, capture spots are directly or indirectly attached or fixed to a substrate (e.g., of a chip). In some embodiments, the capture spots are not directly or indirectly attached or fixed to a substrate, but instead, for example, are disposed within an enclosed or partially enclosed three dimensional space (e.g., wells or divots).

In some embodiments, capture spots are directly or indirectly attached or fixed to a substrate (e.g., of a chip) that is liquid permeable. In some embodiments, capture spots are directly or indirectly attached or fixed to a substrate that is biocompatible. In some embodiments, capture spots are directly or indirectly attached or fixed to a substrate that is a hydrogel.

Figure 12:
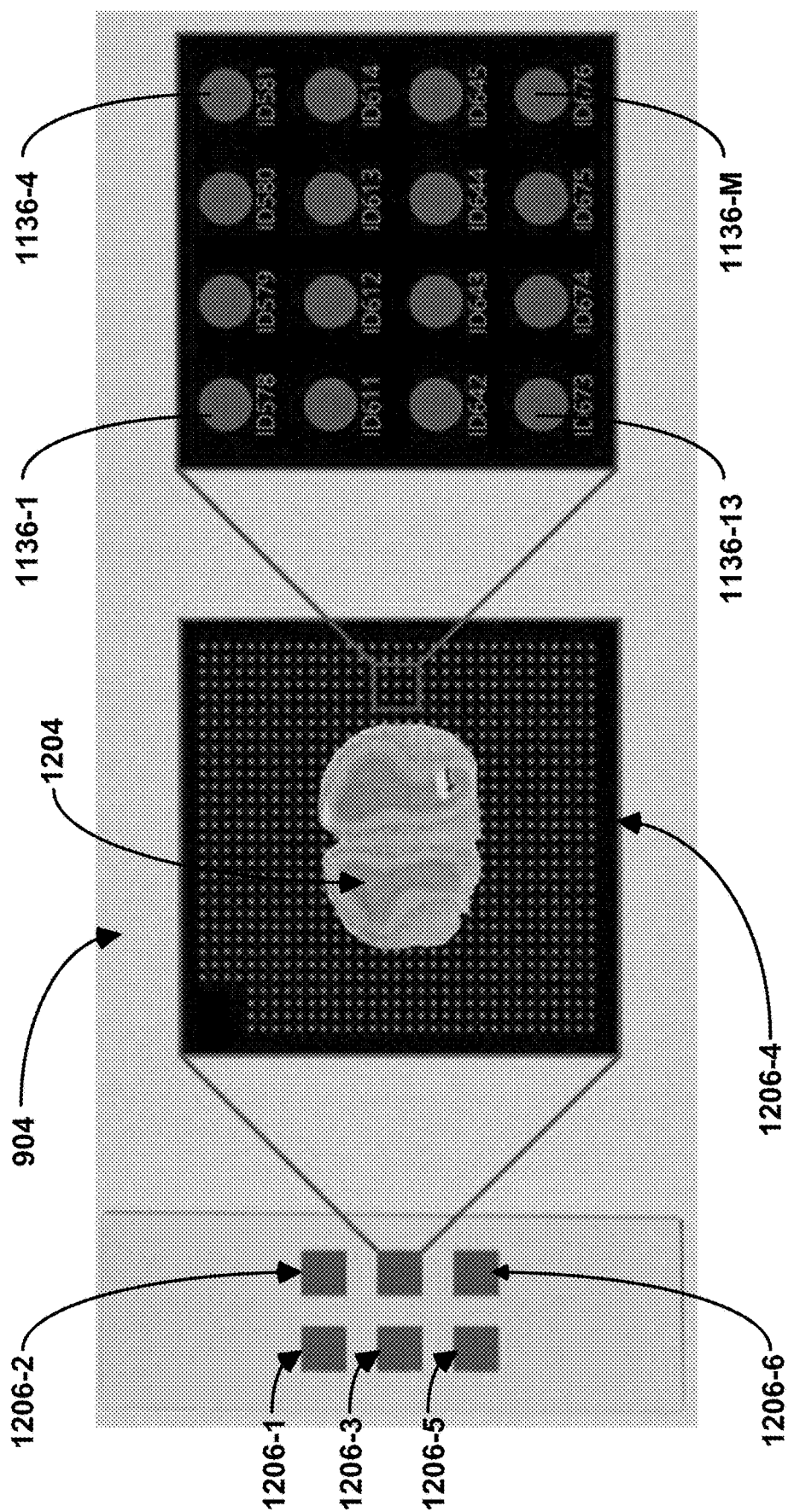
FIG. 12 is a schematic showing the arrangement of barcoded capture spots within an array in accordance with some embodiments of the present disclosure.

FIG. 12 depicts an exemplary arrangement of barcoded capture spots within an array.

From left to right, FIG. 12 shows (L) a slide including six spatially-barcoded arrays, (C) An enlarged schematic of one of the six spatially-barcoded arrays, showing a grid of barcoded capture spots in relation to a sample, and (R) an enlarged schematic of one section of an array, showing the specific identification of multiple capture spots within the array (labelled as ID578, ID579, ID580, etc.).

As used herein, the term "bead array" refers to an array that includes a plurality of beads as the capture spots in the array. In some embodiments, the beads are attached to a substrate (e.g., of a chip). For example, the beads can optionally attach to a substrate such as a microscope slide and in proximity to a sample (e.g., a tissue section that includes cells). The beads can also be suspended in a solution and deposited on a surface (e.g., a membrane, a tissue section, or a substrate (e.g., a microscope slide)).

Examples of arrays of beads on or within a substrate include beads located in wells such as the BeadChip array (available from Illumina Inc., San Diego, Calif.), arrays used in sequencing platforms from 454 LifeSciences (a subsidiary of Roche, Basel, Switzerland), and array used in sequencing platforms from Ion Torrent (a subsidiary of Life Technologies, Carlsbad, Calif.). Examples of bead arrays are described in, e.g., U.S. Pat. Nos. 6,266,459; 6,355,431; 6,770,441; 6,859,570; 6,210,891; 6, 258, 568; and 6,274, 320; U.S. Patent Application Publication Nos. 2009/ 0026082; 2009/0127589; 2010/0137143; and 2010/ 0282617; and PCT Patent Application Publication Nos. WO 00/063437 and WO 2016/162309, the entire contents of each of which is incorporated herein by reference.

(i) Arrays for Analyted Capture

In some embodiments, some or all capture spots in an array include a capture probe. In some embodiments, an array can include a capture probe attached directly or indirectly to the substrate.

The capture probe includes a capture domain (e.g., a nucleotide sequence) that can specifically bind (e.g., hybridize) to a target analyte (e.g., mRNA, DNA, or protein) within a sample. In some embodiments, the binding of the capture probe to the target (e.g., hybridization) is detected and quantified by detection of a visual signal, e.g., a fluorophore, a heavy metal (e.g., silver ion), or chemiluminescent label, which has been incorporated into the target. In some embodiments, the intensity of the visual signal correlates with the relative abundance of each analyte in the sample. Since an array can contain thousands or millions of capture probes (or more), an array of capture spots with capture probes can interrogate many analytes in parallel.

In some embodiments, a substrate includes one or more capture probes that are designed to capture analytes from one or more organisms. In a non-limiting example, a substrate can contain one or more capture probes designed to capture mRNA from one organism (e.g., a human) and one or more capture probes designed to capture DNA from a second organism (e.g., a bacterium).

The capture probes can be attached to a substrate or capture spot using a variety of techniques. In some embodiments, the capture probe is directly attached to a capture spot that is fixed on an array. In some embodiments, the capture probes are immobilized to a substrate by chemical immobilization. For example, a chemical immobilization can take place between functional groups on the substrate and corresponding functional elements on the capture probes. Exemplary corresponding functional elements in the capture probes can either be an inherent chemical group of the capture probe, e.g., a hydroxyl group, or a functional element can be introduced on to the capture probe. An example of a functional group on the substrate is an amine group. In some embodiments, the capture probe to be immobilized includes a functional amine group or is chemically modified in order to include a functional amine group. Means and methods for such a chemical modification are well known in the art.

In some embodiments, the capture probe is a nucleic acid. In some embodiments, the capture probe is immobilized on the capture spot or the substrate via its 5' end. In some embodiments, the capture probe is immobilized on a capture spot or a substrate via its 5' end and includes from the 5' to 3' end: one or more barcodes (e.g., a spatial barcode and/or a UMI) and one or more capture domains. In some embodiments, the capture probe is immobilized on a capture spot via its 5' end and includes from the 5' to 3' end: one barcode (e.g., a spatial barcode or a UMI) and one capture domain. In some embodiments, the capture probe is immobilized on a capture spot or a substrate via its 5' end and includes from the 5' to 3' end: a cleavage domain, a functional domain, one or more barcodes (e.g., a spatial barcode and/or a UMI), and a capture domain.

In some embodiments, the capture probe is immobilized on a capture spot or a substrate via its 5' end and includes from the 5' to 3' end: a cleavage domain, a functional domain, one or more barcodes (e.g., a spatial barcode and/or a UMI), a second functional domain, and a capture domain. In some embodiments, the capture probe is immobilized on a capture spot or a substrate via its 5' end and includes from the 5' to 3' end: a cleavage domain, a functional domain, a spatial barcode, a UMI, and a capture domain. In some embodiments, the capture probe is immobilized on a capture spot or a substrate via its 5' end and does not include a spatial barcode. In some embodiments, the capture probe is immobilized on a capture spot or a substrate via its 5' end and does not include a UMI. In some embodiments, the capture probe includes a sequence for initiating a sequencing reaction.

In some embodiments, the capture probe is immobilized on a capture spot or a substrate via its 3' end. In some embodiments, the capture probe is immobilized on a capture spot or a substrate via its 3' end and includes from the 3' to 5' end: one or more barcodes (e.g., a spatial barcode and/or a UMI) and one or more capture domains. In some embodiments, the capture probe is immobilized on a capture spot or a substrate via its 3' end and includes from the 3' to 5' end: one barcode (e.g., a spatial barcode or a UMI) and one capture domain. In some embodiments, the capture probe is immobilized on a capture spot or a substrate via its 3' end and includes from the 3' to 5' end: a cleavage domain, a functional domain, one or more barcodes (e.g., a spatial barcode and/or a UMI), and a capture domain. In some embodiments, the capture probe is immobilized on a capture spot or a substrate via its 3' end and includes from the 3' to 5' end: a cleavage domain, a functional domain, a spatial barcode, a UMI, and a capture domain.

The localization of the functional group within the capture probe to be immobilized can be used to control and shape the binding behavior and/or orientation of the capture probe, e.g., the functional group can be placed at the 5' or 3' end of the capture probe or within the sequence of the capture probe. In some embodiments, a capture probe can further include a support (e.g., a support attached to the capture probe, a support attached to the capture spot, or a support attached to the substrate). A typical support for a capture probe to be immobilized includes moieties which are capable of binding to such capture probes, e.g., to amine-functionalized nucleic acids. Examples of such supports are carboxy, aldehyde, or epoxy supports.

In some embodiments, the substrates on which capture probes can be immobilized can be chemically activated, e.g., by the activation of functional groups, available on the substrate. The term "activated substrate" relates to a material in which interacting or reactive chemical functional groups are established or enabled by chemical modification procedures. For example, a substrate including carboxyl groups can be activated before use. Furthermore, certain substrates contain functional groups that can react with specific moieties already present in the capture probes.

In some embodiments, a covalent linkage is used to directly couple a capture probe to a substrate. In some embodiments a capture probe is indirectly coupled to a substrate through a linker separating the "first" nucleotide of the capture probe from the support, i.e., a chemical linker. In some embodiments, a capture probe does not bind directly to the array, but interacts indirectly, for example by binding to a molecule which itself binds directly or indirectly to the array. In some embodiments, the capture probe is indirectly attached to a substrate (e.g., via a solution including a polymer).

In some embodiments, where the capture probe is immobilized on the capture spot of the array indirectly, e.g., via hybridization to a surface probe capable of binding the capture probe, the capture probe can further include an upstream sequence (5' to the sequence that hybridizes to the nucleic acid, e.g., RNA of the tissue sample) that is capable of hybridizing to 5' end of the surface probe. Alone, the capture domain of the capture probe can be seen as a capture domain oligonucleotide, which can be used in the synthesis of the capture probe in embodiments where the capture probe is immobilized on the array indirectly.

In some embodiments, a substrate is comprised of an inert material or matrix (e.g., glass slides) that has been functionalized by, for example, treatment with a material comprising reactive groups which enable immobilization of capture probes. See, for example, WO 2017/019456, the entire contents of which are herein incorporated by reference. Non-limiting examples include polyacrylamide hydrogels supported on an inert substrate (e.g., glass slide; see WO 2005/065814 and U.S. Patent Application No. 2008/0280773, the entire contents of which are incorporated herein by reference).

In some embodiments, functionalized biomolecules (e.g., capture probes) are immobilized on a functionalized substrate using covalent methods. Methods for covalent attachment include, for example, condensation of amines and activated carboxylic esters (e.g., N-hydroxysuccinimide esters); condensation of amine and aldehydes under reductive amination conditions; and cycloaddition reactions such as the Diels-Alder [4+2] reaction, 1,3-dipolar cycloaddition reactions, and [2+2] cycloaddition reactions. Methods for covalent attachment also include, for example, click chemistry reactions, including [3+2] cycloaddition reactions (e.g., Huisgen 1,3-dipolar cycloaddition reaction and copper(I)-catalyzed azide-alkyne cycloaddition (CuAAC)); thiol-ene reactions; the Diels-Alder reaction and inverse electron demand Diels-Alder reaction; [4+1] cycloaddition of isonitriles and tetrazines; and nucleophilic ring-opening of small carbocycles (e.g., epoxide opening with amino oligonucleotides). Methods for covalent attachment also include, for example, maleimides and thiols; and para-nitrophenyl ester-functionalized oligonucleotides and polylysine-functionalized substrate. Methods for covalent attachment also include, for example, disulfide reactions; radical reactions (see, e.g., U.S. Pat. No. 5,919,626, the entire contents of which are herein incorporated by reference); and hydrazide-functionalized substrate (e.g., where the hydrazide functional group is directly or indirectly attached to the substrate) and aldehyde-functionalized oligonucleotides (see, e.g., Yershov et al. (1996) Proc. Natl. Acad. Sci. USA 93, 4913-4918, the entire contents of which are herein incorporated by reference).

In some embodiments, functionalized biomolecules (e.g., capture probes) are immobilized on a functionalized substrate using photochemical covalent methods. Methods for photochemical covalent attachment include, for example, immobilization of antraquinone-conjugated oligonucleotides (see, e.g., Koch et al., 2000, Bioconjugate Chem. 11, 474-483, the entire contents of which is herein incorporated by reference).

In some embodiments, functionalized biomolecules (e.g., capture probes are immobilized on a functionalized substrate using non-covalent methods. Methods for non-covalent attachment include, for example, biotin-functionalized oligonucleotides and streptavidin-treated substrates (see, e.g., Holmstrom et al. (1993) Analytical Biochemistry 209, 278-283 and Gilles et al. (1999) Nature Biotechnology 17, 365-370, the entire contents of which are herein incorporated by reference).

In some embodiments, an oligonucleotide (e.g., a capture probe) can be attached to a substrate or capture spot according to the methods set forth in U.S. Pat. Nos. 6,737,236, 7,259,258, 7,375,234, 7,427,678, 5,610,287, 5,807,522, 5,837,860, and 5,472,881; U.S. Patent Application Publication Nos. 2008/0280773 and 2011/0059865; Shalon et al. (1996) Genome Research, 639-645; Rogers et al. (1999) Analytical Biochemistry 266, 23-30; Stimpson et al. (1995) Proc. Natl. Acad. Sci. USA 92, 6379-6383; Beattie et al. (1995) Clin. Chem. 45, 700-706; Lamture et al. (1994) Nucleic Acids Research 22, 2121-2125; Beier et al. (1999) Nucleic Acids Research 27, 1970-1977; Joos et al. (1997) Analytical Biochemistry 247, 96-101; Nikiforov et al. (1995) Analytical Biochemistry 227, 201-209; Timofeev et al. (1996) Nucleic Acids Research 24, 3142-3148; Chrisey et al. (1996) Nucleic Acids Research 24, 3031-3039; Guo et al. (1994) Nucleic Acids Research 22, 5456-5465; Running and Urdea (1990) BioTechniques 8, 276-279; Fahy et al. (1993) Nucleic Acids Research 21, 1819-1826; Zhang et al. (1991) 19, 3929-3933; and Rogers et al. (1997) Gene Therapy 4, 1387-1392. The entire contents of each of the foregoing documents are incorporated herein by reference.

In some embodiments, the surface of a substrate is coated with a cell permissive coating to facilitate adherence of live cells. A "cell-permissive coating" is a coating that allows or helps cells to maintain cell viability (e.g., remain viable) on the substrate. For example, a cell-permissive coating can enhance cell attachment, cell growth, and/or cell differentiation, e.g., a cell-permissive coating can provide nutrients to the live cells. A cell-permissive coating can include a biological material and/or a synthetic material. Non-limiting examples of a cell-permissive coating include coatings that feature one or more extracellular matrix (ECM) components (e.g., proteoglycans and fibrous proteins such as collagen, elastin, fibronectin and laminin), poly-lysine, poly-L-ornithine, and/or a biocompatible silicone (e.g., CYTOSOFT®). For example, a cell-permissive coating that includes one or more extracellular matrix components can include collagen Type I, collagen Type II, collagen Type IV, elastin, fibronectin, laminin, and/or vitronectin. In some embodiments, the cell-permissive coating includes a solubilized basement membrane preparation extracted from the Engelbreth-Holm-Swarm (EHS) mouse sarcoma (e.g., MATRIGEL®). In some embodiments, the cell-permissive coating includes collagen.

A "conditionally removable coating" is a coating that can be removed from the surface of a substrate upon application of a releasing agent. In some embodiments, a conditionally removable coating includes a hydrogel as described in further detail in U.S. patent application Ser. No. 16/992,569, entitled "Systems and Methods for Using the Spatial Distribution of Haplotypes to Determine a Biological Condition," filed Aug. 13, 2020.

(ii) Generation of Capture Probes in an Array Format.

Arrays can be prepared by a variety of methods. In some embodiments, arrays are prepared through the synthesis (e.g., in-situ synthesis) of oligonucleotides on the array, or by jet printing or lithography. For example, light-directed synthesis of high-density DNA oligonucleotides can be achieved by photolithography or solid-phase DNA synthesis. To implement photolithographic synthesis, synthetic linkers modified with photochemical protecting groups can be attached to a substrate and the photochemical protecting groups can be modified using a photolithographic mask (applied to specific areas of the substrate) and light, thereby producing an array having localized photo-deprotection. Many of these methods are known in the art, and are described e.g., in Miller et al., 2009, "Basic concepts of microarrays and potential applications in clinical microbiology." Clinical microbiology reviews 22.4, 611-633; US201314111482A; U.S. Pat. No. 9,593,365B2; US2019203275; and WO2018091676, which are each incorporated herein by reference in the entirety.

(1) Spotting or Printing

In some embodiments, the arrays are "spotted" or "printed" with oligonucleotides and these oligonucleotides (e.g., capture probes) are then attached to the substrate. The oligonucleotides can be applied by either noncontact or contact printing. A noncontact printer can use the same method as computer printers (e.g., bubble jet or inkjet) to expel small droplets of probe solution onto the substrate. The specialized inkjet-like printer can expel nanoliter to picoliter volume droplets of oligonucleotide solution, instead of ink, onto the substrate. In contact printing, each print pin directly applies the oligonucleotide solution onto a specific location on the surface. The oligonucleotides can be attached to the substrate surface by the electrostatic interaction of the negative charge of the phosphate backbone of the DNA with a positively charged coating of the substrate surface or by UV-cross-linked covalent bonds between the thymidine bases in the DNA and amine groups on the treated substrate surface. In some embodiments, the substrate is a glass slide. In some embodiments, the oligonucleotides (e.g., capture probes) are attached to the substrate by a covalent bond to a chemical matrix, e.g., epoxy-silane, amino-silane, lysine, polyacrylamide, etc.

(2) In Situ Synthesis

The arrays can also be prepared by in situ-synthesis. In some embodiments, these arrays can be prepared using photolithography. Photolithography typically relies on UV masking and light-directed combinatorial chemical synthesis on a substrate to selectively synthesize probes directly on the surface of the array, one nucleotide at a time per spot, for many spots simultaneously. In some embodiments, a substrate contains covalent linker molecules that have a protecting group on the free end that can be removed by light. UV light is directed through a photolithographic mask to deprotect and activate selected sites with hydroxyl groups that initiate coupling with incoming protected nucleotides that attach to the activated sites. The mask is designed in such a way that the exposure sites can be selected, and thus specify the coordinates on the array where each nucleotide can be attached. The process can be repeated, a new mask is applied activating different sets of sites and coupling different bases, allowing arbitrary oligonucleotides to be constructed at each site. This process can be used to synthesize hundreds of thousands of different oligonucleotides. In some embodiments, maskless array synthesizer technology can be used. It uses an array of programmable micromirrors to create digital masks that reflect the desired pattern of UV light to deprotect the features.

In some embodiments, the inkjet spotting process can also be used for in-situ oligonucleotide synthesis. The different nucleotide precursors plus catalyst can be printed on the substrate, and are then combined with coupling and deprotection steps. This method relies on printing picoliter volumes of nucleotides on the array surface in repeated rounds of base-by-base printing that extends the length of the oligonucleotide probes on the array.

(3) Electric Fields

Arrays can also be prepared by active hybridization via electric fields to control nucleic acid transport. Negatively charged nucleic acids can be transported to specific sites, or capture spots, when a positive current is applied to one or more test sites on the array. The surface of the array can contain a binding molecule, e.g., streptavidin, which allows for the formation of bonds (e.g., streptavidin-biotin bonds) once electronically addressed biotinylated probes reach their targeted location. The positive current is then removed from the active capture spots, and new test sites can be activated by the targeted application of a positive current. The process are repeated until all sites on the array are covered.

An array for spatial analysis can be generated by various methods as described herein. In some embodiments, the array has a plurality of capture probes comprising spatial barcodes. These spatial barcodes and their relationship to the locations on the array can be determined. In some cases, such information is readily available, because the oligonucleotides are spotted, printed, or synthesized on the array with a pre-determined pattern. In some cases, the spatial barcode can be decoded by methods described herein, e.g., by in-situ sequencing, by various labels associated with the spatial barcodes etc. In some embodiments, an array can be used a template to generate a daughter array. Thus, the spatial barcode can be transferred to the daughter array with a known pattern.

(4) Ligation

In some embodiments, an array comprising barcoded probes can be generated through ligation of a plurality of oligonucleotides. In some instances, an oligonucleotide of the plurality contains a portion of a barcode, and the complete barcode is generated upon ligation of the plurality of oligonucleotides. For example, a first oligonucleotide containing a first portion of a barcode can be attached to a substrate (e.g., using any of the methods of attaching an oligonucleotide to a substrate described herein), and a second oligonucleotide containing a second portion of the barcode can then be ligated onto the first oligonucleotide to generate a complete barcode. Different combinations of the first, second and any additional portions of a barcode can be used to increase the diversity of the barcodes. In instances where the second oligonucleotide is also attached to the substrate prior to ligation, the first and/or the second oligonucleotide can be attached to the substrate via a surface linker which contains a cleavage site. Upon ligation, the ligated oligonucleotide is linearized by cleaving at the cleavage site.

To increase the diversity of the barcodes, a plurality of second oligonucleotides comprising two or more different barcode sequences can be ligated onto a plurality of first oligonucleotides that comprise the same barcode sequence, thereby generating two or more different species of barcodes. To achieve selective ligation, a first oligonucleotide attached to a substrate containing a first portion of a barcode can initially be protected with a protective group (e.g., a photocleavable protective group), and the protective group can be removed prior to ligation between the first and second oligonucleotide. In instances where the barcoded probes on an array are generated through ligation of two or more oligonucleotides, a concentration gradient of the oligonucleotides can be applied to a substrate such that different combinations of the oligonucleotides are incorporated into a barcoded probe depending on its location on the substrate.

Probes can be generated by directly ligating additional oligonucleotides onto existing oligonucleotides via a splint oligonucleotide. In some embodiments, oligonucleotides on an existing array can include a recognition sequence that can hybridize with a splint oligonucleotide. The recognition sequence can be at the free 5' end or the free 3' end of an oligonucleotide on the existing array. Recognition sequences useful for the methods of the present disclosure may not contain restriction enzyme recognition sites or secondary structures (e.g., hairpins), and may include high contents of guanine and gytosine nucleotides.

(5) Polymerases

Barcoded probes on an array can also be generated by adding single nucleotides to existing oligonucleotides on an array, for example, using polymerases that function in a template-independent manner. Single nucleotides can be added to existing oligonucleotides in a concentration gradient, thereby generating probes with varying length, depending on the location of the probes on the array.

(6) Modification of Existing Capture Probes

Arrays can also be prepared by modifying existing arrays, for example, by modifying the oligonucleotides attached to the arrays. For instance, probes can be generated on an array that comprises oligonucleotides that are attached to the array at the 3' end and have a free 5' end. The oligonucleotides can be in situ synthesized oligonucleotides, and can include a barcode. The length of the oligonucleotides can be less than 50 nucleotides (nts) (e.g., less than 45, 40, 35, 30, 25, 20, 15, or 10 nts). To generate probes using these oligonucleotides, a primer complementary to a portion of an oligonucleotide (e.g., a constant sequence shared by the oligonucleotides) can be used to hybridize with the oligonucleotide and extend (using the oligonucleotide as a template) to form a duplex and to create a 3' overhang. The 3' overhang thus allows additional nucleotides or oligonucleotides to be added on to the duplex. A capture probe can be generated by, for instance, adding one or more oligonucleotides to the end of the 3' overhang (e.g., via splint oligonucleotide mediated ligation), where the added oligonucleotides can include the sequence or a portion of the sequence of a capture domain.

In some embodiments, arrays are prepared according to the methods set forth in WO 2012/140224, WO 2014/060483, WO 2016/162309, WO 2017/019456, WO 2018/091676, and WO 2012/140224, and U.S. Patent Application No. 2018/0245142. The entire contents of the foregoing documents are herein incorporated by reference.

In some embodiments, a capture spot on the array includes a bead. In some embodiments, two or more beads are dispersed onto a substrate to create an array, where each bead is a capture spot on the array. Beads can optionally be dispersed into wells on a substrate, e.g., such that only a single bead is accommodated per well.

Further details and non-limiting embodiments relating to beads, bead arrays, bead properties (e.g., structure, materials, construction, cross-linking, degradation, reagents, and/or optical properties), and for covalently and non-covalently bonding beads to substrates are described in U.S. patent application Ser. No. 16/992,569, U.S. Patent Publication No. 20110059865A1, U.S. Provisional Patent Application No. 62/839,346, U.S. Pat. No. 9,012,022, and PCT publication 202020176788A1 entitled "Profiling of biological analyes with spatially barcoded oligonucleotide arrays" each of which is incorporated herein by reference in its entirety.

(i) Capture Spot Sizes

Capture spots on an array can be a variety of sizes. In some embodiments, a capture spot of an array has a diameter or maximum dimension between 1 µm to 100 µm. In some embodiments, a capture spot of an array has a diameter or maximum dimension of between 1 µm to 10 µm, 1 µm to µm, 1 µm to 30 µm, 1 µm to 40 µm, 1 µm to 50 µm, 1 µm to 60 µm, 1 µm to 70 µm, 1 µm to 80 µm, 1 µm to 90 µm, 90 µm to 100 µm, 80 µm to 100 µm, 70 µm to 100 µm, 60 µm to 100 µm, 50 µm to 100 µm, 40 µm to 100 µm, 30 µm to 100 µm, 20 µm to 100 µm, or 10 µm to 100 µm. In some embodiments, the capture spot has a diameter or maximum dimension between 30 µm to 100 µm, 40 µm to 90 µm, 50 µm to 80 µm, 60 µm to 70 µm, or any range within the disclosed sub-ranges. In some embodiments, the capture spot has a diameter or maximum dimension no larger than 95 µm, 90 µm, 85 µm, 80 µm, 75 µm, 70 µm, 65 µm, 60 µm, 55 µm, 50 µm, 45 µm, 40 µm, 35 µm, 30 µm, µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm. In some embodiments, the capture spot has a diameter or maximum dimension of approximately 65 µm.

In some embodiments, a plurality of capture spots has a mean diameter or mean maximum dimension between 1 µm to 100 µm. For example, between 1 µm to 10 µm, 1 µm to 20 µm, 1 µm to 30 µm, 1 µm to 40 µm, 1 µm to 50 µm, 1 µm to 60 µm, 1 µm to 70 µm, 1 µm to 80 µm, 1 µm to 90 µm, 90 µm to 100 µm, 80 µm to 100 µm, 70 µm to 100 µm, 60 µm to 100 µm, 50 µm to 100 µm, 40 µm to 100 µm, 30 µm to 100 µm, 20 µm to 100 µm, or 10 µm to 100 µm. In some embodiments, the plurality of capture spots has a mean diameter or mean maximum dimension between 30 µm to 100 µm, 40 µm to 90 µm, 50 µm to 80 µm, 60 µm to 70 µm, or any range within the disclosed sub-ranges. In some embodiments, the plurality of capture spots has a mean diameter or a mean maximum dimension no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm. In some embodiments, the plurality of capture spots has a mean average diameter or a mean maximum dimension of approximately 65 µm.

In some embodiments, where the capture spot is a bead, the bead can have a diameter or maximum dimension no larger than 100 µm (e.g., no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm).

In some embodiments, a plurality of beads has an average diameter no larger than 100 µm. In some embodiments, a plurality of beads has an average diameter or maximum dimension no larger than 95 µm, 90 µm, 85 µm, 80 µm, 75 µm, 70 µm, 65 µm, 60 µm, 55 µm, 50 µm, 45 µm, 40 µm, 35

μm, 30 μm, 25 μm, 20 μm, 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm.

In some embodiments, the volume of the bead can be at least about 1 μm$^3$, e.g., at least 1 μm$^3$, 2 μm$^3$, 3 μm$^3$, 4 μm$^3$, 5 μm$^3$, 6 μm$^3$, 7 μm$^3$, 8 μm$^3$, 9 μm$^3$, 10 μm$^3$, 12 μm$^3$, 14 μm$^3$, 16 μm$^3$, 18 μm$^3$, 20 μm$^3$, 25 μm$^3$, 30 μm$^3$, 35 μm$^3$, 40 μm$^3$, 45 μm$^3$, 50 μm$^3$, 55 μm$^3$, 60 μm$^3$, 65 μm$^3$, 70 μm$^3$, 75 μm$^3$, 80 μm$^3$, 85 μm$^3$, 90 μm$^3$, 95 μm$^3$, 100 μm$^3$, 125 μm$^3$, 150 μm$^3$, 175 μm$^3$, 200 μm$^3$, 250 μm$^3$, 300 μm$^3$, 350 μm$^3$, 400 μm$^3$, 450 μm$^3$, μm$^3$, 500 μm$^3$, 550 μm$^3$, 600 μm$^3$, 650 μm$^3$, 700 μm$^3$, 750 μm$^3$, 800 μm$^3$, 850 μm$^3$, 900 μm$^3$, 950 μm$^3$, 1000 μm$^3$, 1200 μm$^3$, 1400 μm$^3$, 1600 μm$^3$, 1800 μm$^3$, 2000 μm$^3$, 2200 μm$^3$, 2400 μm$^3$, 2600 μm$^3$, 2800 μm$^3$, 3000 μm$^3$, or greater.

In some embodiments, the bead can have a volume of between about 1 μm$^3$ and 100 μm$^3$, such as between about 1 μm$^3$ and 10 μm$^3$, between about 10 μm$^3$ and 50 μm$^3$, or between about 50 μm$^3$ and 100 μm$^3$. In some embodiments, the bead can include a volume of between about 100 μm$^3$ and 1000 μm$^3$, such as between about 100 μm$^3$ and 500 μm$^3$ or between about 500 μm$^3$ and 1000 μm$^3$. In some embodiments, the bead can include a volume between about 1000 μm$^3$ and 3000 μm$^3$, such as between about 1000 μm$^3$ and 2000 μm$^3$ or between about 2000 μm$^3$ and 3000 μm$^3$. In some embodiments, the bead can include a volume between about 1 μm$^3$ and 3000 μm$^3$, such as between about 1 μm$^3$ and 2000 μm$^3$, between about 1 μm$^3$ and 1000 μm$^3$, between about 1 μm$^3$ and 500 μm$^3$, or between about 1 μm$^3$ and 250 μm$^3$.

The capture spot can include one or more cross-sections that can be the same or different. In some embodiments, the capture spot can have a first cross-section that is different from a second cross-section. The capture spot can have a first cross-section that is at least about 0.0001 micrometer, 0.001 micrometer, 0.01 micrometer, 0.1 micrometer, or 1 micrometer. In some embodiments, the capture spot can include a cross-section (e.g., a first cross-section) of at least about 1 micrometer (m), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 am, 55 μm, 60 μm, 65 μm, 70 μm, 75 μm, 80 μm, 85 μm, 90 μm, 100 μm, 120 μm, 140 μm, 160 μm, 180 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), or greater. In some embodiments, the capture spot can include a cross-section (e.g., a first cross-section) of between about 1 μm and 500 μm, such as between about 1 μm and 100 μm, between about 100 μm and 200 am, between about 200 μm and 300 μm, between about 300 μm and 400 μm, or between about 400 μm and 500 μm. For example, the capture spot can include a cross-section (e.g., a first cross-section) of between about 1 μm and 100 μm. In some embodiments, the capture spot can have a second cross-section that is at least about 1 μm. For example, the capture spot can include a second cross-section of at least about 1 micrometer (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 100 μm, 120 μm, 140 μm, 160 μm, 180 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), or greater. In some embodiments, the capture spot can include a second cross-section of between about 1 μm and 500 μm, such as between about 1 μm and 100 μm, between about 100 μm and 200 μm, between about 200 μm and 300 μm, between about 300 μm and 400 μm, or between about 400 μm and 500 μm. For example, the capture spot can include a second cross-section of between about 1 μm and 100 μm.

In some embodiments, capture spots can be of a nanometer scale (e.g., capture spots can have a diameter or maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). A plurality of capture spots can have an average diameter or average maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). In some embodiments, a capture spot has a diameter or size that is about the size of a single cell (e.g., a single cell under evaluation).

Capture spots can be of uniform size or heterogeneous size. "Polydispersity" generally refers to heterogeneity of sizes of molecules or particles. The polydispersity (PDI) can be calculated using the equation $PDI = Mw/Mn$, where Mw is the weight-average molar mass and Mn is the number-average molar mass. In certain embodiments, capture spots can be provided as a population or plurality of capture spots having a relatively monodisperse size distribution. Where it can be desirable to provide relatively consistent amounts of reagents, maintaining relatively consistent capture spot characteristics, such as size, can contribute to the overall consistency.

In some embodiments, the beads provided herein can have size distributions that have a coefficient of variation in their cross-sectional dimensions of less than 50%, less than 40%, less than 30%, less than 20%, less than 15%, less than 10%, less than 5%, or lower. In some embodiments, a plurality of beads provided herein has a polydispersity index of less than 50%, less than 45%, less than 40%, less than 35%, less than 30%, less than 25%, less than 20%, less than 15%, less than 10%, less than 5%, or lower.

(ii) Capture Spot Density

In some embodiments, an array (e.g., two-dimensional array) comprises a plurality number of capture spots. In some embodiments, an array includes between 4000 and 10,000 capture spots, or any range within 4000 to 6000 capture spots. For example, an array includes between 4,000 to 4,400 capture spots, 4,000 to 4,800 capture spots, 4,000 to 5,200 capture spots, 4,000 to 5,600 capture spots, 5,600 to 6,000 capture spots, 5,200 to 6,000 capture spots, 4,800 to 6,000 capture spots, or 4,400 to 6,000 capture spots. In some embodiments, the array includes between 4,100 and 5,900 capture spots, between 4,200 and 5,800 capture spots, between 4,300 and 5,700 capture spots, between 4,400 and 5,600 capture spots, between 4,500 and 5,500 capture spots, between 4,600 and 5,400 capture spots, between 4,700 and 5,300 capture spots, between 4,800 and 5,200 capture spots, between 4,900 and 5,100 capture spots, or any range within the disclosed sub-ranges. For example, the array can include about 4,000 capture spots, about 4,200 capture spot, about 4,400 capture spots, about 4,800 capture spots, about 5,000 capture spots, about 5,200 capture spots, about 5,400 capture spots, about 5,600 capture spots, or about 6,000 capture spots. In some embodiments, the array comprises at least 4,000 capture spots. In some embodiments, the array includes approximately 5,000 capture spots.

In some embodiments, the capture spots of the array can be arranged in a pattern. In some embodiments, the center of a capture spot of an array is between 1 µm and 100 µm from the center of another capture spot of the array. For example, the center of a capture spot is between 20 µm to µm, 20 µm to 60 µm, 20 µm to 80 µm, 80 µm to 100 µm, 60 µm to 100 µm, or 40 µm to 100 µm from the center of another capture spot of the array. In some embodiments, the center of a capture spot of an array is between 30 µm and 100 µm, 40 µm and 90 µm, 50 µm and 80 µm, 60 µm and 70 µm, or any range within the disclosed sub-ranges from the center of another capture spot of the array. In some embodiments, the center of a capture spot of an array is approximately 65 µm from the center of another capture spot of the array. In some embodiments, the center of a capture spot of an array is between 80 µm to 120 µm from the center of another capture spot of the array.

In some embodiments, a plurality of capture spots of an array are uniformly positioned. In some embodiments, a plurality of capture spots of an array are not uniformly positioned. In some embodiments, the positions of a plurality of capture spots of an array are predetermined. In some embodiments, the positioned of a plurality of capture spots of an array are not predetermined.

In some embodiments, the size and/or shape of a plurality of capture spots of an array are approximately uniform. In some embodiments, the size and/or shape of a plurality of capture spots of an array is substantially not uniform.

In some embodiments, an array is approximately 8 mm by 8 mm. In some embodiments, an array is smaller than 8 mm by 8 mm.

In some embodiments, the array can be a high density array. In some embodiments, the high density array can be arranged in a pattern. In some embodiments, the high-density pattern of the array is produced by compacting or compressing capture spots together in one or more dimensions. In some embodiments, a high-density pattern may be created by spot printing or other techniques described herein. In some embodiments, the center of a capture spots of the array is between 80 µm and 120 µm from the center of another capture spot of the array. In some embodiments, the center of a capture spot of the array is between 85 µm and 115 µm, between 90 µm and 110 µm, 95 µm and 105 µm, or any range within the disclosed sub-ranges from the center of another capture spot of the array. In some embodiments, the center of a capture spot of the array is approximately 100 µm from the center of another capture spot of the array.

(iii) Array Resolution

As used herein, a "low resolution" array (e.g., a low resolution spatial array) refers to an array with capture spots having an average diameter of about 20 microns or greater. In some embodiments, substantially all (e.g., 80% or more) of the capture probes within a single capture spot include the same barcode (e.g., spatial barcode) such that upon deconvolution, resulting sequencing data from the detection of one or more analytes can be correlated with the spatial barcode of the capture spot, thereby identifying the location of the capture spot on the array, and thus determining the location of the one or more analytes in the sample.

A "high-resolution" array refers to an array with capture spots having an average diameter of about 1 micron to about 10 microns. This range in average diameter of capture spots corresponds to the approximate diameter of a single mammalian cell. Thus, a high-resolution spatial array is capable of detecting analytes at, or below, mammalian single-cell scale.

In some embodiments, resolution of an array can be improved by constructing an array with smaller capture spots. In some embodiments, resolution of an array can be improved by increasing the number of capture spots in the array. In some embodiments, the resolution of an array can be improved by packing capture spots closer together. For example, arrays including 5,000 capture spots were determined to provide higher resolution as compared to arrays including 1,000 capture spots (data not shown).

In some embodiments, the capture spots of the array may be arranged in a pattern, and in some cases, high-density pattern. In some embodiments, the high-density pattern of the array is produced by compacting or compressing capture spots together in one or more dimensions. In some embodiments, a high-density pattern may be created by spot printing or other techniques described herein. The number of median genes captures per cell and the median UMI counts per cell were higher when an array including 5,000 capture spots was used as compared to array including 1,000 capture spots (data not shown).

In some embodiments, an array includes a capture spot, where the capture spot incudes one or more capture probes (e.g., any of the capture probes described herein).

(e) Analyte Capture

In this section, general aspects of systems and methods for capturing analytes are described. Individual method steps and system features can be present in combination in many different embodiments; the specific combinations described herein do not in any way limit other combinations of steps and features.

Generally, analytes can be captured when contacting a sample with, e.g., a substrate comprising capture probes (e.g., substrate with capture probes embedded, spotted, printed on the substrate or a substrate with capture spots (e.g., beads, wells) comprising capture probes).

As used herein, "contact," "contacted," and/or "contacting," a sample with a substrate comprising capture spots refers to any contact (e.g., direct or indirect) such that capture probes can interact (e.g., capture) with analytes from the sample. For example, the substrate may be near or adjacent to the sample without direct physical contact, yet capable of capturing analytes from the sample. In some embodiments the sample is in direct physical contact with the substrate. In some embodiments, the sample is in indirect physical contact with the substrate. For example, a liquid layer may be between the sample and the substrate. In some embodiments, the analytes diffuse through the liquid layer. In some embodiments the capture probes diffuse through the liquid layer. In some embodiments reagents may be delivered via the liquid layer between the sample and the substrate. In some embodiments, indirect physical contact may be the presence of a second substrate (e.g., a hydrogel, a film, a porous membrane) between the sample and the first substrate comprising capture spots with capture probes. In some embodiments, reagents are delivered by the second substrate to the sample.

(i) Diffusion-Resistant Media/Lids

To increase efficiency by encouraging analyte diffusion toward the spatially-labelled capture probes, a diffusion-resistant medium can be used. In general, molecular diffusion of biological analytes occurs in all directions, including toward the capture probes (e.g. toward the spatially-barcoded array), and away from the capture probes (e.g. into the bulk solution). Increasing diffusion toward the spatially-barcoded array reduces analyte diffusion away from the spatially-barcoded array and increases the capturing efficiency of the capture probes.

In some embodiments, a sample is placed on the top of a spatially-barcoded substrate and a diffusion-resistant medium is placed on top of the sample. For example, the diffusion-resistant medium can be placed onto an array that has been placed in contact with a sample. In some embodiments, the diffusion-resistant medium and spatially-labelled array are the same component. For example, the diffusion-resistant medium can contain spatially-labelled capture probes within or on the diffusion-resistant medium (e.g., coverslip, slide, hydrogel, or membrane). In some embodiments, a sample is placed on a support and a diffusion-resistant medium is placed on top of the sample. Additionally, a spatially-barcoded capture probe array can be placed in close proximity over the diffusion-resistant medium. For example, a diffusion-resistant medium may be sandwiched between a spatially-labelled array and a sample on a support. In some embodiments, the diffusion-resistant medium is disposed or spotted onto the sample. In other embodiments, the diffusion-resistant medium is placed in close proximity to the sample.

In general, the diffusion-resistant medium can be any material known to limit diffusivity of biological analytes. For example, the diffusion-resistant medium can be a solid lid (e.g., coverslip or glass slide). In some embodiments, the diffusion-resistant medium may be made of glass, silicon, paper, hydrogel polymer monoliths, or other material. In some embodiments, the glass side can be an acrylated glass slide. In some embodiments, the diffusion-resistant medium is a porous membrane. In some embodiments, the material may be naturally porous. In some embodiments, the material may have pores or wells etched into solid material. In some embodiments, the pore size can be manipulated to minimize loss of target analytes. In some embodiments, the membrane chemistry can be manipulated to minimize loss of target analytes. In some embodiments, the diffusion-resistant medium (i.e. hydrogel) is covalently attached to a solid support (i.e. glass slide). In some embodiments, the diffusion-resistant medium can be any material known to limit diffusivity of polyA transcripts. In some embodiments, the diffusion-resistant medium can be any material known to limit the diffusivity of proteins. In some embodiments, the diffusion-resistant medium can be any material know to limit the diffusivity of macromolecular constituents.

In some embodiments, a diffusion-resistant medium includes one or more diffusion-resistant media. For example, one or more diffusion-resistant media can be combined in a variety of ways prior to placing the media in contact with a sample including, without limitation, coating, layering, or spotting. As another example, a hydrogel can be placed onto a sample followed by placement of a lid (e.g., glass slide) on top of the hydrogel.

In some embodiments, a force (e.g., hydrodynamic pressure, ultrasonic vibration, solute contrasts, microwave radiation, vascular circulation, or other electrical, mechanical, magnetic, centrifugal, and/or thermal forces) is applied to control diffusion and enhance analyte capture. In some embodiments, one or more forces and one or more diffusion-resistant media are used to control diffusion and enhance capture. For example, a centrifugal force and a glass slide can used contemporaneously. Any of a variety of combinations of a force and a diffusion-resistant medium can be used to control or mitigate diffusion and enhance analyte capture.

In some embodiments, the diffusion-resistant medium, along with the spatially-barcoded array and sample, is submerged in a bulk solution. In some embodiments, the bulk solution includes permeabilization reagents. In some embodiments, the diffusion-resistant medium includes at least one permeabilization reagent. In some embodiments, the diffusion-resistant medium (i.e. hydrogel) is soaked in permeabilization reagents before contacting the diffusion-resistant medium to the sample. In some embodiments, the diffusion-resistant medium can include wells (e.g., micro-, nano-, or picowells) containing a permeabilization buffer or reagents. In some embodiments, the diffusion-resistant medium can include permeabilization reagents. In some embodiments, the diffusion-resistant medium can contain dried reagents or monomers to deliver permeabilization reagents when the diffusion-resistant medium is applied to a sample. In some embodiments, the diffusion-resistant medium is added to the spatially-barcoded array and sample assembly before the assembly is submerged in a bulk solution. In some embodiments, the diffusion-resistant medium is added to the spatially-barcoded array and sample assembly after the sample has been exposed to permeabilization reagents. In some embodiments, the permeabilization reagents are flowed through a microfluidic chamber or channel over the diffusion-resistant medium. In some embodiments, the flow controls the sample's access to the permeabilization reagents. In some embodiments, the target analytes diffuse out of the sample and toward a bulk solution and get embedded in a spatially-labelled capture probe-embedded diffusion-resistant medium.

Figure 13:
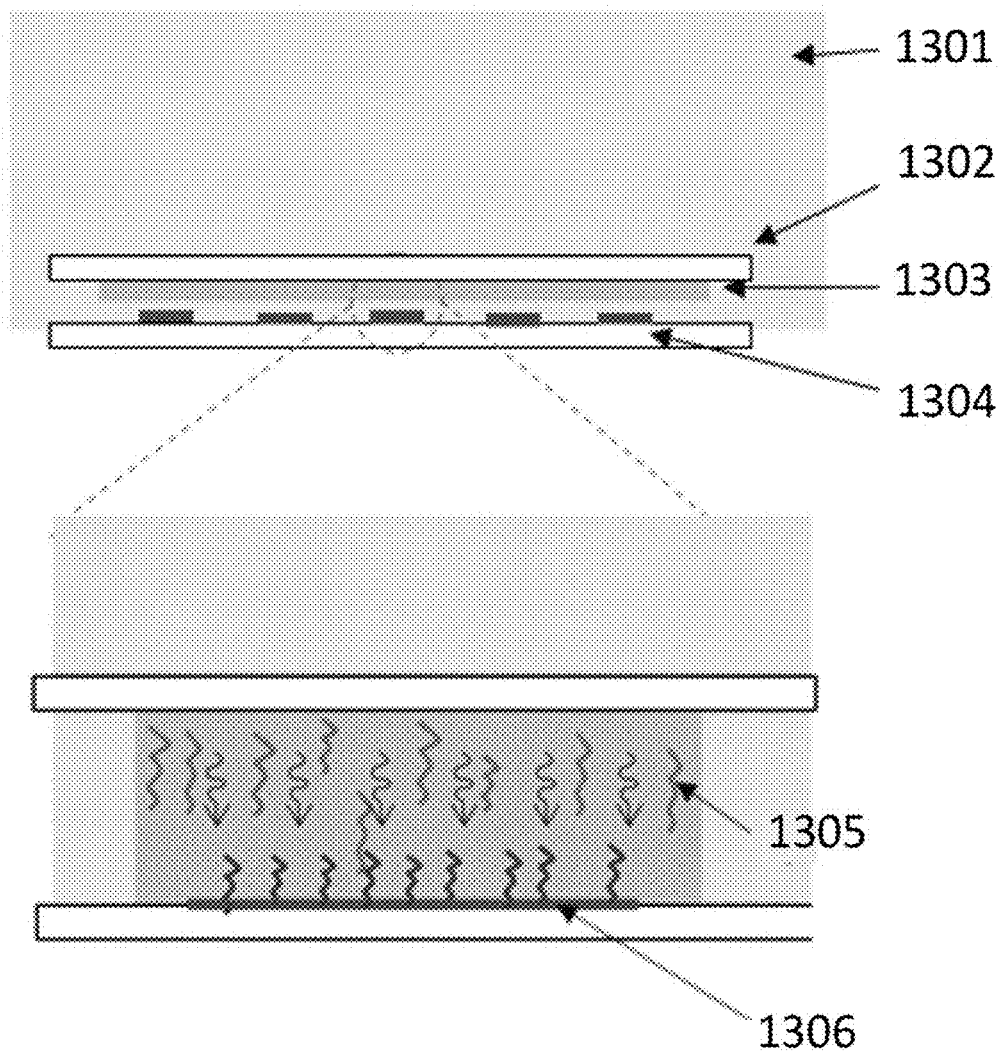
FIG. 13 is a schematic illustrating a side view of a diffusion-resistant medium, e.g., a lid in accordance with some embodiments of the present disclosure.

FIG. 13 is an illustration of an exemplary use of a diffusion-resistant medium. A diffusion-resistant medium 1302 can be contacted with a sample 1303. In FIG. 13, a glass slide 1304 is populated with spatially-barcoded capture probes 1306, and the sample 1303, 1305 is contacted with the array 1304, 1306. A diffusion-resistant medium 1302 can be applied to the sample 1303, where the sample 1303 is sandwiched between a diffusion-resistant medium 1302 and a capture probe coated slide 1304. When a permeabilization solution 1301 is applied to the sample, using the diffusion-resistant medium/lid 1302 directs migration of the analytes 1305 toward the capture probes 1306 by reducing diffusion of the analytes out into the medium. Alternatively, the lid may contain permeabilization reagents.

(ii) Conditions for Capture

Capture probes on the substrate (or on a capture spot on the substrate) interact with released analytes through a capture domain, described elsewhere, to capture analytes. In some embodiments, certain steps are performed to enhance the transfer or capture of analytes by the capture probes of the array. Examples of such modifications include, but are not limited to, adjusting conditions for contacting the substrate with a sample (e.g., time, temperature, orientation, pH levels, pre-treating of samples, etc.), using force to transport analytes (e.g., electrophoretic, centrifugal, mechanical, etc.), performing amplification reactions to increase the amount of biological analytes (e.g., PCR amplification, in situ amplification, clonal amplification), and/or using labeled probes for detecting of amplicons and barcodes.

In some embodiments, capture of analytes is facilitated by treating the sample with permeabilization reagents. If a sample is not permeabilized sufficiently, the amount of analyte captured on the substrate can be too low to enable adequate analysis. Conversely, if the sample is too permeable, the analyte can diffuse away from its origin in the sample, such that the relative spatial relationship of the analytes within the sample is lost. Hence, a balance between permeabilizing the sample enough to obtain good signal intensity while still maintaining the spatial resolution of the analyte distribution in the sample is desired. Methods of preparing samples to facilitation are known in the art and can be modified depending on the sample and how the sample is prepared (e.g., fresh frozen, FFPE, etc).

(iii) Passive Capture Methods

In some embodiments, analytes are migrated from a sample to a substrate. Methods for facilitating migration can be passive (e.g., diffusion) and/or active (e.g., electrophoretic migration of nucleic acids). Non-limiting examples of passive migration can include simple diffusion and osmotic pressure created by the rehydration of dehydrated objects.

Passive migration by diffusion uses concentration gradients. Diffusion is movement of untethered objects toward equilibrium. Therefore, when there is a region of high object concentration and a region of low object concentration, the object (capture probe, the analyte, etc.) moves to an area of lower concentration. In some embodiments, untethered analytes move down a concentration gradient.

In some embodiments, different reagents are added to the sample, such that the sample is rehydrated while improving capture of analytes. In some embodiments, the sample is rehydrated with permeabilization reagents. In some embodiments, the sample is rehydrated with a staining solution (e.g., hematoxylin and eosin stain).

(iv) Active Capture Methods

In some examples of any of the methods described herein, an analyte in a cell or a sample can be transported (e.g., passively or actively) to a capture probe (e.g., a capture probe affixed to a solid surface).

For example, analytes in a cell or a sample can be transported to a capture probe (e.g., an immobilized capture probe) using an electric field (e.g., using electrophoresis), a pressure gradient, fluid flow, a chemical concentration gradient, a temperature gradient, and/or a magnetic field. For example, analytes can be transported through, e.g., a gel (e.g., hydrogel matrix), a fluid, or a permeabilized cell, to a capture probe (e.g., an immobilized capture probe).

In some examples, an electrophoretic field can be applied to analytes to facilitate migration of the analytes towards a capture probe. In some examples, a sample contacts a substrate and capture probes fixed on a substrate (e.g., a slide, cover slip, or bead), and an electric current is applied to promote the directional migration of charged analytes towards the capture probes fixed on the substrate. An electrophoresis assembly, where a cell or a sample is in contact with a cathode and capture probes (e.g., capture probes fixed on a substrate), and where the capture probes (e.g., capture probes fixed on a substrate) is in contact with the cell or sample and an anode, can be used to apply the current.

Electrophoretic transfer of analytes can be performed while retaining the relative spatial alignment of the analytes in the sample. As such, an analyte captured by the capture probes (e.g., capture probes fixed on a substrate) retains the spatial information of the cell or the sample.

In some examples, a spatially-addressable microelectrode array is used for spatially-constrained capture of at least one charged analyte of interest by a capture probe. The microelectrode array can be configured to include a high density of discrete sites having a small area for applying an electric field to promote the migration of charged analyte(s) of interest. For example, electrophoretic capture can be performed on a region of interest using a spatially-addressable microelectrode array.

(v) Region of Interest

A sample can have regions that show morphological feature(s) that may indicate the presence of disease or the development of a disease phenotype. For example, morphological features at a specific site within a tumor biopsy sample can indicate the aggressiveness, therapeutic resistance, metastatic potential, migration, stage, diagnosis, and/or prognosis of cancer in a subject. A change in the morphological features at a specific site within a tumor biopsy sample often correlate with a change in the level or expression of an analyte in a cell within the specific site, which can, in turn, be used to provide information regarding the aggressiveness, therapeutic resistance, metastatic potential, migration, stage, diagnosis, and/or prognosis of cancer in a subject. A region or area within a sample that is selected for specific analysis (e.g., a region in a sample that has morphological features of interest) is often described as "a region of interest."

A region of interest in a sample can be used to analyze a specific area of interest within a sample, and thereby, focus experimentation and data gathering to a specific region of a biological sample (rather than an entire biological sample). This results in increased time efficiency of the analysis of a sample.

A region of interest can be identified in a sample using a variety of different techniques, e.g., expansion microscopy, bright field microscopy, dark field microscopy, phase contrast microscopy, electron microscopy, fluorescence microscopy, reflection microscopy, interference microscopy, and confocal microscopy, and combinations thereof. For example, the staining and imaging of a sample can be performed to identify a region of interest. In some examples, the region of interest can correspond to a specific structure of cytoarchitecture. In some embodiments, a sample can be stained prior to visualization to provide contrast between the different regions of the sample. The type of stain can be chosen depending on the type of sample and the region of the cells to be stained. In some embodiments, more than one stain can be used to visualize different aspects of the sample, e.g., different regions of the sample, specific cell structures (e.g., organelles), or different cell types. In other embodiments, the sample can be visualized or imaged without staining the sample.

In some embodiments, imaging can be performed using one or more fiducial markers, i.e., objects placed in the field of view of an imaging system which appear in the image produced. Fiducial markers are typically used as a point of reference or measurement scale. Fiducial markers can include, but are not limited to, detectable labels such as fluorescent, radioactive, chemiluminescent, calorimetric, and colorimetric labels. The use of fiducial markers to stabilize and orient samples is described, for example, in Carter et al., 2007, *Applied Optics* 46:421-427), the entire contents of which are incorporated herein by reference.

In some embodiments, a fiducial marker can be present on a substrate to provide orientation of the sample. In some embodiments, a microsphere can be coupled to a substrate to aid in orientation of the sample. In some examples, a microsphere coupled to a substrate can produce an optical signal (e.g., fluorescence). In another example, a microsphere can be attached to a portion (e.g., corner) of an array in a specific pattern or design (e.g., hexagonal design) to aid in orientation of a sample on an array of capture spots on the substrate. In some embodiments, a fiducial marker can be an immobilized molecule with which a detectable signal molecule can interact to generate a signal. For example, a marker nucleic acid can be linked or coupled to a chemical moiety capable of fluorescing when subjected to light of a specific wavelength (or range of wavelengths). Such a marker nucleic acid molecule can be contacted with an array before, contemporaneously with, or after the tissue sample is stained to visualize or image the tissue section. Although not required, it can be advantageous to use a marker that can be detected using the same conditions (e.g., imaging conditions) used to detect a labelled cDNA.

In some embodiments, fiducial markers are included to facilitate the orientation of a tissue sample or an image thereof in relation to an immobilized capture probes on a substrate. Any number of methods for marking an array can be used such that a marker is detectable only when a tissue section is imaged. For instance, a molecule, e.g., a fluorescent molecule that generates a signal, can be immobilized directly or indirectly on the surface of a substrate. Markers can be provided on a substrate in a pattern (e.g., an edge, one or more rows, one or more lines, etc.).

In some embodiments, a fiducial marker can be randomly placed in the field of view. For example, an oligonucleotide containing a fluorophore can be randomly printed, stamped, synthesized, or attached to a substrate (e.g., a glass slide) at a random position on the substrate. A tissue section can be contacted with the substrate such that the oligonucleotide containing the fluorophore contacts, or is in proximity to, a cell from the tissue section or a component of the cell (e.g., an mRNA or DNA molecule). An image of the substrate and the tissue section can be obtained, and the position of the fluorophore within the tissue section image can be determined (e.g., by reviewing an optical image of the tissue section overlaid with the fluorophore detection). In some embodiments, fiducial markers can be precisely placed in the field of view (e.g., at known locations on a substrate). In this instance, a fiducial marker can be stamped, attached, or synthesized on the substrate and contacted with a sample. Typically, an image of the sample and the fiducial marker is taken, and the position of the fiducial marker on the substrate can be confirmed by viewing the image.

In some examples, fiducial markers can surround the array. In some embodiments the fiducial markers allow for detection of, e.g., mirroring. In some embodiments, the fiducial markers may completely surround the array. In some embodiments, the fiducial markers may not completely surround the array. In some embodiments, the fiducial markers identify the corners of the array. In some embodiments, one or more fiducial markers identify the center of the array. In some embodiments, the fiducial markers comprise patterned spots, where the diameter of one or more patterned spot fiducial markers is approximately 100 micrometers. The diameter of the fiducial markers can be any useful diameter including, but not limited to, 50 micrometers to 500 micrometers in diameter. The fiducial markers may be arranged in such a way that the center of one fiducial marker is between 100 micrometers and 200 micrometers from the center of one or more other fiducial markers surrounding the array. In some embodiments, the array with the surrounding fiducial markers is approximately 8 mm by 8 mm. In some embodiments, the array without the surrounding fiducial markers is smaller than 8 mm by 8 mm.

In some embodiments, staining and imaging a sample prior to contacting the sample with a spatial array is performed to select samples for spatial analysis. In some embodiments, the staining includes applying a fiducial marker as described above, including fluorescent, radioactive, chemiluminescent, calorimetric, or colorimetric detectable markers. In some embodiments, the staining and imaging of samples allows the user to identify the specific sample (or region of interest) the user wishes to assess.

In some embodiments, a lookup table (LUT) can be used to associate one property with another property of a capture spot. These properties include, e.g., locations, barcodes (e.g., nucleic acid barcode molecules), spatial barcodes, optical labels, molecular tags, and other properties.

In some embodiments, a lookup table can associate a nucleic acid barcode molecule with a capture spot. In some embodiments, an optical label of a capture spot can permit associating the capture spot with a biological particle (e.g., cell or nuclei). The association of a capture spot with a biological particle can further permit associating a nucleic acid sequence of a nucleic acid molecule of the biological particle to one or more physical properties of the biological particle (e.g., a type of a cell or a location of the cell). For example, based on the relationship between the barcode and the optical label, the optical label can be used to determine the location of a capture spot, thus associating the location of the capture spot with the barcode sequence of the capture spot. Subsequent analysis (e.g., sequencing) can associate the barcode sequence and the analyte from the sample. Accordingly, based on the relationship between the location and the barcode sequence, the location of the biological analyte can be determined (e.g., in a specific type of cell or in a cell at a specific location of the sample).

In some embodiments, a capture spot can have a plurality of nucleic acid barcode molecules attached thereto. The plurality of nucleic acid barcode molecules can include barcode sequences. The plurality of nucleic acid molecules attached to a given capture spot can have the same barcode sequences, or two or more different barcode sequences. Different barcode sequences can be used to provide improved spatial location accuracy.

In some embodiments, a substrate is treated in order to minimize or reduce non-specific analyte hybridization within or between capture spots. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Publication Nos. U.S. 2017/0253918 and U.S. 2018/0052081, can be used. The entire contents of each of the foregoing documents are incorporated herein by reference.

Treatment can include adding a functional group that is reactive or capable of being activated such that it becomes reactive after receiving a stimulus (e.g., photoreactive). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

In some examples, an array (e.g., any of the exemplary arrays described herein) can be contained with only a portion of a sample (e.g., a cell, a feature, or a region of interest). In some examples, a sample is contacted with only a portion of an array (e.g., any of the exemplary arrays described herein). In some examples, a portion of the array can be deactivated such that it does not interact with the analytes in the sample (e.g., optical deactivation, chemical deactivation, heat deactivation, or blocking of the capture probes in the array (e.g., using blocking probes)). In some examples, a region of interest can be removed from a sample and then the region of interest can be contacted to the array (e.g., any of the arrays described herein). A region of interest can be removed from a sample using microsurgery, laser capture microdissection, chunking, a microtome, dicing, trypsinization, labelling, and/or fluorescence-assisted cell sorting.

(f) Analysis of Captured Analytes

In some embodiments, after contacting a sample with a substrate that includes capture probes, a removal step can optionally be performed to remove all or a portion of the sample from the substrate. In some embodiments, the removal step includes enzymatic and/or chemical degradation of cells of the sample. For example, the removal step can include treating the sample with an enzyme (e.g., a proteinase, e.g., proteinase K) to remove at least a portion of the sample from the substrate. In some embodiments, the removal step can include ablation of the tissue (e.g., laser ablation).

In some embodiments, a method for spatially detecting an analyte (e.g., detecting the location of an analyte, e.g., a biological analyte) from a sample (e.g., present in a biological sample), comprises: (a) optionally staining and/or imaging a sample on a substrate; (b) permeabilizing (e.g., providing a solution comprising a permeabilization reagent to) the sample on the substrate; (c) contacting the sample with an array comprising a plurality of capture probes, where a capture probe of the plurality captures the biological analyte; and (d) analyzing the captured biological analyte, thereby spatially detecting the biological analyte; where the sample is fully or partially removed from the substrate.

In some embodiments, a sample is not removed from the substrate. For example, the sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the sample is not removed from the substrate prior to analysis of an analyte bound to a capture probe after it is released from the substrate. In some embodiments, the sample remains on the substrate during removal of a capture probe from the substrate and/or analysis of an analyte bound to the capture probe after it is released from the substrate. In some embodiments, analysis of an analyte bound to capture probe from the substrate can be performed without subjecting the sample to enzymatic and/or chemical degradation of the cells (e.g., permeabilized cells) or ablation of the tissue (e.g., laser ablation).

In some embodiments, at least a portion of the sample is not removed from the substrate. For example, a portion of the sample can remain on the substrate prior to releasing a capture probe (e.g., a capture prove bound to an analyte) from the substrate and/or analyzing an analyte bound to a capture probe released from the substrate. In some embodiments, at least a portion of the sample is not subjected to enzymatic and/or chemical degradation of the cells (e.g., permeabilized cells) or ablation of the tissue (e.g., laser ablation) prior to analysis of an analyte bound to a capture probe from the support.

In some embodiments, a method for spatially detecting an analyte (e.g., detecting the location of an analyte, e.g., a biological analyte) from a sample (e.g., present in a biological sample) comprises: (a) optionally staining and/or imaging a sample on a substrate; (b) permeabilizing (e.g., providing a solution comprising a permeabilization reagent to) the sample on the substrate; (c) contacting the sample with an array comprising a plurality of capture probes, where a capture probe of the plurality captures the biological analyte; and (d) analyzing the captured biological analyte, thereby spatially detecting the biological analyte; where the sample is not removed from the substrate.

In some embodiments, a method for spatially detecting a biological analyte of interest from a biological sample comprises: (a) staining and imaging a sample on a support; (b) providing a solution comprising a permeabilization reagent to the sample on the support; (c) contacting the sample with an array on a substrate, where the array comprises one or more capture probe pluralities thereby allowing the one or more pluralities of capture probes to capture the biological analyte of interest; and (d) analyzing the captured biological analyte, thereby spatially detecting the biological analyte of interest; where the sample is not removed from the support.

In some embodiments, the method further includes selecting a region of interest in the sample to subject to spatial transcriptomic analysis. In some embodiments, one or more of the one or more capture probes include a capture domain. In some embodiments, one or more of the one or more capture probe pluralities comprise a unique molecular identifier (UMI). In some embodiments, one or more of the one or more capture probe pluralities comprise a cleavage domain. In some embodiments, the cleavage domain comprises a sequence recognized and cleaved by a uracil-DNA glycosylase, apurinic/apyrimidinic (AP) endonuclease (APE1), U uracil-specific excision reagent (USER), and/or an endonuclease VIII. In some embodiments, one or more capture probes do not comprise a cleavage domain and is not cleaved from the array.

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, the methods described herein can be used to assess analyte levels and/or expression in a cell or a sample over time (e.g., before or after treatment with an agent or different stages of differentiation). In some examples, the methods described herein can be performed on multiple similar samples or cells obtained from the subject at a different time points (e.g., before or after treatment with an agent, different stages of differentiation, different stages of disease progression, different ages of the subject, or before or after development of resistance to an agent).

Further details and non-limiting embodiments relating to removal of sample from the array, release and amplification of analytes, analysis of captured analytes (e.g. by sequencing and/or multiplexing), and spatial resolution of analyte information (e.g., using lookup tables) are described in U.S. patent application Ser. No. 16/992,569 entitled "Systems and Methods for Using the Spatial Distribution of Haplotypes to Determine a Biological Condition," filed Aug. 13, 2019, which is hereby incorporated herein by reference.

III. Specific Embodiments of Systems and Methods for Spatial Analysis of Analytes Using Fiducial Alignment This disclosure also provides methods and systems for spatial analysis of analytes. Provided below are detailed descriptions and explanations of various embodiments of the present disclosure. These embodiments are non-limiting and do not preclude any alternatives, variations, changes, and substitutions that can occur to those skilled in the art from the scope of this disclosure.

(a) Systems for Spatial Analysis of Analytes

Figure 11A:
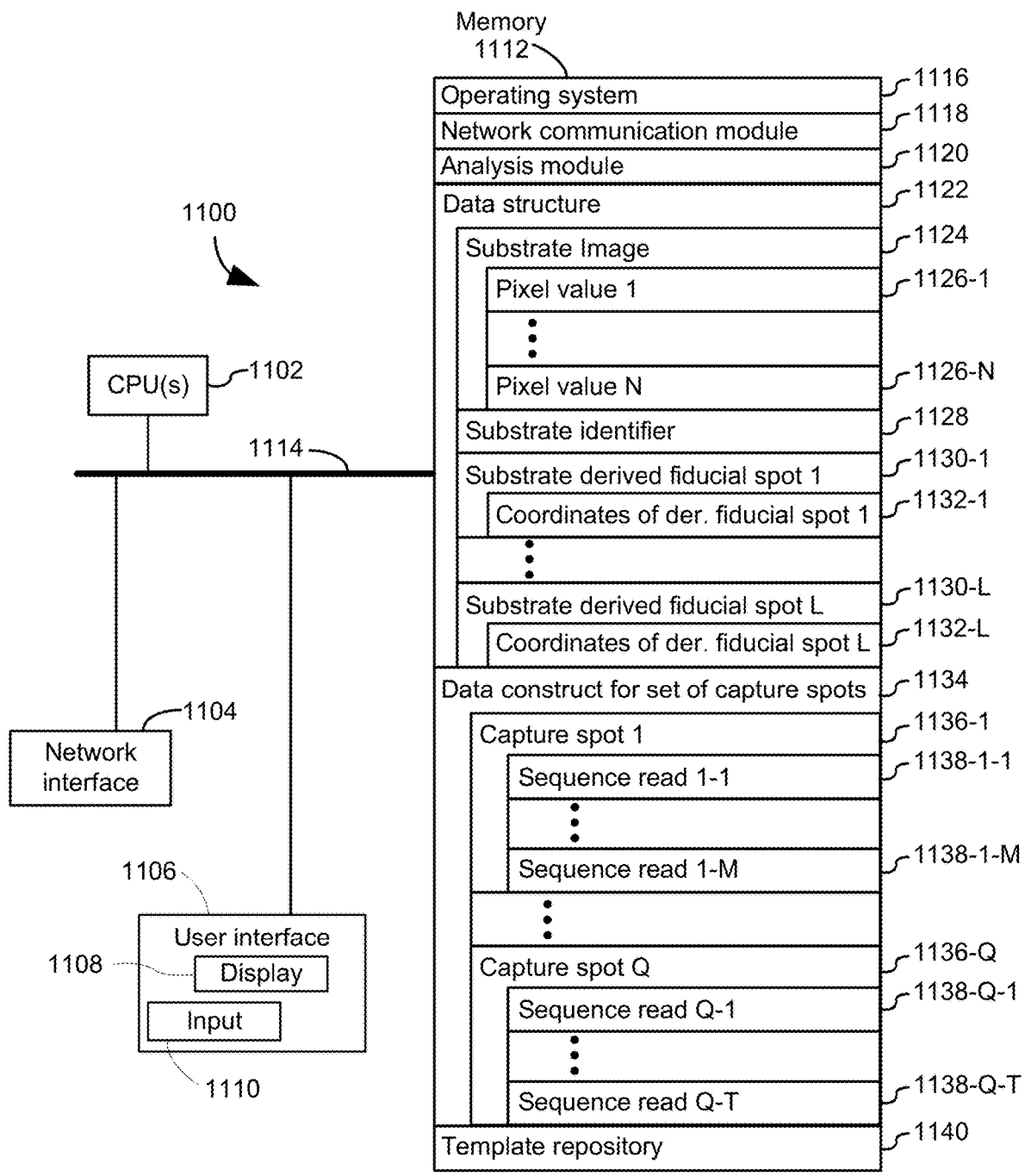

FIG. 11 is a block diagram illustrating an exemplary, non-limiting system for spatial analysis of analytes in accordance with some implementations. The system 1100 in some implementations includes one or more processing units CPU(s) 1102 (also referred to as processors), one or more network interfaces 1104, a user interface 1106, a memory 1112, and one or more communication buses 1114 for interconnecting these components. The communication buses 1114 optionally include circuitry (sometimes called a chipset) that interconnects and controls communications between system components. The memory 1112 typically includes high-speed random access memory, such as DRAM, SRAM, DDR RAM, ROM, EEPROM, flash memory, CD-ROM, digital versatile disks (DVD) or other optical storage, magnetic cassettes, magnetic tape, magnetic disk storage or other magnetic storage devices, other random access solid state memory devices, or any other medium which can be used to store desired information; and optionally includes non-volatile memory, such as one or more magnetic disk storage devices, optical disk storage devices, flash memory devices, or other non-volatile solid state storage devices. The memory 1112 optionally includes one or more storage devices remotely located from the CPU(s) 1102. The memory 1112, or alternatively the non-volatile memory device(s) within the memory 1112, comprises a non-transitory computer readable storage medium. It will be appreciated that this memory 1112 can be distributed across one or more computers. In some implementations, the memory 1112 or alternatively the non-transitory computer readable storage medium stores the following programs, modules and data structures, or a subset thereof:

- an optional operating system 1116, which includes procedures for handling various basic system services and for performing hardware dependent tasks;
- an optional network communication module (or instructions) 1118 for connecting the device 1100 with other devices, or a communication network;
- an analysis module 1120 for spatial analysis of analytes;
- a data structure 1122 comprising a (i) substrate image 1124, the substrate image comprising a plurality of pixel values 1126-1, . . . , 1126-N and (ii) a substrate identifier 1128;
- a plurality of derived fiducial spots 1130-1, . . . , 1130-L, and corresponding coordinates 1132-1, . . . , 1132-L identified in the substrate image 1124;
- a data construct 1134 for a set of capture spots in the substrate, the data construct comprising, for each capture spot 1136-1, . . . , 1136-Q, sequencing reads 1138-1-1, . . . , 1138-1-M, . . . 1138-Q-1, . . . , 1138-Q-T data, where the sequence reads 1138 include unique spatial barcodes 1150 (e.g., 1150-1-1-1) and analyte encoding portions 1152 (e.g., 1152-1-1-1); and
- a template repository 1140 comprising a plurality of templates 1142-1, . . . 1142-Q, respectively comprising corresponding coordinates systems 1144-1, . . . , 1144-Q, reference fiducial spots 1146-1-1, . . . , 1146-1-K, 1146-Q-1, . . . , 1146-Q-P, and corresponding coordinates 1148-1-1, . . . , 1148-1-K, 1148-Q-1, . . . , 1146-Q-P.

In some implementations, the user interface 1106 includes an input device (e.g., a keyboard, a mouse, a touchpad, a track pad, and/or a touch screen) 1110 for a user to interact with the system 1100 and a display 1108.

In some implementations, one or more of the above identified elements are stored in one or more of the previously mentioned memory devices, and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 1112 optionally stores a subset of the modules and data structures identified above. Furthermore, in some embodiments, the memory stores additional modules and data structures not described above. In some embodiments, one or more of the above identified elements is stored in a computer system, other than that of system 1100, that is addressable by system 1100 so that system 1100 may retrieve all or a portion of such data when needed.

Although FIG. 11 shows an exemplary system 1100, the figure is intended more as functional description of the various features that may be present in computer systems than as a structural schematic of the implementations described herein. In practice, and as recognized by those of ordinary skill in the art, items shown separately could be combined and some items could be separated.

(b) Methods for Spatial Analysis of Analytes.

FIG. 10 is a flow chart 1000 illustrating a method for spatial analysis of analytes 1002. In some embodiments, the method takes place at a computer system 1100 having one or more processors 1102, and memory 1112 storing one or more programs for execution by the one or more processors 1102. It will be appreciated that the memory can be on a single computer, distributed across several computers, in one or more virtual machines and/or in a cloud computing architecture.

Referring to block 1004, the disclosed method comprises obtaining a data structure 1122 in electronic form comprising (i) an image 1124 of a sample (e.g., sectioned tissue sample 1204 of FIG. 12) on a substrate (e.g., from a subject) and (ii) a substrate identifier 1128 that is unique to the substrate. The substrate includes a plurality of fiducial markers and a set of capture spots 1136.

An image can be obtained in any electronic image file format, including but not limited to JPEG/JFIF, TIFF, Exif, PDF, EPS, GIF, BMP, PNG, PPM, PGM, PBM, PNM, WebP, HDR raster formats, HEIF, BAT, BPG, DEEP, DRW, ECW, FITS, FLIF, ICO, ILBM, IMG, PAM, PCX, PGF, JPEG XR, Layered Image File Format, PLBM, SGI, SID, CD5, CPT, PSD, PSP, XCF, PDN, CGM, SVG, PostScript, PCT, WMF, EMF, SWF, XAML, and/or RAW.

In some embodiments, the image is acquired using transmission light microscopy and comprises an array of pixel values 1126. In some embodiments the array of pixel values comprises at least a least 100, 10,000, 100,000, $1\times10^6$, $2\times10^6$, $3\times10^6$, $5\times10^6$, $8\times10^6$, $10\times10^6$, or $15\times10^6$ pixel values. In some embodiments, the sample is subjected to immunohistochemistry prior to image acquisition and fluorescence microscopy is used to acquire the image. In some such embodiments, the image is acquired using Epi-illumination mode, where both the illumination and detection are performed from one side of the sample. In some such embodiments, the image is acquired using confocal microscopy, two-photon imaging, wide-field multiphoton microscopy, single plane illumination microscopy or light sheet fluorescence microscopy. See, for example, *Adaptive Optics for Biological Imaging*, 2013, Kubby ed., CRC Press, Boca Raton, Fla.; and *Confocal and Two-Photon Microscopy: Foundations, Applications and Advances*, 2002, Diaspro ed., Wiley Liss, New York, N.Y.; and *Handbook of Biological Confocal Microscopy*, 2002, Pawley ed., Springer Science+

Business Media, LLC, New York, N.Y. each of which is hereby incorporated by reference.

Figure 14:
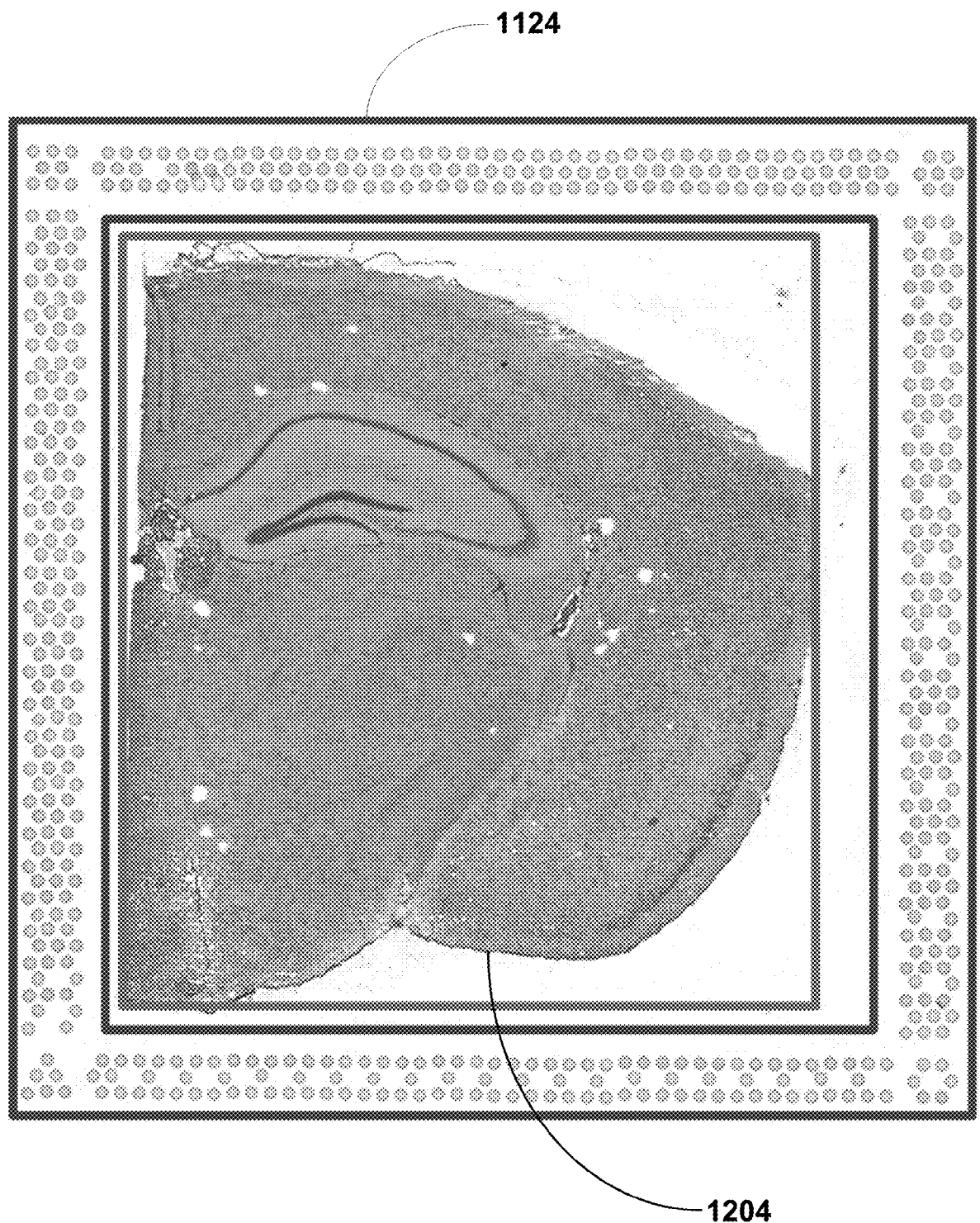
FIG. 14 illustrates a substrate with an image of a sample (e.g., tissue sample) on the substrate, in accordance with an embodiment of the present disclosure.
Figure 15:
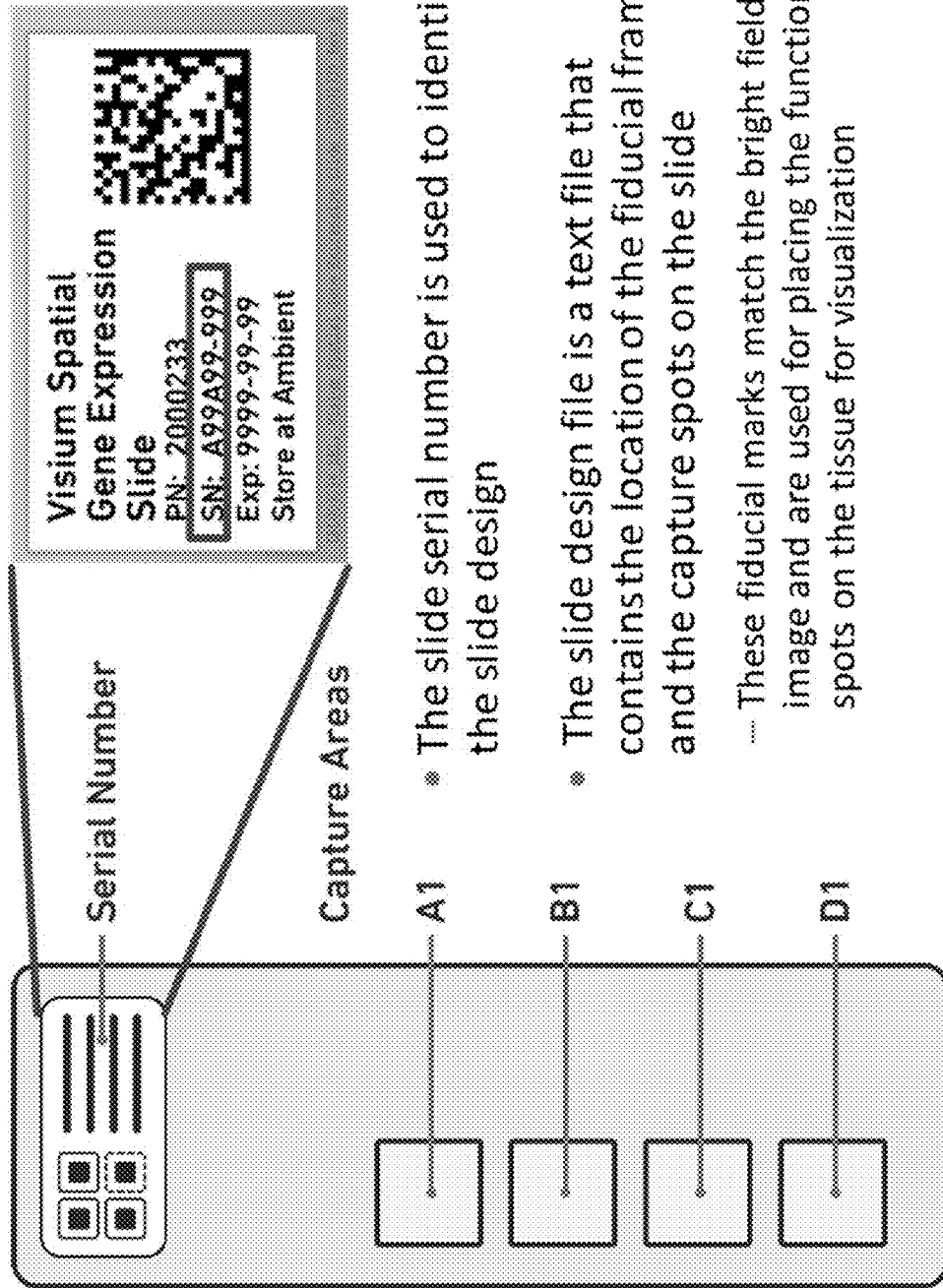
FIG. 15 illustrates a substrate that has a number of capture areas and a substrate identifier, in accordance with an embodiment of the present disclosure.
Figure 16:
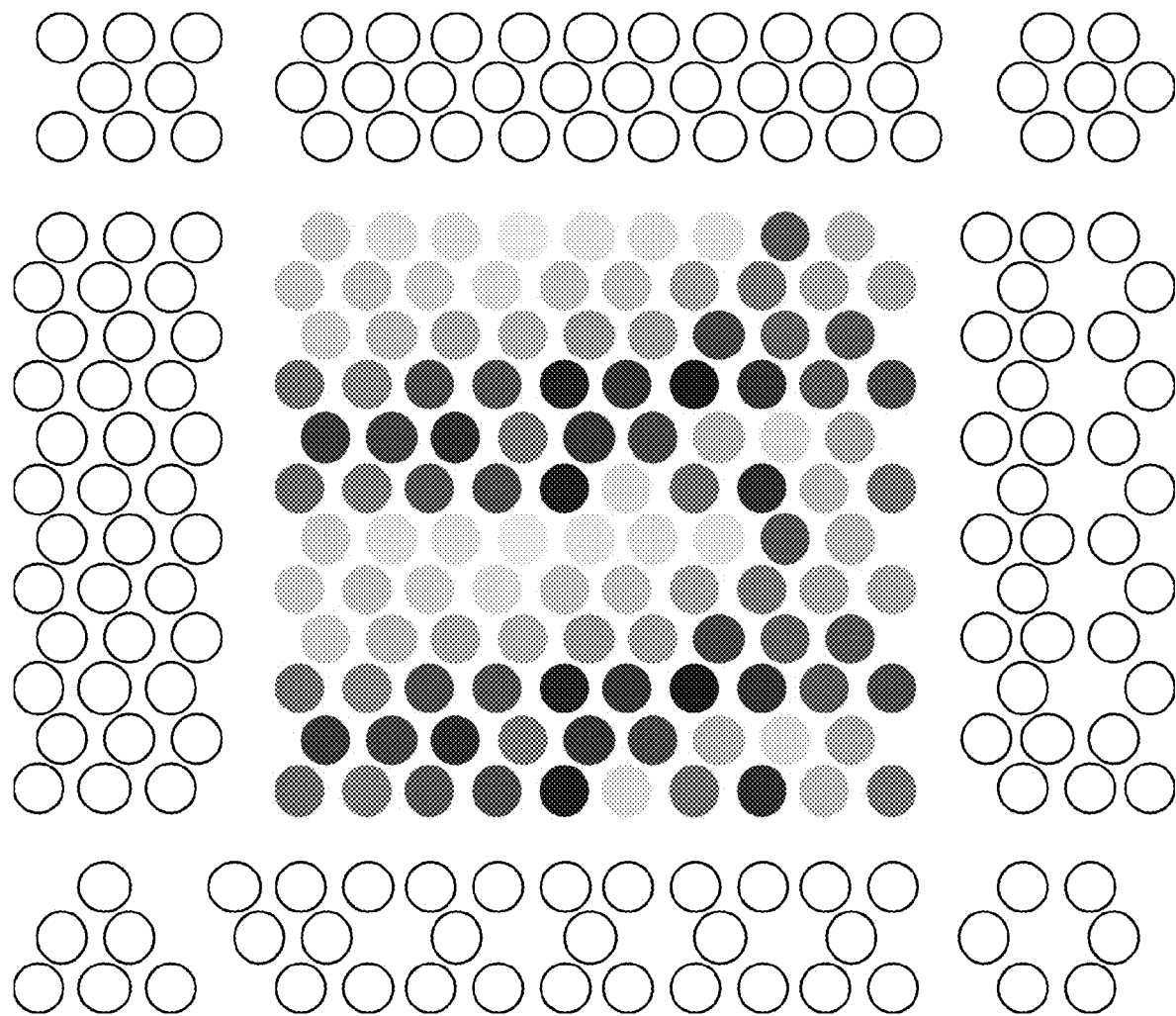
FIG. 16 illustrates a substrate that has a plurality of fiducial markers and a set of capture spots, in accordance with an embodiment of the present disclosure.

As an illustration, FIG. 14 shows an example of an image 1124 of a sample on a substrate in accordance with some embodiments. In some embodiments, substrates are used to provide support to a sample, particularly, for example, a thin tissue section. In some embodiments, a substrate is a support that allows for positioning of samples, analytes, capture spots, and/or capture probes on the substrate.

In some embodiments, the image is acquired using a Nikon Eclipse Ti2 with brightfield and fluorescence capacity (TRITC) or an ImageXpress Nano Automated Cell Imaging System. In some embodiments the image is acquired with a microscope having a 4× (Plan APO λ; NA 0.20), 10× (Plan APO λ; NA 0.45), or 20× (Plan APO λ; NA 0.75) objective lens.

In some embodiments, the image is a color image (e.g., 3×8 bit, 2424×2424 pixel resolution). In some embodiments, the image is a monochrome image (e.g., 14 bit, 2424×2424 pixel resolution).

In some embodiments, the exposure time for the image is between 2 and 10 milliseconds. In some embodiments, the sample is exposed to a light source (or equivalent) with a wavelength range of 380-680 nm is during the acquisition of the image. In some embodiments, the minimum capture resolution is 2.18 μm/pixel.

In some embodiments, the image is obtained in any electronic color mode, including but not limited to grayscale, bitmap, indexed, RGB, CMYK, HSV, lab color, duotone, and/or multichannel. In some embodiments, the image is manipulated (e.g., stitched, compressed and/or flattened). In some embodiments, the image file size is between 1 KB and 1 MB, between 1 MB and 0.5 GB, between 0.5 GB and 5 GB, between 5 GB and 10 GB, or greater than 10 GB.

In some embodiments, the image is represented as an array (e.g., matrix) comprising a plurality of pixels, such that the location of each respective pixel in the plurality of pixels in the array (e.g., matrix) corresponds to its original location in the image. In some embodiments, the image is represented as a vector comprising a plurality of pixels, such that each respective pixel in the plurality of pixels in the vector comprises spatial information corresponding to its original location in the image.

In some embodiments, a substrate can comprise any suitable support material, including, but not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, TEFLON™, cyclic olefins, polyimides, etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate. In some embodiments, a substrate can be printed, patterned, or otherwise modified to comprise capture spots that allow association with analytes upon contacting a sample (e.g., a tissue section). Further detailed embodiments of substrate properties, structure, and/or modifications are described above in the Detailed Description (e.g., under II. General Spatial Array-Based Analytical Methodology; (c) Substrate).

Referring to FIG. 12, in some embodiments, the substrate comprises a capture area 1206, where the capture area comprises a plurality of barcoded capture spots 1136 for one or more reactions and/or assays, and where a reaction comprises one or more tissue types for spatial analysis. In some embodiments, the substrate comprises 2, 3, 4, 5, 6, 7, 8, 9, 10, 11, 12, 13, 14, 15, 16, 17, 18, 19, 20, more than 20, more than 30, more than 40, or more than 50 capture areas 1206 for a plurality of reactions and/or assays. For example, in some embodiments, the substrate is a spatial gene expression slide (e.g., Visium) comprising four capture areas 1206, each capture area having the dimensions 6.5 mm×6.5 mm, such that the substrate comprises a capacity for four reactions and up to four tissue types. In some such embodiments, each capture area comprises 5,000 barcoded capture spots 1136, where each capture spot is 55 μm in diameter and the distance between the centers of two respective capture spots is 100 μm. See, 10×, 2019, "Visium Spatial Gene Expression Solution," where is hereby incorporated herein by reference. Further specific embodiments of capture spots are detailed below in the present disclosure. See also, U.S. Provisional Patent Application No. 62/886,233 entitled "Systems and Methods for Using the Spatial Distribution of Haplotypes to Determine a Biological Condition," filed Aug. 13, 2019, and U.S. Provisional Patent Application No. 62/839,346 entitled "Spatial Transcriptomics of Biological Analytes in Tissue Samples," filed Apr. 26, 2019, each of which is hereby incorporated by reference.

Referring again to block 1004, the sample is obtained (e.g., from a subject). As defined above, in some embodiments, a subject is a mammal such as a rodent, mouse, rat, rabbit, guinea pig, ungulate, horse, sheep, pig, goat, cow, cat, dog, primate (e.g., human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. These examples are non-limiting and do not preclude substitution of any alternative subjects that will occur to one skilled in the art.

In some embodiments, the sample is a tissue sample, and the tissue sample is obtained from any tissue and/or organ derived from any subject, including but not limited to those subjects listed above. In some embodiments, a tissue sample is obtained from, e.g., heart, kidney, ovary, breast, lymph node, adipose, brain, small intestine, stomach, liver, quadriceps, lung, testes, thyroid, eyes, tongue, large intestine, spleen, and/or mammary gland, skin, muscle, diaphragm, pancreas, bladder, prostate, among others. Tissue samples can be obtained from healthy or unhealthy tissue (e.g., inflamed, tumor, carcinoma, or other). Additional examples of tissue samples are shown in Table 1 and catalogued, for example, in 10×, 2019, "Visium Spatial Gene Expression Solution," which is hereby incorporated herein by reference.

TABLE 1

Examples of tissue samples

| Organism | Tissue | Healthy/Diseased |
|---|---|---|
| Human | Brain | Cerebrum Glioblastoma Multiforme |
| Human | Breast | Healthy |
| Human | Breast | Invasive Ductal Carcinoma |
| Human | Breast | Invasive Lobular Carcinoma |
| Human | Heart | Healthy |

TABLE 1-continued

Examples of tissue samples

| Organism | Tissue | Healthy/Diseased |
|---|---|---|
| Human | Kidney | Healthy |
| Human | Kidney | Nephritis |
| Human | Large Intestine | Colorectal Cancer |
| Human | Lung | Papillary Carcinoma |
| Human | Lymph Node | Healthy |
| Human | Lymph Node | Inflamed |
| Human | Ovaries | Tumor |
| Human | Spleen | Inflamed |
| Mouse | Brain | Healthy |
| Mouse | Eyes | Healthy |
| Mouse | Heart | Healthy |
| Mouse | Kidney | Healthy |
| Mouse | Large Intestine | Healthy |
| Mouse | Liver | Healthy |
| Mouse | Lungs | Healthy |
| Mouse | Ovary | Healthy |
| Mouse | Quadriceps | Healthy |
| Mouse | Small Intestine | Healthy |
| Mouse | Spleen | Healthy |
| Mouse | Stomach | Healthy |
| Mouse | Testes | Healthy |
| Mouse | Thyroid | Healthy |
| Mouse | Tongue | Healthy |
| Rat | Brain | Healthy |
| Rat | Heart | Healthy |
| Rat | Kidney | Healthy |
| Mouse | Tongue | Healthy |
| Rat | Brain | Healthy |
| Rat | Heart | Healthy |
| Rat | Kidney | Healthy |

In some embodiments, the sectioned tissue is prepared by tissue sectioning, as described above in the Detailed Description (e.g., under I. Introduction; (d) Biological Samples; (ii) Preparation of Biological Samples; (1) Tissue Sectioning). Briefly, in some embodiments, thin sections of tissue are prepared from a sample (e.g., using a mechanical cutting apparatus such as a vibrating blade microtome, or by applying a touch imprint of a sample to a suitable substrate material). In some embodiments, a sample is frozen, fixed and/or cross-linked, or encased in a matrix (e.g., a resin or paraffin block) prior to sectioning to preserve the integrity of the sample during sectioning. Further implementations of sample preparation are provided above in the Detailed Description (e.g., under I. Introduction; (d) Biological Samples; (ii) Preparation of Biological Samples; (2) Freezing, (3) Formalin Fixation and Paraffin Embedding, (4) Fixation, and (5) Embedding). As an example, referring to FIG. 3, preparation of a biological sample using tissue sectioning comprises a first step 301 of an exemplary workflow for spatial analysis.

Figure 9:
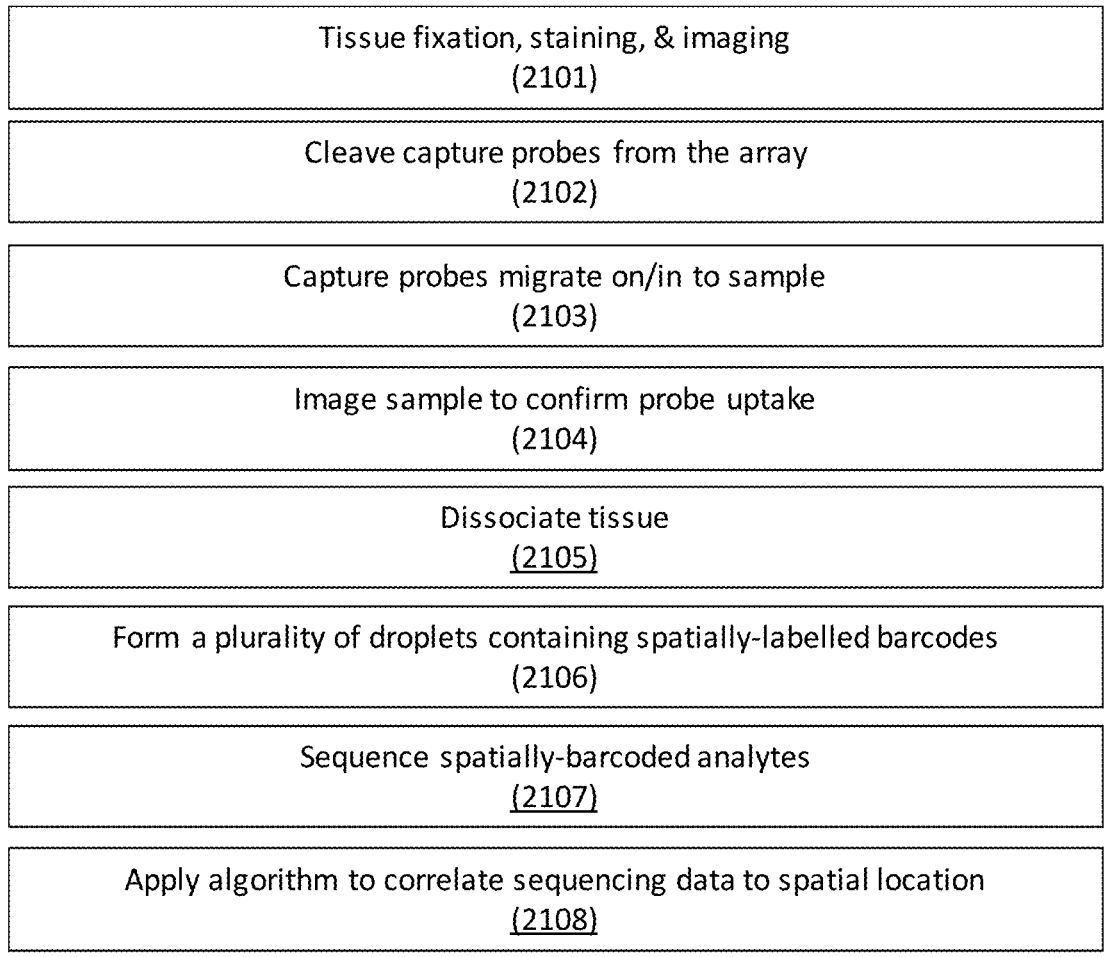
FIG. 9 shows an exemplary spatial analysis workflow in which optional steps are indicated by dashed boxes in accordance with an embodiment of the present disclosure.

Referring to block 1006, in some embodiments, the sample is a sectioned tissue sample having a depth of 100 microns or less. In some embodiments, the sectioned tissue sample has a depth of 80 microns or less, 70 microns or less, 60 microns or less, 50 microns or less, 40 microns or less, 30 microns or less, or 20 microns or less. In some embodiments, the sectioned tissue sample has a depth of between 10 microns and 20 microns. See, 10×, 2019, "Visium Spatial Gene Expression Solution." In some embodiments, the sectioned tissue sample has a depth of between 1 and 10 microns. Further embodiments of sectioned tissue samples are provided above in the Detailed Description (e.g., under I. Introduction; (d) Biological Samples; (ii) Preparation of Biological Samples; (1) Tissue Sectioning). In some embodiments, a tissue section is a similar size and shape to the substrate on which it is on. In some embodiments, a tissue section is a different size and shape from the substrate on which it is on. In some embodiments, a tissue section overlays all or a portion of the substrate. For example, FIG. 9A illustrates a tissue section with dimensions roughly comparable to the substrate, such that a large proportion of the substrate is in contact with the tissue section.

In some embodiments, a tissue section on a substrate is a single uniform section. In some alternative embodiments, multiple tissue sections are on a substrate. In some such embodiments, a single capture area 1206 on a substrate can contain multiple tissue sections, where each tissue section is obtained from either the same sample and/or subject or from different samples and/or subjects. In some embodiments, a tissue section is a single tissue section that comprises one or more regions where no cells are present (e.g., holes, tears, or gaps in the tissue). Thus, in some embodiments such as the above, an image of a tissue section on a substrate can contain regions where tissue is present and regions where tissue is not present.

Referring to block 1008 and as illustrated for example in FIG. 12, in some embodiments, each respective capture spot 1136 in the set of capture spots is (i) at a different position in a two-dimensional array and (ii) associates with one or more analytes from the tissue. Further, in such embodiments, each respective capture spot in the set of capture spots is characterized by at least one unique spatial barcode in a plurality of spatial barcodes.

Referring to block 1010, in some embodiments, the one or more analytes comprise five or more analytes, ten or more analytes, fifty or more analytes, one hundred or more analytes, five hundred or more analytes, 1000 or more analytes, 2000 or more analytes, between 2000 and 10,000 analytes, between 5,000 and 20,000 analytes, or between 10,000 and 100,000 analytes.

Referring to block 1012, in some embodiments, the unique spatial barcode encodes a unique predetermined value selected from the set $\{1, \ldots, 1024\}$, $\{1, \ldots, 4096\}$, $\{1, \ldots, 16384\}$, $\{1, \ldots, 65536\}$, $\{1, \ldots, 262144\}$, $\{1, \ldots, 1048576\}$, $\{1, \ldots, 4194304\}$, $\{1, \ldots, 16777216\}$, $\{1, \ldots, 67108864\}$, or $\{1, \ldots, 1 \times 10^{12}\}$.

Referring to block 1014, in some embodiments, the one or more analytes is a plurality of analytes. A respective capture spot 1136 in the set of capture spots includes a plurality of capture probes. Each capture probe in the plurality of capture probes includes a capture domain that is characterized by a capture domain type in a plurality of capture domain types. Each respective capture domain type in the plurality of capture domain types is configured to bind to a different analyte in the plurality of analytes.

Thus, in some such embodiments, each capture domain type corresponds to a specific analyte (e.g., a specific oligonucleotide or binding moiety for a specific gene). In some embodiments, each capture domain type in the plurality of capture domain types is configured to bind to the same analyte (e.g., specific binding complementarity to mRNA for a single gene) or to different analytes (e.g., specific binding complementarity to mRNA for a plurality of genes).

Referring to block 1016, in some embodiments, the plurality of capture domain types comprises between 5 and 15,000 capture domain types and the respective capture spot 1136 includes at least five, at least 10, at least 100, at least 1000 capture probes, at least 5000 capture probes or at least 10,000 capture probes for each capture domain type in the plurality of capture domain types.

Referring to block 1018, in some embodiments, the one or more analytes is a plurality of analytes. A respective capture spot in the set of capture spots includes a plurality of capture probes, each capture probe in the plurality of capture probes including a capture domain that is characterized by a single capture domain type configured to bind to each analyte in the plurality of analytes in an unbiased manner. Thus, in some such embodiments, the capture domain comprises a non-specific capture moiety (e.g., an oligo-dT binding moiety).

Referring to block 1020, in some embodiments, each respective capture spot in the set of capture spots is contained within a 100 micron by 100 micron square on the substrate (e.g., on the substrate of the substrate). In some embodiments, each respective capture spot in the set of capture spots is contained within a 50 micron by 50 micron square on the substrate. In some embodiments, each respective capture spot in the set of capture spots is contained within a 10 micron by 10 micron square on the substrate. In some embodiments, each respective capture spot in the set of capture spots is contained within a 1 micron by 1 micron square on the substrate. In some embodiments, each respective capture spot in the set of capture spots is contained within a 0.5 micron by 0.5 micron square on the substrate. In some embodiments, each respective capture spot in the set of capture spots is contained within a 0.3 micron by 0.3 micron square on the substrate. In some embodiments, each respective capture spot in the set of capture spots is contained within a 0.2 micron by 0.2 micron square on the substrate.

Referring to block 1022, in some embodiments, a distance between a center of each respective capture spot to a neighboring capture spot in the set of capture spots on the substrate is between 300 nanometers and 300 microns. In some embodiments, a distance between a center of each respective capture spot to a neighboring capture spot is between 300 nanometers and 15 microns, between 800 nanometers and 10 microns, or between two microns and seven microns. In some embodiments, a distance between a center of each respective spot to a neighboring capture spot is between 100 microns and 200 microns.

Figure 10B:
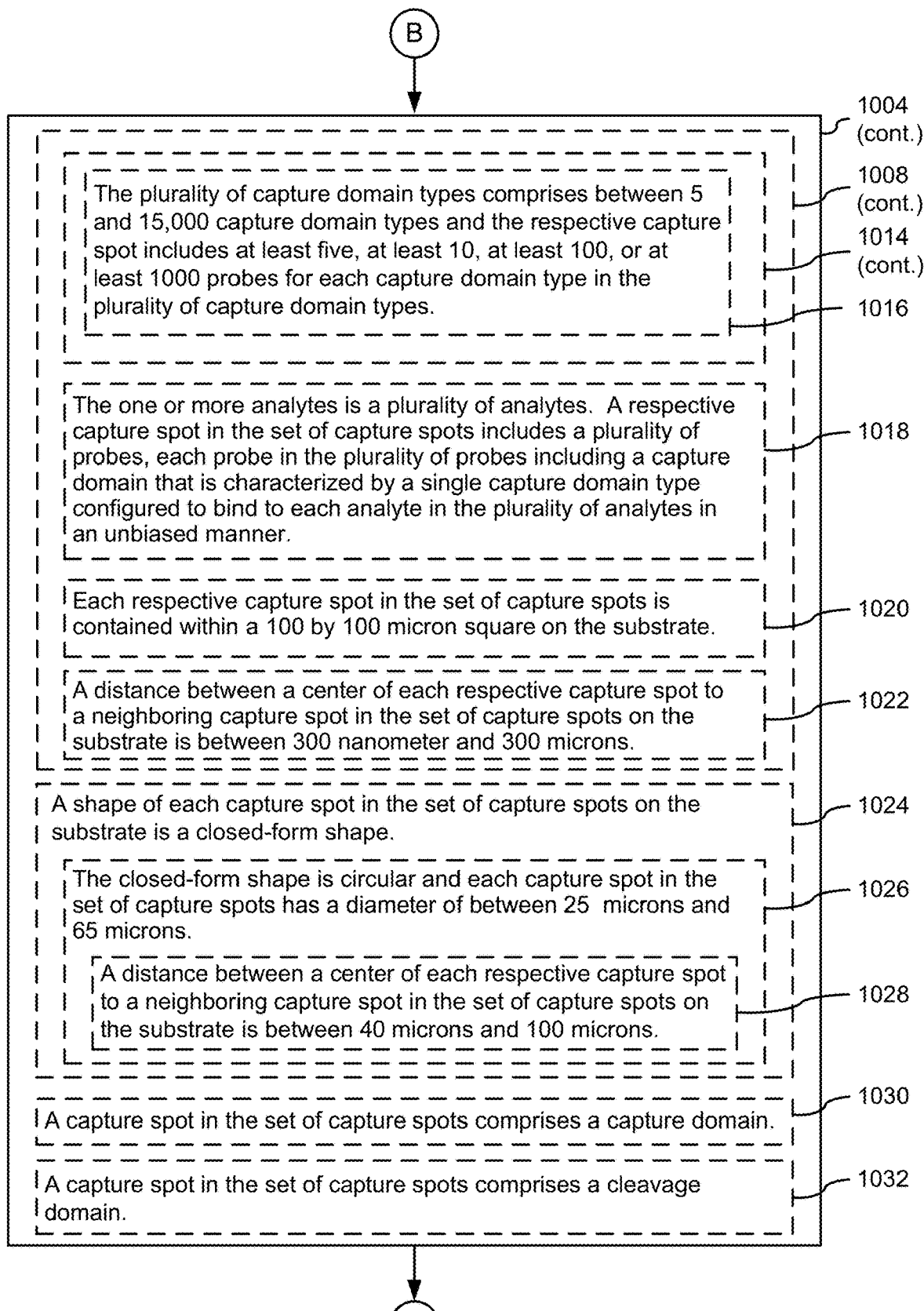

Referring to block 1024 of FIG. 10B, in some embodiments, a shape of each capture spot in the set of capture spots on the substrate is a closed-form shape. In some embodiments, the closed-form shape is circular, elliptical, or an N-gon, where N is a value between 1 and 20. In some embodiments, the closed-form shape is hexagonal. Referring to block 1026, in some such embodiments, the closed-form shape is circular and each capture spot in the set of capture spots has a diameter of between 25 microns and 65 microns. In some embodiments, the closed-form shape is circular or hexagonal, and each capture spot in the set of capture spots has a diameter of between 30 nanometers and 200 microns, and/or a diameter of 100 microns or less. In some embodiments, the closed-form shape is circular and each capture spot in the set of capture spots has a diameter of between 30 microns and 200 microns. In some embodiments, the closed-form shape is circular or hexagonal and each capture spot in the set of capture spots has a diameter of between 0.5 microns and 60 microns. Referring to block 1028, in some embodiments, a distance between a center of each respective capture spot to a neighboring capture spot in the set of capture spots on the substrate is between 40 microns and 100 microns. In some embodiments, a distance between a center of each respective capture spot to a neighboring capture spot in the set of capture spots on the substrate is between 300 nanometers and 300 microns. In some embodiments, a distance between a center of each respective spot to a neighboring capture spot in the set of capture spots on the substrate is between 700 nanometers and 10 microns. In some embodiments, a distance between a center of each respective spot to a neighboring capture spot in the set of capture spots on the substrate is between 800 nanometers and 3 microns.

In some embodiments, the positions of a plurality of capture spots of an array are predetermined. In some embodiments, the positioned of a plurality of capture spots of an array are not predetermined. In some embodiments, the substrate comprises fiducial markers, and the position of the fiducial markers is predetermined such that they can be mapped to a spatial location. In some embodiments, a substrate comprises a number of capture spots that is between 500 and 1000, between 1000 and 5000, between 5000 and 10,000, between 10,000 and 15,000, between 15,000 and 20,000, or between 20,000 and 100,000. In some embodiments, a substrate comprises between 1000 and 5000 capture spots, or between 4000 and 100,000 capture spotes where capture spots are arranged on the substrate hexagonally or in a grid.

Referring to block 1030, in some embodiments, a capture spot 1136 in the set of capture spots comprises a capture domain. Referring to block 1032, in some embodiments, a capture spot in the set of capture spots comprises a cleavage domain. Referring to block 1034, in some embodiments, each capture spot in the set of spots is attached directly or attached indirectly to the substrate.

Referring to block 1036, in some embodiments, each respective capture spot includes 1000 or more capture probes, 2000 or more capture probes, 10,000 or more capture probes, 100,000 or more capture probes, $1 \times 10^6$ or more capture probes, $2 \times 10^6$ or more capture probes, or $5 \times 10^6$ or more capture probes. Referring to block 1038, in some embodiments, each capture probe in the respective capture spot includes a poly-A sequence or a poly-T sequence and the unique spatial barcode that characterizes the respective capture spot. Referring to block 1040 and block 1042, in some embodiments, each capture probe in the respective capture spot includes the same spatial barcode or a different spatial barcode from the plurality of spatial barcodes.

Numerous alternative combinations of capture domain types, capture spot sizes, arrays, probes, spatial barcodes analytes, and/or other features of capture spots including but not limited to dimensions, designs, and modifications are also possible, and are discussed in detail at length above (e.g., in Section (II) General Spatial Array-Based Analytical Methodology; Subsections (b) Capture Probes, (c) Substrate, and (d) Arrays).

Referring again to block 1004, the image is obtained as an array of pixel values. As an example, referring to FIG. 3, imaging of a tissue sample and/or an array on a substrate comprises a second step 302 of an exemplary workflow for spatial analysis. An image can be obtained in any electronic image file format, including but not limited to JPEG/JFIF, TIFF, Exif, PDF, EPS, GIF, BMP, PNG, PPM, PGM, PBM, PNM, WebP, HDR raster formats, HEIF, BAT, BPG, DEEP, DRW, ECW, FITS, FLIF, ICO, ILBM, IMG, PAM, PCX, PGF, JPEG XR, Layered Image File Format, PLBM, SGI, SID, CD5, CPT, PSD, PSP, XCF, PDN, CGM, SVG, PostScript, PCT, WMF, EMF, SWF, XAML, and/or RAW. In some embodiments the array of pixel values comprises at least a least 100, 10,000, 100,000, $1 \times 10^6$, $2 \times 10^6$, $3 \times 10^6$, $5 \times 10^6$, $8 \times 10^6$, $10 \times 10^6$, or $15 \times 10^6$ pixel values.

In some embodiments, the image is obtained in any electronic color mode, including but not limited to grayscale, bitmap, indexed, RGB, CMYK, HSV, lab color, duotone, and/or multichannel. In some embodiments, the image is manipulated (e.g., stitched, compressed and/or flattened). In some embodiments, the image file size is between 1 KB and 1 MB, between 1 MB and 0.5 GB, between 0.5 GB and 5 GB, between 5 GB and 10 GB, or greater than 10 GB.

In some embodiments, the image is represented as an array (e.g., matrix) comprising a plurality of pixels, such that the location of each respective pixel in the plurality of pixels in the array (e.g., matrix) corresponds to its original location in the image. In some embodiments, the image is represented as a vector comprising a plurality of pixels, such that each respective pixel in the plurality of pixels in the vector comprises spatial information corresponding to its original location in the image.

Referring again to block 1004, the substrate that is imaged includes a plurality of fiducial markers. Fiducial markers are described in further detail in the Detailed Description above (e.g., at II. General Spatial Array-Based Analytical Methodology; (c) Substrate and (e) Analyte Capture; (v) Region of Interest). Briefly, in some embodiments, fiducial markers are included on the substrate as one or more markings on the surface of the substrate of the substrate. In some embodiments, fiducial markers serve as guides for correlating spatial information with the characterization of the analyte of interest. In some embodiments, fiducial markers are prepared on the substrate using any one of the following non-limiting techniques: chrome-deposition on glass, gold nanoparticles, laser-etching, tubewriter-ink, microspheres, Epson 802, HP 65 Black XL, permanent marker, fluorescent oligos, amine iron oxide nanoparticles, amine thulium doped upconversion nanophosphors, and/or amine Cd-based quantum dots. Other techniques for fiducial marker preparation include sand-blasting, printing, depositing, or physical modification of the substrate surface. In some embodiments, fiducial markers do not bind to analytes, either directly or indirectly.

In some embodiments, the fiducial markers are non-transiently attached to the outer boundary of the substrate (e.g., the outerboundry of the capture area 1206) and the sample is overlayed within the boundary of the fiducial markers. In some embodiments, the fiducial markers are transiently attached to the outer boundary of the substrate (e.g., by attachment of an adaptor, a slide holder, and/or a cover slip). In some embodiments, the fiducial markers are transiently attached to the outer boundary of the substrate before or after the sample is on the substrate. In some embodiments, the fiducial markers are transiently or non-transiently attached to the substrate after the sample is on but prior to obtaining the image.

FIG. 12 illustrates an image 1124 of a tissue 1204 on a substrate, where the image includes a plurality of fiducial markers, in accordance with some embodiments. The fiducial markers are arranged along the external border of the substrate, surrounding the capture spot array and the tissue overlay. In some such embodiments, the fiducial markers comprise patterned spots, and the patterned spots indicate the edges and corners of the capture spot array. In some such embodiments, a different pattern of fiducial markers is provided at each corner, allowing the image to be correlated with spatial information using any orientation (e.g., rotated and/or mirror image).

In some embodiments, the image is acquired using transmission light microscopy. In some embodiments, the sample is stained prior to imaging using, e.g., fluorescent, radioactive, chemiluminescent, calorimetric, or colorimetric detectable markers. In some embodiments, the sample is stained using live/dead stain (e.g., trypan blue). In some embodiments, samples are stained as indicated in the Detailed Description above (e.g., at I. Introduction; (d) Biological Samples; (ii) Preparation of Biological Samples; (6) Staining). In some embodiments, the image is acquired using optical microscopy (e.g., bright field, dark field, dispersion staining, phase contrast, differential interference contrast, interference reflection, fluorescence, confocal, single plane illumination, wide-field multiphoton, deconvolution, transmission electron microscopy, and/or scanning electron microscopy). In some embodiments, the image is acquired after staining the tissue section but prior to analyte capture. In some embodiments, the sample is subjected to immunohistochemistry prior to image acquisition and fluorescence microscopy is used to acquire the image. In some such embodiments, the image is acquired using Epi-illumination mode, where both the illumination and detection are performed from one side of the sample. In some such embodiments, the image is acquired using confocal microscopy, two-photon imaging, wide-field multiphoton microscopy, single plane illumination microscopy or light sheet fluorescence microscopy. See, for example, *Adaptive Optics for Biological Imaging,* 2013, Kubby ed., CRC Press, Boca Raton, Fla.; and *Confocal and Two-Photon Microscopy: Foundations, Applications and Advances,* 2002, Diaspro ed., Wiley Liss, New York, N.Y.; and *Handbook of Biological Confocal Microscopy,* 2002, Pawley ed., Springer Science+ Business Media, LLC, New York, N.Y. each of which is hereby incorporated by reference.

Figure 10C:
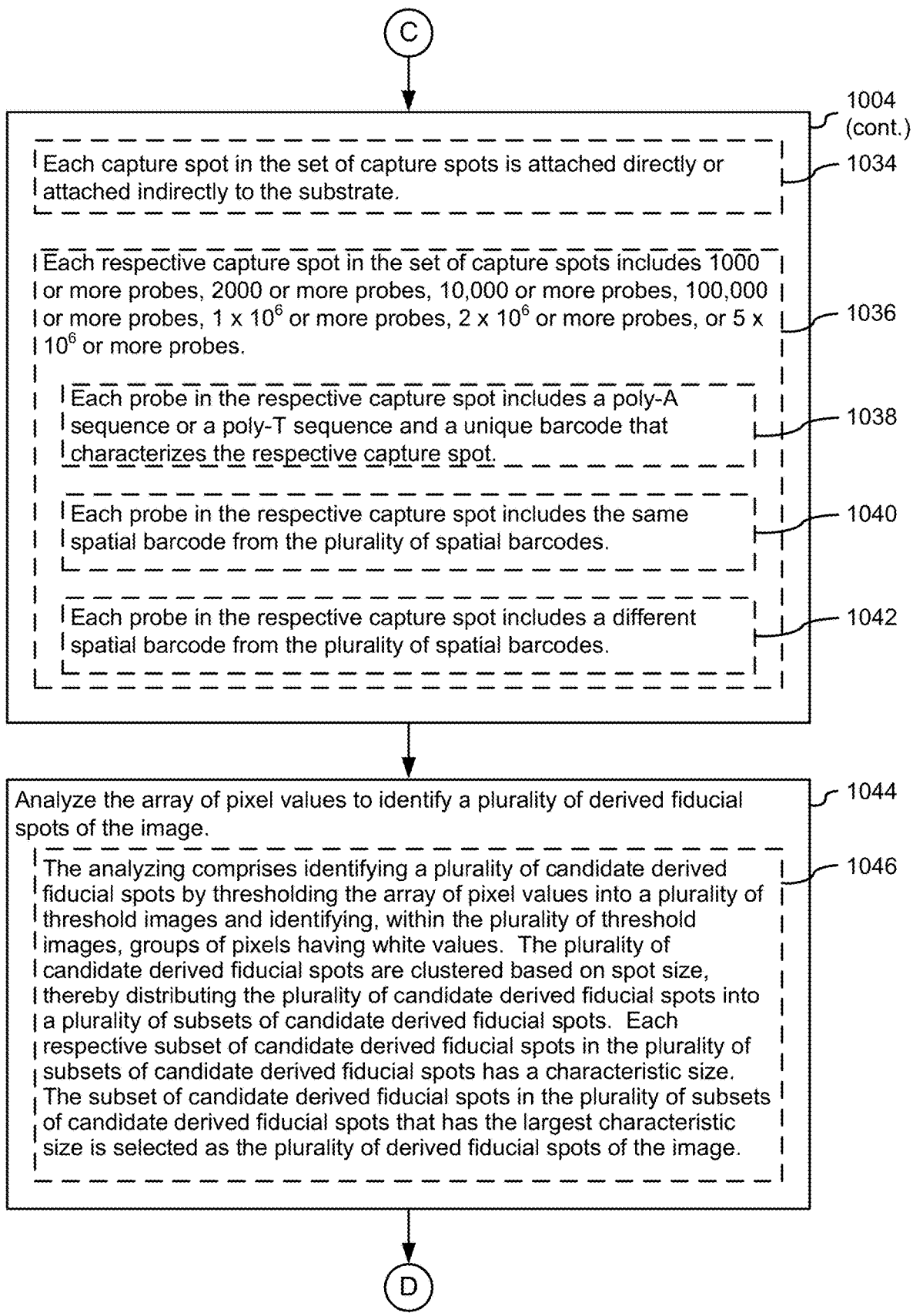

Referring to block 1044 of FIG. 10C, the array of pixel values are analyzed to identify a plurality of derived fiducial spots of the image. Referring to block 1046 of FIG. 10C, in some embodiments this is performed by identifying a plurality of candidate derived fiducial spots within the image by thresholding the array of pixel values within the image with a plurality of different threshold values thereby achieving a plurality of threshold images and identifying, within the plurality of threshold images, groups of pixels having white values. In one such embodiment, for one such threshold value T, each respective pixel$_{i,j}$ in the image is replaced with a black pixel if the respective pixel$_{i,j}$ intensity is less than the threshold value (Ii,j<T), or a white pixel if the respective pixel$_{i,j}$ intensity is greater than the threshold value (Ii,j>T). In some embodiments, the value for the threshold is selected automatically using the image. See for example, Sezgin and Sankur, 2004, "Survey over image thresholding techniques and quantitative performance evaluation," Journal of Electronic Imaging 13(1), 146-165 for disclosure on methods for thresholding, including selecting suitable thresholding values, and types of thresholding including histogram shape-based methods. As disclosed in Sezgin and Sankur, Id., suitable thresholding methods include, but are not limited to histogram shape-base thresholding methods where, for example, the peaks, valleys and curvatures of the smoothed histogram are analyzed. Suitable thresholding methods also include clustering-based methods where gray-level samples are clustered in two parts as background and foreground (object), or alternately are modeled as a mixture of two Gaussians.

Suitable thresholding methods also include entropy-based methods that use the entropy of the foreground and background regions, the cross-entropy between the original and binarized image, etc. See, for example, Zhang, 2011, "Optimal multi-level Thresholding based on Maximum Tsallis Entropy via an Artificial Bee Colony Approach," Entropy 13(4): pp. 841-859, which is hereby incorporated by reference. Suitable thresholding methods further include object attribute-based thresholding methods that search for a measure of similarity between the gray-level and the binarized images, such as fuzzy shape similarity, edge coincidence, etc. Suitable thresholding methods further include spatial methods [that] use higher-order probability distribution and/or correlation between pixels.

Suitable thresholding methods further include local methods that adapt the threshold value on each pixel to the local image characteristics. In such local thresholding methods, a different T is selected for each pixel in the image.

Thus as the above disclosed, in some embodiments several different values of T are used to threshold an image whereas in other embodiments a single T is used to threshold an image. The net result of the thresholding is the identification of plurality of candidate derived fiducial spots. Under classical thresholding, these candidate derived fiducial spots are groups of white pixels. However, the present disclosure is not so limited and one of skill in the art will fully appreciate that white and black can be reversed, such that the candidate derived fiducial spots are groups of black pixels. However, the ease of describing the workflow, the candidate derived fiducial spots will be considered groups of white pixels identified by the thresholding.

Figure 17:
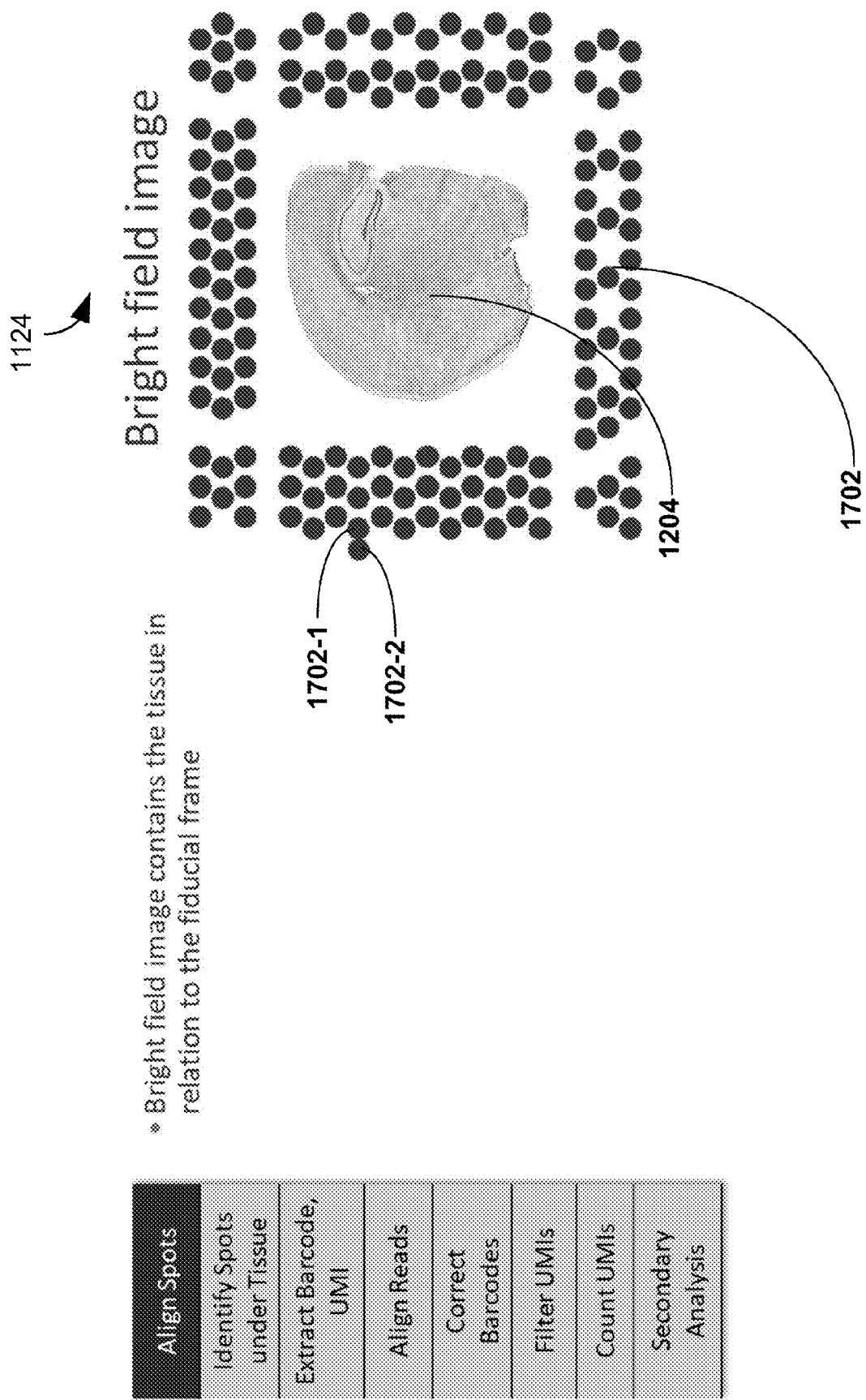
FIG. 17 illustrates an image of a sample (e.g., tissue sample) on a substrate, where the sample is positioned within a plurality of fiducial markers, in accordance with an embodiment of the present disclosure.

FIG. 17 illustrates an image 1124 that includes the sample 1204 and a plurality of candidate derived fiducial spots 1702 on the perimeter of the image. In some embodiments, there are between 5 and 1000 candidate derived fiducial spots 1702, between 5 and 500 candidate derived fiducial spots 1702, or between 5 and 300 candidate derived fiducial spots 1702.

Continuing to refer to block 1046 of FIG. 10C, the plurality of candidate derived fiducial spots are clustered based on spot size (e.g., spot size area, spot size diameter, spot size circumference), thereby distributing the plurality of candidate derived fiducial spots into a plurality of subsets of candidate derived fiducial spots.

Clustering is described at pages 211-256 of Duda and Hart, *Pattern Classification and Scene Analysis,* 1973, John Wiley & Sons, Inc., New York, (hereinafter "Duda 1973") which is hereby incorporated by reference in its entirety. As described in Section 6.7 of Duda 1973, the clustering problem is one of finding natural groupings in a dataset. To identify natural groupings, two issues are addressed. First, a way to measure similarity (or dissimilarity) between two samples is determined. This metric (e.g., similarity measure) is used to ensure that the samples in one cluster are more like one another than they are to samples in other clusters. Second, a mechanism for partitioning the data into clusters using the similarity measure is determined. Similarity measures are discussed in Section 6.7 of Duda 1973, where it is stated that one way to begin a clustering investigation is to define a distance function and to compute the matrix of distances between all pairs of samples in the training set. If distance is a good measure of similarity, then the distance between reference entities in the same cluster will be significantly less than the distance between the reference entities in different clusters. However, as stated on page 215 of Duda 1973, clustering does not require the use of a distance metric. For example, a nonmetric similarity function $s(x, x')$ can be used to compare two vectors x and x'. Conventionally, $s(x, x')$ is a symmetric function whose value is large when x and x' are somehow "similar." An example of a nonmetric similarity function $s(x, x')$ is provided on page 218 of Duda 1973. Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973. More recently, Duda et al., *Pattern Classification,* $2^{nd}$ edition, John Wiley & Sons, Inc. New York, has been published. Pages 537-563 describe clustering that may be used in accordance with block 1046 of FIG. 10C in detail. More information on suitable clustering techniques is found in Kaufman and Rousseeuw, 1990, *Finding Groups in Data: An Introduction to Cluster Analysis,* Wiley, New York, N.Y.; Everitt, 1993, Cluster analysis (3d ed.), Wiley, New York, N.Y.; and Backer, 1995, Computer-Assisted Reasoning in Cluster Analysis, Prentice Hall, Upper Saddle River, N.J., each of which is hereby incorporated by reference. Particular exemplary clustering techniques that can be used in the present disclosure include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. In some embodiments, the clustering comprises unsupervised clustering where no preconceived notion of what clusters should form when the training set is clustered are imposed.

In some embodiments, the plurality of candidate derived fiducial spots are clustered into two, three, four, five, six, seven, eight, nine, ten, eleven, twelve, thirteen, fourteen, fifteen, sixteen, seventeen, eighteen, nineteen, or twenty subsets. In some embodiments, the candidate derived fiducial spots are clustered into between two and 100 subsets. Each respective subset of candidate derived fiducial spots in the plurality of subsets of candidate derived fiducial spots has a characteristic size. For instance in some embodiments, the characteristic size is the average number of pixels in each candidate derived fiducial spot in the respective subset. The subset of candidate derived fiducial spots in the plurality of subsets of candidate derived fiducial spots that has the largest characteristic size is selected as the plurality of derived fiducial spots of the image. For instance, consider the case where the plurality of candidate derived fiducial spots are clustered into two subsets, subset A and subset B, and the average size of the candidate derived fiducial spots in subset A is 49 pixels and the average size of the candidate derived fiducial spots in subset B is 58 pixels. In this instance, the candidate derived fiducial spots in subset B would be chosen as the derived fiducial spots of the image and the candidate derived fiducial spots in subset A would be discarded as noise.

Figure 10D:
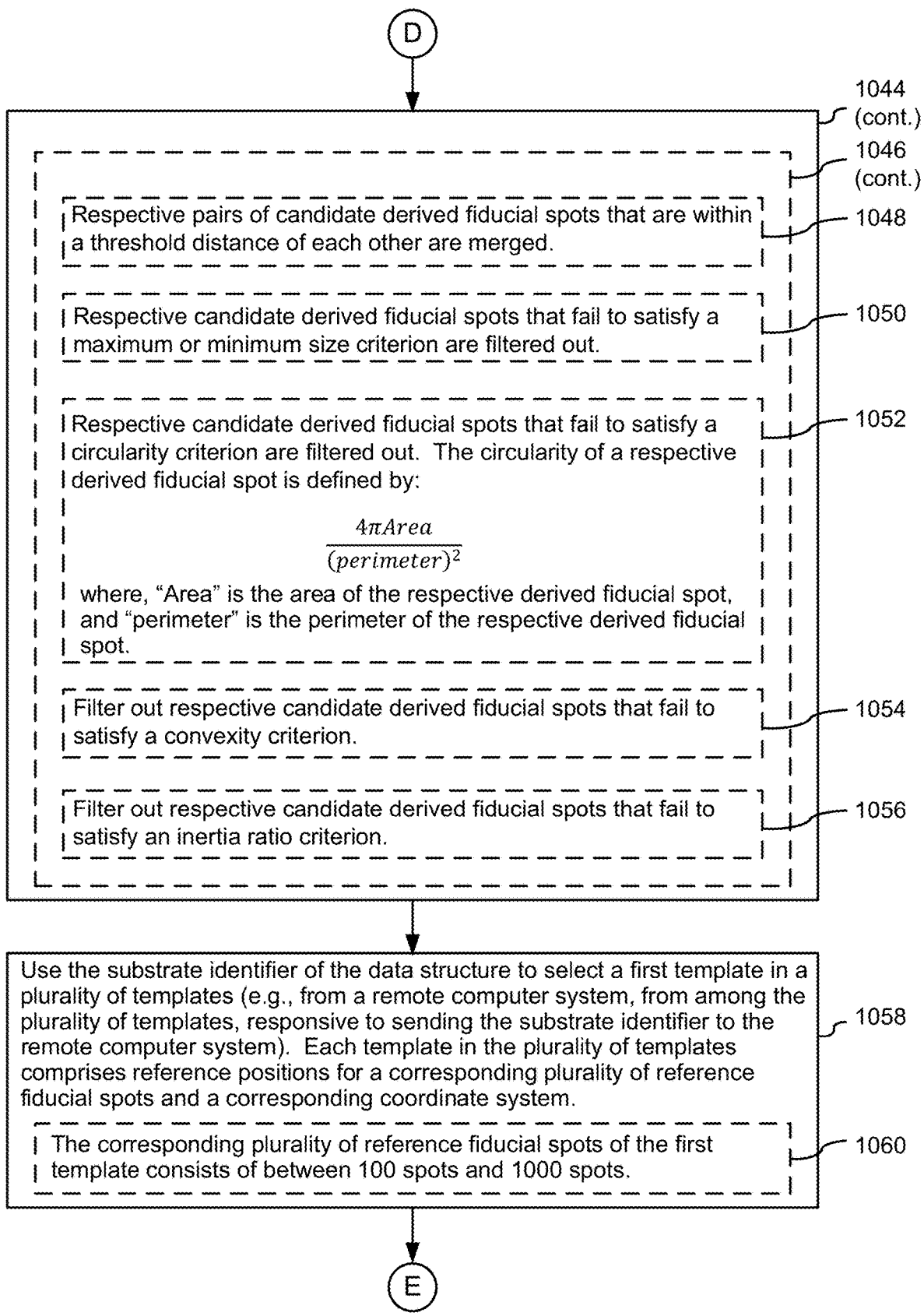

Referring to block 1048 of FIG. 10D and with further reference to FIG. 17, in some embodiments, respective pairs of candidate derived fiducial spots that are within a threshold distance of each other are merged. In some embodiments, this threshold distance is a threshold number of pixels, such as one pixel, two pixels, three pixels, four pixels, five pixels, six pixels, seven pixels, eight pixels, nine pixels, ten pixels, twenty pixels, etc. In some embodiments, this threshold distance is a threshold distance between spot centers. For instance, in some embodiments, a respective pair of candidate derived fiducial spots whose centers that are within 0.5 µM, within 1 µM, within 2 µM, within 3 µM, within 4 µM, within 5 µM, within 10 µM or within 20 µM of each other are merged. In some embodiments, the resultant merged candidate derived fiducial spot is taken midway between the original pair of candidate derived fiducial spots that is merged. In FIG. 17, the respective pair of candidate derived fiducial spots 1702-1/1702-2 is merged because they fail a distance threshold. In some embodiments, the threshold distance filter is applied to candidate derived fiducial spots.

In alternative embodiments, the threshold distance filter is not applied to candidate derived fiducial spots but rather is applied to derived fiducial spots after completion of block 1046.

Referring to block 1050 of FIG. 10D, in some embodiments respective candidate derived fiducial spots that fail to satisfy a maximum or minimum size criterion are filtered out. In some embodiments, this size filter is applied to candidate derived fiducial spots. In alternative embodiments, this size filter is not applied to candidate derived fiducial spots but rather is applied to derived fiducial spots after completion of block 1046. In some embodiments, application of this size filter causes respective candidate derived fiducial spots having less than 50 pixels, 200 pixels, 150 pixels, 100 pixels, 50 pixels, 40 pixels, 35 pixels, 30 pixels, 25 pixels, 20 pixels, 18 pixels, 16 pixels, 14 pixels, 12 pixels, 10 pixels, 9 pixels, 8 pixels, 7 pixels, 6 pixels, 5 pixels, or 4 pixels or less to be discarded. In some embodiments, application of this size filter causes respective candidate derived fiducial spots having more than 200 pixels, 150 pixels, 100 pixels, 50 pixels, 40 pixels, 35 pixels, 30 pixels, 25 pixels, 20 pixels, 18 pixels, 16 pixels, 14 pixels, 12 pixels, or 10 pixels to be discarded.

Referring to block 1052 of FIG. 10D, in some embodiments respective candidate derived fiducial spots that fail to satisfy a circularity criterion are filtered out. In some embodiments, this circularity filter is applied to candidate derived fiducial spots. In alternative embodiments, this circularity is not applied to candidate derived fiducial spots but rather is applied to derived fiducial spots after completion of block 1046. In some such embodiments, the circularity of a respective derived fiducial spot is defined by:

$$\text{circularity} = \frac{4\pi \text{Area}}{(\text{perimeter})^2}$$

where, "Area" is the area of the respective derived fiducial spot, and "perimeter" is the perimeter of the respective derived fiducial spot. Thus, in such embodiments, when this circularity criterion falls outside a suitable range, the respective candidate derived fiducial spot is deemed to not be circular, and thus not possibly representative of a true fiducial spot on the substrate, which in some embodiments are printed such that they are circular. In some embodiments, the circularity of each respective candidate derived fiducial spot is determined using a single-trace method for roundness determination. In some embodiments, the circularity of each respective candidate derived fiducial spot is determined using a multiple-trace method for roundness determination.

In some embodiments, the circularity of each respective candidate derived fiducial spot is determined using a least squares reference circle (LSCI) approach in which reference circle is fitted to the respective candidate derived fiducial spot such that the sum of the squares of the departure of the respective candidate derived fiducial spot from that reference circle is a minimum. Out-of-roundness is then expressed in terms of the maximum departure of the profile from the LSCI, i.e. the highest peak to the lowest valley. In such embodiments, when the out-of-roundness exceeds an acceptable threshold value, the respective candidate derived fiducial spot is discarded. In other embodiments, roundness is measured using a minimum circumcised circle method, minimum zone circle method. See, for example, Petrick et al., 2009, Measurement 2009, Proceedings of the 7th International Conference, Smolenice, Slovakia, pp. 352-355 which is hereby incorporated by reference. The exact threshold used to discard respective candidate derived fiducial spots (or candidate derived fiducial spots) using any of the disclosed methods for calculating circularity, or any method for calculating eccentricity known in the art, is application dependent and, in many instances, is dynamically optimized for a given dataset.

Referring to block 1054 of FIG. 10D, in some embodiments, respective candidate derived fiducial spots that fail to satisfy a convexity criterion are discarded. In some embodiments, this convexity filter is applied to candidate derived fiducial spots. In alternative embodiments, this convexity filter is not applied to candidate derived fiducial spots but rather is applied to derived fiducial spots after completion of block 1046. In some embodiments, the convexity filter requires that each respective candidate derived fiducial spot fall into a range between a minimum convexity (less than or equal to one) and a maximum convexity. In some embodiments, the convexity of a respective candidate derived fiducial spot is calculated by the formula:

$$\text{convexity} = \frac{\text{Area}}{\text{Area of Convex Hull}}$$

where, "Area" is the area of the respective candidate derived fiducial spot, and "Area of Convex Hull" is the area of the convex hull of the respective derived fiducial spot. See Andrew, 1979, "Another efficient algorithm for convex hulls in two dimensions," Information Processing Letters 9 (5), pp. 216-219; and Brown, 1979, "Voronoi diagrams from convex hulls," Information Processing Letters 9(5), pp. 223-228 for calculation of convex hulls. For more information on calculating convexity generally, see Emerging Technology in Modeling and Graphics: Processing of IEM Graph 2018, Jyotsna Kumar Mandal, Debika ed., which is hereby incorporated by reference. In some embodiments, the convexity filter requires that each respective candidate derived fiducial spot fall into a range between a minimum convexity of 0.10, 0.15, 0.20, 0.25, 0.30, 0.35, or 0.45 and a maximum convexity of 0.95, 0.90, 0.85, 0.80, 0.75, 0.70, 0.65, or 0.60.

Referring to block 1056 of FIG. 10D, in some embodiments, respective candidate derived fiducial spots that fail to satisfy an inertia ratio criterion are discarded. In some embodiments, this inertia ratio filter is applied to candidate derived fiducial spots. In alternative embodiments, this inertia ratio filter is not applied to candidate derived fiducial spots but rather is applied to derived fiducial spots after completion of block 1056. In some embodiments, the inertia ratio filter requires that each respective candidate derived fiducial spot fall into a range between a minimum inertia (less than or equal to one) and a maximum inertia. For more information on calculating inertia generally, see *Emerging Technology in Modeling and Graphics: Processing of IEM Graph* 2018, Springer Singapore, Jyotsna Kumar Mandal, Debika eds., which is hereby incorporated by reference. In some embodiments, the inertia filter requires that each respective candidate derived fiducial spot fall into a range between a minimum inertia of 0.40, 0.45, 0.50, 0.55, 0.60, 0.65, or 0.70 and a maximum inertia of 1 (full circle).

Referring to block 1058 of FIG. 10D, the substrate identifier 1128 of the data structure 1122 is used to select a first template in a plurality of templates (e.g., from a remote computer system, from among the plurality of templates, responsive to sending the substrate identifier to the remote computer system). In other words, the substrate identifier of the substrate that is presently being analyzed is used to identify a template that has a matching substrate identifier. For instance, referring to FIG. 11B, in some embodiments, the plurality of templates is found in a template repository 1140. Each template 1142 in the plurality of templates includes at least one chip identifier 1128 that it can be used for and comprises reference positions 1148 (coordinates) for a corresponding plurality of reference fiducial spots 1146 and a corresponding coordinate system 1144. In some embodiments, the coordinate system is inferred from the coordinates 1148. In some embodiments, the coordinate system 1144 comprises the location (coordinates) of capture spots 1136 on the chip substrate has a substrate identifier 1128 that matches the substrate identifier of the template 1142.

In some embodiments, a template 1142 is formed from a substrate printing instruction file (e.g., a GenePix Array List (GAL) file) that specifies how to print the array capture spots 1136 on the substrate. In some such embodiments, the substrate printing instruction file is analyzed to create a template 1142 for each substrate and this template is provided when the matching substrate identifier 1128 is provided. For information on example substrate printing instruction files, see Zhai, 2001, "Making GenePix Array List (GAL) Files," GenePix Application Note, Molecular Devices, pp. 1-9, which is hereby incorporated by reference. FIG. 18 illustrates an example of the formation of a template 1142 from a GAL file.

Figure 19:
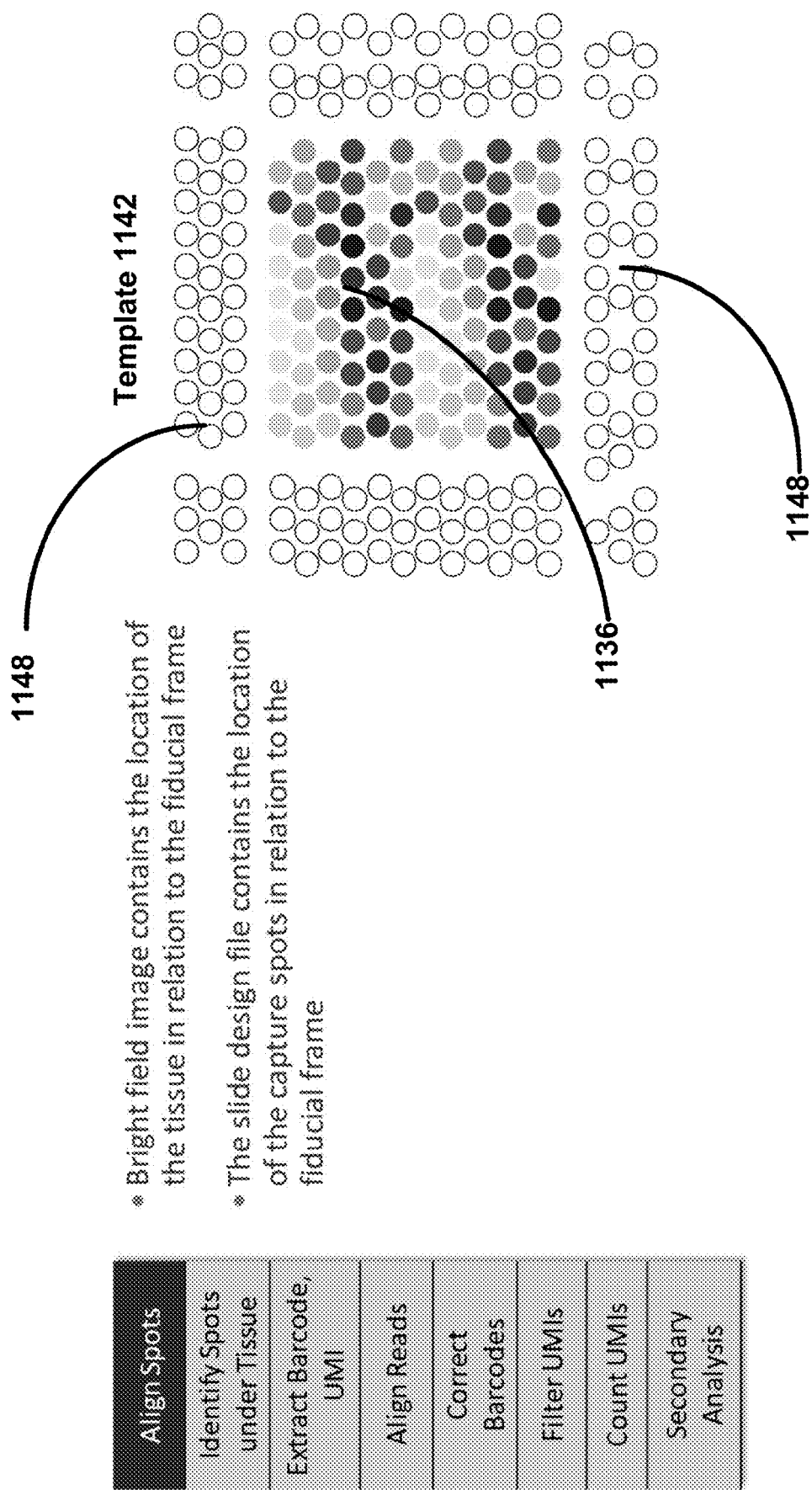
FIG. 19 illustrates how the template specifies the locations of the set of capture spots of a substrate in relation to the reference fiducial spots of the substrate using a corresponding coordinate system in accordance with an embodiment of the present disclosure.

Referring to block 1060 of FIG. 10D, in some embodiments, the corresponding plurality of reference fiducial spots 1146 of the first template 1142 consists of between 100 fiducial spots and 1000 fiducial spots, between 200 fiducial spots and 800 fiducial spots, between 300 fiducial spots and 700 fiducial spots or between 500 and 600 fiducial spots. That is, the template 1142 has between 100 fiducial spots and 1000 fiducial spots because that is how many fiducial spots are on the substrate that corresponds to the template. In some embodiments, the template 1142 and the corresponding substrate have less than 100 fiducial spots, less than 50 fiducial spots or less than 25 fiducial spots. In some embodiments, the template 1142 and the corresponding substrate have more than 1000 fiducial spots, more than 1500 fiducial spots or more than 3000 fiducial spots. FIG. 19 illustrates the positions of fiducial spots at the perimeter of the substrate. As further illustrated in FIG. 19, the substrate also includes capture spots 1136 and the coordinate system 1144 of the template 1142 specifies the location of these capture spots on the substrate and, in some embodiments, precisely which capture probes have been printed at each capture spot. In some embodiments, each capture spot has been printed with the same capture probes. In other embodiments, each capture spot is printed with an independent set of capture probes and the template 1142 tracks not only the position on the substrate of each respective capture spot, but also the independent set of capture probes that have been printed on the respective capture spot. In some embodiments, the coordinate system 1144 provides an explicit location of each capture spot 1136 on the substrate. In some embodiments, the coordinate system 1144 provides an orientation of the substrate relative to the fiducial spots and the orientation is used to reference a list of capture spot locations in a data source that is external to the template 1142. One of skill in the art will appreciate that there are a number of ways to implement the template coordinate system 1144 based on the present disclosure (e.g., as an explicit list of capture spot locations, as an orientation derived from the fiducial spots coupled with an external list of capture spot locations, etc.) and all such methods are encompassed by the present disclosure.

Figure 10E:
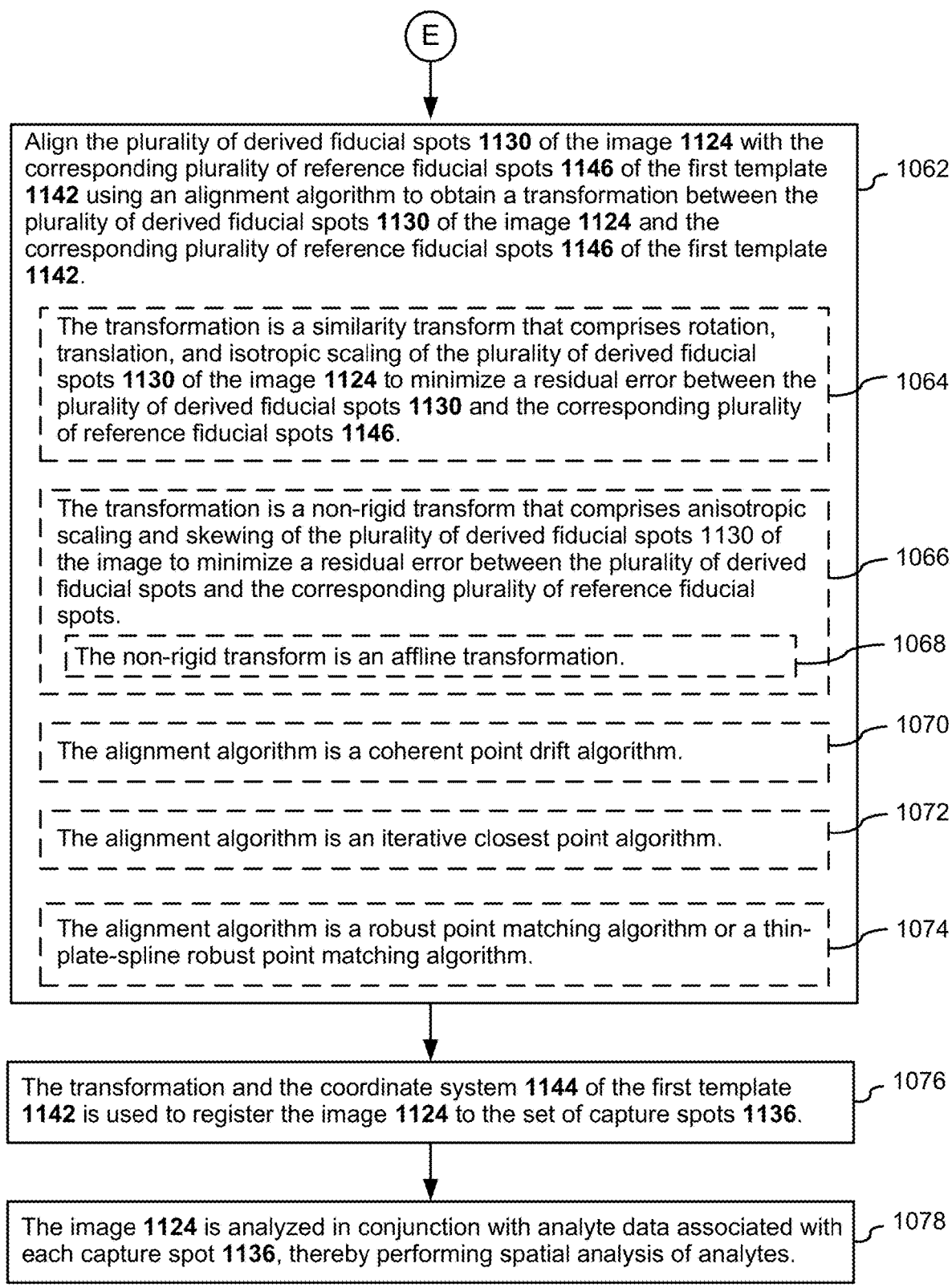

Referring to block 1062 of FIG. 10E, the plurality of derived fiducial spots 1130 of the image 1124 is aligned with the corresponding plurality of reference fiducial spots 1146 of the first template 1142 using an alignment algorithm to obtain a transformation between the plurality of derived fiducial spots 1130 of the image 1124 and the corresponding plurality of reference fiducial spots 1146 of the first template 1142. This is a point set registration problem, the goal of which is to assign correspondences between two sets of points (the plurality of derived fiducial spots 1130 of the image 1124 and the plurality of reference fiducial spots 1146 of the template 1142) and/or to recover the transformation that maps one point set to the other. In some embodiments, in order to determine which of the eight possible orientations a substrate is in (four 90 degree rotations plus reflection), all eight orientations are concurrently run and the orientation with the lowest residual error is chosen, as long as the second lowest residual error is significantly higher.

Referring to block 1064 of FIG. 10E, in some embodiments, the transformation between the plurality of derived fiducial spots 1130 of the image 1124 and the corresponding plurality of reference fiducial spots 1146 of the template 1142 is a similarity transform. A similarity transformation allows only for translation, rotation and isotropic scaling. Thus, when a similarity transformation is used, the plurality of derived fiducial spots 1130 of the image 1124 are rotated, translated, and/or isotropically scaled to minimize a residual error between the plurality of derived fiducial spots 1130 and the corresponding plurality of reference fiducial spots 1146.

In some embodiments, the transformation between the plurality of derived fiducial spots 1130 of the image 1124 and the corresponding plurality of reference fiducial spots 1146 of the template 1142 is a rigid transform. A rigid transformation allows only for translation and rotation. Thus, when a rigid transformation is used, the plurality of derived fiducial spots 1130 of the image 1124 are rotated and/or translated to minimize a residual error between the plurality of derived fiducial spots 1130 and the corresponding plurality of reference fiducial spots 1146.

Referring to block 1066 of FIG. 10E, in some embodiments the transformation is a non-rigid transform that comprises anisotropic scaling and skewing of the plurality of derived fiducial spots 1130 of the image 1124 to minimize a residual error between the plurality of derived fiducial spots 1130 and the corresponding plurality of reference fiducial spots 1146. Referring to block 1068 of FIG. 10E, in some embodiments the non-rigid transform is an affline transformation. Referring to block 1070 of FIG. 10E, in some embodiments the alignment algorithm is a coherent point drift algorithm. See Myronenko et al., 2007, "Non-rigid point set registration: Coherent Point Drift," NIPS, 1009-1016; and Myronenko and Song, "Point Set Registration: Coherent Point Drift," arXiv:0905.2635v1, 15 May 2009, each of which is hereby incorporated by reference, for disclosure on the coherent point drift algorithm. In some embodiments, the coherent point drift algorithm that is used is an implementation in Python called pycpd." See, the Internet at github.com/siavashk/pycpd, which is hereby incorporated by reference.

Referring to block 1072 of FIG. 10E, in some embodiments the alignment algorithm is an iterative closest point algorithm. See, for example, Chetverikov et al., 2002, "The Trimmed Iterative Closest Point Algorithm," Object recognition supported by user interaction for service robots, Quebec City, Quebec, Canada, ISSN: 1051-4651; and Chetverikov et al., 2005, "Robust Euclidean alignment of 3D point sets; the trimmed iterative closest point algorithm," Image and Vision Computing 23(3), pp. 299-309, each of which is hereby incorporated by reference.

Referring to block 1074 of FIG. 10E, in some embodiments the alignment algorithm is a robust point matching algorithm (See, for example, Chui and Rangarajanb, 2003, "A new point matching algorithm for non-rigid registration," Computer Vision and Image Understanding 89(2-3), pp. 114-141, which is hereby incorporated by reference) or a thin-plate-spline robust point matching algorithm (See, for example, Yang, 2011, "The thin plate spline robust point matching (TPS-RPM) algorithm: A revisit," Pattern Recognition Letters 32(7), pp. 910-918, which is hereby incorporated by reference.)

Figure 20:
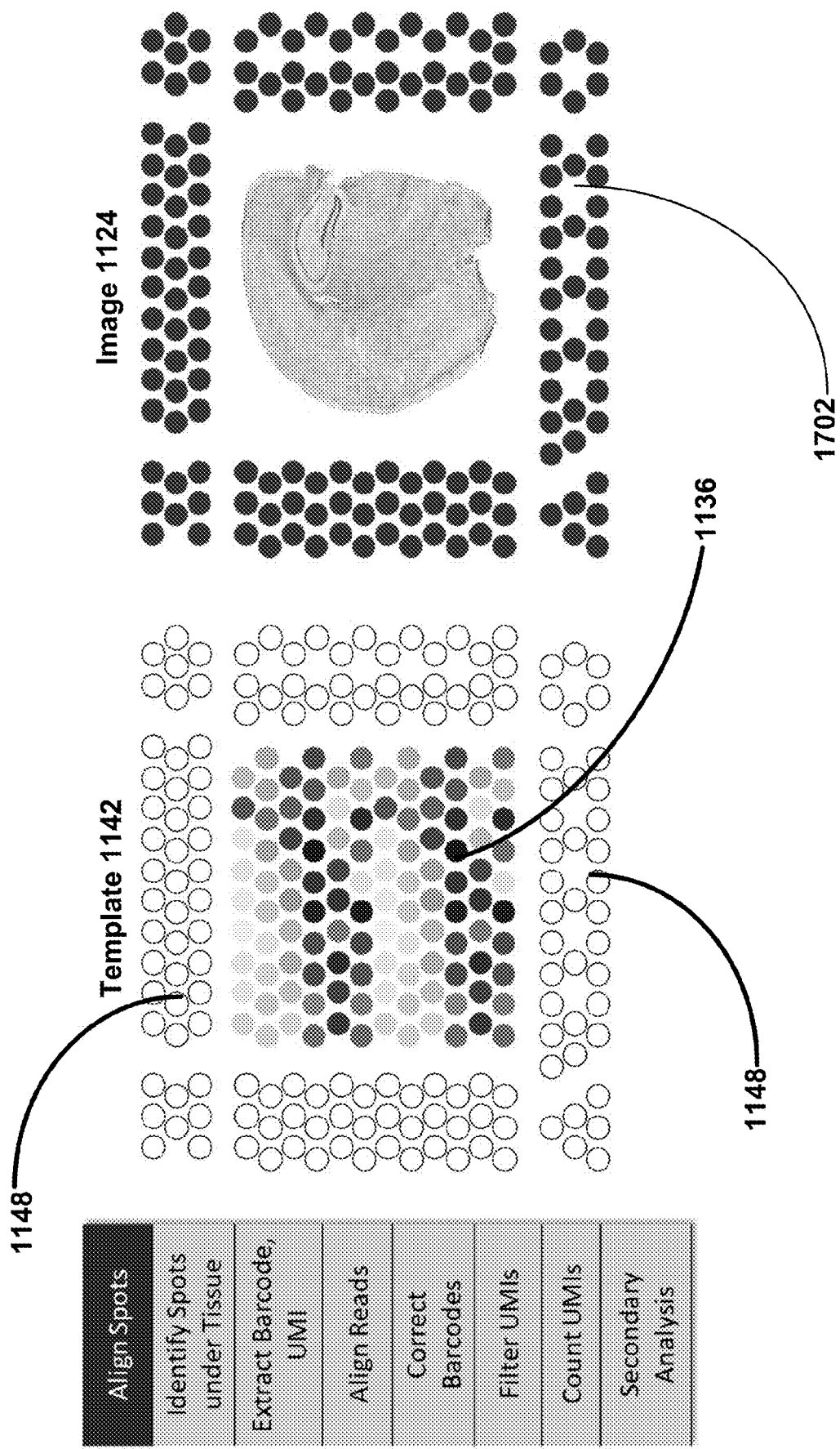
FIG. 20 illustrates the substrate design, including a plurality of fiducial markers and a set of capture spots, to the image, which includes corresponding derived fiducial spots, in accordance with an embodiment of the present disclosure.

Referring to block 1076 of FIG. 10E, the transformation and the coordinate system 1144 of the first template 1142 is used to register the image 1124 to the set of capture spots 1136. FIGS. 20 and 21 illustrate. In FIG. 20, the alignment causes the transformation that maps the substrate derived fiducial spots 1130 of the image onto the fiducial spots 1148 of the template 1142. Upon such a mapping, as illustrated in FIG. 21, it is now possible to determine the location of each capture spot 1136 in the image 1124.

Figure 24:
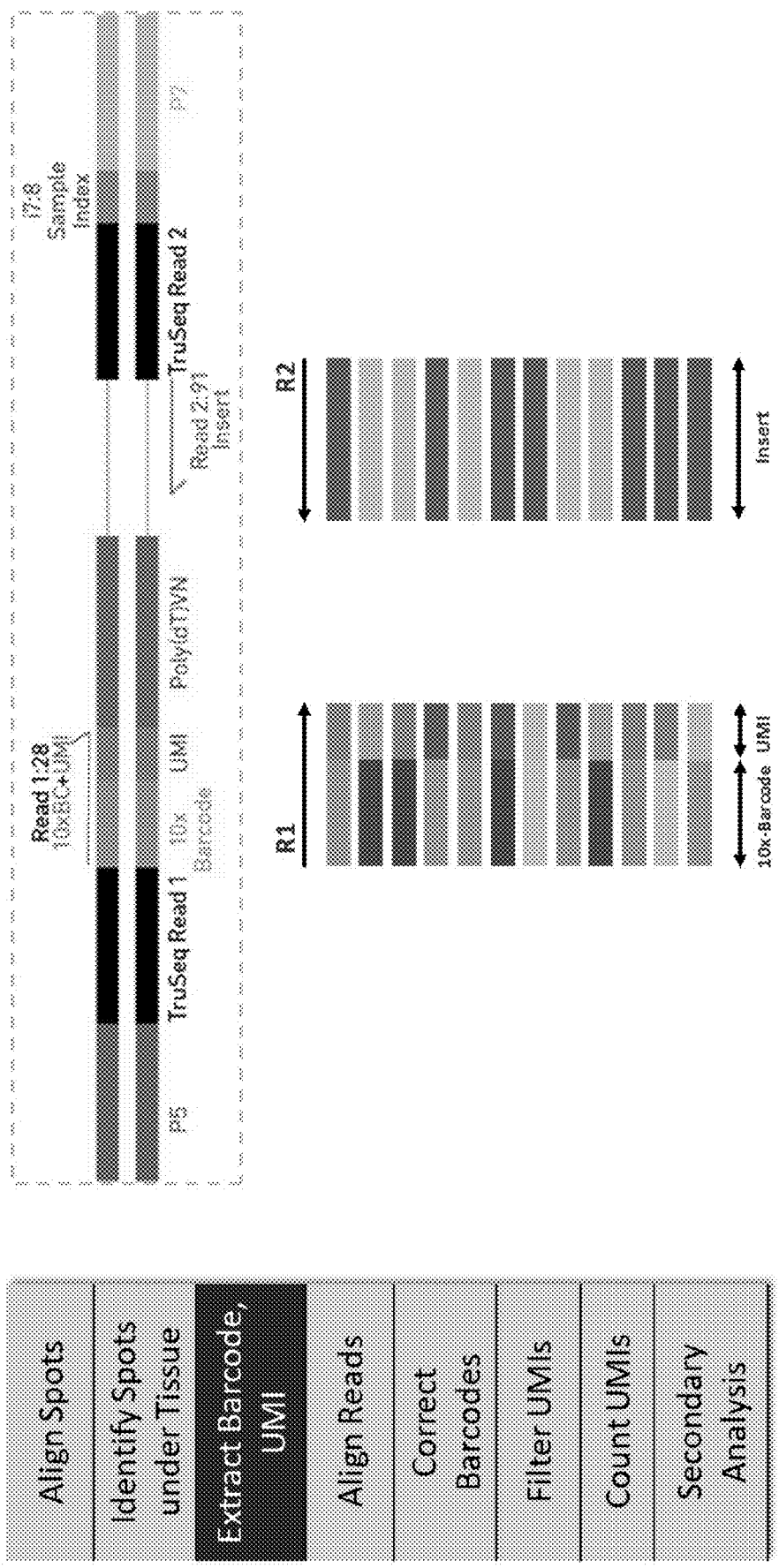
FIG. 24 illustrates extraction of barcodes and UMIs from each sequence read in nucleic acid sequencing data associated with a substrate in accordance with an embodiment of the present disclosure.
Figure 25:
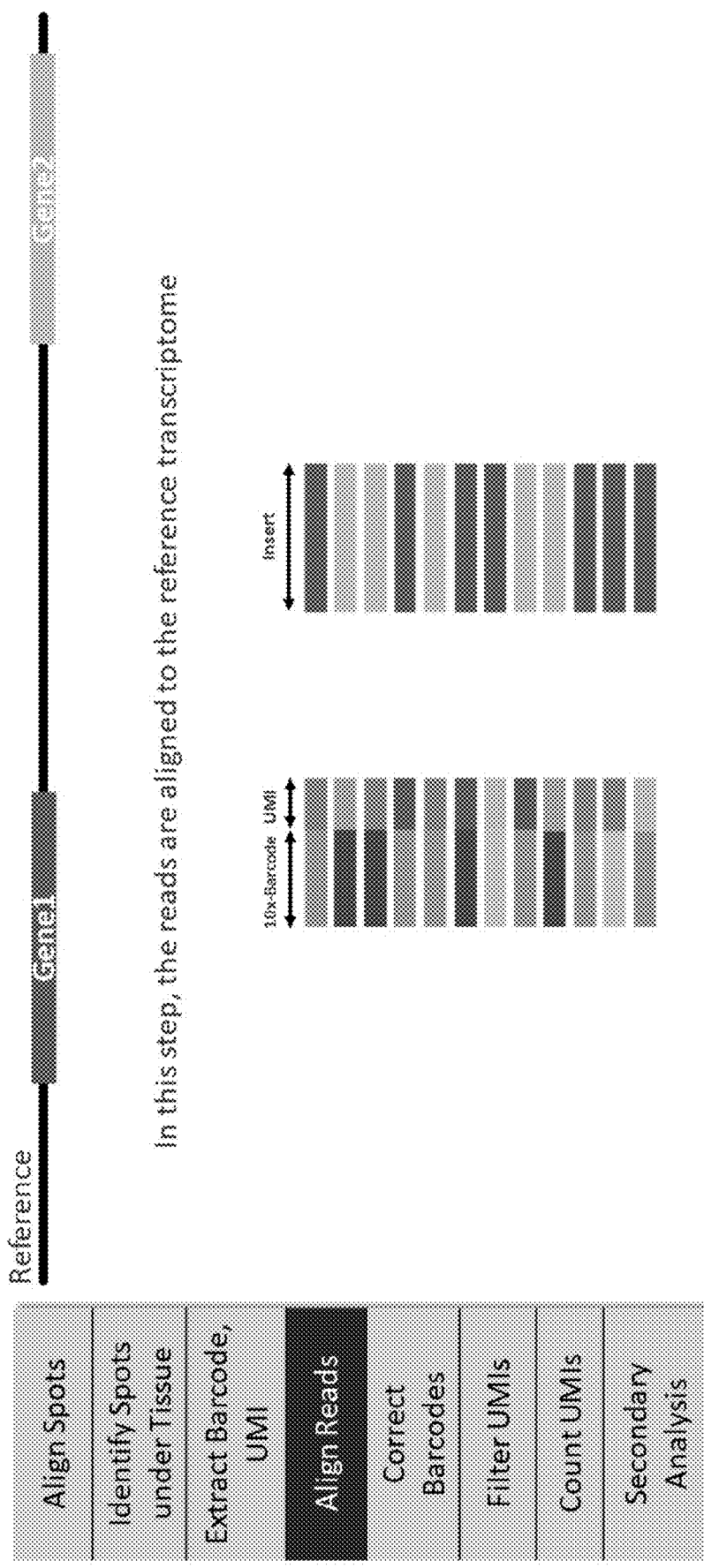
FIG. 25 illustrates alignment of the sequence reads with a reference genome in accordance with an embodiment of the present disclosure.
Figure 26:
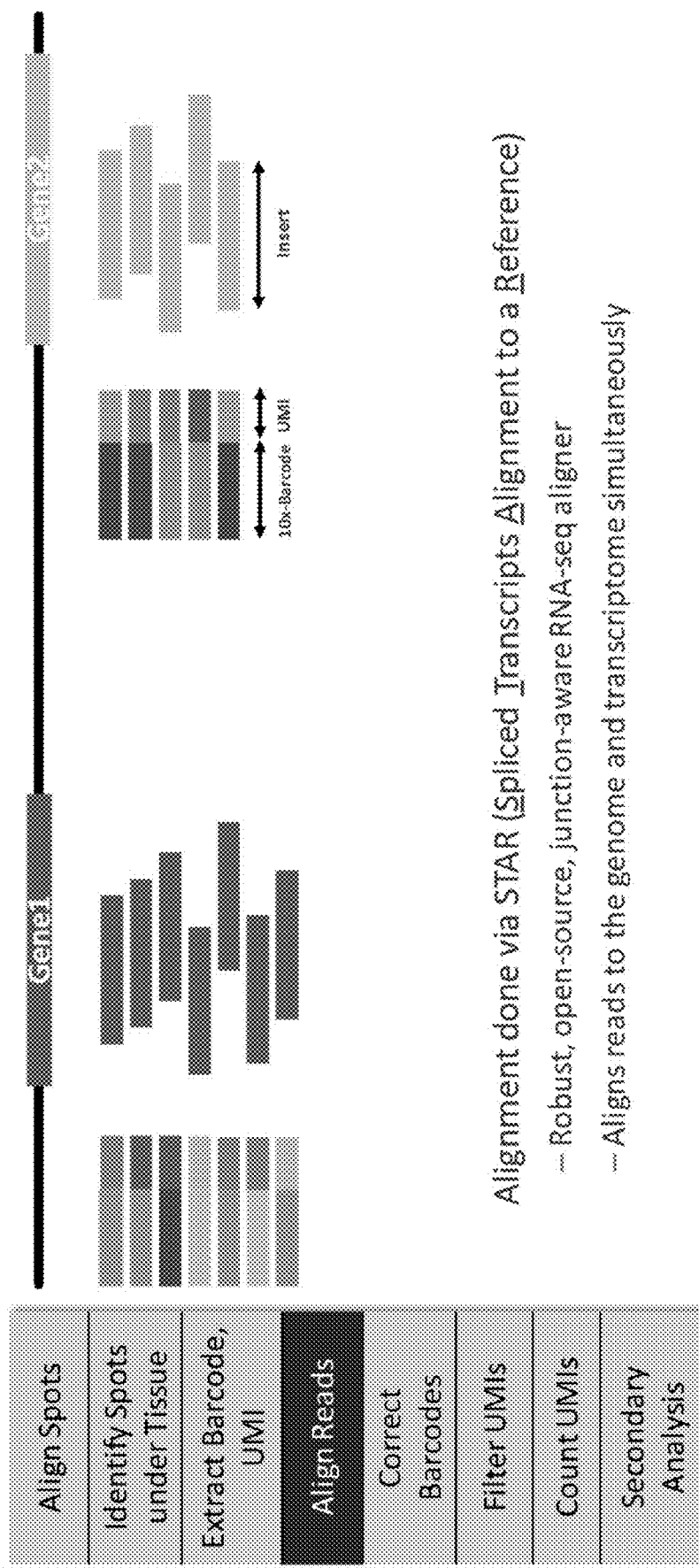
FIG. 26 illustrates how sequence reads don't all map to exactly the same place, even if they share a barcode and UMI, due to the random fragmentation that happens during workflow steps in accordance with an embodiment of the present disclosure.
Figure 27:
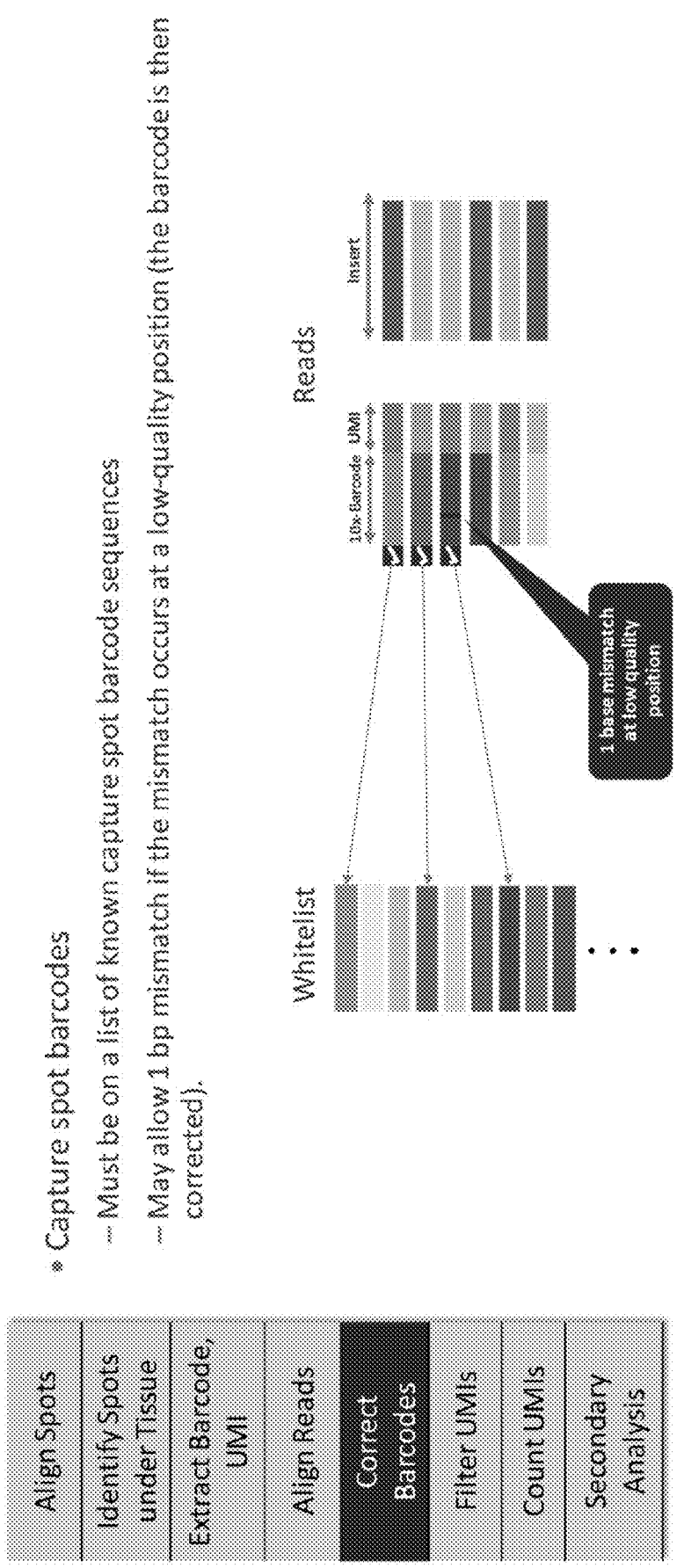
FIG. 27 illustrates how the barcode of each sequence read is validated against a whitelist of actual barcodes (e.g., in some embodiments the whitelist corresponds to the Chromium Single Cell 3' v3 chemistry gel beads that have about 3.6 million distinct barcodes and thus a whitelist of 3.6 million barcodes) in accordance with an embodiment of the present disclosure.
Figure 28:
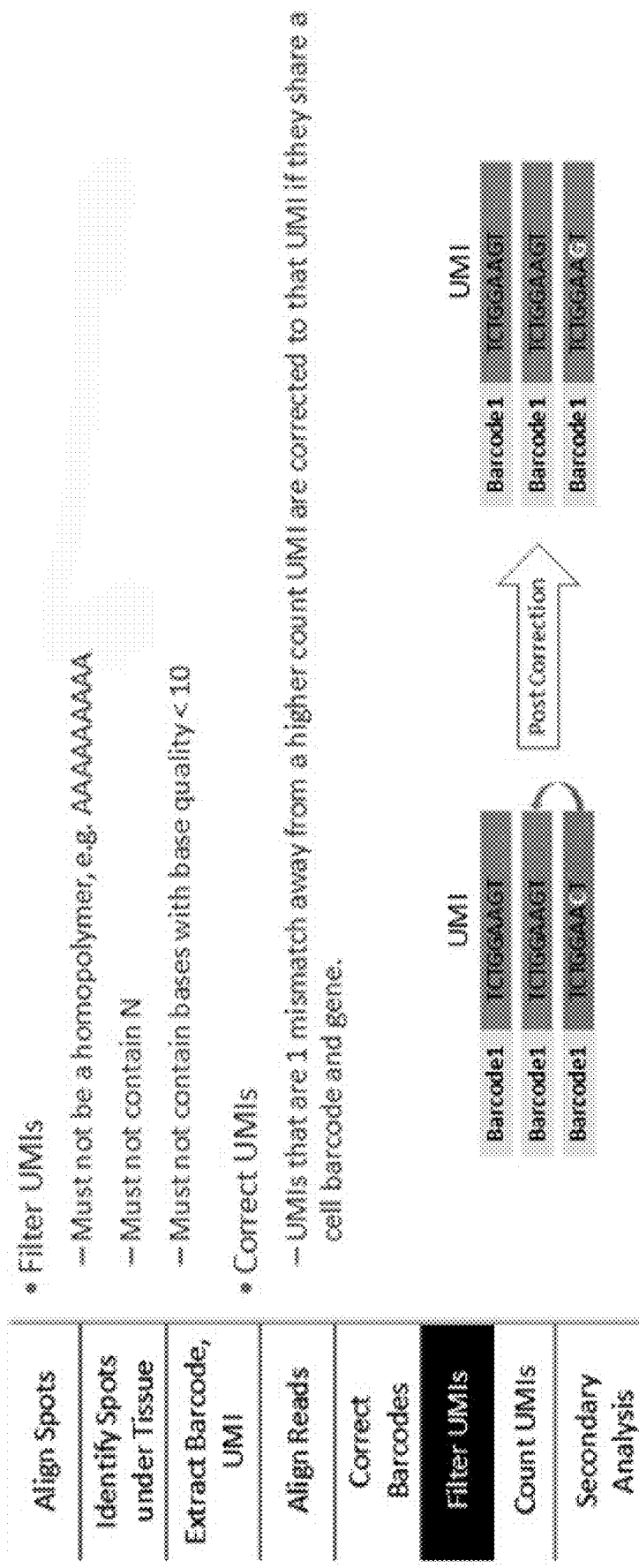
FIG. 28 illustrates how the unique molecular identifiers (UMIs) of sequence reads that are 1 mismatch away from a higher count UMI are corrected to that UMI if they share a cell barcode and gene in accordance with some embodiments of the present disclosure.
Figure 29:
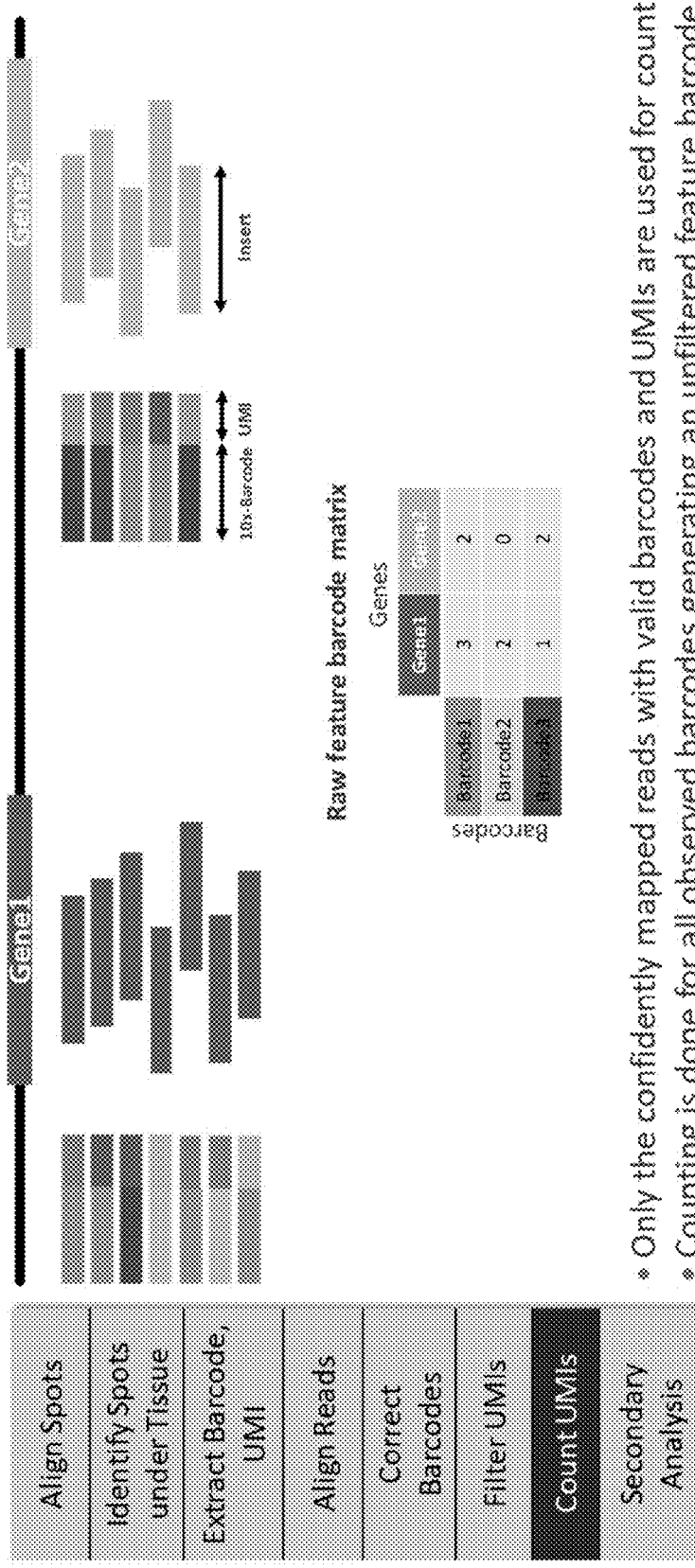
FIG. 29 illustrates how using only the confidently mapped reads with valid barcodes and UMIs are used to form UMI counts for a raw feature barcode matrix in accordance with some embodiments of the present disclosure.
Figure 30:
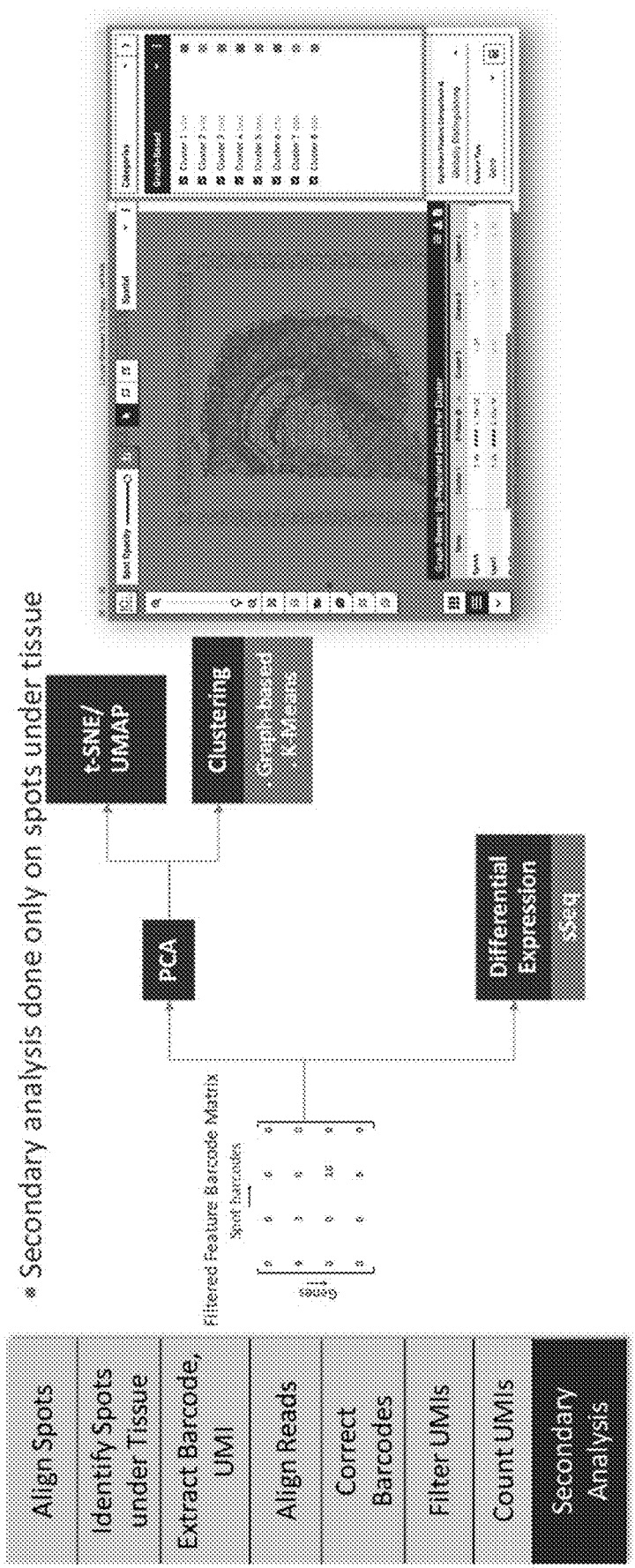
FIG. 30 illustrates how secondary analysis is done on barcodes called as cells (filtered feature barcode matrix), in which principal components analysis on normalized filtered gene-cell matrix is used to reduce G genes to top 10 metagenes, t-SNE is run in PCA space to generate a two-dimensional projection, graph-based (Louvain) and k-means clustering (k=2 . . . 10) is performed in PCA-space to identify clusters of cells, and sSeq (negative-binomial test) algorithm is used to find genes that most uniquely define each cluster, in accordance with an embodiment of the present disclosure.

Referring to block 1078 of FIG. 10E, the image 1124 is analyzed in conjunction with spatial analyte data such as nucleic acid sequencing data (e.g., sequence reads 1138) associated with each capture spot 1136, thereby performing spatial nucleic acid analysis. Methods for such analysis are disclosed in 62/938,336, entitled "Pipeline for spatial analysis of anlytes," filed Nov. 21, 2019, each of which is hereby incorporated by reference. This is illustrated in FIG. 22, after the capture spots are overlaid on the image, the spots that are under the tissue sample of the tissue can be identified and the nucleic acid sequencing data of each such capture spot can be analyzed using, for example, the techniques disclosed in the present disclosure as well as those detailed in United States Provisional Patent Application Nos. 62/886,233, entitled "Systems and Methods for Using the Spatial Distribution of Haplotypes to Determine a Biological Condition," filed Aug. 13, 2019; 62/909,071, entitled "Systems and Methods for Visualizing a Pattern in a Dataset," filed Oct. 1, 2019; 62/839,346, entitled "Spatial Transcriptomics of Biological Analytes in Tissue Samples," filed Apr. 26, 2019, and 62/938,336, entitled "Pipeline for spatial analysis of anlytes," filed Nov. 21, 2019, each of which is hereby incorporated by reference. Such analysis is further illustrated in FIG. 23, which specifies that the capture spots 1136 that are under tissue are used to generate a filtered barcode matrix that is used for secondary analysis that is further illustrated in FIGS. 24-35. In particular, FIG. 24 illustrates how the spatial barcodes 1150 and UMIs are extracted from each sequence read 1136 (e.g., using Read 1) that has been obtained, as further explained in U.S. Provisional Application No. 62/839,346, entitled "Spatial Transcriptomics of Biological Analytes in Tissue Samples," filed Apr. 26, 2019, which is hereby incorporated by reference. FIG. 25 illustrates how the sequence reads 1138 are aligned to the reference genome (e.g., using the Read 2 insert read). FIG. 26 illustrates how sequence reads 1138 don't all map to exactly the same place, even if they share a barcode and UMI, due to the random fragmentation that happens during the workflow steps. FIG. 27 illustrates how the spatial barcodes in the sequence reads in the capture spots must be in a list of known capture spot spatial barcodes. For instance, if the Chromium Single Cell 3' v3 chemistry gel beads (10×, Pleasanton, Calif.) are used to perform sequencing of analytes from capture spots in accordance with U.S. Provisional Application No. 62/839,346, entitled "Spatial Transcriptomics of Biological Analytes in Tissue Samples," filed Apr. 26, 2019, each spatial barcode 1150 must be in the set of 3.6 million distinct cell barcodes in the Chromium Single Cell 3' v3 chemistry gel beads. As detailed in FIG. 27, in some embodiments a single mismatch in the barcode is permitted. In other embodiments, no mismatch in the spatial barcode 1150 is permitted and sequence reads that have a spatial barcode 1150 that is not in the set of spatial barcode of the sequencing kit used (e.g., the Chromium Single Cell 3' v3 chemistry gel beads) are discarded. FIG. 28 illustrates how unique molecule identifiers (UMIs) are used to assess and filter out sequence reads 1138 as well in some embodiments. Thus, referring to FIG. 29, in some embodiments only confidently mapped sequence reads 1138 with valid spatial barcodes 1150 and UMIs are used. In some embodiments the UMI of sequence reads are corrected to more abundant UMIs that are one mismatch away in sequence. In some embodiments, sequence reads that are duplicates of the same RNA molecule are recorded and only the unique UMIs are counted as unique RNA molecules. In such embodiments, these UMI counts form the raw feature barcode matrix. FIG. 30 further illustrates how the image 1124 is analyzed in conjunction with nucleic acid sequencing data associated with each capture spot 1136. In some embodiments, the raw feature barcode matrix is subjected to a dimension reduction algorithm such as principal components analysis to reduce G genes to top 10 metagenes. Then, t-SNE is run in the PCA space to generate a two-dimensional projection. Further, graph-based (Louvain) and k-means clustering (k=2 . . . 10) in PCA-space is used to identify clusters of cells. In some embodiments an sSeq (negative-binomial test) algorithm is used to find genes that most uniquely define each cluster. See, for example, U.S. Provisional Application No. 62/909,071, entitled "Systems and Methods for Visualizing a Pattern in a Dataset," filed Oct. 1, 2019, which is hereby incorporated by reference.

Figure 31:
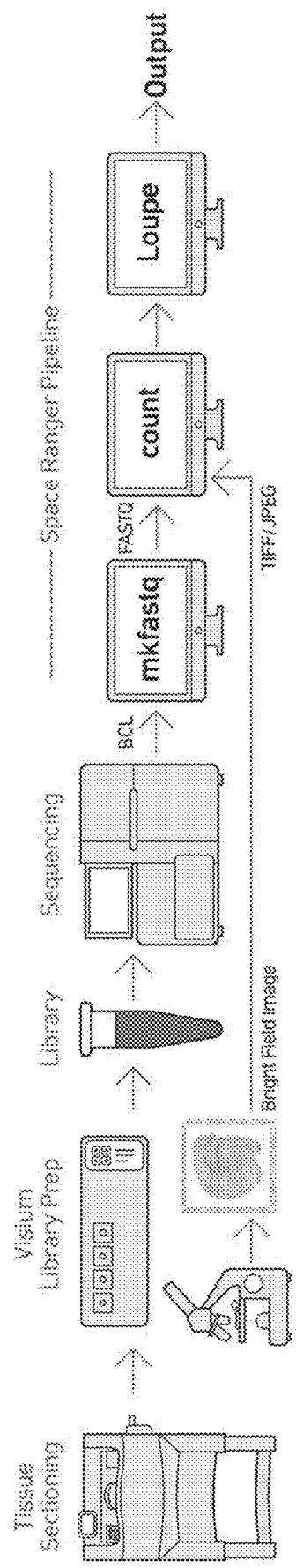
FIG. 31 illustrates a pipeline for analyzing an image (e.g., tissue image) in conjunction with nucleic acid sequencing data associated with each capture spot in a plurality of capture spots, thereby performing spatial nucleic acid analysis in accordance with the present disclosure.
Figure 32:
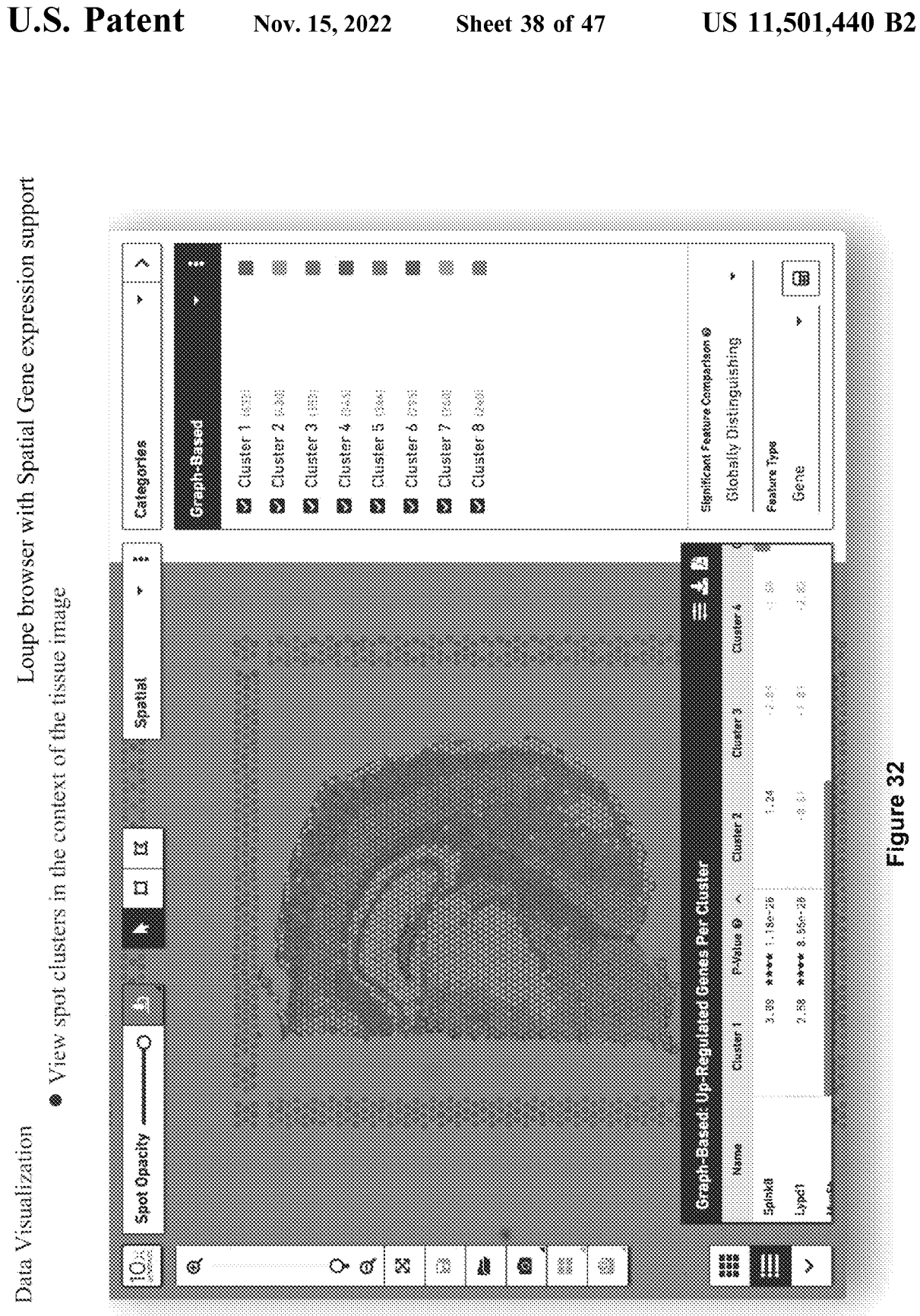
FIG. 32 illustrates how analysis of the tissue image in conjunction with nucleic acid sequencing data can be used to view capture spot clusters in the context of the image in accordance with the present disclosure.
Figure 33:
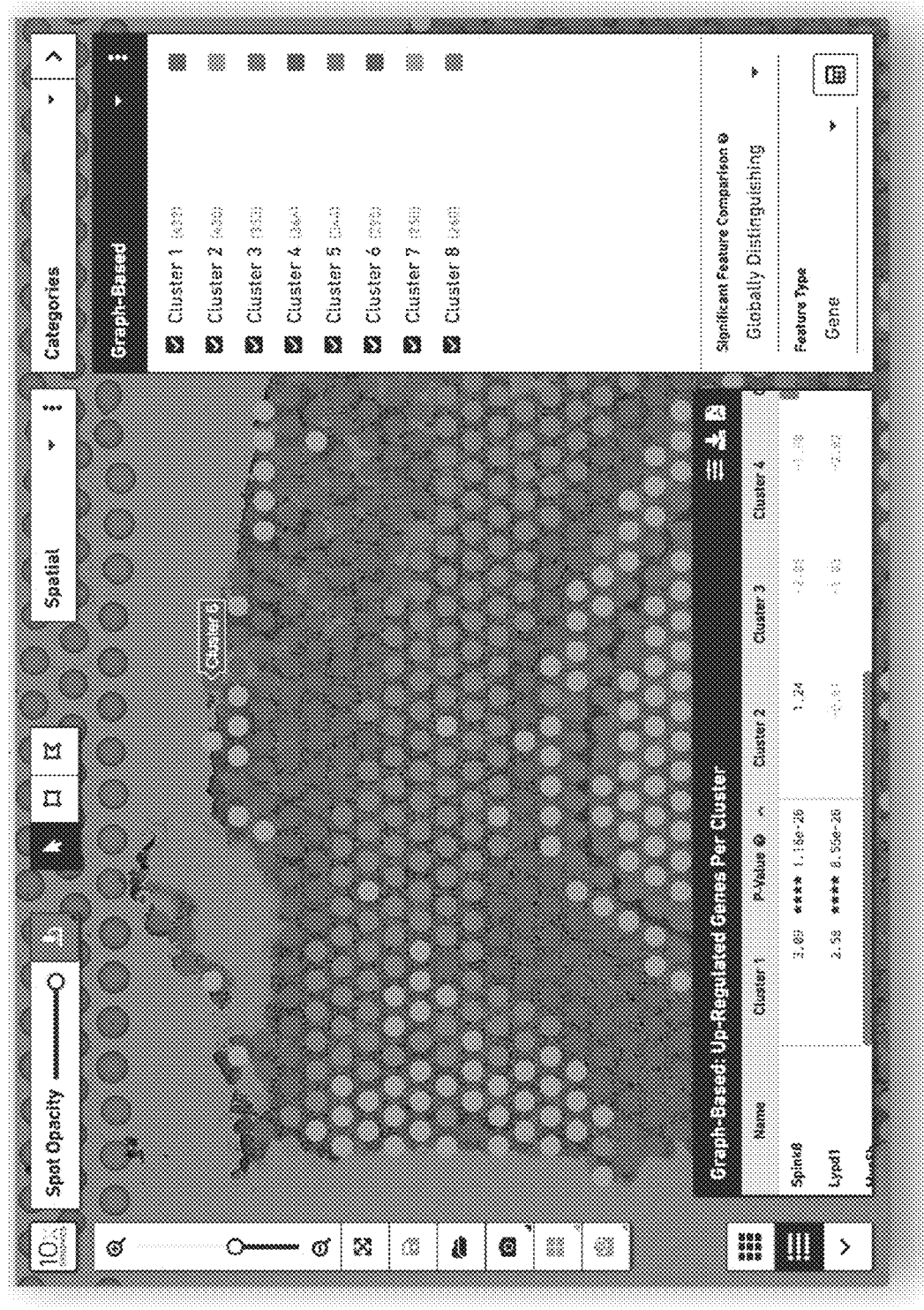
FIG. 33 illustrates how analysis of the tissue image in conjunction with nucleic acid sequencing data can include zooming into the overlay of capture spot clusters in the context of the image in order to see more detail in accordance with some embodiments of the present disclosure.
Figure 34:
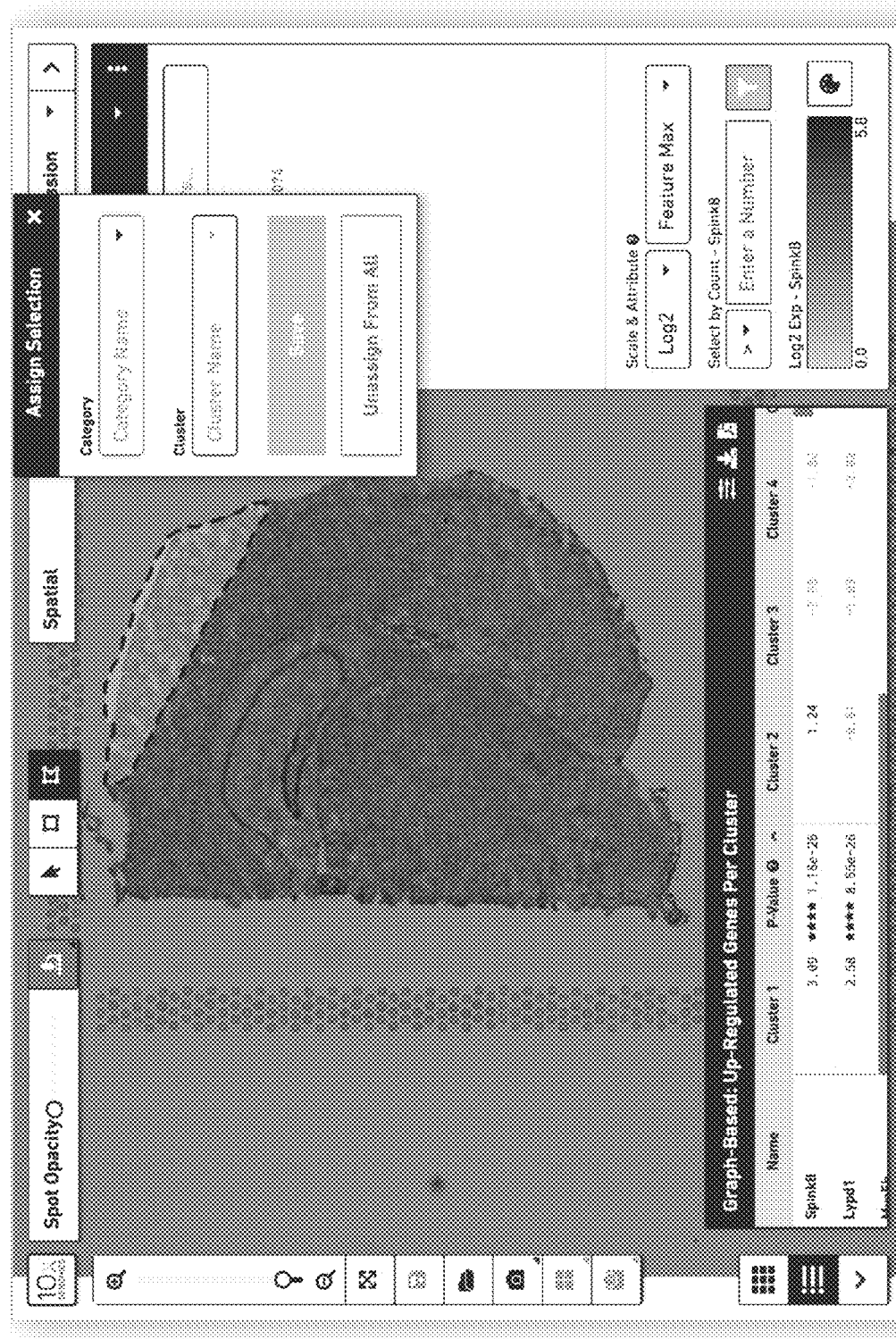
FIG. 34 illustrates how analysis of the tissue image in conjunction with nucleic acid sequencing data can be used to create custom categories and clusters for differential expression analysis in accordance with some embodiments of the present disclosure.
Figure 35:
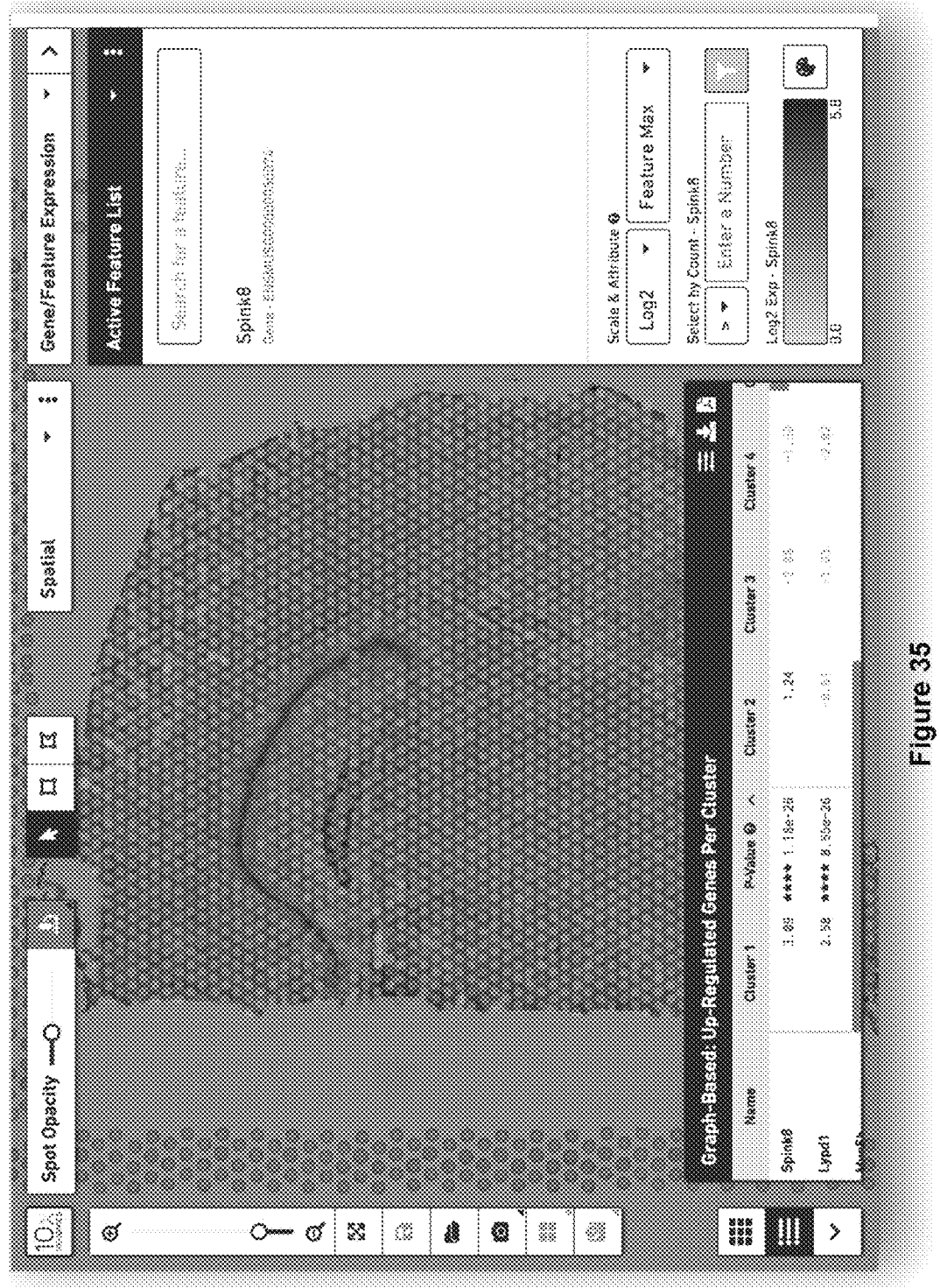
FIG. 35 illustrates how analysis of the tissue image in conjunction with nucleic acid sequencing data can be used to see expressed genes in the context of the tissue image in accordance with some embodiments of the present disclosure.

FIG. 31 illustrates how the acquisition of the image 1124 runs parallel, and in conjunction to, the above-described spatial sequencing. FIG. 32 illustrates the end result of this parallel analysis, where the image 1124 is displayed in conjunction with nucleic acid sequencing data associated with each capture spot 1136 in accordance with some embodiments of the present disclosure. FIG. 33 illustrates how the image and the corresponding analysis of nucleic acid sequencing data can be zoomed in to see further detail as disclosed in U.S. application Ser. No. 17/039,935, entitled "Systems and Methods for Identifying Morphological Patterns in Tissue Samples," filed Sep. 30, 2020, which is hereby incorporated by reference. FIG. 34 illustrates how custom categories and clusters for differential expression analysis can be performed as part of the analysis of the image 1124 after the in conjunction with nucleic acid sequencing data associated with each capture spot 1136 in accordance with some embodiments of the present disclosure. FIG. 35 illustrates how the spatial expression of genes in the context of the image 1124 can be performed as part of the analysis of the image 1124 in conjunction with nucleic acid sequencing data associated with each capture spot 1136 in accordance with some embodiments of the present disclosure. See, for example, U.S. Provisional Application No. 62/909,071, entitled "Systems and Methods for Visualizing a Pattern in a Dataset," filed Oct. 1, 2019, which is hereby incorporated by reference.

Exemplary Embodiment

Figure 36:
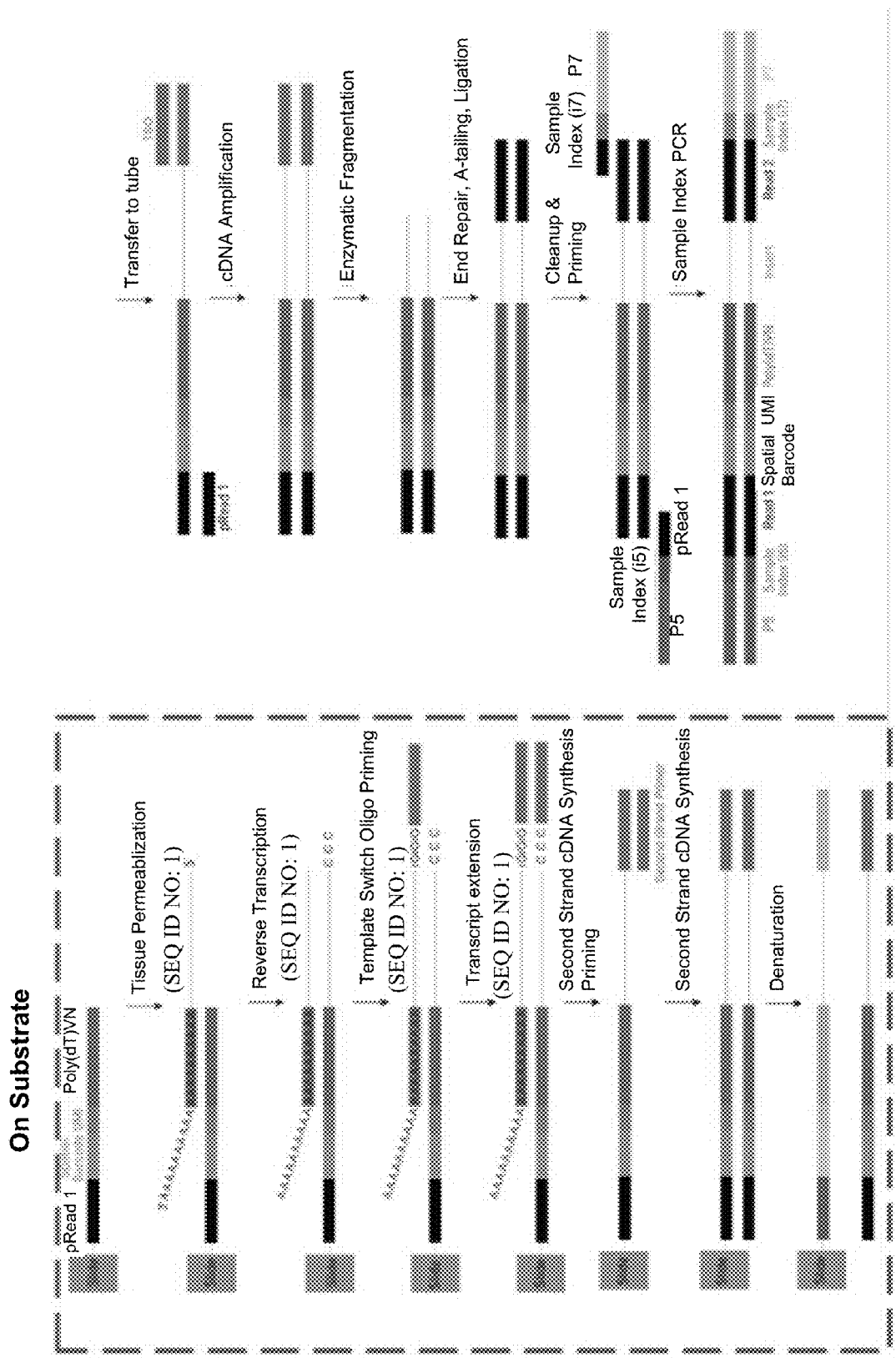
FIG. 36 illustrates a reaction scheme for the preparation of sequence reads for spatial analysis in accordance with some embodiments of the present disclosure.

The following example provides reaction schemes for the preparation of sequence reads for spatial analysis. FIG. 36 also provides a reaction scheme for the preparation of sequence reads for spatial analysis.

In some non-limiting examples of the workflows described herein, the sample can be immersed in 100% chilled methanol and incubated for 30 minutes at −20° C. After 20 minutes, the sample can be removed and rinsed in ultrapure water. After rinsing the sample, fresh eosin solution is prepared, and the sample can be covered in isopropanol. After incubating the sample in isopropanol for 1 minute, the reagent can be removed by holding the slide at an angle, where the bottom edge of the slide can be in contact with a laboratory wipe and air dried. The sample can be uniformly covered in hematoxylin solution and incubated for 7 minutes at room temperature. After incubating the sample in hematoxylin for 7 minutes, the reagent can be removed by holding the slide at an angle, where the bottom edge of the slide can be in contact with a laboratory wipe. The slide containing the sample can be immersed in water and the excess liquid can be removed. After that, the sample can be covered with blueing buffer and can be incubated for 2 minutes at room temperature. The slide containing the sample can again be immersed in water, and uniformly covered with eosin solution and incubated for 1 minute at room temperature. The slide can be air-dried for no more than 30 minutes and incubated for 5 minutes at 37° C. The sample can be imaged using brightfield imaging setting.

Further, the sample can be processed by the following exemplary steps for sample permeabilization and cDNA generation. The sample can be exposed to a permeabilization enzyme and incubated at 37° C. for the pre-determined permeabilization time (which is tissue type specific). The permeabilization enzyme can be removed and the sample prepared for analyte capture by adding 0.1×SSC buffer. The sample can then subjected to a pre-equilibration thermocycling protocol (e.g., lid temperature and pre-equilibrate at 53° C., reverse transcription at 53° C. for 45 minutes, and then hold at 4° C.) and the SSC buffer can be removed. A Master Mix, containing nuclease-free water, a reverse transcriptase reagent, a template switch oligo, a reducing agent, and a reverse transcriptase enzyme can be added to the sample and substrate, and the sample with the Master Mix can be subjected to a thermocycling protocol (e.g., perform reverse transcription at 53° C. for 45 minutes and hold at 4° C.). Second strand synthesis can be performed on the substrate by subjecting the substrate to a thermocycling protocol (e.g., pre-equilibrate at 65° C., second strand synthesis at 65° C. for 15 minutes, then hold at 4° C.). The Master Mix reagents can be removed from the sample and 0.8M KOH can be applied and incubated for 5 minutes at room temperature. The KOH can be removed and elution buffer can be added and removed from the sample. A Second Strand Mix, including a second strand reagent, a second strand primer, and a second strand enzyme, can be added to the sample and the sample can be sealed and incubated. At the end of the incubation, the reagents can be removed and elution buffer can be added and removed from the sample, and 0.8 M KOH can be added again to the sample and the sample can be incubated for 10 minutes at room temperature. Tris-HCl can be added and the reagents can be mixed. The sample can be transferred to a new tube, vortexed, and placed on ice.

Further the sample can be processed by the following exemplary steps for cDNA amplification and quality control. A qPCR Mix, including nuclease-free water, qPCR Master Mix, and cDNA primers, can be prepared and pipetted into wells in a qPCR plate. A small amount of sample can be added to the plated qPCR Mix, and thermocycled according to a predetermined thermocycling protocol (e.g., step 1: 98° C. for 3 minutes, step 2: 98° C. for 5 seconds, step 3: 63° C. for 30 seconds, step 4: record amplification signal, step 5: repeating 98° C. for 5 seconds, 63° C. for 30 seconds for a total of 25 cycles). After completing the thermocycling, a cDNA amplification mix, including amplification mix and cDNA primers, can be prepared and combined with the remaining sample and mixed. The sample can then be incubated and thermocycled (e.g., lid temperature at 105° C. for ~45-60 minutes; step 1: 98° C. for 3 minutes, step 2: 98° C. for 15 seconds, step 3: 63° C. for 20 seconds, step 4: 72° C. for one minute, step 5: [the number of cycles determined by qPCR Cq Values], step 6: 72° C. for 1 minute, and step 7: hold at 4° C.). The sample can then be stored at 4° C. for up to 72 hours or at −20° C. for up to 1 week, or resuspended in 0.6× SPRIselect Reagent and pipetted to ensure proper mixing. The sample can then be incubated at 5 minutes at room temperature, and cleared by placing the sample on a magnet (e.g., the magnet is in the high position). The supernatant can be removed and 80% ethanol can be added to the pellet, and incubated for 30 seconds. The ethanol can be removed and the pellet can be washed again. The sample can then be centrifuged and placed on a magnet (e.g., the magnet is on the low position). Any remaining ethanol can be removed and the sample can be air dried for up to 2 minutes. The magnet can be removed and elution buffer can be added to the sample, mixed, and incubated for 2 minutes at room temperature. The sample can then be placed on the magnet (e.g., on low position) until the solution clears. The sample can be transferred to a new tube strip and stored at 4° C. for up to 72 hours or at −20° C. for up to 4 weeks. A portion of the sample can be run on an Agilent Bioanalyzer High Sensitivity chip, where a region can be selected and the cDNA concentration can be measured to calculate the total cDNA yield. Alternatively, the quantification can be determined by Agilent Bioanalyzer or Agilent TapeStation.

Further, the sample can be processed by the following exemplary steps for spatial gene expression library construction. A Fragmentation Mix, including a fragmentation buffer and fragmentation enzyme, can be prepared on ice. Elution buffer and fragmentation mix can be added to each sample, mixed, and centrifuged. The sample mix can then be placed in a thermocycler and cycled according to a predetermined protocol (e.g., lid temperature at 65° C. for ~35 minutes, pre-cool block down to 4° C. before fragmentation at 32° C. for 5 minutes, End-repair and A-tailing at 65° C. for 30 minutes, and holding at 4° C.). The 0.6× SPRIselect Reagent can be added to the sample and incubated at 5 minutes at room temperature. The sample can be placed on a magnet (e.g., in the high position) until the solution clears, and the supernatant can be transferred to a new tube strip. 0.8× SPRIselect Reagent can be added to the sample, mixed, and incubated for 5 minutes at room temperature. The sample can be placed on a magnet (e.g., in the high position) until the solution clears. The supernatant can be removed and 80% ethanol can be added to the pellet, the pellet can be incubated for 30 seconds, and the ethanol can be removed. The ethanol wash can be repeated and the sample placed on a magnet (e.g., in the low position) until the solution clears. The remaining ethanol can be removed and elution buffer can be added to the sample, mixed, and incubated for 2 minutes at room temperature. The sample can be placed on a magnet (e.g., in the high position) until the solution clears, and a portion of the sample can be moved to a new tube strip. An Adaptor Ligation Mix, including ligation buffer, DNA ligase, and adaptor oligos, can be prepared and centrifuged. The Adaptor Ligation Mix can be added to the sample, pipette-mixed, and centrifuged briefly. The sample can then be thermocycled according to a predetermined protocol (e.g., lid temperature at 30° C. for ~15 minutes, step 1: 20° C. for 15 minutes, step 2: 4° C. hold). The sample can be vortexed to resuspend SPRIselect Reagent, additional 0.8× SPRIselect Reagent can be added to the sample and incubated for 5 minutes at room temperature, and placed on a magnet (e.g., in the high position) until the solution clears. The supernatant can be removed and the pellet can be washed with 80% ethanol, incubated for 30 seconds, and the ethanol can be removed. The ethanol wash can be repeated, and the sample can be centrifuged briefly before placing the sample on a magnet (e.g., in the low position). Any remaining ethanol can be removed and the sample can be air dried for a maximum of 2 minutes. The magnet can be removed, and elution buffer can be added to the sample, and the sample can be pipette-mixed, incubated for 2 minutes at room temperature, and placed on a magnet (e.g., in the low position) until the solution clears. A portion of the sample can be transferred to a new tube strip. Amplification mix, can be prepared and combined with the sample. An individual Dual Index TT Set A can be added to the sample, pipette-mixed and subjected to a pre-determined thermocycling protocol (e.g., lid temperature at 105° C. for ~25-40 minutes, step 1: 98° C. for 45 seconds, step 2: 98° C. for 20 seconds, step 3: 54° C. for 30 seconds; step 4: 72° C. for 20 seconds, step 5: reverting to step 2 for a predetermined number of cycles, step 6: 72° C. for 1 minute, and 4° C. on hold). Vortex to resuspend the SPRIselect Reagent, additional 0.6× SPRIselect Reagent can be added to each sample, mixed, and incubated for 5 minutes at room temperature. The sample can be placed on a magnet (e.g., in the high position) until the solution clears, and the supernatant can be transferred to a new tube strip. The 0.8× SPRIselect Reagent can be added to each sample, pipette-mixed, and incubated for 5 minutes at room temperature. The sample can then be placed on a magnet (e.g., in the high position) until the solution clears. The supernatant can be removed, and the pellet can be washed with 80% ethanol, incubated for 30 seconds, and then the ethanol can be removed. The ethanol wash can be repeated, the sample centrifuged, and placed on a magnet (e.g., in the low position) to remove any remaining ethanol. The sample can be removed from the magnet and Elution Buffer can be added to the sample, pipette-mixed, and incubated for 2 minutes at room temperature. The sample can be placed on a magnet (e.g., in the low position) until the solution clears and a portion of the sample can be transferred to a new tube strip. The sample can be stored at 4° C. for up to 72 hours, or at −20° C. for long-term storage. The average fragment size can be determined using a Bioanalyzer trace or an Agilent TapeStation.

The library can be sequenced using available sequencing platforms, including, MiSeq, NextSeq 500/550, HiSeq 2500, HiSeq 3000/4000, NovaSeq, and iSeq.

In non-limiting examples of any of the workflows described herein, a nucleic acid molecule is produced that includes a contiguous nucleotide sequence comprising: (a) a first primer sequence (e.g., Read 1); (b) a spatial barcode; (c) a unique molecular sequence (UMI); (d) a capture domain; (e) a sequence complementary to a sequence present in a nucleic acid from a sample; (f) a second primer sequence (e.g., Read 2) that is substantially complementary to a sequence of a template switching oligonucleotide (TSO). In some embodiments of these nucleic acid molecules, the nucleic acid molecule is a single-stranded nucleic acid molecule. In some embodiments of these nucleic acid molecules, the nucleic acid molecule is a double-stranded nucleic acid molecule. In some embodiments of these nucleic acid molecules, (a) through (f) are positioned in a 5' to 3' direction in the contiguous nucleotide sequence. In some embodiments of any of these nucleic acid molecules, the nucleic acid molecule is attached to a substrate (e.g., a slide). In some embodiments of any of these nucleic acid molecules, the 5' end of the contiguous nucleic acid sequence is attached to the substrate (e.g., a slide). In some embodiments of any of these nucleic acid molecules, the contiguous nucleotide sequence is a chimeric RNA and DNA sequence. In some embodiments of any of these nucleic acid molecules, the contiguous nucleotide sequence is a DNA sequence.

In non-limiting examples of any of the workflows described herein, a nucleic acid molecule is produced that includes a contiguous nucleotide sequence comprising: (a) a sequence complementary to a first primer sequence (e.g., a sequence complementary to Read 1); (b) a sequence complementary to a spatial barcode; (c) a sequence complementary to a unique molecular sequence; (d) a sequence complementary to a capture domain; (e) a sequence present in a nucleic acid from a sample; and (f) a sequence of a template switching oligonucleotide (TSO). In some embodiments of any of these nucleic acid molecules, the nucleic acid molecule is single-stranded. In some embodiments of any of these nucleic acid molecules, the nucleic acid molecule is double-stranded. In some embodiments of any of these nucleic acid molecules, the contiguous nucleotide sequence is a DNA sequence. In some embodiments of any of these nucleic acid molecules, (a) through (f) are positioned in a 3' to 5' direction in the contiguous nucleotide sequence.

In non-limiting examples of any of the workflows described herein, a nucleic acid molecule is produced that includes a contiguous nucleotide sequence comprising: (a) a first primer sequence (e.g., Read 1); (b) a spatial barcode; (c) a unique molecular sequence (UMI); (d) a capture domain; (e) a sequence complementary to a sequence present in a nucleic acid from a sample; and (f) a second primer sequence (Read 2). In some embodiments of any of these nucleic acid molecules, the nucleic acid molecule is a single-stranded nucleic acid molecule. In some embodiments of any of these nucleic acid molecules, the nucleic acid molecule is a double-stranded nucleic acid molecule. In some embodiments of any of these nucleic acid molecules, (a) through (f) are positioned in a 5' to 3' direction in the contiguous nucleotide sequence. In some embodiments of any of these nucleic acid molecules, the contiguous nucleotide sequence is a DNA sequence. In some embodiments of any of these nucleic acid molecules, the contiguous nucleotide sequence further comprises 3' to (f): (g) a sequence complementary to a first adaptor sequence; and (h) a sequence complementary to a third primer sequence. In some embodiments of any of the nucleic acid molecules, the first adaptor sequence is an i7 sample index sequence. In some embodiments of any of these nucleic acid molecules, the third primer sequence is a P7 primer sequence. See, Illumina, Indexed Sequencing Overview Guides, February 2018, Document 15057455v04; and Illumina Adapter Sequences, May 2019, Document #1000000002694v11, each of which is hereby incorporated by reference, for information on P5, P7, i7, i5, TruSeq Read 2, indexed sequencing, and other reagents described herein. In some embodiments of any of these nucleic acid molecules, (h) is 3' positioned relative to (g) in the contiguous nucleotide sequence. In some embodiments of any of these nucleic acid molecules, the contiguous nucleotide sequence further comprises 5' to (a): (i) a second adaptor sequence; and (ii) a fourth primer sequence. In some embodiments of any of these nucleic acid molecules, the second adaptor sequence is an i5 sample index sequence. In some embodiments of any of these nucleic acid molecules, the fourth primer sequence is a P5 primer sequence. In some embodiments of any of these nucleic acid molecules, (ii) is 5' positioned relative to (i) in the contiguous nucleotide sequence.

In non-limiting examples of any of the workflows described herein, a nucleic acid molecule is produced that includes a contiguous nucleotide sequence comprising: (a) a sequence complementary to a first primer sequence; (b) a sequence complementary to a spatial barcode; (c) a sequence complementary to a unique molecular sequence; (d) a sequence complementary to a capture domain; (e) a sequence present in a nucleic acid from a sample; and (f) a sequence complementary to a second primer sequence. In some embodiments of these nucleic acid molecules, a sequence complementary to a first primer sequence is a sequence complementary to Read 1. In some embodiments of these nucleic acid molecules, a sequence complementary to a second primer sequence is a sequence complementary to Read 2. In some embodiments of any of these nucleic acid molecules, the nucleic acid molecule is a single-stranded nucleic acid molecule. In some embodiments of any of these nucleic acid molecules, the nucleic acid molecule is a double-stranded nucleic acid molecule. In some embodiments of any of these nucleic acid molecules, (a) through (f) are positioned in a 3' to 5' direction in the contiguous nucleotide sequence. In some embodiments of any of these nucleic acid molecules, the contiguous nucleotide sequence is a DNA sequence. In some embodiments of any of these nucleic acid molecules, the contiguous nucleotide sequence further comprises 5' to (f): (g) a first adaptor sequence; and (h) a third primer sequence. In some embodiments of any of these nucleic acid molecules, the first adaptor sequence is an i7 sample index sequence. In some embodiments of any of these nucleic acid molecules, the third primer sequence is a P7 primer sequence. In some embodiments of any of these nucleic acid molecules, (h) is 5' positioned relative to (g) in the contiguous nucleotide sequence. In some embodiments of any of these nucleic acid molecules, the contiguous nucleotide sequence further comprises 3' to (a): (i) a sequence complementary to a second adaptor sequence; and (ii) a sequence complementary to a fourth primer sequence. In some embodiments of any of these nucleic acid molecules, the second adaptor sequence is an i5 sample index sequence. In some embodiments of any of these nucleic acid molecules, the fourth primer sequence is a P5 primer sequence. In some embodiments of any of these nucleic acid molecules, (ii) is 3' positioned relative to (i) in the contiguous nucleotide sequence.

REFERENCES CITED AND ALTERNATIVE EMBODIMENTS

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

The present invention can be implemented as a computer program product that comprises a computer program mechanism embedded in a nontransitory computer readable storage medium. For instance, the computer program product could contain the program modules shown in FIGS. 11A and 11B, and/or described in FIGS. 10A, 10B, 10C, 10D, and 10E. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of spatial analysis of analytes comprising:
A) obtaining a data structure in electronic form comprising (i) an image of a sample on a substrate and (ii) a substrate identifier unique to the substrate, wherein:
the substrate includes a plurality of fiducial markers,
the substrate includes a set of capture spots, wherein the set of capture spots comprises at least 1000 capture spots; and
the image comprises an array of pixel values, wherein the array of pixel values comprises at least 100,000 pixel values;
B) analyzing the array of pixel values to identify a plurality of derived fiducial spots of the image;
C) using the substrate identifier of the data structure to select a first template in a plurality of templates, wherein each template in the plurality of templates comprises reference positions for a corresponding plurality of reference fiducial spots and a corresponding coordinate system;
D) aligning the plurality of derived fiducial spots of the image with the corresponding plurality of reference fiducial spots of the first template using an alignment algorithm to obtain a transformation between the plurality of derived fiducial spots of the image and the corresponding plurality of reference fiducial spots of the first template;
E) using the transformation and the coordinate system of the first template to register the image to the set of capture spots; and
F) analyzing the image after the using E) in conjunction with spatial analyte data associated with each capture spot, thereby performing spatial analysis of analytes.

2. The method of claim 1, wherein the B) analyzing comprises:
identifying a plurality of candidate derived fiducial spots by thresholding the array of pixel values into a plurality of threshold images and identifying, within the plurality of threshold images, groups of pixels having white values,
clustering the plurality of candidate derived fiducial spots based on spot size, thereby distributing the plurality of candidate derived fiducial spots into a plurality of subsets of candidate derived fiducial spots, wherein each respective subset of candidate derived fiducial spots in the plurality of subsets of candidate derived fiducial spots has a characteristic size, and
selecting the subset of candidate derived fiducial spots in the plurality of subsets of candidate derived fiducial spots that has the largest characteristic size as the plurality of derived fiducial spots of the image.

3. The method of claim 2, wherein the identifying further comprises merging respective pairs of candidate derived fiducial spots that are within a threshold distance of each other.

4. The method of claim 2, wherein the identifying further comprises filtering out respective candidate derived fiducial spots that fail to satisfy a maximum or minimum size criterion.

5. The method of claim 2, wherein the identifying further comprises filtering out respective candidate derived fiducial spots that fail to satisfy a circularity criterion, a convexity criterion, or an inertia ratio criterion.

6. The method of claim 1, wherein the transformation comprises:
a similarity transform that comprises rotation, translation, and isotropic scaling of the plurality of derived fiducial spots of the image to minimize a residual error between the plurality of derived fiducial spots and the corresponding plurality of reference fiducial spots, or
a non-rigid transform that comprises anisotropic scaling and skewing of the plurality of derived fiducial spots of the image to minimize a residual error between the plurality of derived fiducial spots and the corresponding plurality of reference fiducial spots.

7. The method of claim 1, wherein the transformation is a non-rigid transform and wherein the non-rigid transform is an affine transformation.

8. The method of claim 1, wherein the alignment algorithm is a coherent point drift algorithm, an Iterative Closest Point algorithm, a Robust Point Matching algorithm, or a Thin-Plate-Spline Robust Point Matching algorithm.

9. The method of claim 1, wherein the corresponding plurality of reference fiducial spots of the first template consists of between 100 spots and 1000 spots.

10. The method of claim 1, wherein:
the sample is a sectioned tissue sample,
each respective capture spot in the set of capture spots is
 (i) at a different position in a two-dimensional array and
 (ii) associates with one or more analytes from the sectioned tissue sample, and
each respective capture spot in the set of capture spots is characterized by at least one unique spatial barcode in a plurality of spatial barcodes.

11. The method of claim 1, wherein a capture spot in the set of capture spots comprises a capture domain or a cleavage domain.

12. The method of claim 1, wherein each capture spot in the set of capture spots is attached directly or attached indirectly to the substrate.

13. The method of claim 10, wherein the one or more analytes comprise five or more analytes, ten or more analytes, fifty or more analytes, one hundred or more analytes, five hundred or more analytes, 1000 or more analytes, 2000 or more analytes, or between 2000 and 10,000 analytes.

14. The method of claim 10, wherein the unique spatial barcode encodes a unique predetermined value selected from the set $\{1, \ldots, 1024\}$, $\{1, \ldots, 4096\}$, $\{1, \ldots, 16384\}$, $\{1, \ldots, 65536\}$, $\{1, \ldots, 262144\}$, $\{1, \ldots, 1048576\}$, $\{1, \ldots, 4194304\}$, $\{1, \ldots, 16777216\}$, $\{1, \ldots, 67108864\}$, or $\{1, \ldots, 1 \times 10^{12}\}$.

15. The method of claim 1, wherein each respective capture spot in the set of capture spots includes 1000 or more capture probes, 2000 or more capture probes, 10,000 or more capture probes, 100,000 or capture more probes, $1 \times 10^6$ or more capture probes, $2 \times 10^6$ or more capture probes, or $5 \times 10^6$ or more capture probes.

16. The method of claim 15, wherein each capture probe in the respective capture spot includes a poly-A sequence or a poly-T sequence and a unique spatial barcode that characterizes the respective capture spot.

17. The method of claim 15, wherein each capture probe in the respective capture spot includes the same spatial barcode from the plurality of spatial barcodes.

18. The method of claim 15, wherein each capture probe in the respective capture spot includes a different spatial barcode from the plurality of spatial barcodes.

19. The method of claim 1, wherein the sample is a sectioned tissue sample and wherein the sectioned tissue sample has a depth of 100 microns or less.

20. The method of claim 10, wherein
the one or more analytes is a plurality of analytes,
a respective capture spot in the set of capture spots includes a plurality of capture probes, each probe in the plurality of capture probes including a capture domain that is characterized by a capture domain type in a plurality of capture domain types, and
each respective capture domain type in the plurality of capture domain types is configured to bind to a different analyte in the plurality of analytes.

21. The method of claim 20, wherein the plurality of capture domain types comprises between 5 and 15,000 capture domain types and the respective capture spot includes at least five, at least 10, at least 100, or at least 1000 capture probes for each capture domain type in the plurality of capture domain types.

22. The method of claim 10, wherein:
the one or more analytes is a plurality of analytes, and
a respective capture spot in the set of capture spots includes a plurality of capture probes, each capture probe in the plurality of capture probes including a capture domain that is characterized by a single capture domain type configured to bind to each analyte in the plurality of analytes in an unbiased manner.

23. The method of claim 10, wherein each respective capture spot in the set of capture spots is contained within a 100 micron by 100 micron square on the substrate.

24. The method of claim 10, wherein a distance between a center of each respective capture spot to a neighboring capture spot in the set of capture spots on the substrate is between 40 microns and 300 microns.

25. The method of claim 1, wherein a shape of each capture spot in the set of capture spots on the substrate is circular and each capture spot in the set of capture spots has a diameter of between 2 microns and 7 microns.

26. The method of claim 1, wherein a distance between a center of each respective capture spot to a neighboring capture spot in the set of capture spots on the substrate is between 2 microns and 7 microns.

27. The method of claim 1, wherein the image is acquired using transmission light microscopy or fluorescent microscopy.

28. The method of claim 1, wherein the spatial analyte data associated with each capture spot is nucleic acid sequencing data associated with each capture spot.

29. The method of claim 10, wherein the one or more analytes are nucleic acids, RNA, DNA, or proteins.

30. A computer system comprising:
one or more processors;
memory; and
one or more programs, wherein the one or more programs are stored in the memory and configured to be executed by the one or more processors, the one or more programs for spatial analysis of analytes, the one or more programs including instructions for:
A) obtaining a data structure in electronic form comprising (i) an image of a sample on a substrate, and (ii) a substrate identifier unique to the substrate, wherein:
the substrate includes a plurality of fiducial markers,
the substrate includes a set of capture spots, wherein the set of capture spots comprises at least 1000 capture spots; and
the image comprises an array of pixel values, wherein the array of pixel values comprises at least 100,000 pixel values;
B) analyzing the array of pixel values to identify a plurality of derived fiducial spots of the image;
C) using the substrate identifier of the data structure to select a first template in a plurality of templates, wherein each template in the plurality of templates comprises reference positions for a corresponding plurality of reference fiducial spots and a corresponding coordinate system;
D) aligning the plurality of derived fiducial spots of the image with the corresponding plurality of reference fiducial spots of the first template using an alignment algorithm to obtain a transformation between the plurality of derived fiducial spots of the image and the corresponding plurality of reference fiducial spots of the first template;

E) using the transformation and the coordinate system of the first template to register the image to the set of capture spots; and F) analyzing the image after the using E) in conjunction with spatial nucleic analyte data associated with each capture spot.

31. A non-transitory computer readable storage medium storing one or more programs, the one or more programs comprising instructions, which when executed by an electronic device with one or more processors and a memory cause the electronic device to perform spatial analysis of analytes by a method comprising:

A) obtaining a data structure in electronic form comprising (i) an image of a sample on a substrate, and (ii) a substrate identifier unique to the substrate, wherein:
   the substrate includes a plurality of fiducial markers,
   the substrate includes a set of capture spots, wherein the set of capture spots comprises at least 1000 capture spots; and
   the image comprises an array of pixel values, wherein the array of pixel values comprises at least 100,000 pixel values;

B) analyzing the array of pixel values to identify a plurality of derived fiducial spots of the image;

C) using the substrate identifier of the data structure to select a first template in a plurality of templates, wherein each template in the plurality of templates comprises reference positions for a corresponding plurality of reference fiducial spots and a corresponding coordinate system;

D) aligning the plurality of derived fiducial spots of the image with the corresponding plurality of reference fiducial spots of the first template using an alignment algorithm to obtain a transformation between the plurality of derived fiducial spots of the image and the corresponding plurality of reference fiducial spots of the first template;

E) using the transformation and the coordinate system of the first template to register the image to the set of capture spots; and F) analyzing the image after the using E) in conjunction with spatial analyte data associated with each capture spot.

* * * * *

SEQUENCE LISTING

<160> NUMBER OF SEQ ID NOS: 4

<210> SEQ ID NO 1
<211> LENGTH: 20
<212> TYPE: RNA
<213> ORGANISM: Artificial Sequence
<220> FEATURE:
<223> OTHER INFORMATION: Hypothetical Nucleic Acid

<400> SEQUENCE: 1
aaaaaaaaaa aaaaaaaaaa                                              20

<210> SEQ ID NO 2
<211> LENGTH: 23
<212> TYPE: RNA
<213> ORGANISM: Artificial Sequence
<220> FEATURE:
<223> OTHER INFORMATION: Hypothetical Nucleic Acid -continued

```
<400> SEQUENCE: 2
aaaaaaaaaa aaaaaaaaaa aaa                                              23

<210> SEQ ID NO 3
<211> LENGTH: 23
<212> TYPE: RNA
<213> ORGANISM: Artificial Sequence
<220> FEATURE:
<223> OTHER INFORMATION: Hypothetical Nucleic Acid

<400> SEQUENCE: 3
uuuuuuuuuu uuuuuuuuuu uuu                                              23

<210> SEQ ID NO 4
<211> LENGTH: 18
<212> TYPE: DNA
<213> ORGANISM: Artificial Sequence
<220> FEATURE:
<223> OTHER INFORMATION: Hypothetical Nucleic Acid

<400> SEQUENCE: 4
tttttttttt tttttttt                                                    18
```